(12) United States Patent
Feldmann et al.

(10) Patent No.: US 7,569,389 B2
(45) Date of Patent: *Aug. 4, 2009

(54) NUCLEOTIDE SEQUENCES AND POLYPEPTIDES ENCODED THEREBY USEFUL FOR MODIFYING PLANT CHARACTERISTICS

(75) Inventors: Kenneth A. Feldmann, Newbury Park, CA (US); Vyacheslav Brover, Simi Valley, CA (US); Vladimir Makarov, Thousand Oaks, CA (US); Timothy Swaller, Thousand Oaks, CA (US)

(73) Assignee: Ceres, Inc., Rancho Conejo, CA (US)

( * ) Notice: Subject to any disclaimer, the term of this patent is extended or adjusted under 35 U.S.C. 154(b) by 162 days.

This patent is subject to a terminal disclaimer.

(21) Appl. No.: 11/241,607

(22) Filed: Sep. 30, 2005

(65) Prior Publication Data

US 2007/0039067 A1    Feb. 15, 2007

Related U.S. Application Data

(60) Provisional application No. 60/615,270, filed on Sep. 30, 2004, provisional application No. 60/638,820, filed on Dec. 22, 2004, provisional application No. 60/637,210, filed on Dec. 16, 2004, provisional application No. 60/614,271, filed on Sep. 30, 2004, provisional application No. 60/614,332, filed on Sep. 30, 2004, provisional application No. 60/627,206, filed on Nov. 12, 2004.

(51) Int. Cl.
C12N 15/82 (2006.01)
C12N 5/04 (2006.01)

(52) U.S. Cl. ................. 435/468; 435/419; 800/290; 800/298

(58) Field of Classification Search .............. None
See application file for complete search history.

(56) References Cited

U.S. PATENT DOCUMENTS 7,109,033 B2 * 9/2006 Harper et al. ............ 435/419

FOREIGN PATENT DOCUMENTS

EP    1 033 405 A2 * 9/2000

* cited by examiner

Primary Examiner—James Martinell
(74) Attorney, Agent, or Firm—Birch, Stewart, Kolasch & Birch LLP

(57) ABSTRACT

Isolated polynucleotides and polypeptides encoded thereby are described, together with the use of those products for making transgenic plants.

16 Claims, No Drawings

NUCLEOTIDE SEQUENCES AND POLYPEPTIDES ENCODED THEREBY USEFUL FOR MODIFYING PLANT CHARACTERISTICS

CROSS REFERENCE TO RELATED APPLICATION

This Nonprovisional application claims priority under 35 U.S.C. § 119(e) on U.S. Provisional Application No(s). 60/615,270 filed on Sep. 30, 2004, Application No. 60/638,820 filed on Dec. 22, 2004, Application No. 60/637,210 filed on Dec. 16, 2004, Application No. 60/614,271 filed on Sep. 30, 2004, Application No. 60/614,332 filed on Sep. 30, 2004 and Application No. 60/627,206 filed on Nov. 12, 2004, the entire contents of which are hereby incorporated by reference.

This application contains a CDR, the entire contents of which are hereby incorporated by reference. The CDR contains the following files:

| File Name | File Size | File Date |
|---|---|---|
| 2005-09-30 Table 1.doc | 768 KB | Sep. 30, 2005 | alleles available, the combinations required and the ability to create and find the correct combinations necessary to give the desired properties to the plant. Molecular genetics technologies are now capable of providing new genes, new alleles and the means of creating and selecting plants with the new, desired characteristics.

Plants specifically improved for agriculture, horticulture, forestry and other industries (such as paper, bioconversion, textile, plants as chemical factories, etc.) can be obtained using molecular technologies. As an example, great agronomic value can result from modulating the size of a plant as a whole or of any of its organs. The green revolution came about as a result of creating dwarf wheat plants which produced a higher seed yield than taller plants because they could withstand higher levels and inputs of fertilizer and water.

Similarly, modulation of the size and stature of an entire plant, or a particular portion of a plant, allows production of plants better suited for a particular industry. For example, reductions in the height of specific ornamentals, crops and tree species can be beneficial by allowing easier harvesting. Alternatively, increasing height may be beneficial by providing more biomass. Other examples of commercially desirable traits include increasing the length of the floral stems of cut flowers, increasing or altering leaf size and shape, enhancing the size of seeds and/or fruits, enhancing yields by specifically stimulating hormone (e.g. Brassinolide) synthesis and stimulating early flowering or evoking late flowering by alter-

TABLES

The patent contains table(s) that have been included at the end of the specification.

FIELD OF THE INVENTION

The present invention relates to isolated polynucleotides, polypeptides encoded thereby, and the use of those products for making transgenic plants or organisms, such as transgenic plants.

BACKGROUND OF THE INVENTION

There are more than 300,000 species of plants. They show a wide diversity of forms, ranging from delicate liverworts, adapted for life in a damp habitat, to cacti, capable of surviving in the desert. The plant kingdom includes herbaceous plants, such as corn, whose life cycle is measured in months, to the giant redwood tree, which can live for thousands of years. This diversity reflects the adaptations of plants to survive in a wide range of habitats. This is seen most clearly in the flowering plants (*phylum Angiospermophyta*), which are the most numerous, with over 250,000 species. They are also the most widespread, being found from the tropics to the arctic.

The process of plant breeding involving man's intervention in natural breeding and selection is some 20,000 years old. It has produced remarkable advances in adapting existing species to serve new purposes. The world's economics was largely based on the successes of agriculture for most of these 20,000 years.

Plant breeding involves choosing parents, making crosses to allow recombination of gene (alleles) and searching for and selecting improved forms. Success depends on the genes/ ing levels of gibberellic acid or other hormones in specific cells. Changes in organ size and biomass also result in changes in the mass of constituent molecules such as secondary products.

To summarize, molecular genetic technologies provide the ability to modulate and manipulate growth, development and biochemistry of the entire plant as well as at the cell, tissue and organ levels. Thus, plant morphology, development and biochemistry are altered to maximize or minimize the desired plant trait.

SUMMARY OF THE INVENTION

The present invention, therefore, relates to isolated polynucleotides, polypeptides encoded thereby, and the use of those products for making transgenic organisms, such as plants, bacteria, yeast, fungi and mammals, depending upon the desired characteristics.

In the field of agriculture and forestry efforts are constantly being made to produce plants with improved characteristics, such as increased overall yield or increased yield of biomass or chemical components, in particular in order to guarantee the supply of the constantly increasing world population with food and to guarantee the supply of reproducible raw materials. Conventionally, people try to obtain plants with an increased yield by breeding, but this is time-consuming and labor-intensive. Furthermore, appropriate breeding programs must be performed for each relevant plant species.

Over the last two decades, progress has been made by the genetic manipulation of plants. That is, by introducing into plants recombinant nucleic acid molecules and expressing them as exogenous genes or using them to silence endogenous genes within these plants. Such approaches have the advantage of not usually being limited to one plant species, but being transferable to other plant species and other organisms as well. EP-A 0 511 979, for example, discloses that the expression of a prokaryotic asparagine synthetase in plant cells inter alia leads to an increase in biomass production. Similarly, WO 96/21737 describes the production of plants with increased yield from the expression of deregulated or unregulated fructose-1,6-bisphosphatase due to an increased rate of the photosynthesis. Nevertheless, there is still a need for generally applicable processes that lead to improved characteristics (such as yield) in relevant plants associated with a wide array of industrial purposes.

BRIEF DESCRIPTION OF THE TABLES

Table 1 Knock-in Table

The Knock-In Table presents the results of knock-in experiments wherein plants are grown from tissues transformed with a marker gene-containing insert and phenotypes are ascertained from the transformed plants. Each section of the Table relating to information on a new transformant begins with a heading "Knock-in phenotype in gene (cDNA_id):" followed by a number which represents the Ceres internal code for a proprietary cDNA sequence. The transformant described is prepared by procedures described herein and the marker gene-containing insert interrupts the Ceres proprietary cDNA_id (corresponding to the cDNA_id in the Reference and Sequence Tables) identified. The following information is presented for each section.

Clone ID—presents the clone number of the Ceres proprietary clone that is the source of the cDNA_id.

Promoter—Identifies the promoter utilized.

Phenotype ID—represents an internal identification code.

Unique Fl plant ID—represents the internal code for the F1 plant for which a phenotype is described.

Assay—presents the type of growth analyzed (e.g. soil gross morphology), followed by the assay name which corresponds to the type/location of the tissue that was observed, the name of the assay conducted for which the result provided the identified phenotype.

Phenotype—describes the phenotype noted for the F1 generation transformant.

Notes—provide additional information on the described phenotype for the transformant.

Each knock-in that represents a transformant with an interruption in the identified cDNA_id may be correlated with more than one identified phenotype.

DETAILED DESCRIPTION OF THE INVENTION

1. Definitions

The following terms are utilized throughout this application:

Domain: Domains are fingerprints or signatures that can be used to characterize protein families and/or parts of proteins. Such fingerprints or signatures can comprise conserved (1) primary sequence, (2) secondary structure, and/or (3) three-dimensional conformation. Generally, each domain has been associated with either a family of proteins or motifs. Typically, these families and/or motifs have been correlated with specific in-vitro and/or in-vivo activities. A domain can be any length, including the entirety of the sequence of a protein. Detailed descriptions of the domains, associated families and motifs, and correlated activities of the polypeptides of the instant invention are described below. Usually, the polypeptides with designated domain(s) can exhibit at least one activity that is exhibited by any polypeptide that comprises the same domain(s). Domains also define areas of non-coding sequences such as promoters and mRNAs.

Endogenous: The term "endogenous," within the context of the current invention refers to any polynucleotide, polypeptide or protein sequence which is a natural part of a cell or organism regenerated from said cell.

Exogenous: "Exogenous," as referred to within, is any polynucleotide, polypeptide or protein sequence, whether chimeric or not, that is initially or subsequently introduced into the genome of an individual host cell or the organism regenerated from said host cell by any means other than by a sexual cross. Examples of means by which this can be accomplished are described below, and include *Agrobacterium*-mediated transformation (of dicots—e.g. Salomon et al. (1984) *EMBO J.* 3:141; Herrera-Estrella et al. (1983) *EMBO J.* 2:987; of monocots, representative papers are those by Escudero et al. (1996) *Plant J.* 10:355; Ishida et al. (1996) *Nature Biotechnology* 14:745; May et al. (1995) *Bio/Technology* 13:486), biolistic methods (Armaleo et al. (1990) *Current Genetics* 17:97), electroporation, in planta techniques, and the like. The term "exogenous" as used herein is also intended to encompass inserting a naturally found element into a non-naturally found location.

Gene: The term "gene," as used in the context of the current invention, encompasses all regulatory and coding sequence contiguously associated with a single hereditary unit with a genetic function. Genes can include non-coding sequences that modulate the genetic function that include, but are not limited to, those that specify polyadenylation, transcriptional regulation, DNA conformation, chromatin conformation, extent and position of base methylation and binding sites of proteins that control all of these. Genes comprised of "exons" (coding sequences), which may be interrupted by "introns" (non-coding sequences), encode proteins. A gene's genetic function may require only RNA expression or protein production, or may only require binding of proteins and/or nucleic acids without associated expression. In certain cases, genes adjacent to one another may share sequence in such a way that one gene will overlap the other. A gene can be found within the genome of an organism, artificial chromosome, plasmid, vector, etc., or as a separate isolated entity.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence originates from, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

Homologous gene: In the current invention, "homologous gene" refers to a gene that shares sequence similarity with the gene of interest. This similarity may be in only a fragment of the sequence and often represents a functional domain such as, examples including without limitation a DNA binding domain, a domain with tyrosine kinase activity, or the like. The functional activities of homologous genes are not necessarily the same.

Misexpression: The term "misexpression" refers to an increase or a decrease in the transcription of a coding region into a complementary RNA sequence as compared to the parental wild-type. This term also encompasses expression of a gene or coding region for a different time period as compared to the wild-type and/or from a non-natural location within the plant genome.

Percentage of sequence identity: "Percentage of sequence identity," as used herein, is determined by comparing two optimally aligned sequences over a comparison window, where the fragment of the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman (1981) *Add. APL. Math.* 2:482, by the homology alignment algorithm of Needleman and Wunsch (1970) *J. Mol. Biol.* 48:443, by the search for similarity method of Pearson and Lipman (1988) *Proc. Natl. Acad. Sci.* (*USA*) 85: 2444, by computerized implementations of algorithms such as GAP, BESTFIT, BLAST, PASTA, and TFASTA (Accelrys, Inc., 10188 Telesis Court, Suite 100 San Diego, Calif. 92121) or by inspection. Typically, the default values of 5.00 for gap weight and 0.30 for gap weight length are used. The term "substantial sequence identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

Regulatory Sequence: The term "regulatory sequence," as used in the current invention, refers to any nucleotide sequence that influences transcription or translation initiation and rate, and stability and/or mobility of the transcript or polypeptide product. Regulatory sequences include, but are not limited to, promoters, promoter control elements, protein binding sequences, 5' and 3' UTRs, transcriptional start site, termination sequence, polyadenylation sequence, introns, certain sequences within a coding sequence, etc.

Stringency: "Stringency" as used herein is a function of probe length, probe composition (G+C content), and salt concentration, organic solvent concentration, and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m-5°$ C. to $T_m-10°$ C. Medium or moderate stringency conditions are those providing $T_m-20°$ C. to $T_m-29°$ C. Low stringency conditions are those providing a condition of $T_m-40°$ C. to $T_m-48°$ C. The relationship of hybridization conditions to $T_m$ (in ° C.) is expressed in the mathematical equation $$T_m=81.5-16.6(\log_{10}[Na^+])+0.41(\% \ G+C)-(600/N) \quad (1)$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m=81.5+16.6 \log \{[Na^+]/(1+0.7[Na^+])\}+0.41(\% \ G+C)-500/L0.63(\% \ formamide) \quad (2)$$

where L is the length of the probe in the hybrid. (P. Tijessen, "Hybridization with Nucleic Acid Probes" in Laboratory Techniques in Biochemistry and Molecular Biology, P. C. vand der Vliet, ed., c. 1993 by Elsevier, Amsterdam.) The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used (Bonner et al. (1973) *J. Mol. Biol.* 81:123), stringency conditions in polynucleotide hybridization reactions can be adjusted to favor hybridization of polynucleotides from identical genes or related family members.

Equation (2) is derived assuming equilibrium and therefore, hybridizations according to the present invention are most preferably performed under conditions of probe excess and for sufficient time to achieve equilibrium. The time required to reach equilibrium can be shortened by inclusion of a hybridization accelerator such as dextran sulfate or another high volume polymer in the hybridization buffer.

Stringency conditions can be selected during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

Substantially free of: A composition containing A is "substantially free of "B when at least 85% by weight of the total A+B in the composition is A. Preferably, A comprises at least about 90% by weight of the total of A+B in the composition, more preferably at least about 95% or even 99% by weight. For example, a plant gene or DNA sequence can be considered substantially free of other plant genes or DNA sequences.

Translational start site: In the context of the current invention, a "translational start site" is usually an ATG in the cDNA transcript, more usually the first ATG. A single cDNA, however, may have multiple translational start sites.

Transcription start site: "Transcription start site" is used in the current invention to describe the point at which transcription is initiated. This point is typically located about 25 nucleotides downstream from a TFIID binding site, such as a TATA box. Transcription can initiate at one or more sites within the gene, and a single gene may have multiple transcriptional start sites, some of which may be specific for transcription in a particular cell-type or tissue.

Untranslated region (UTR): A "UTR" is any contiguous series of nucleotide bases that is transcribed, but is not translated. These untranslated regions may be associated with particular functions such as increasing mRNA message stability. Examples of UTRs include, but are not limited to polyadenylation signals, terminations sequences, sequences located between the transcriptional start site and the first exon (5' UTR) and sequences located between the last exon and the end of the mRNA (3' UTR).

Variant: The term "variant" is used herein to denote a polypeptide or protein or polynucleotide molecule that differs from others of its kind in some way. For example, polypeptide and protein variants can consist of changes in amino acid sequence and/or charge and/or post-translational modifications (such as glycosylation, etc).

2. Important Characteristics of the Polynucleotides of the Invention

The genes and polynucleotides of the present invention are of interest because when they are misexpressed (i.e. when over expressed at a non-natural location or in an increased amount) or when they allow silencing endogenous genes, they produce plants with important modified characteristics as discussed below. These traits can be used to exploit or maximize plant products or to minimize undesirable characteristics. For example, an increase in plant height is beneficial in species grown or harvested for their main stem or trunk, such as ornamental cut flowers, fiber crops (e.g. flax, kenaf, hesperaloe, hemp) and wood producing trees. Increase in inflorescence thickness is also desirable for some ornamentals, while increases in the number, shape and size of leaves can lead to increased production/harvest from leaf crops such as lettuce, spinach, cabbage, switch grass and tobacco. Likewise, a decrease in plant height is beneficial in species that are particularly susceptible to lodging or uprooting due to wind stress.

The polynucleotides and polypeptides of the invention were isolated from different plant species as noted in the Sequence Listing. The polynucleotides and polypeptides are useful to confer on transgenic plants the properties identified for each sequence in the relevant portion (miscellaneous feature section) of the Sequence Listing. The miscellaneous feature section of the sequence listing contains, for each sequence, a description of the domain or other characteristic from which the sequence has the function known in the art for other sequences. Some identified domains are indicated with "PFam Name", signifying that the pfam name and description can be found in the pfam database available via the internet. Other domains are indicated by reference to a "GI Number" from the public sequence database maintained by GenBank under the NCBI, including the non-redundant (NR) database.

The sequences of the invention can be applied to substrates for use in microarray applications such as, but not limited to, assays of global gene expression under varying development and growth conditions. The microarrays are also used for diagnostic or forensic purposes. Arrays can be produced using different procedures such as those from Affymetrix or Agilent. Protocols for these procedures can be obtained from these companies or found via the internet.

The polynucleotides, or fragments thereof, can also be used as probes and primers. Probe length varies depending on the application. For use as primers, probes are 12-40 nucleotides, preferably 18-30 nucleotides long. For use in mapping, probes are preferably 50 to 500 nucleotides, preferably 100-250 nucleotides long. For Southern hybridizations, probes as long as several kilobases are used.

The probes and/or primers are produced by synthetic procedures such as the triester method of Matteucci et al. (1981) *J. Am. Chem. Soc.* 103:3185 or according to Urdea et al. (1981) *Proc. Natl. Acad.* 80:7461 or using commercially available automated oligonucleotide synthesizers.

The polynucleotides of the invention can be utilized in a number of methods known to those skilled in the art as probes and/or primers to isolate and detect polynucleotides including, without limitation: Southerns, Northerns, Branched DNA hybridization assays, polymerase chain reaction microarray assays and variations thereof. Specific methods given by way of examples, and discussed below include:

Hybridization
Methods of Mapping
Southern Blotting
Isolating cDNA from Related Organisms
Isolating and/or Identifying Homologous and Orthologous Genes. Also, the nucleic acid molecules of the invention can be used in other methods, such as high density oligonucleotide hybridizing assays, described, for example, in U.S. Pat. Nos. 6,004,753 and 5,945,306.

The polynucleotides or fragments thereof of the present invention can be used as probes and/or primers for detection and/or isolation of related polynucleotide sequences through hybridization. Hybridization of one nucleic acid to another constitutes a physical property that defines the polynucleotide of the invention and the identified related sequences. Also, such hybridization imposes structural limitations on the pair. A good general discussion of the factors for determining hybridization conditions is provided by Sambrook et al. ("Molecular Cloning, a Laboratory Manual, 2nd ed.,. 1989 by Cold Spring Harbor Laboratory Press, Cold Spring Harbor, N.Y.; see esp., chapters 11 and 12). Additional considerations and details of the physical chemistry of hybridization are provided by G. H. Keller and M. M. Manak "DNA Probes", $2^{nd}$ Ed. pp. 1-25, c. 1993 by Stockton Press, New York, N.Y.

When using the polynucleotides to identify homologous genes in other species, the practitioner will preferably adjust the amount of target DNA of each species so that, as nearly as is practical, the same number of genome equivalents are present for each species examined. This prevents faint signals from species having large genomes, and thus small numbers of genome equivalents per mass of DNA, from erroneously being interpreted as absence of the corresponding gene in the genome.

The probes and/or primers of the instant invention can also be used to detect or isolate nucleotides that are "identical" to the probes or primers. Two nucleic acid sequences or polypeptides are said to be "identical" if the sequence of nucleotides or amino acid residues, respectively, in the two sequences is the same when aligned for maximum correspondence as described below.

Isolated polynucleotides within the scope of the invention also include allelic variants of the specific sequences presented in the Sequence Listing. The probes and/or primers of the invention are also used to detect and/or isolate polynucleotides exhibiting at least 80% sequence identity with the sequences of the Sequence Listing or fragments thereof. Related polynucleotide sequences can also be identified according to the methods described in U.S. Patent Publication 20040137466A1, dated Jul. 15, 2004 to Jofuku et al.

With respect to nucleotide sequences, degeneracy of the genetic code provides the possibility to substitute at least one nucleotide of the nucleotide sequence of a gene with a different nucleotide without changing the amino acid sequence of the polypeptide. Hence, the DNA of the present invention also has any base sequence that has been changed from a sequence in the Sequence Listing by substitution in accordance with degeneracy of genetic code. References describing codon usage include: Carels et al. (1998) *J. Mol. Evol.* 46: 45 and Fennoy et al. (1993) *Nucl. Acids Res.* 21(23): 5294.

The polynucleotides of the invention are also used to create various types of genetic and physical maps of the genome of the plant species listed in the Sequence Listing. Some are absolutely associated with particular phenotypic traits, allowing construction of gross genetic maps. Creation of such maps is based on differences or variants, generally referred to as polymorphisms, between different parents used in crosses. Common methods of detecting polymorphisms that can be used are restriction fragment length polymorphisms (RFLPs), single nucleotide polymorphisms (SNPs) or simple sequence repeats (SSRs).

The use of RFLPs and of recombinant inbred lines for such genetic mapping is described for *Arabidopsis* by Alonso-Blanco et al. (*Methods in Molecular Biology*, vol. 82, "*Arabidopsis Protocols*", pp. 137-146, J. M. Martinez-Zapater and J. Salinas, eds., c. 1998 by Humana Press, Totowa, NJ) and for corn by Burr ("Mapping Genes with Recombinant Inbreds", pp. 249-254. In Freeling, M. and V. Walbot (Ed.), *The Maize Handbook*, c. 1994 by Springer-Verlag New York, Inc.: New York, N.Y., USA; Berlin Germany; Burr et al. *Genetics* (1998) 118: 519; Gardiner, J. et al. (1993) *Genetics* 134: 917). This procedure, however, is not limited to plants and is used for other organisms (such as yeast) or for individual cells.

The polynucleotides of the present invention are also used for simple sequence repeat (SSR) mapping. Rice SSR mapping is described by Morgante et al. (*The Plant Journal* (1993) 3: 165), Panaud et al. (*Genome* (1995) 38: 1170); Senior et al. (*Crop Science* (1996) 36: 1676), Taramino et al. (*Genome* (1996) 39: 277) and Ahn et al. (*Molecular and General Genetics* (1993) 241: 483-90). SSR mapping is achieved using various methods. In one instance, polymorphisms are identified when sequence specific probes contained within a polynucleotide flanking an SSR are made and used in polymerase chain reaction (PCR) assays with template DNA from two or more individuals of interest. Here, a change in the number of tandem repeats between the SSR-flanking sequences produces differently sized fragments (U.S. Pat. No. 5,766,847). Alternatively, polymorphisms are identified by using the PCR fragment produced from the SSR-flanking sequence specific primer reaction as a probe against Southern blots representing different individuals (U. H. Refseth et al. (1997) *Electrophoresis* 18: 1519).

The polynucleotides of the invention can further be used to identify certain genes or genetic traits using, for example, known AFLP technologies, such as in EP0534858 and U.S. Pat. No. 5,878,215.

The polynucleotides of the present invention are also used for single nucleotide polymorphism (SNP) mapping.

Genetic and physical maps of crop species have many uses. For example, these maps are used to devise positional cloning strategies for isolating novel genes from the mapped crop species. In addition, because the genomes of closely related species are largely syntenic (i.e. they display the same ordering of genes within the genome), these maps are used to isolate novel alleles from relatives of crop species by positional cloning strategies.

The various types of maps discussed above are used with the polynucleotides of the invention to identify Quantitative Trait Loci (QTLs). Many important crop traits, such as the solids content of tomatoes, are quantitative traits and result from the combined interactions of several genes. These genes reside at different loci in the genome, often times on different chromosomes, and generally exhibit multiple alleles at each locus. The polynucleotides of the invention are used to identify QTLs and isolate specific alleles as described by de Vicente and Tanksley (*Genetics* (1993) 134:585). Once a desired allele combination is identified, crop improvement is accomplished either through biotechnological means or by directed conventional breeding programs (for review see Tanksley and McCouch (1997) *Science* 277:1063). In addition to isolating QTL alleles in present crop species, the polynucleotides of the invention are also used to isolate alleles from the corresponding QTL of wild relatives.

In another embodiment, the polynucleotides are used to help create physical maps of the genome of the plant species mentioned in the Sequence Listing and related species thereto. Where polynucleotides are ordered on a genetic map, as described above, they are used as probes to discover which clones in large libraries of plant DNA fragments in YACs, BACs, etc. contain the same polynucleotide or similar sequences, thereby facilitating the assignment of the large DNA fragments to chromosomal positions. Subsequently, the large BACs, YACs, etc. are ordered unambiguously by more detailed studies of their sequence composition (e.g. Marra et al. (1997) Genomic Research 7:1072-1084) and by using their end or other sequences to find the identical sequences in other cloned DNA fragments. The overlapping of DNA sequences in this way allows building large contigs of plant sequences to be built that, when sufficiently extended, provide a complete physical map of a chromosome. Sometimes the polynucleotides themselves provide the means of joining cloned sequences into a contig. All scientific and patent publications cited in this paragraph are hereby incorporated by reference.

U.S. Pat. Nos. 6,287,778 and 6,500,614, both hereby incorporated by reference, describe scanning multiple alleles of a plurality of loci using hybridization to arrays of oligonucleotides. These techniques are useful for each of the types of mapping discussed above.

Following the procedures described above and using a plurality of the polynucleotides of the present invention, any individual is genotyped. These individual genotypes are used for the identification of particular cultivars, varieties, lines, ecotypes and genetically modified plants or can serve as tools for subsequent genetic studies involving multiple phenotypic traits.

Identification and isolation of orthologous genes from closely related species and alleles within a species is particularly desirable because of their potential for crop improvement. Many important crop traits result from the combined interactions of the products of several genes residing at different loci in the genome. Generally, alleles at each of these loci make quantitative differences to the trait. Once a more favorable allele combination is identified, crop improvement is accomplished either through biotechnological means or by directed conventional breeding programs (Tanksley et al. (1997) *Science* 277:1063).

3. Use of the Genes to Make Transgenic Plants

To use the sequences of the present invention or a combination of them or parts and/or mutants and/or fusions and/or variants of them, recombinant DNA constructs are prepared which comprise the polynucleotide sequences of the invention inserted into a vector, and which are suitable for transformation of plant cells. The construct is made using standard recombinant DNA techniques (Sambrook et al. 1989) and is introduced to the species of interest by *Agrobacterium*-mediated transformation or by other means of transformation as referenced below.

The sequences of the present invention can be in sense orientation or in anti-sense orientation.

If a decrease in the transcription or translation product of an endogenous gene (gene silencing) is desired, the sequence of interest is transcribed as an antisense nucleic acid or an interfering RNA similar or identical to part of the endogenous gene. Antisense nucleic acids or interfering RNAs are about 10 nucleotides to about 2,500 nucleotides in length. For example, the nucleic acid of the present invention can be used as an antisense nucleic acid to its corresponding endogenous gene. Alternatively, the transcription product of a nucleic acid of the invention can be similar or identical to the sense coding sequence of its corresponding endogenous gene, but is an RNA that is unpolyadenylated, lacks a 5' cap structure, or contains an unsplicable intron. The nucleic acid of the present invention in sense orientation can also be used as a partial or full-length coding sequence that results in inhibition of the expression of an endogenous polypeptide by co-suppression. Methods of co-suppression using a full-length cDNA sequence as well as a partial cDNA sequence are known in the art (see, for example, U.S. Pat. No. 5,231,020).

Alternatively, a nucleic acid can be transcribed into a ribozyme that affects expression of an mRNA (see U.S. Pat. No. 6,423,885). Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art (see, for example, U.S. Pat. No. 5,254,678). Hammerhead ribozyme sequences can be embedded in a stable RNA such as a transfer RNA (tRNA) to increase cleavage efficiency in vivo (Perriman et al. (1995) *Proc. Natl. Acad. Sci.* USA, 92(13):6175-6179; de Feyter and Gaudron *Methods in Molecular Biology*, Vol. 74, Chapter 43, "Expressing Ribozymes in Plants", Edited by Turner, P. C, Humana Press Inc., Totowa, NJ). RNA endoribonucleases such as the one that occurs naturally in *Tetrahymena thermophila* and which have been described extensively by Cech and collaborators can also be useful (see, for example, U.S. Pat. No. 4,987,071).

A nucleic acid of the present invention can also be used for its transcription into an interfering RNA. Such an RNA can be one that can anneal to itself, for example a double stranded RNA having a stem-loop structure. One strand of the stem portion of a double stranded RNA can comprise a sequence that is similar or identical to the sense coding sequence of an endogenous polypeptide and that is about 10 nucleotides to about 2,500 nucleotides in length. Generally, the length of the nucleic acid sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA can comprise an antisense sequence of an endogenous polypeptide and can have a length that is shorter, the same as, or longer than the length of the corresponding sense sequence. The loop portion of a double stranded RNA can be from 10 nucleotides to 500 nucleotides in length, for example from 15 nucleotides to 100 nucleotides, from 20 nucleotides to 300 nucleotides or from 25 nucleotides to 400 nucleotides in length. The loop portion of the RNA can include an intron (see, for example the following publications: WO 98/53083; WO 99/32619; WO 98/36083; WO 99/53050; US 20040214330; US 20030180945; U.S. Pat. Nos. 5,034,323; 6,452,067; 6,777,588; 6,573,099 and 6,326, 527). Interfering RNA also can be constructed as described in Brummell, et al. (2003) Plant J. 33:793-800.

The vector backbone for the recombinant constructs is any of those typical in the art such as plasmids (such as Ti plasmids), viruses, artificial chromosomes, BACs, YACs and PACs and vectors of the sort described by (a) BAC: Shizuya et al. (1992) Proc. Natl. Acad. Sci. USA 89: 8794-8797; Hamilton et al. (1996) Proc. Natl. Acad. Sci. USA 93: 9975-9979;
(b) YAC: Burke et al. (1987) Science 236:806-812;
(c) PAC: Sternberg N. et al. (1990) Proc Natl Acad Sci USA. Jan; 87(1):103-7;
(d) Bacteria-Yeast Shuttle Vectors: Bradshaw et al. (1995) Nucl Acids Res 23: 4850-4856;
(e) Lambda Phage Vectors: Replacement Vector, e.g., Frischauf et al. (1983) J. Mol Biol 170: 827-842; or Insertion vector, e.g., Huynh et al., In: Glover NM (ed) DNA Cloning: A practical Approach, Vol. 1 Oxford: IRL Press (1985); T-DNA gene fusion vectors: Walden et al. (1990) Mol Cell Biol 1: 175-194; and
(g) Plasmid vectors: Sambrook et al., infra.

Typically, the construct comprises a vector containing a sequence of the present invention with any desired transcriptional and/or translational regulatory sequences, such as promoters, UTRs, and 3' end termination sequences. Vectors can also include origins of replication, scaffold attachment regions (SARs), markers, homologous sequences, introns, etc. The vector may also comprise a marker gene that confers a selectable phenotype on plant cells. The marker may encode biocide resistance, particularly antibiotic resistance, such as resistance to kanamycin, G418, bleomycin, hygromycin, or herbicide resistance, such as resistance to chlorosulfuron, glyphosate or phosphinotricin.

A plant promoter fragment is used that directs transcription of the gene in all tissues of a regenerated plant and/or is a constitutive promoter. Alternatively, the plant promoter directs transcription of a sequence of the invention in a specific tissue (tissue-specific promoter) or is otherwise under more precise environmental control, such as chemicals, cold, heat, drought, salt and many others (inducible promoter).

If proper polypeptide production is desired, a polyadenylation region at the 3'-end of the coding region is typically included. The polyadenylation region is derived from the natural gene, from a variety of other plant genes, or from T-DNA, synthesized in the laboratory.

Transformation

Techniques for transforming a wide variety of higher plant species are well known and described in the technical and scientific literature. See, e.g. Weising et al. (1988) *Ann. Rev. Genet.* 22:421 and Christou (1995) Euphytica, v. 85, n.1-3: 13-27.

The person skilled in the art knows processes for the transformation of monocotyledonous and dicotyledonous plants. A variety of techniques are available for introducing DNA into a plant host cell. These techniques comprise transformation of plant cells by DNA injection, DNA electroporation, use of bolistics methods, protoplast fusion and via T-DNA using *Agrobacterium tumefaciens* or *Agrobacterium rhizogenes*, as well as further possibilities, or other bacterial hosts for Ti plasmid vectors. See for example, Broothaerts et al. (2005) Gene Transfer to Plants by Diverse Species of Bacteria, *Nature*, Vol. 433, pp. 629-633.

DNA constructs of the invention are introduced into the cell or the genome of the desired plant host by a variety of conventional techniques. For example, the DNA construct is introduced using techniques such as electroporation, microinjection and polyethylene glycol precipitation of plant cell protoplasts or protoplast fusion. Electroporation techniques are described in Fromm et al. (1985) *Proc. Natl. Acad. Sci. USA* 82:5824. Microinjection techniques are known in the art and well described in the scientific and patent literature. The plasmids do not have to fulfill specific requirements for use in DNA electroporation or DNA injection into plant cells. Simple plasmids such as pUC derivatives can be used.

The introduction of DNA constructs using polyethylene glycol precipitation is described in Paszkowski et al. (1984) *EMBO J.* 3:2717. Introduction of foreign DNA using protoplast fusion is described by Willmitzer (Willmitzer, L. (1993) Transgenic plants. In: Biotechnology, A Multi-Volume Comprehensive Treatise (H. J. Rehm, G. Reed, A. Puhler, P. Stadler, eds.), Vol. 2, 627-659, VCH Weinheim-New York-Basel-Cambridge).

Alternatively, the DNA constructs of the invention are introduced directly into plant tissue using ballistic methods, such as DNA particle bombardment. Ballistic transformation techniques are described in Klein et al. (1987) *Nature* 327: 773. Introduction of foreign DNA using ballistics is described by Willmitzer (Willmitzer, L., 1993 Transgenic plants. In: Biotechnology, A Multi-Volume Comprehensive Treatise (H. J. Rehm, G. Reed, A. Pühler, P. Stadler, eds.), Vol. 2, 627-659, VCH Weinheim-New York-Basel-Cambridge).

DNA constructs are also introduced with the help of *Agrobacteria*. The use of *Agrobacteria* for plant cell transformation is extensively examined and sufficiently disclosed in the specification of EP-A 120 516, and in Hoekema (In: The Binary Plant Vector System Offsetdrukkerij Kanters B.V., Alblasserdam (1985), Chapter V), Fraley et al. (Crit. Rev. Plant. Sci. 4, 146) and DePicker et al. (EMBO J. 4 (1985), 277-287). Using this technique, the DNA constructs of the invention are combined with suitable T-DNA flanking regions and introduced into a conventional *Agrobacterium tumefaciens* host vector. The virulence functions of the *Agrobacterium tumefaciens* host direct the insertion of the construct and adjacent marker(s) into the plant cell DNA when the cell is infected by the bacteria (McCormac et al. (1997) *Mol. Biotechnol.* 8:199; Hamilton (1997) *Gene* 200:107; Salomon et al. (1984) *EMBO J.* 3:141; Herrera-Estrella et al. (1983) *EMBO J.* 2:987). *Agrobacterium tumefaciens*-mediated transformation techniques, including disarming and use of binary or co-integrate vectors, are well described in the scientific literature. See, for example Hamilton (1997) *Gene* 200:107; Müller et al. (1987) *Mol. Gen. Genet.* 207:171; Komari et al. (1996) *Plant J.* 10:165; Venkateswarlu et al. (1991) *Biotechnology* 9:1103 and Gleave (1992) *Plant Mol. Biol.* 20:1203; Graves and Goldman (1986) *Plant Mol. Biol.* 7:34 and Gould et al. (1991) *Plant Physiology* 95:426.

For plant cell T-DNA transfer of DNA, plant organs, e.g. infloresences, plant explants, plant cells that have been cultured in suspension or protoplasts are co-cultivated with *Agrobacterium tumefaciens* or *Agrobacterium rhizogenes* or other suitable T-DNA hosts. Whole plants are regenerated from the infected plant material or seeds generated from infected plant material using a suitable medium that contains antibiotics or biocides for the selection of transformed cells or by spraying the biocide on plants to select the transformed plants. Plants obtained in this way are then examined for the presence of the DNA introduced. The transformation of dicotyledonous plants via Ti-plasmid-vector systems and *Agrobacterium tumefaciens* is well established.

Monocotyledonous plants are also transformed by means of *Agrobacterium* based vectors (See Chan et al. (1993) Plant Mol. Biol. 22: 491-506; Hiei et al. (1994) Plant J. 6:271-282; Deng et al. (1990) Science in China 33:28-34; Wilmink et al. Plant (1992) Cell Reports 11:76-80; May et al. (1995) Bio/Technology 13:486-492; Conner and Domisse (1992) Int. J. Plant Sci. 153:550-555; Ritchie et al. (1993) Transgenic Res. 2:252-265). Maize transformation in particular is described in the literature (see, for example, WO95/06128, EP 0 513 849; EP 0 465 875; Fromm et al., (1990) Biotechnology 8:833-844; Gordon-Kamm et al. (1990) Plant Cell 2:603-618; Koziel et al. (1993) Biotechnology 11:194-200). In EP 292 435 and in Shillito et al. (Bio/Technology (1989) 7:581) fertile plants are obtained from a mucus-free, soft (friable) maize callus. Prioli and Söndahl (Bio/Technology (1989) 7, 589) also report regenerating fertile plants from maize protoplasts of the maize Cateto inbred line, Cat 100-1.

Other cereal species have also been successfully transformed, such as barley (Wan and Lemaux, see above; Ritala et al., see above) and wheat (Nehra et al. (1994) Plant J. 5, 285-297).

Alternatives to *Agrobacterium* transformation for plants are ballistics, protoplast fusion, electroporation of partially permeabilized cells and use of glass fibers (See Wan and Lemaux (1994) Plant Physiol. 104:37-48; Vasil et al. (1993) Bio/Technology 11:1553-1558; Ritala et al. (1994) Plant Mol. Biol. 24:317-325; Spencer et al. (1990) Theor. Appl. Genet. 79:625-631).

Introduced DNA is usually stable after integration into the plant genome and is transmitted to the progeny of the transformed cell or plant. Generally the transformed plant cell contains a selectable marker that makes the transformed cells resistant to a biocide or an antibiotic such as kanamycin, G 418, bleomycin, hygromycin, phosphinotricin or others. Therefore, the individually chosen marker should allow the selection of transformed cells from cells lacking the introduced DNA.

The transformed cells grow within the plant in the usual way (McCormick et al. (1986) Plant Cell Reports 5, 81-84) and the resulting plants are cultured normally. Transformed plant cells obtained by any of the above transformation techniques are cultured to regenerate a whole plant that possesses the transformed genotype and thus the desired phenotype. Such regeneration techniques rely on manipulation of certain phytohormones in a tissue culture growth medium, typically relying on a biocide and/or herbicide marker that has been introduced together with the desired nucleotide sequences.

Plant regeneration from cultured protoplasts is described in Evans et al., *Protoplasts Isolation and Culture* in "Handbook of Plant Cell Culture," pp. 124-176, MacMillan Publishing Company, New York, 1983; and Binding, *Regeneration of Plants, Plant Protoplasts*, pp. 21-73, CRC Press, Boca Raton, 1988. Regeneration also occurs from plant callus, explants, organs, or parts thereof. Such regeneration techniques are described generally in Klee et al. (1987) *Ann. Rev. of Plant Phys.* 38:467. Regeneration of monocots (rice) is described by Hosoyama et al. (*Biosci. Biotechnol. Biochem.* (1994) 58:1500) and by Ghosh et al. (*J. Biotechnol.* (1994) 32:1). Useful and relevant procedures for transient expression are also described in U.S. Application No. 60/537,070 filed on Jan. 16, 2004 and PCT Application No. PCT/US2005/001153 filed on Jan. 14, 2005.

After transformation, seeds are obtained from the plants and used for testing stability and inheritance. Generally, two or more generations are cultivated to ensure that the phenotypic feature is stably maintained and transmitted.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The nucleotide sequences according to the invention generally encode an appropriate protein from any organism, in particular from plants, fungi, bacteria or animals. The sequences preferably encode proteins from plants or fungi. Preferably, the plants are higher plants, in particular starch or oil storing useful plants, such as potato or cereals such as rice, maize, wheat, barley, rye, triticale, oat, millet, etc., as well as spinach, tobacco, sugar beet, soya, cotton etc.

In principle, the process according to the invention can be applied to any plant. Therefore, monocotyledonous as well as dicotyledonous plant species are particularly suitable. The process is preferably used with plants that are interesting for agriculture, horticulture, biomass for conversion, textile, plants as chemical factories and/or forestry.

Thus, the invention has use over a broad range of plants, preferably higher plants, pertaining to the classes of Angiospermae and Gymnospermae. Plants of the subclasses of the Dicotylodenae and the Monocotyledonae are particularly suitable. Dicotyledonous plants belong to the orders of the Magniolales, Illiciales, Laurales, Piperales Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, Santales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales. Monocotyledonous plants belong to the orders of the Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales. Plants belonging to the class of the Gymnospermae are Pinales, Ginkgoales, Cycadales and Gnetales.

Examples of species represented in these orders are tobacco, oilseed rape, sugar beet, potato, tomato, lettuce, cucumber, pepper, bean, pea, citrus fruit, apple, pear, berries, plum, melon, eggplant, cotton, soybean, sunflower, rose, poinsettia, petunia, guayule, cabbage, spinach, alfalfa, artichoke, corn, wheat, rye, barley, grasses such as switch grass or turf grass, millet, hemp, banana, poplar, eucalyptus trees, conifers.

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

TABLE 1

| Knock-in phenotype in gene(cDNA_id): 3265003 | |
|---|---|
| clone ID: | 536796 |
| Promoter: | 35S |
| unique F1 plant ID: | R1 PLANT:ME05809-01 |
| phenotype ID: | 98827 |
| assay: | Soil Gross Morphology: First flower buds visible |
| phenotype: | ROSETTE LEAVES - Short Petioles |
| notes: | NONE |
| unique F1 plant ID: | R1 PLANT:ME05809-01 |
| phenotype ID: | 98828 |
| assay: | Soil Gross Morphology: First flower buds visible |
| phenotype: | ROSETTE LEAVES - Oval Shaped |
| notes: | NONE |
| unique F1 plant ID: | R1 PLANT:ME05809-02 |
| phenotype ID: | 98846 |
| assay: | Soil Gross Morphology: First flower buds visible |
| phenotype: | ROSETTE LEAVES - Short Petioles |
| notes: | NONE |
| unique F1 plant ID: | R1 PLANT:ME05809-02 |
| phenotype ID: | 98847 |
| assay: | Soil Gross Morphology: First flower buds visible |
| phenotype: | ROSETTE LEAVES - Oval Shaped |
| notes: | NONE |
| unique F1 plant ID: | R1 PLANT:ME05809-04 |
| phenotype ID: | 98885 |
| assay: | Soil Gross Morphology: First flower buds visible |
| phenotype: | ROSETTE LEAVES - Short Petioles |
| notes: | NONE |
| unique F1 plant ID: | R1 PLANT:ME05809-04 |
| phenotype ID: | 98886 |
| assay: | Soil Gross Morphology: First flower buds visible |
| phenotype: | ROSETTE LEAVES - Oval Shaped |
| notes: | NONE |
| unique F1 plant ID: | R1 PLANT:ME05809-05 |
| phenotype ID: | 98906 |
| assay: | Soil Gross Morphology: First flower buds visible |
| phenotype: | ROSETTE LEAVES - Short Petioles |
| notes: | NONE |
| unique F1 plant ID: | R1 PLANT:ME05809-05 |
| phenotype ID: | 98907 |
| assay: | Soil Gross Morphology: First flower buds visible |
| phenotype: | ROSETTE LEAVES - Oval Shaped |
| notes: | NONE |
| unique F1 plant ID: | R1 PLANT:ME05809-05 |

TABLE 1-continued

| | |
|---|---|
| phenotype ID: | 98908 |
| assay: | Soil Gross Morphology: 50% of flowers to be produced have opened |
| phenotype: | ROSETTE LEAVES - Short Petioles |
| notes: | NONE |
| unique F1 plant ID: | R1 PLANT:ME05809-05 |
| phenotype ID: | 98909 |
| assay: | Soil Gross Morphology: 50% of flowers to be produced have opened |
| phenotype: | WHOLE PLANT - Small |
| notes: | 50 pct wt |
| unique F1 plant ID: | R1 PLANT:ME05809-06 |
| phenotype ID: | 98931 |
| assay: | Soil Gross Morphology: First flower buds visible |
| phenotype: | ROSETTE LEAVES - Short Petioles |
| notes: | NONE |
| unique F1 plant ID: | R1 PLANT:ME05809-06 |
| phenotype ID: | 98932 |
| assay: | Soil Gross Morphology: First flower buds visible |
| phenotype: | ROSETTE LEAVES - Oval Shaped |
| notes: | NONE |
| unique F1 plant ID: | R1 PLANT:ME05809-07 |
| phenotype ID: | 98946 |
| assay: | Soil Gross Morphology: First flower buds visible |
| phenotype: | ROSETTE LEAVES - Short Petioles |
| notes: | NONE |
| unique F1 plant ID: | R1 PLANT:ME05809-07 |
| phenotype ID: | 98947 |
| assay: | Soil Gross Morphology: First flower buds visible |
| phenotype: | ROSETTE LEAVES - Oval Shaped |
| notes: | NONE |
| unique F1 plant ID: | R1 PLANT:ME05809-09 |
| phenotype ID: | 98978 |
| assay: | Soil Gross Morphology: 8 rosette leaves 1 mm in length |
| phenotype: | WHOLE PLANT - Other |
| notes: | pale green |
| unique F1 plant ID: | R1 PLANT:ME05809-09 |
| phenotype ID: | 98979 |
| assay: | Soil Gross Morphology: 8 rosette leaves 1 mm in length |
| phenotype: | ROSETTE LEAVES - Short Petioles |
| notes: | NONE |
| unique F1 plant ID: | R1 PLANT:ME05809-09 |
| phenotype ID: | 98980 |
| assay: | Soil Gross Morphology: 8 rosette leaves 1 mm in length |
| phenotype: | ROSETTE LEAVES - Serrate Margins |
| notes: | NONE |
| unique F1 plant ID: | R1 PLANT:ME05809-09 |
| phenotype ID: | 98981 |
| assay: | Soil Gross Morphology: 8 rosette leaves 1 mm in length |
| phenotype: | INFLORESCENCE - Late Flowering |
| notes: | NONE |
| unique F1 plant ID: | R1 PLANT:ME05809-09 |
| phenotype ID: | 98982 |
| assay: | Soil Gross Morphology: 8 rosette leaves 1 mm in length |
| phenotype: | WHOLE PLANT - Small |
| notes: | 10 pct wt |
| Knock-in phenotype in gene(cDNA_id): 4865327 | |
| clone ID: | 1120124 |
| Promoter: | 34414F |
| unique F1 plant ID: | R1 PLANT:ME09398-01 |
| phenotype ID: | 124913 |
| assay: | Soil Gross Morphology: 6 rosette leaves 1 mm in length |
| phenotype: | INFLORESCENCE - Late Flowering |
| notes: | NONE |
| unique F1 plant ID: | R1 PLANT:ME09398-04 |
| phenotype ID: | 124980 |
| assay: | Soil Gross Morphology: 5 rosette leaves 1 mm in length |
| phenotype: | ROSETTE LEAVES - Oval Shaped |
| notes: | NONE |
| unique F1 plant ID: | R1 PLANT:ME09398-04 |
| phenotype ID: | 124981 |
| assay: | Soil Gross Morphology: 5 rosette leaves 1 mm in length |
| phenotype: | INFLORESCENCE - Other |
| notes: | possible meristem defect |
| unique F1 plant ID: | R1 PLANT:ME09398-04 |
| phenotype ID: | 124982 |
| assay: | Soil Gross Morphology: 6 rosette leaves 1 mm in length |
| phenotype: | INFLORESCENCE - Late Flowering |
| notes: | NONE |
| unique F1 plant ID: | R1 PLANT:ME09398-07 |

TABLE 1-continued

| | |
|---|---|
| phenotype ID: | 125050 |
| assay: | Soil Gross Morphology: 7 rosette leaves 1 mm in length |
| phenotype: | ROSETTE LEAVES - Oval Shaped |
| notes: | NONE |
| unique F1 plant ID: | R1 PLANT:ME09398-07 |
| phenotype ID: | 125051 |
| assay: | Soil Gross Morphology: 7 rosette leaves 1 mm in length |
| phenotype: | INFLORESCENCE - Other |
| notes: | possible meristem defect |
| unique F1 plant ID: | R1 PLANT:ME09398-07 |
| phenotype ID: | 125052 |
| assay: | Soil Gross Morphology: 6 rosette leaves 1 mm in length |
| phenotype: | INFLORESCENCE - Late Flowering |
| notes: | NONE |
| unique F1 plant ID: | R1 PLANT:ME09398-09 |
| phenotype ID: | 125086 |
| assay: | Soil Gross Morphology: 6 rosette leaves 1 mm in length |
| phenotype: | INFLORESCENCE - Late Flowering |
| notes: | NONE |
| unique F1 plant ID: | R1 PLANT:ME05235-01 |
| phenotype ID: | 89471 |
| assay: | Soil Gross Morphology: First flower open |
| phenotype: | WHOLE PLANT - Small |
| notes: | 15 pct. size of wt |
| unique F1 plant ID: | R1 PLANT:ME05235-01 |
| phenotype ID: | 89472 |
| assay: | Soil Gross Morphology: First flower open |
| phenotype: | WHOLE PLANT - Dark Green |
| notes: | NONE |
| unique F1 plant ID: | R1 PLANT:ME05235-02 |
| phenotype ID: | 89478 |
| assay: | Soil Gross Morphology: First flower open |
| phenotype: | WHOLE PLANT - Small |
| notes: | 20 pct. size of wt |
| unique F1 plant ID: | R1 PLANT:ME05235-02 |
| phenotype ID: | 89479 |
| assay: | Soil Gross Morphology: First flower open |
| phenotype: | WHOLE PLANT - Dark Green |
| notes: | NONE |
| unique F1 plant ID: | R1 PLANT:ME05235-03 |
| phenotype ID: | 89482 |
| assay: | Soil Gross Morphology: First flower open |
| phenotype: | WHOLE PLANT - Small |
| notes: | 20 pct. size of wt |
| unique F1 plant ID: | R1 PLANT:ME05235-03 |
| phenotype ID: | 89483 |
| assay: | Soil Gross Morphology: First flower open |
| phenotype: | WHOLE PLANT - Dark Green |
| notes: | NONE |
| unique F1 plant ID: | R1 PLANT:ME05235-04 |
| phenotype ID: | 89488 |
| assay: | Soil Gross Morphology: First flower open |
| phenotype: | WHOLE PLANT - Small |
| notes: | 20 pct. size of wt |
| unique F1 plant ID: | R1 PLANT:ME05235-04 |
| phenotype ID: | 89489 |
| assay: | Soil Gross Morphology: First flower open |
| phenotype: | WHOLE PLANT - Dark Green |
| notes: | NONE |
| unique F1 plant ID: | R1 PLANT:ME05235-05 |
| phenotype ID: | 89494 |
| assay: | Soil Gross Morphology: First flower open |
| phenotype: | WHOLE PLANT - Small |
| notes: | 15 pct. size of wt |
| unique F1 plant ID: | R1 PLANT:ME05235-05 |
| phenotype ID: | 89495 |
| assay: | Soil Gross Morphology: First flower open |
| phenotype: | WHOLE PLANT - Dark Green |
| notes: | NONE |
| unique F1 plant ID: | R1 PLANT:ME05235-06 |
| phenotype ID: | 89496 |
| assay: | Soil Gross Morphology: First flower open |
| phenotype: | WHOLE PLANT - Small |
| notes: | 15 pct. size of wt |
| unique F1 plant ID: | R1 PLANT:ME05235-06 |
| phenotype ID: | 89497 |
| assay: | Soil Gross Morphology: First flower open |
| phenotype: | WHOLE PLANT - Dark Green |
| notes: | NONE |

TABLE 1-continued

| | |
|---|---|
| unique F1 plant ID: | R1 PLANT:ME05235-07 |
| phenotype ID: | 89502 |
| assay: | Soil Gross Morphology: First flower open |
| phenotype: | WHOLE PLANT - Small |
| notes: | 15 pct. size of wt |
| unique F1 plant ID: | R1 PLANT:ME05235-07 |
| phenotype ID: | 89503 |
| assay: | Soil Gross Morphology: First flower open |
| phenotype: | WHOLE PLANT - Dark Green |
| notes: | NONE |
| unique F1 plant ID: | R1 PLANT:ME05235-08 |
| phenotype ID: | 89506 |
| assay: | Soil Gross Morphology: First flower open |
| phenotype: | WHOLE PLANT - Small |
| notes: | 15 pct. size of wt |
| unique F1 plant ID: | R1 PLANT:ME05235-08 |
| phenotype ID: | 89507 |
| assay: | Soil Gross Morphology: First flower open |
| phenotype: | WHOLE PLANT - Dark Green |
| notes: | NONE |
| unique F1 plant ID: | R1 PLANT:ME05235-09 |
| phenotype ID: | 89515 |
| assay: | Soil Gross Morphology: First flower open |
| phenotype: | WHOLE PLANT - Small |
| notes: | 15 pct. size of wt |
| unique F1 plant ID: | R1 PLANT:ME05235-09 |
| phenotype ID: | 89516 |
| assay: | Soil Gross Morphology: First flower open |
| phenotype: | WHOLE PLANT - Dark Green |
| notes: | NONE |
| unique F1 plant ID: | R1 PLANT:ME05235-10 |
| phenotype ID: | 89521 |
| assay: | Soil Gross Morphology: First flower open |
| phenotype: | WHOLE PLANT - Small |
| notes: | 30 pct. size of wt |
| unique F1 plant ID: | R1 PLANT:ME05235-10 |
| phenotype ID: | 89522 |
| assay: | Soil Gross Morphology: First flower open |
| phenotype: | WHOLE PLANT - Dark Green |
| notes: | NONE |

Knock-in phenotype in gene(cDNA_id): 12324135

| | |
|---|---|
| clone ID: | 949 |
| Promoter: | 35S |
| unique F1 plant ID: | R1 PLANT:ME04316-02 |
| phenotype ID: | 83424 |
| assay: | Soil Gross Morphology: 50% of flowers to be produced have opened |
| phenotype: | WHOLE PLANT - Large |
| notes: | NONE |
| unique F1 plant ID: | R1 PLANT:ME04316-06 |
| phenotype ID: | 83467 |
| assay: | Soil Gross Morphology: 50% of flowers to be produced have opened |
| phenotype: | WHOLE PLANT - Large |
| notes: | NONE |
| unique F1 plant ID: | R1 PLANT:ME04316-07 |
| phenotype ID: | 83479 |
| assay: | Soil Gross Morphology: 50% of flowers to be produced have opened |
| phenotype: | WHOLE PLANT - Large |
| notes: | NONE |
| unique F1 plant ID: | R1 PLANT:ME04316-09 |
| phenotype ID: | 83499 |
| assay: | Soil Gross Morphology: 50% of flowers to be produced have opened |
| phenotype: | WHOLE PLANT - Large |
| notes: | NONE |

Knock-in phenotype in gene(cDNA_id): 12325093

| | |
|---|---|
| clone ID: | 40729 |
| Promoter: | 35S |
| unique F1 plant ID: | R1 PLANT:ME04213-01 |
| phenotype ID: | 82613 |
| assay: | Soil Gross Morphology: 50% of flowers to be produced have opened |
| phenotype: | WHOLE PLANT - Small |
| notes: | 10 percent wt |
| unique F1 plant ID: | R1 PLANT:ME04213-01 |
| phenotype ID: | 82614 |
| assay: | Soil Gross Morphology: 50% of flowers to be produced have opened |
| phenotype: | SILIQUES - Short |
| notes: | NONE |
| unique F1 plant ID: | R1 PLANT:ME04213-01 |

TABLE 1-continued

| | |
|---|---|
| phenotype ID: | 82615 |
| assay: | Soil Gross Morphology: 50% of flowers to be produced have opened |
| phenotype: | FLOWER - Reduced fertility |
| notes: | NONE |
| unique F1 plant ID: | R1 PLANT:ME04213-01 |
| phenotype ID: | 82616 |
| assay: | Soil Gross Morphology: 50% of flowers to be produced have opened |
| phenotype: | SILIQUES - Other |
| notes: | misshapen |
| unique F1 plant ID: | R1 PLANT:ME04213-01 |
| phenotype ID: | 82617 |
| assay: | Soil Gross Morphology: 50% of flowers to be produced have opened |
| phenotype: | INFLORESCENCE - Short |
| notes: | NONE |
| unique F1 plant ID: | R1 PLANT:ME04213-01 |
| phenotype ID: | 82618 |
| assay: | Soil Gross Morphology: 50% of flowers to be produced have opened |
| phenotype: | INFLORESCENCE - Short Internode |
| notes: | NONE |
| unique F1 plant ID: | R1 PLANT:ME04213-01 |
| phenotype ID: | 82619 |
| assay: | Soil Gross Morphology: 50% of flowers to be produced have opened |
| phenotype: | FLOWER - Reduced fertility |
| notes: | NONE |
| unique F1 plant ID: | R1 PLANT:ME04213-02 |
| phenotype ID: | 82671 |
| assay: | Soil Gross Morphology: 50% of flowers to be produced have opened |
| phenotype: | FLOWER - Reduced fertility |
| notes: | NONE |
| unique F1 plant ID: | R1 PLANT:ME04213-02 |
| phenotype ID: | 82672 |
| assay: | Soil Gross Morphology: 50% of flowers to be produced have opened |
| phenotype: | INFLORESCENCE - Short |
| notes: | NONE |
| unique F1 plant ID: | R1 PLANT:ME04213-02 |
| phenotype ID: | 82673 |
| assay: | Soil Gross Morphology: 50% of flowers to be produced have opened |
| phenotype: | SILIQUES - Short |
| notes: | NONE |
| unique F1 plant ID: | R1 PLANT:ME04213-02 |
| phenotype ID: | 82674 |
| assay: | Soil Gross Morphology: 50% of flowers to be produced have opened |
| phenotype: | FLOWER - Other |
| notes: | a lot of flowers |
| unique F1 plant ID: | R1 PLANT:ME04213-02 |
| phenotype ID: | 82675 |
| assay: | Soil Gross Morphology: 50% of flowers to be produced have opened |
| phenotype: | FLOWER - Reduced fertility |
| notes: | NONE |
| unique F1 plant ID: | R1 PLANT:ME04213-02 |
| phenotype ID: | 82676 |
| assay: | Soil Gross Morphology: 50% of flowers to be produced have opened |
| phenotype: | INFLORESCENCE - Reduced Apical Dominance |
| notes: | NONE |
| unique F1 plant ID: | R1 PLANT:ME04213-02 |
| phenotype ID: | 82677 |
| assay: | Soil Gross Morphology: 50% of flowers to be produced have opened |
| phenotype: | INFLORESCENCE - Short Internode |
| notes: | NONE |
| unique F1 plant ID: | R1 PLANT:ME04213-02 |
| phenotype ID: | 82678 |
| assay: | Soil Gross Morphology: 50% of flowers to be produced have opened |
| phenotype: | FLOWER - Other |
| notes: | flowers bunched at top of bolt |
| unique F1 plant ID: | R1 PLANT:ME04213-02 |
| phenotype ID: | 82679 |
| assay: | Soil Gross Morphology: 50% of flowers to be produced have opened |
| phenotype: | FLOWER - Reduced fertility |
| notes: | NONE |
| unique F1 plant ID: | R1 PLANT:ME04213-02 |
| phenotype ID: | 82680 |
| assay: | Soil Gross Morphology: 50% of flowers to be produced have opened |
| phenotype: | INFLORESCENCE - Short Internode |
| notes: | NONE |
| unique F1 plant ID: | R1 PLANT:ME04213-02 |
| phenotype ID: | 82681 |
| assay: | Soil Gross Morphology: 50% of flowers to be produced have opened |
| phenotype: | FLOWER - Other |
| notes: | some of secondary inflorescence are producing flowers very close to rosette |

TABLE 1-continued

| | |
|---|---|
| unique F1 plant ID: | R1 PLANT:ME04213-02 |
| phenotype ID: | 82682 |
| assay: | Soil Gross Morphology: 50% of flowers to be produced have opened |
| phenotype: | WHOLE PLANT - Late Senescence |
| notes: | NONE |
| unique F1 plant ID: | R1 PLANT:ME04213-02 |
| phenotype ID: | 82683 |
| assay: | Soil Gross Morphology: 50% of flowers to be produced have opened |
| phenotype: | INFLORESCENCE - Short |
| notes: | NONE |
| unique F1 plant ID: | R1 PLANT:ME04213-02 |
| phenotype ID: | 82684 |
| assay: | Soil Gross Morphology: 50% of flowers to be produced have opened |
| phenotype: | FLOWER - Other |
| notes: | extra flowers |
| unique F1 plant ID: | R1 PLANT:ME04213-03 |
| phenotype ID: | 82727 |
| assay: | Soil Gross Morphology: 50% of flowers to be produced have opened |
| phenotype: | WHOLE PLANT - Late Senescence |
| notes: | NONE |
| unique F1 plant ID: | R1 PLANT:ME04213-03 |
| phenotype ID: | 82728 |
| assay: | Soil Gross Morphology: 50% of flowers to be produced have opened |
| phenotype: | SILIQUES - Short |
| notes: | NONE |
| unique F1 plant ID: | R1 PLANT:ME04213-03 |
| phenotype ID: | 82729 |
| assay: | Soil Gross Morphology: 50% of flowers to be produced have opened |
| phenotype: | FLOWER - Reduced fertility |
| notes: | NONE |
| unique F1 plant ID: | R1 PLANT:ME04213-03 |
| phenotype ID: | 82730 |
| assay: | Soil Gross Morphology: First flower open |
| phenotype: | WHOLE PLANT - Small |
| notes: | NONE |
| unique F1 plant ID: | R1 PLANT:ME04213-03 |
| phenotype ID: | 82731 |
| assay: | Soil Gross Morphology: 50% of flowers to be produced have opened |
| phenotype: | WHOLE PLANT - Small |
| notes: | 10 percent wt |
| unique F1 plant ID: | R1 PLANT:ME04213-03 |
| phenotype ID: | 82732 |
| assay: | Soil Gross Morphology: 50% of flowers to be produced have opened |
| phenotype: | INFLORESCENCE - Short |
| notes: | NONE |
| unique F1 plant ID: | R1 PLANT:ME04213-03 |
| phenotype ID: | 82733 |
| assay: | Soil Gross Morphology: First flower open |
| phenotype: | ROSETTE LEAVES - Serrate Margins |
| notes: | NONE |
| unique F1 plant ID: | R1 PLANT:ME04213-03 |
| phenotype ID: | 82734 |
| assay: | Soil Gross Morphology: 50% of flowers to be produced have opened |
| phenotype: | INFLORESCENCE - Short Internode |
| notes: | NONE |
| unique F1 plant ID: | R1 PLANT:ME04213-03 |
| phenotype ID: | 82735 |
| assay: | Soil Gross Morphology: 50% of flowers to be produced have opened |
| phenotype: | FLOWER - Reduced fertility |
| notes: | NONE |
| unique F1 plant ID: | R1 PLANT:ME04213-03 |
| phenotype ID: | 82736 |
| assay: | Soil Gross Morphology: 50% of flowers to be produced have opened |
| phenotype: | INFLORESCENCE - Weak |
| notes: | NONE |
| unique F1 plant ID: | R1 PLANT:ME04213-03 |
| phenotype ID: | 82737 |
| assay: | Soil Gross Morphology: 50% of flowers to be produced have opened |
| phenotype: | INFLORESCENCE - Reduced Apical Dominance |
| notes: | NONE |
| unique F1 plant ID: | R1 PLANT:ME04213-03 |
| phenotype ID: | 82738 |
| assay: | Soil Gross Morphology: 50% of flowers to be produced have opened |
| phenotype: | ROSETTE LEAVES - Serrate Margins |
| notes: | NONE |
| unique F1 plant ID: | R1 PLANT:ME04213-03 |
| phenotype ID: | 82739 |
| assay: | Soil Gross Morphology: First flower open |
| phenotype: | ROSETTE LEAVES - Other |

TABLE 1-continued

| | |
|---|---|
| notes: | round leaves |
| unique F1 plant ID: | R1 PLANT:ME04213-03 |
| phenotype ID: | 82740 |
| assay: | Soil Gross Morphology: 50% of flowers to be produced have opened |
| phenotype: | WHOLE PLANT - Small |
| notes: | 25 pct wt |
| unique F1 plant ID: | R1 PLANT:ME04213-03 |
| phenotype ID: | 82741 |
| assay: | Soil Gross Morphology: 50% of flowers to be produced have opened |
| phenotype: | ROSETTE LEAVES - Other |
| notes: | misshapen |
| unique F1 plant ID: | R1 PLANT:ME04213-04 |
| phenotype ID: | 82797 |
| assay: | Soil Gross Morphology: First flower buds visible |
| phenotype: | WHOLE PLANT - Small |
| notes: | NONE |
| unique F1 plant ID: | R1 PLANT:ME04213-04 |
| phenotype ID: | 82798 |
| assay: | Soil Gross Morphology: 50% of flowers to be produced have opened |
| phenotype: | ROSETTE LEAVES - Other |
| notes: | misshapen |
| unique F1 plant ID: | R1 PLANT:ME04213-04 |
| phenotype ID: | 82799 |
| assay: | Soil Gross Morphology: 50% of flowers to be produced have opened |
| phenotype: | ROSETTE LEAVES - Serrate Margins |
| notes: | NONE |
| unique F1 plant ID: | R1 PLANT:ME04213-04 |
| phenotype ID: | 82800 |
| assay: | Soil Gross Morphology: 50% of flowers to be produced have opened |
| phenotype: | INFLORESCENCE - Short Internode |
| notes: | NONE |
| unique F1 plant ID: | R1 PLANT:ME04213-04 |
| phenotype ID: | 82801 |
| assay: | Soil Gross Morphology: First flower buds visible |
| phenotype: | ROSETTE LEAVES - Lanceolate Shaped |
| notes: | NONE |
| unique F1 plant ID: | R1 PLANT:ME04213-04 |
| phenotype ID: | 82802 |
| assay: | Soil Gross Morphology: 50% of flowers to be produced have opened |
| phenotype: | FLOWER - Reduced fertility |
| notes: | NONE |
| unique F1 plant ID: | R1 PLANT:ME04213-04 |
| phenotype ID: | 82803 |
| assay: | Soil Gross Morphology: 50% of flowers to be produced have opened |
| phenotype: | WHOLE PLANT - Small |
| notes: | 25 pct wt |
| unique F1 plant ID: | R1 PLANT:ME04213-09 |
| phenotype ID: | 83078 |
| assay: | Soil Gross Morphology: First flower buds visible |
| phenotype: | INFLORESCENCE - Late Flowering |
| notes: | NONE |
| unique F1 plant ID: | R1 PLANT:ME04213-09 |
| phenotype ID: | 83079 |
| assay: | Soil Gross Morphology: First flower buds visible |
| phenotype: | WHOLE PLANT - Dark Green |
| notes: | NONE |
| unique F1 plant ID: | R1 PLANT:ME04213-09 |
| phenotype ID: | 83080 |
| assay: | Soil Gross Morphology: First flower buds visible |
| phenotype: | WHOLE PLANT - Misc. Dwarf |
| notes: | dwarf-lik |
| unique F1 plant ID: | R1 PLANT:ME04213-09 |
| phenotype ID: | 83081 |
| assay: | Soil Gross Morphology: First flower buds visible |
| phenotype: | ROSETTE LEAVES - Other |
| notes: | extra leaves |
| unique F1 plant ID: | R1 PLANT:ME04213-09 |
| phenotype ID: | 83082 |
| assay: | Soil Gross Morphology: First flower buds visible |
| phenotype: | INFLORESCENCE - Late Flowering |
| notes: | NONE |
| unique F1 plant ID: | R1 PLANT:ME04213-09 |
| phenotype ID: | 83083 |
| assay: | Soil Gross Morphology: First flower buds visible |
| phenotype: | WHOLE PLANT - Small |
| notes: | 10 percent weight |
| unique F1 plant ID: | R1 PLANT:ME04213-09 |
| phenotype ID: | 83084 |
| assay: | Soil Gross Morphology: First flower buds visible |

TABLE 1-continued

| | |
|---|---|
| phenotype: | ROSETTE LEAVES - Oval Shaped |
| notes: | NONE |

Knock-in phenotype in gene(cDNA__id): 12328728

| | |
|---|---|
| clone ID: | 99298 |
| Promoter: | 35S |
| unique F1 plant ID: | R1 PLANT:ME04092-01 |
| phenotype ID: | 81879 |
| assay: | Soil Gross Morphology: Flowering complete |
| phenotype: | WHOLE PLANT - Late Senescence |
| notes: | NONE |
| unique F1 plant ID: | R1 PLANT:ME04092-02 |
| phenotype ID: | 81880 |
| assay: | Soil Gross Morphology: Flowering complete |
| phenotype: | WHOLE PLANT - Late Senescence |
| notes: | NONE |
| unique F1 plant ID: | R1 PLANT:ME04092-03 |
| phenotype ID: | 81881 |
| assay: | Soil Gross Morphology: Flowering complete |
| phenotype: | WHOLE PLANT - Late Senescence |
| notes: | NONE |

Knock-in phenotype in gene(cDNA__id): 12330060

| | |
|---|---|
| clone ID: | 4043 |
| Promoter: | 35S |
| unique F1 plant ID: | R1 PLANT:ME04356-02 |
| phenotype ID: | 83272 |
| assay: | Soil Gross Morphology: 10% of flowers to be produced have opened |
| phenotype: | WHOLE PLANT - Yellow-Green Viable 1 |
| notes: | NONE |
| unique F1 plant ID: | R1 PLANT:ME04356-02 |
| phenotype ID: | 83273 |
| assay: | Soil Gross Morphology: 10% of flowers to be produced have opened |
| phenotype: | ROSETTE LEAVES - Curled 3 |
| notes: | NONE |
| unique F1 plant ID: | R1 PLANT:ME04356-02 |
| phenotype ID: | 83274 |
| assay: | Soil Gross Morphology: 30% of flowers to be produced have opened |
| phenotype: | WHOLE PLANT - Small |
| notes: | 25 percent weight |
| unique F1 plant ID: | R1 PLANT:ME04356-02 |
| phenotype ID: | 83275 |
| assay: | Soil Gross Morphology: 10% of flowers to be produced have opened |
| phenotype: | WHOLE PLANT - Small |
| notes: | 25 pct wt |
| unique F1 plant ID: | R1 PLANT:ME04356-02 |
| phenotype ID: | 83276 |
| assay: | Soil Gross Morphology: 30% of flowers to be produced have opened |
| phenotype: | WHOLE PLANT - Yellow-Green Viable 1 |
| notes: | NONE |
| unique F1 plant ID: | R1 PLANT:ME04356-04 |
| phenotype ID: | 83285 |
| assay: | Soil Gross Morphology: 10% of flowers to be produced have opened |
| phenotype: | WHOLE PLANT - Small |
| notes: | 25 pct wt |
| unique F1 plant ID: | R1 PLANT:ME04356-04 |
| phenotype ID: | 83286 |
| assay: | Soil Gross Morphology: 10% of flowers to be produced have opened |
| phenotype: | WHOLE PLANT - Yellow-Green Viable 1 |
| notes: | NONE |
| unique F1 plant ID: | R1 PLANT:ME04356-04 |
| phenotype ID: | 83287 |
| assay: | Soil Gross Morphology: 30% of flowers to be produced have opened |
| phenotype: | ROSETTE LEAVES - Lanceolate Shaped |
| notes: | NONE |
| unique F1 plant ID: | R1 PLANT:ME04356-04 |
| phenotype ID: | 83288 |
| assay: | Soil Gross Morphology: 30% of flowers to be produced have opened |
| phenotype: | WHOLE PLANT - Small |
| notes: | 25 percent weight |
| unique F1 plant ID: | R1 PLANT:ME04356-05 |
| phenotype ID: | 83289 |
| assay: | Soil Gross Morphology: 10% of flowers to be produced have opened |
| phenotype: | ROSETTE LEAVES - Curled 2 |
| notes: | NONE |
| unique F1 plant ID: | R1 PLANT:ME04356-05 |
| phenotype ID: | 83290 |
| assay: | Soil Gross Morphology: 10% of flowers to be produced have opened |
| phenotype: | WHOLE PLANT - Small |

TABLE 1-continued

| | |
|---|---|
| notes: | 25 pct wt |
| unique F1 plant ID: | R1 PLANT:ME04356-05 |
| phenotype ID: | 83291 |
| assay: | Soil Gross Morphology: 30% of flowers to be produced have opened |
| phenotype: | ROSETTE LEAVES - Other |
| notes: | misshapen leaves |
| unique F1 plant ID: | R1 PLANT:ME04356-05 |
| phenotype ID: | 83292 |
| assay: | Soil Gross Morphology: 30% of flowers to be produced have opened |
| phenotype: | ROSETTE LEAVES - Other |
| notes: | fewer leaves |
| unique F1 plant ID: | R1 PLANT:ME04356-05 |
| phenotype ID: | 83293 |
| assay: | Soil Gross Morphology: 10% of flowers to be produced have opened |
| phenotype: | WHOLE PLANT - Yellow-Green Viable 1 |
| notes: | NONE |

Knock-in phenotype in gene(cDNA_id): 12339505

| | |
|---|---|
| clone ID: | 37298 |
| Promoter: | 35S |
| unique F1 plant ID: | R1 PLANT:ME05593-04 |
| phenotype ID: | 98513 |
| assay: | Soil Gross Morphology: 30% of flowers to be produced have opened |
| phenotype: | INFLORESCENCE - Short |
| notes: | 15 pct wt |
| unique F1 plant ID: | R1 PLANT:ME05593-04 |
| phenotype ID: | 98514 |
| assay: | Soil Gross Morphology: 30% of flowers to be produced have opened |
| phenotype: | FLOWER - Other |
| notes: | flowers bunched at top of bolt |
| unique F1 plant ID: | R1 PLANT:ME05593-04 |
| phenotype ID: | 98515 |
| assay: | Soil Gross Morphology: First flower buds visible |
| phenotype: | ROSETTE LEAVES - Disorganized Rosette |
| notes: | NONE |
| unique F1 plant ID: | R1 PLANT:ME05593-04 |
| phenotype ID: | 98516 |
| assay: | Soil Gross Morphology: First flower buds visible |
| phenotype: | ROSETTE LEAVES - Other |
| notes: | misshapen |
| unique F1 plant ID: | R1 PLANT:ME05593-04 |
| phenotype ID: | 98517 |
| assay: | Soil Gross Morphology: First flower buds visible |
| phenotype: | INFLORESCENCE - Reduced Apical Dominance |
| notes: | NONE |
| unique F1 plant ID: | R1 PLANT:ME05593-04 |
| phenotype ID: | 98518 |
| assay: | Soil Gross Morphology: First flower buds visible |
| phenotype: | WHOLE PLANT - Dark Green |
| notes: | NONE |
| unique F1 plant ID: | R1 PLANT:ME05593-05 |
| phenotype ID: | 98558 |
| assay: | Soil Gross Morphology: 30% of flowers to be produced have opened |
| phenotype: | INFLORESCENCE - Other |
| notes: | increased secondary inflorescence |
| unique F1 plant ID: | R1 PLANT:ME05593-05 |
| phenotype ID: | 98559 |
| assay: | Soil Gross Morphology: 30% of flowers to be produced have opened |
| phenotype: | INFLORESCENCE - Other |
| notes: | multiple siliques/branches emerging from same node |
| unique F1 plant ID: | R1 PLANT:ME05593-05 |
| phenotype ID: | 98560 |
| assay: | Soil Gross Morphology: 30% of flowers to be produced have opened |
| phenotype: | INFLORESCENCE - Other |
| notes: | secondary inflorescence are 50 pct shorter than wt |
| unique F1 plant ID: | R1 PLANT:ME05593-05 |
| phenotype ID: | 98561 |
| assay: | Soil Gross Morphology: 30% of flowers to be produced have opened |
| phenotype: | ROSETTE LEAVES - Disorganized Rosette |
| notes: | slightly disorganized |
| unique F1 plant ID: | R1 PLANT:ME05593-06 |
| phenotype ID: | 98592 |
| assay: | Soil Gross Morphology: 2 rosette leaves 1 mm in length |
| phenotype: | WHOLE PLANT - Dark Green |
| notes: | NONE |
| unique F1 plant ID: | R1 PLANT:ME05593-06 |
| phenotype ID: | 98593 |
| assay: | Soil Gross Morphology: 2 rosette leaves 1 mm in length |
| phenotype: | ROSETTE LEAVES - Other |

TABLE 1-continued

| | |
|---|---|
| notes: | few rosette leaves |
| unique F1 plant ID: | R1 PLANT:ME05593-06 |
| phenotype ID: | 98594 |
| assay: | Soil Gross Morphology: 2 rosette leaves 1 mm in length |
| phenotype: | ROSETTE LEAVES - Other |
| notes: | misshapen |
| unique F1 plant ID: | R1 PLANT:ME05593-06 |
| phenotype ID: | 98595 |
| assay: | Soil Gross Morphology: 2 rosette leaves 1 mm in length |
| phenotype: | WHOLE PLANT - Small |
| notes: | 15 pct wt |
| unique F1 plant ID: | R1 PLANT:ME05593-06 |
| phenotype ID: | 98596 |
| assay: | Soil Gross Morphology: 2 rosette leaves 1 mm in length |
| phenotype: | INFLORESCENCE - Late Flowering |
| notes: | NONE |
| unique F1 plant ID: | R1 PLANT:ME05593-07 |
| phenotype ID: | 98649 |
| assay: | Soil Gross Morphology: 30% of flowers to be produced have opened |
| phenotype: | WHOLE PLANT - Other |
| notes: | slightly fasciated |
| unique F1 plant ID: | R1 PLANT:ME05593-07 |
| phenotype ID: | 98650 |
| assay: | Soil Gross Morphology: First flower buds visible |
| phenotype: | ROSETTE LEAVES - Disorganized Rosette |
| notes: | NONE |
| unique F1 plant ID: | R1 PLANT:ME05593-07 |
| phenotype ID: | 98651 |
| assay: | Soil Gross Morphology: First flower buds visible |
| phenotype: | ROSETTE LEAVES - Other |
| notes: | misshapen |
| unique F1 plant ID: | R1 PLANT:ME05593-07 |
| phenotype ID: | 98652 |
| assay: | Soil Gross Morphology: First flower buds visible |
| phenotype: | INFLORESCENCE - Reduced Apical Dominance |
| notes: | NONE |
| unique F1 plant ID: | R1 PLANT:ME05593-07 |
| phenotype ID: | 98653 |
| assay: | Soil Gross Morphology: First flower buds visible |
| phenotype: | WHOLE PLANT - Dark Green |
| notes: | NONE |
| unique F1 plant ID: | R1 PLANT:ME05593-10 |
| phenotype ID: | 98789 |
| assay: | Soil Gross Morphology: 30% of flowers to be produced have opened |
| phenotype: | INFLORESCENCE - Other |
| notes: | 1st secondary branches emerging close to rosette |
| unique F1 plant ID: | R1 PLANT:ME05593-10 |
| phenotype ID: | 98790 |
| assay: | Soil Gross Morphology: 30% of flowers to be produced have opened |
| phenotype: | ROSETTE LEAVES - Disorganized Rosette |
| notes: | NONE |
| | Knock-in phenotype in gene(cDNA_id): 12341440 |
| clone ID: | 241379 |
| Promoter: | 35S |
| unique F1 plant ID: | R1 PLANT:ME03149-01 |
| phenotype ID: | 71408 |
| assay: | Soil Gross Morphology: First flower open |
| phenotype: | INFLORESCENCE - Asecondary Branching |
| notes: | NONE |
| unique F1 plant ID: | R1 PLANT:ME03149-01 |
| phenotype ID: | 71409 |
| assay: | Soil Gross Morphology: First flower open |
| phenotype: | INFLORESCENCE - No Branching |
| notes: | NONE |
| unique F1 plant ID: | R1 PLANT:ME03149-01 |
| phenotype ID: | 71410 |
| assay: | Soil Gross Morphology: First flower open |
| phenotype: | WHOLE PLANT - Small |
| notes: | 20pct. of wt |
| unique F1 plant ID: | R1 PLANT:ME03149-01 |
| phenotype ID: | 71411 |
| assay: | Soil Gross Morphology: First flower open |
| phenotype: | ROSETTE LEAVES - Lanceolate Shaped |
| notes: | NONE |
| unique F1 plant ID: | R1 PLANT:ME03149-03 |
| phenotype ID: | 71446 |
| assay: | Soil Gross Morphology: First flower buds visible |
| phenotype: | ROSETTE LEAVES - Lanceolate Shaped |

TABLE 1-continued

| | |
|---|---|
| notes: | NONE |
| unique F1 plant ID: | R1 PLANT:ME03149-03 |
| phenotype ID: | 71447 |
| assay: | Soil Gross Morphology: First flower buds visible |
| phenotype: | ROSETTE LEAVES - Other |
| notes: | few leaves |
| unique F1 plant ID: | R1 PLANT:ME03149-03 |
| phenotype ID: | 71448 |
| assay: | Soil Gross Morphology: First flower buds visible |
| phenotype: | INFLORESCENCE - Asecondary Branching |
| notes: | NONE |
| unique F1 plant ID: | R1 PLANT:ME03149-03 |
| phenotype ID: | 71449 |
| assay: | Soil Gross Morphology: First flower buds visible |
| phenotype: | INFLORESCENCE - No Branching |
| notes: | NONE |
| unique F1 plant ID: | R1 PLANT:ME03149-03 |
| phenotype ID: | 71450 |
| assay: | Soil Gross Morphology: First flower buds visible |
| phenotype: | WHOLE PLANT - Small |
| notes: | 20pct. of wt |
| unique F1 plant ID: | R1 PLANT:ME03149-10 |
| phenotype ID: | 71558 |
| assay: | Soil Gross Morphology: First flower buds visible |
| phenotype: | ROSETTE LEAVES - Curled 2 |
| notes: | NONE |
| unique F1 plant ID: | R1 PLANT:ME03149-10 |
| phenotype ID: | 71559 |
| assay: | Soil Gross Morphology: First flower buds visible |
| phenotype: | INFLORESCENCE - Short |
| notes: | NONE |
| unique F1 plant ID: | R1 PLANT:ME03149-10 |
| phenotype ID: | 71560 |
| assay: | Soil Gross Morphology: First flower buds visible |
| phenotype: | INFLORESCENCE - Other |
| notes: | no flowers apparent on inflorescence |
| unique F1 plant ID: | R1 PLANT:ME03149-10 |
| phenotype ID: | 71561 |
| assay: | Soil Gross Morphology: First flower buds visible |
| phenotype: | INFLORESCENCE - Asecondary Branching |
| notes: | NONE |
| unique F1 plant ID: | R1 PLANT:ME03149-10 |
| phenotype ID: | 71562 |
| assay: | Soil Gross Morphology: First flower buds visible |
| phenotype: | INFLORESCENCE - No Branching |
| notes: | NONE |
| unique F1 plant ID: | R1 PLANT:ME03149-10 |
| phenotype ID: | 71563 |
| assay: | Soil Gross Morphology: First flower buds visible |
| phenotype: | CAULINE LEAVES - Curled 1 |
| notes: | NONE |
| unique F1 plant ID: | R1 PLANT:ME03149-10 |
| phenotype ID: | 71564 |
| assay: | Soil Gross Morphology: First flower buds visible |
| phenotype: | ROSETTE LEAVES - Disorganized Rosette |
| notes: | NONE |
| unique F1 plant ID: | R1 PLANT:ME03149-10 |
| phenotype ID: | 71565 |
| assay: | Soil Gross Morphology: First flower buds visible |
| phenotype: | ROSETTE LEAVES - Lanceolate Shaped |
| notes: | NONE |
| unique F1 plant ID: | R1 PLANT:ME03149-10 |
| phenotype ID: | 71566 |
| assay: | Soil Gross Morphology: First flower buds visible |
| phenotype: | WHOLE PLANT - Yellow-Green Viable 1 |
| notes: | NONE |
| | Knock-in phenotype in gene(cDNA__id): 12343471 |
| clone ID: | 6397 |
| Promoter: | 35S |
| unique F1 plant ID: | R1 PLANT:ME01699-04 |
| phenotype ID: | 54284 |
| assay: | Soil Gross Morphology: 50% of flowers to be produced have opened |
| phenotype: | INFLORESCENCE - Other |
| notes: | extra branching |
| unique F1 plant ID: | R1 PLANT:ME01699-04 |
| phenotype ID: | 54285 |
| assay: | Soil Gross Morphology: 50% of flowers to be produced have opened |
| phenotype: | FLOWER - Reduced fertility |

TABLE 1-continued

| | |
|---|---|
| notes: | NONE |
| unique F1 plant ID: | R1 PLANT:ME01699-05 |
| phenotype ID: | 54302 |
| assay: | Soil Gross Morphology: 50% of flowers to be produced have opened |
| phenotype: | FLOWER - Reduced fertility |
| notes: | NONE |
| unique F1 plant ID: | R1 PLANT:ME01699-05 |
| phenotype ID: | 54303 |
| assay: | Soil Gross Morphology: 50% of flowers to be produced have opened |
| phenotype: | FLOWER - Other |
| notes: | extra flowers |
| unique F1 plant ID: | R1 PLANT:ME01699-07 |
| phenotype ID: | 54340 |
| assay: | Soil Gross Morphology: 30% of flowers to be produced have opened |
| phenotype: | INFLORESCENCE - Other |
| notes: | extra secondary branching |

Knock-in phenotype in gene(cDNA__id): 12392187

| | |
|---|---|
| clone ID: | 481710 |
| Promoter: | 35S |
| unique F1 plant ID: | R1 PLANT:ME05778-01 |
| phenotype ID: | 98831 |
| assay: | Soil Gross Morphology: 9 rosette leaves 1 mm in length |
| phenotype: | INFLORESCENCE - Late Flowering |
| notes: | slight |
| unique F1 plant ID: | R1 PLANT:ME05778-01 |
| phenotype ID: | 98832 |
| assay: | Soil Gross Morphology: 9 rosette leaves 1 mm in length |
| phenotype: | ROSETTE LEAVES - Short Petioles |
| notes: | NONE |
| unique F1 plant ID: | R1 PLANT:ME05778-01 |
| phenotype ID: | 98833 |
| assay: | Soil Gross Morphology: 9 rosette leaves 1 mm in length |
| phenotype: | ROSETTE LEAVES - Oval Shaped |
| notes: | NONE |
| unique F1 plant ID: | R1 PLANT:ME05778-01 |
| phenotype ID: | 98834 |
| assay: | Soil Gross Morphology: 9 rosette leaves 1 mm in length |
| phenotype: | WHOLE PLANT - Dark Green |
| notes: | NONE |
| unique F1 plant ID: | R1 PLANT:ME05778-02 |
| phenotype ID: | 98849 |
| assay: | Soil Gross Morphology: 7 rosette leaves 1 mm in length |
| phenotype: | INFLORESCENCE - Late Flowering |
| notes: | slight |
| unique F1 plant ID: | R1 PLANT:ME05778-02 |
| phenotype ID: | 98850 |
| assay: | Soil Gross Morphology: 7 rosette leaves 1 mm in length |
| phenotype: | ROSETTE LEAVES - Short Petioles |
| notes: | NONE |
| unique F1 plant ID: | R1 PLANT:ME05778-02 |
| phenotype ID: | 98851 |
| assay: | Soil Gross Morphology: 7 rosette leaves 1 mm in length |
| phenotype: | ROSETTE LEAVES - Oval Shaped |
| notes: | NONE |
| unique F1 plant ID: | R1 PLANT:ME05778-02 |
| phenotype ID: | 98852 |
| assay: | Soil Gross Morphology: 7 rosette leaves 1 mm in length |
| phenotype: | WHOLE PLANT - Dark Green |
| notes: | NONE |
| unique F1 plant ID: | R1 PLANT:ME05778-03 |
| phenotype ID: | 98871 |
| assay: | Soil Gross Morphology: 8 rosette leaves 1 mm in length |
| phenotype: | INFLORESCENCE - Late Flowering |
| notes: | slight |
| unique F1 plant ID: | R1 PLANT:ME05778-03 |
| phenotype ID: | 98872 |
| assay: | Soil Gross Morphology: 8 rosette leaves 1 mm in length |
| phenotype: | ROSETTE LEAVES - Short Petioles |
| notes: | NONE |
| unique F1 plant ID: | R1 PLANT:ME05778-03 |
| phenotype ID: | 98873 |
| assay: | Soil Gross Morphology: 8 rosette leaves 1 mm in length |
| phenotype: | ROSETTE LEAVES - Oval Shaped |
| notes: | NONE |
| unique F1 plant ID: | R1 PLANT:ME05778-03 |
| phenotype ID: | 98874 |
| assay: | Soil Gross Morphology: 8 rosette leaves 1 mm in length |
| phenotype: | WHOLE PLANT - Dark Green |

TABLE 1-continued

| | |
|---|---|
| notes: | NONE |
| unique F1 plant ID: | R1 PLANT:ME05778-04 |
| phenotype ID: | 98895 |
| assay: | Soil Gross Morphology: 8 rosette leaves 1 mm in length |
| phenotype: | INFLORESCENCE - Late Flowering |
| notes: | slight |
| unique F1 plant ID: | R1 PLANT:ME05778-04 |
| phenotype ID: | 98896 |
| assay: | Soil Gross Morphology: 8 rosette leaves 1 mm in length |
| phenotype: | ROSETTE LEAVES - Short Petioles |
| notes: | NONE |
| unique F1 plant ID: | R1 PLANT:ME05778-04 |
| phenotype ID: | 98897 |
| assay: | Soil Gross Morphology: 8 rosette leaves 1 mm in length |
| phenotype: | ROSETTE LEAVES - Oval Shaped |
| notes: | NONE |
| unique F1 plant ID: | R1 PLANT:ME05778-04 |
| phenotype ID: | 98898 |
| assay: | Soil Gross Morphology: 8 rosette leaves 1 mm in length |
| phenotype: | WHOLE PLANT - Dark Green |
| notes: | NONE |
| unique F1 plant ID: | R1 PLANT:ME05778-05 |
| phenotype ID: | 98920 |
| assay: | Soil Gross Morphology: 7 rosette leaves 1 mm in length |
| phenotype: | INFLORESCENCE - Late Flowering |
| notes: | slight |
| unique F1 plant ID: | R1 PLANT:ME05778-05 |
| phenotype ID: | 98921 |
| assay: | Soil Gross Morphology: 7 rosette leaves 1 mm in length |
| phenotype: | ROSETTE LEAVES - Short Petioles |
| notes: | NONE |
| unique F1 plant ID: | R1 PLANT:ME05778-05 |
| phenotype ID: | 98922 |
| assay: | Soil Gross Morphology: 7 rosette leaves 1 mm in length |
| phenotype: | ROSETTE LEAVES - Oval Shaped |
| notes: | NONE |
| unique F1 plant ID: | R1 PLANT:ME05778-05 |
| phenotype ID: | 98923 |
| assay: | Soil Gross Morphology: 7 rosette leaves 1 mm in length |
| phenotype: | WHOLE PLANT - Dark Green |
| notes: | NONE |
| unique F1 plant ID: | R1 PLANT:ME05778-06 |
| phenotype ID: | 98935 |
| assay: | Soil Gross Morphology: 7 rosette leaves 1 mm in length |
| phenotype: | INFLORESCENCE - Late Flowering |
| notes: | slight |
| unique F1 plant ID: | R1 PLANT:ME05778-06 |
| phenotype ID: | 98936 |
| assay: | Soil Gross Morphology: 7 rosette leaves 1 mm in length |
| phenotype: | ROSETTE LEAVES - Short Petioles |
| notes: | NONE |
| unique F1 plant ID: | R1 PLANT:ME05778-06 |
| phenotype ID: | 98937 |
| assay: | Soil Gross Morphology: 7 rosette leaves 1 mm in length |
| phenotype: | ROSETTE LEAVES - Oval Shaped |
| notes: | NONE |
| unique F1 plant ID: | R1 PLANT:ME05778-06 |
| phenotype ID: | 98938 |
| assay: | Soil Gross Morphology: 7 rosette leaves 1 mm in length |
| phenotype: | WHOLE PLANT - Dark Green |
| notes: | NONE |
| unique F1 plant ID: | R1 PLANT:ME05778-07 |
| phenotype ID: | 98950 |
| assay: | Soil Gross Morphology: 7 rosette leaves 1 mm in length |
| phenotype: | INFLORESCENCE - Late Flowering |
| notes: | slight |
| unique F1 plant ID: | R1 PLANT:ME05778-07 |
| phenotype ID: | 98951 |
| assay: | Soil Gross Morphology: 7 rosette leaves 1 mm in length |
| phenotype: | ROSETTE LEAVES - Short Petioles |
| notes: | NONE |
| unique F1 plant ID: | R1 PLANT:ME05778-07 |
| phenotype ID: | 98952 |
| assay: | Soil Gross Morphology: 7 rosette leaves 1 mm in length |
| phenotype: | ROSETTE LEAVES - Oval Shaped |
| notes: | NONE |
| unique F1 plant ID: | R1 PLANT:ME05778-07 |
| phenotype ID: | 98953 |
| assay: | Soil Gross Morphology: 7 rosette leaves 1 mm in length |

TABLE 1-continued

| | |
|---|---|
| phenotype: | WHOLE PLANT - Dark Green |
| notes: | NONE |
| unique F1 plant ID: | R1 PLANT:ME05778-08 |
| phenotype ID: | 98970 |
| assay: | Soil Gross Morphology: 7 rosette leaves 1 mm in length |
| phenotype: | INFLORESCENCE - Late Flowering |
| notes: | slight |
| unique F1 plant ID: | R1 PLANT:ME05778-08 |
| phenotype ID: | 98971 |
| assay: | Soil Gross Morphology: 7 rosette leaves 1 mm in length |
| phenotype: | ROSETTE LEAVES - Short Petioles |
| notes: | NONE |
| unique F1 plant ID: | R1 PLANT:ME05778-08 |
| phenotype ID: | 98972 |
| assay: | Soil Gross Morphology: 7 rosette leaves 1 mm in length |
| phenotype: | ROSETTE LEAVES - Oval Shaped |
| notes: | NONE |
| unique F1 plant ID: | R1 PLANT:ME05778-08 |
| phenotype ID: | 98973 |
| assay: | Soil Gross Morphology: 7 rosette leaves 1 mm in length |
| phenotype: | WHOLE PLANT - Dark Green |
| notes: | NONE |
| unique F1 plant ID: | R1 PLANT:ME05778-09 |
| phenotype ID: | 98984 |
| assay: | Soil Gross Morphology: 6 rosette leaves 1 mm in length |
| phenotype: | INFLORESCENCE - Late Flowering |
| notes: | slight |
| unique F1 plant ID: | R1 PLANT:ME05778-09 |
| phenotype ID: | 98985 |
| assay: | Soil Gross Morphology: 6 rosette leaves 1 mm in length |
| phenotype: | ROSETTE LEAVES - Short Petioles |
| notes: | NONE |
| unique F1 plant ID: | R1 PLANT:ME05778-09 |
| phenotype ID: | 98986 |
| assay: | Soil Gross Morphology: 6 rosette leaves 1 mm in length |
| phenotype: | ROSETTE LEAVES - Oval Shaped |
| notes: | NONE |
| unique F1 plant ID: | R1 PLANT:ME05778-09 |
| phenotype ID: | 98987 |
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME05778-10 |
| phenotype ID: | 99012 |
| assay: | Soil Gross Morphology: 8 rosette leaves 1 mm in length |
| phenotype: | INFLORESCENCE - Late Flowering |
| notes: | slight |
| unique F1 plant ID: | R1 PLANT:ME05778-10 |
| phenotype ID: | 99013 |
| assay: | Soil Gross Morphology: 8 rosette leaves 1 mm in length |
| phenotype: | ROSETTE LEAVES - Short Petioles |
| notes: | NONE |
| unique F1 plant ID: | R1 PLANT:ME05778-10 |
| phenotype ID: | 99014 |
| assay: | Soil Gross Morphology: 8 rosette leaves 1 mm in length |
| phenotype: | ROSETTE LEAVES - Oval Shaped |
| notes: | NONE |
| unique F1 plant ID: | R1 PLANT:ME05778-10 |
| phenotype ID: | 99015 |
| assay: | Soil Gross Morphology: 8 rosette leaves 1 mm in length |
| phenotype: | WHOLE PLANT - Dark Green |
| notes: | NONE |
| | Knock-in phenotype in gene(cDNA__id): 12394681 |
| clone ID: | 157547 |
| Promoter: | 35S |
| unique F1 plant ID: | R1 PLANT:ME03646-06 |
| phenotype ID: | 71886 |
| assay: | Soil Gross Morphology: First flower buds visible |
| phenotype: | ROSETTE LEAVES - Oval Shaped |
| notes: | NONE |
| unique F1 plant ID: | R1 PLANT:ME03646-06 |
| phenotype ID: | 71887 |
| assay: | Soil Gross Morphology: First flower buds visible |
| phenotype: | WHOLE PLANT - Dark Green |
| notes: | NONE |
| unique F1 plant ID: | R1 PLANT:ME03646-06 |
| phenotype ID: | 71888 |
| assay: | Soil Gross Morphology: First flower buds visible |

TABLE 1-continued

| | |
|---|---|
| phenotype: | INFLORESCENCE - No Branching |
| notes: | NONE |
| unique F1 plant ID: | R1 PLANT:ME03646-06 |
| phenotype ID: | 71889 |
| assay: | Soil Gross Morphology: First flower buds visible |
| phenotype: | WHOLE PLANT - Small |
| notes: | 10pct. of wt |
| unique F1 plant ID: | R1 PLANT:ME03646-06 |
| phenotype ID: | 71890 |
| assay: | Soil Gross Morphology: First flower buds visible |
| phenotype: | INFLORESCENCE - Late Flowering |
| notes: | NONE |
| unique F1 plant ID: | R1 PLANT:ME04159-01 |
| phenotype ID: | 82584 |
| assay: | Soil Gross Morphology: First flower buds visible |
| phenotype: | INFLORESCENCE - Short |
| notes: | NONE |
| unique F1 plant ID: | R1 PLANT:ME04159-01 |
| phenotype ID: | 82585 |
| assay: | Soil Gross Morphology: First flower buds visible |
| phenotype: | ROSETTE LEAVES - Other |
| notes: | fewer rosette leaves |
| unique F1 plant ID: | R1 PLANT:ME04159-01 |
| phenotype ID: | 82586 |
| assay: | Soil Gross Morphology: 50% of flowers to be produced have opened |
| phenotype: | FLOWER - Sterile |
| notes: | NONE |
| unique F1 plant ID: | R1 PLANT:ME04159-01 |
| phenotype ID: | 82587 |
| assay: | Soil Gross Morphology: 50% of flowers to be produced have opened |
| phenotype: | WHOLE PLANT - Small |
| notes: | 10 percent weight |
| unique F1 plant ID: | R1 PLANT:ME04159-01 |
| phenotype ID: | 82588 |
| assay: | Soil Gross Morphology: First flower buds visible |
| phenotype: | WHOLE PLANT - Small |
| notes: | 10 percent weight |
| unique F1 plant ID: | R1 PLANT:ME04159-03 |
| phenotype ID: | 82702 |
| assay: | Soil Gross Morphology: 10% of flowers to be produced have opened |
| phenotype: | ROSETTE LEAVES - Serrate Margins |
| notes: | NONE |
| unique F1 plant ID: | R1 PLANT:ME04159-03 |
| phenotype ID: | 82703 |
| assay: | Soil Gross Morphology: 10% of flowers to be produced have opened |
| phenotype: | ROSETTE LEAVES - Other |
| notes: | misshapen leaves |
| unique F1 plant ID: | R1 PLANT:ME04159-07 |
| phenotype ID: | 82937 |
| assay: | Soil Gross Morphology: 10% of flowers to be produced have opened |
| phenotype: | ROSETTE LEAVES - Serrate Margins |
| notes: | NONE |
| unique F1 plant ID: | R1 PLANT:ME04159-07 |
| phenotype ID: | 82938 |
| assay: | Soil Gross Morphology: 10% of flowers to be produced have opened |
| phenotype: | ROSETTE LEAVES - Other |
| notes: | misshapen leaves |
| unique F1 plant ID: | R1 PLANT:ME04159-09 |
| phenotype ID: | 83060 |
| assay: | Soil Gross Morphology: First flower open |
| phenotype: | ROSETTE LEAVES - Disorganized Rosette |
| notes: | NONE |
| unique F1 plant ID: | R1 PLANT:ME04159-09 |
| phenotype ID: | 83061 |
| assay: | Soil Gross Morphology: First flower open |
| phenotype: | INFLORESCENCE - Late Flowering |
| notes: | NONE |
| unique F1 plant ID: | R1 PLANT:ME04159-09 |
| phenotype ID: | 83062 |
| assay: | Soil Gross Morphology: First flower open |
| phenotype: | INFLORESCENCE - Short |
| notes: | NONE |
| unique F1 plant ID: | R1 PLANT:ME04159-09 |
| phenotype ID: | 83063 |
| assay: | Soil Gross Morphology: 50% of flowers to be produced have opened |
| phenotype: | FLOWER - Sterile |
| notes: | NONE |
| unique F1 plant ID: | R1 PLANT:ME04159-09 |
| phenotype ID: | 83064 |

TABLE 1-continued

| | |
|---|---|
| assay: | Soil Gross Morphology: First flower open |
| phenotype: | ROSETTE LEAVES - Other |
| notes: | misshapen leaves |
| unique F1 plant ID: | R1 PLANT:ME04159-10 |
| phenotype ID: | 83123 |
| assay: | Soil Gross Morphology: 50% of flowers to be produced have opened |
| phenotype: | INFLORESCENCE - Other |
| notes: | reduced branching |
| unique F1 plant ID: | R1 PLANT:ME04159-10 |
| phenotype ID: | 83124 |
| assay: | Soil Gross Morphology: 50% of flowers to be produced have opened |
| phenotype: | FLOWER - Sterile |
| notes: | NONE |

Knock-in phenotype in gene(cDNA_id): 12396606

| | |
|---|---|
| clone ID: | 11929 |
| Promoter: | 35S |
| unique F1 plant ID: | R1 PLANT:ME02560-03 |
| phenotype ID: | 54987 |
| assay: | Soil Gross Morphology: First flower buds visible |
| phenotype: | ROSETTE LEAVES - Other |
| notes: | few rosette leaves |
| unique F1 plant ID: | R1 PLANT:ME02560-04 |
| phenotype ID: | 55033 |
| assay: | Soil Gross Morphology: First flower buds visible |
| phenotype: | ROSETTE LEAVES - Curled 2 |
| notes: | NONE |
| unique F1 plant ID: | R1 PLANT:ME02560-05 |
| phenotype ID: | 55081 |
| assay: | Soil Gross Morphology: First flower buds visible |
| phenotype: | ROSETTE LEAVES - Curled 2 |
| notes: | NONE |

Knock-in phenotype in gene(cDNA_id): 12421991

| | |
|---|---|
| clone ID: | 641 |
| Promoter: | 35S |
| unique F1 plant ID: | R1 PLANT:ME02715-01 |
| phenotype ID: | 55469 |
| assay: | Soil Gross Morphology: 30% of flowers to be produced have opened |
| phenotype: | FLOWER - Reduced fertility |
| notes: | NONE |
| unique F1 plant ID: | R1 PLANT:ME02715-01 |
| phenotype ID: | 55470 |
| assay: | Soil Gross Morphology: 50% of flowers to be produced have opened |
| phenotype: | FLOWER - Reduced fertility |
| notes: | NONE |
| unique F1 plant ID: | R1 PLANT:ME02715-04 |
| phenotype ID: | 55682 |
| assay: | Soil Gross Morphology: 30% of flowers to be produced have opened |
| phenotype: | FLOWER - Reduced fertility |
| notes: | NONE |
| unique F1 plant ID: | R1 PLANT:ME02715-04 |
| phenotype ID: | 55683 |
| assay: | Soil Gross Morphology: 50% of flowers to be produced have opened |
| phenotype: | FLOWER - Reduced fertility |
| notes: | NONE |
| unique F1 plant ID: | R1 PLANT:ME02715-06 |
| phenotype ID: | 55842 |
| assay: | Soil Gross Morphology: 50% of flowers to be produced have opened |
| phenotype: | FLOWER - Reduced fertility |
| notes: | NONE |
| unique F1 plant ID: | R1 PLANT:ME02715-06 |
| phenotype ID: | 55843 |
| assay: | Soil Gross Morphology: 30% of flowers to be produced have opened |
| phenotype: | FLOWER - Reduced fertility |
| notes: | NONE |
| unique F1 plant ID: | R1 PLANT:ME02715-07 |
| phenotype ID: | 55911 |
| assay: | Soil Gross Morphology: 30% of flowers to be produced have opened |
| phenotype: | FLOWER - Reduced fertility |
| notes: | NONE |
| unique F1 plant ID: | R1 PLANT:ME02715-07 |
| phenotype ID: | 55912 |
| assay: | Soil Gross Morphology: 50% of flowers to be produced have opened |
| phenotype: | FLOWER - Reduced fertility |
| notes: | NONE |
| unique F1 plant ID: | R1 PLANT:ME02715-10 |
| phenotype ID: | 56111 |
| assay: | Soil Gross Morphology: 50% of flowers to be produced have opened |

TABLE 1-continued

| | |
|---|---|
| phenotype: | FLOWER - Reduced fertility |
| notes: | NONE |
| unique F1 plant ID: | R1 PLANT:ME02715-10 |
| phenotype ID: | 56112 |
| assay: | Soil Gross Morphology: 30% of flowers to be produced have opened |
| phenotype: | FLOWER - Reduced fertility |
| notes: | NONE |

Knock-in phenotype in gene(cDNA_id): 12438838

| | |
|---|---|
| clone ID: | 572121 |
| Promoter: | 326D |
| unique F1 plant ID: | R1 PLANT:ME09212-01 |
| phenotype ID: | 124829 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09212-01 |
| phenotype ID: | 124830 |
| assay: | Soil Gross Morphology: 30% of flowers to be produced have opened |
| phenotype: | INFLORESCENCE - Reduced Apical Dominance |
| notes: | NONE |
| unique F1 plant ID: | R1 PLANT:ME09212-02 |
| phenotype ID: | 124838 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09212-02 |
| phenotype ID: | 124839 |
| assay: | Soil Gross Morphology: 30% of flowers to be produced have opened |
| phenotype: | INFLORESCENCE - Reduced Apical Dominance |
| notes: | NONE |
| unique F1 plant ID: | R1 PLANT:ME09212-03 |
| phenotype ID: | 124840 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09212-03 |
| phenotype ID: | 124841 |
| assay: | Soil Gross Morphology: 30% of flowers to be produced have opened |
| phenotype: | INFLORESCENCE - Reduced Apical Dominance |
| notes: | NONE |
| unique F1 plant ID: | R1 PLANT:ME09370-03 |
| phenotype ID: | 124898 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09370-03 |
| phenotype ID: | 124899 |
| assay: | Soil Gross Morphology: 30% of flowers to be produced have opened |
| phenotype: | INFLORESCENCE - Reduced Apical Dominance |
| notes: | NONE |
| unique F1 plant ID: | R1 PLANT:ME03166-02 |
| phenotype ID: | 71365 |
| assay: | Soil Gross Morphology: Flowering complete |
| phenotype: | FLOWER - Reduced fertility |
| notes: | NONE |
| unique F1 plant ID: | R1 PLANT:ME03166-02 |
| phenotype ID: | 71366 |
| assay: | Soil Gross Morphology: Flowering complete |
| phenotype: | SILIQUES - Short |
| notes: | NONE |
| unique F1 plant ID: | R1 PLANT:ME03166-03 |
| phenotype ID: | 71367 |
| assay: | Soil Gross Morphology: Flowering complete |
| phenotype: | FLOWER - Reduced fertility |
| notes: | NONE |
| unique F1 plant ID: | R1 PLANT:ME03166-03 |
| phenotype ID: | 71368 |
| assay: | Soil Gross Morphology: Flowering complete |
| phenotype: | SILIQUES - Short |
| notes: | NONE |
| unique F1 plant ID: | R1 PLANT:ME03166-04 |
| phenotype ID: | 71369 |
| assay: | Soil Gross Morphology: Flowering complete |
| phenotype: | SILIQUES - Short |
| notes: | NONE |
| unique F1 plant ID: | R1 PLANT:ME03166-04 |
| phenotype ID: | 71370 |
| assay: | Soil Gross Morphology: Flowering complete |

TABLE 1-continued

| | |
|---|---|
| phenotype: | FLOWER - Reduced fertility |
| notes: | NONE |
| unique F1 plant ID: | R1 PLANT:ME03166-05 |
| phenotype ID: | 71371 |
| assay: | Soil Gross Morphology: Flowering complete |
| phenotype: | SILIQUES - Short |
| notes: | NONE |
| unique F1 plant ID: | R1 PLANT:ME03166-05 |
| phenotype ID: | 71372 |
| assay: | Soil Gross Morphology: Flowering complete |
| phenotype: | FLOWER - Reduced fertility |
| notes: | NONE |

Knock-in phenotype in gene(cDNA_id): 12447172

| | |
|---|---|
| clone ID: | 681088 |
| Promoter: | 35S |
| unique F1 plant ID: | R1 PLANT:ME03190-01 |
| phenotype ID: | 71413 |
| assay: | Soil Gross Morphology: 50% of flowers to be produced have opened |
| phenotype: | ROSETTE LEAVES - Curled 1 |
| notes: | NONE |
| unique F1 plant ID: | R1 PLANT:ME03190-01 |
| phenotype ID: | 71414 |
| assay: | Soil Gross Morphology: 50% of flowers to be produced have opened |
| phenotype: | WHOLE PLANT - Small |
| notes: | 25pct. of wt |
| unique F1 plant ID: | R1 PLANT:ME03190-02 |
| phenotype ID: | 71429 |
| assay: | Soil Gross Morphology: 50% of flowers to be produced have opened |
| phenotype: | ROSETTE LEAVES - Curled 1 |
| notes: | NONE |
| unique F1 plant ID: | R1 PLANT:ME03190-02 |
| phenotype ID: | 71430 |
| assay: | Soil Gross Morphology: 50% of flowers to be produced have opened |
| phenotype: | WHOLE PLANT - Small |
| notes: | 50pct. of wt |
| unique F1 plant ID: | R1 PLANT:ME03190-03 |
| phenotype ID: | 71455 |
| assay: | Soil Gross Morphology: 10% of flowers to be produced have opened |
| phenotype: | WHOLE PLANT - Small |
| notes: | 70pct.of wt |
| unique F1 plant ID: | R1 PLANT:ME03190-03 |
| phenotype ID: | 71456 |
| assay: | Soil Gross Morphology: 10% of flowers to be produced have opened |
| phenotype: | ROSETTE LEAVES - Curled 1 |
| notes: | less so |
| unique F1 plant ID: | R1 PLANT:ME03190-04 |
| phenotype ID: | 71482 |
| assay: | Soil Gross Morphology: 10% of flowers to be produced have opened |
| phenotype: | ROSETTE LEAVES - Curled 1 |
| notes: | NONE |
| unique F1 plant ID: | R1 PLANT:ME03190-04 |
| phenotype ID: | 71483 |
| assay: | Soil Gross Morphology: 10% of flowers to be produced have opened |
| phenotype: | WHOLE PLANT - Small |
| notes: | 10pct. of wt |
| unique F1 plant ID: | R1 PLANT:ME03190-09 |
| phenotype ID: | 71538 |
| assay: | Soil Gross Morphology: 50% of flowers to be produced have opened |
| phenotype: | WHOLE PLANT - Small |
| notes: | 50pct. of wt |
| unique F1 plant ID: | R1 PLANT:ME03190-09 |
| phenotype ID: | 71539 |
| assay: | Soil Gross Morphology: 50% of flowers to be produced have opened |
| phenotype: | ROSETTE LEAVES - Lanceolate Shaped |
| notes: | NONE |

Knock-in phenotype in gene(cDNA_id): 12447204

| | |
|---|---|
| clone ID: | 641355 |
| Promoter: | 13879D |
| unique F1 plant ID: | R1 PLANT:ME09414-01 |
| phenotype ID: | 124915 |
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME09414-01 |
| phenotype ID: | 124916 |
| assay: | Soil Gross Morphology: 6 rosette leaves 1 mm in length |
| phenotype: | WHOLE PLANT - Small |

TABLE 1-continued

| | |
|---|---|
| notes: | 50 pct wt |
| unique F1 plant ID: | R1 PLANT:ME09414-01 |
| phenotype ID: | 124917 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09414-02 |
| phenotype ID: | 124939 |
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME09414-02 |
| phenotype ID: | 124940 |
| assay: | Soil Gross Morphology: 6 rosette leaves 1 mm in length |
| phenotype: | WHOLE PLANT - Small |
| notes: | 50 pct wt |
| unique F1 plant ID: | R1 PLANT:ME09414-02 |
| phenotype ID: | 124941 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09414-03 |
| phenotype ID: | 124960 |
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME09414-03 |
| phenotype ID: | 124961 |
| assay: | Soil Gross Morphology: 6 rosette leaves 1 mm in length |
| phenotype: | WHOLE PLANT - Small |
| notes: | 50 pct wt |
| unique F1 plant ID: | R1 PLANT:ME09414-03 |
| phenotype ID: | 124962 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09414-04 |
| phenotype ID: | 124988 |
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME09414-04 |
| phenotype ID: | 124989 |
| assay: | Soil Gross Morphology: 6 rosette leaves 1 mm in length |
| phenotype: | WHOLE PLANT - Small |
| notes: | 50 pct wt |
| unique F1 plant ID: | R1 PLANT:ME09414-04 |
| phenotype ID: | 124990 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09414-05 |
| phenotype ID: | 125006 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09414-06 |
| phenotype ID: | 125031 |
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME09414-06 |
| phenotype ID: | 125032 |
| assay: | Soil Gross Morphology: 6 rosette leaves 1 mm in length |
| phenotype: | WHOLE PLANT - Small |
| notes: | 50 pct wt |
| unique F1 plant ID: | R1 PLANT:ME09414-06 |
| phenotype ID: | 125033 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09414-07 |
| phenotype ID: | 125057 |
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME09414-07 |
| phenotype ID: | 125058 |
| assay: | Soil Gross Morphology: 6 rosette leaves 1 mm in length |

TABLE 1-continued

| | |
|---|---|
| phenotype: | WHOLE PLANT - Small |
| notes: | 50 pct wt |
| unique F1 plant ID: | R1 PLANT:ME09414-07 |
| phenotype ID: | 125059 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09414-08 |
| phenotype ID: | 125075 |
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME09414-08 |
| phenotype ID: | 125076 |
| assay: | Soil Gross Morphology: 6 rosette leaves 1 mm in length |
| phenotype: | WHOLE PLANT - Small |
| notes: | 50 pct wt |
| unique F1 plant ID: | R1 PLANT:ME09414-08 |
| phenotype ID: | 125077 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09414-09 |
| phenotype ID: | 125098 |
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME09414-09 |
| phenotype ID: | 125099 |
| assay: | Soil Gross Morphology: 6 rosette leaves 1 mm in length |
| phenotype: | WHOLE PLANT - Small |
| notes: | 50 pct wt |
| unique F1 plant ID: | R1 PLANT:ME09414-09 |
| phenotype ID: | 125100 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09414-10 |
| phenotype ID: | 125128 |
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME09414-10 |
| phenotype ID: | 125129 |
| assay: | Soil Gross Morphology: 6 rosette leaves 1 mm in length |
| phenotype: | WHOLE PLANT - Small |
| notes: | 50 pct wt |
| unique F1 plant ID: | R1 PLANT:ME09414-10 |
| phenotype ID: | 125130 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09407-01 |
| phenotype ID: | 124914 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09407-02 |
| phenotype ID: | 124935 |
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME09407-02 |
| phenotype ID: | 124936 |
| assay: | Soil Gross Morphology: 6 rosette leaves 1 mm in length |
| phenotype: | ROSETTE LEAVES - Glossy |
| notes: | NONE |
| unique F1 plant ID: | R1 PLANT:ME09407-02 |
| phenotype ID: | 124937 |
| assay: | Soil Gross Morphology: 6 rosette leaves 1 mm in length |
| phenotype: | WHOLE PLANT - Small |
| notes: | 50 pct wt |
| unique F1 plant ID: | R1 PLANT:ME09407-02 |
| phenotype ID: | 124938 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09407-03 |
| phenotype ID: | 124956 |

TABLE 1-continued

| | |
|---|---|
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME09407-03 |
| phenotype ID: | 124957 |
| assay: | Soil Gross Morphology: 6 rosette leaves 1 mm in length |
| phenotype: | ROSETTE LEAVES - Glossy |
| notes: | NONE |
| unique F1 plant ID: | R1 PLANT:ME09407-03 |
| phenotype ID: | 124958 |
| assay: | Soil Gross Morphology: 6 rosette leaves 1 mm in length |
| phenotype: | WHOLE PLANT - Small |
| notes: | 50 pct wt |
| unique F1 plant ID: | R1 PLANT:ME09407-03 |
| phenotype ID: | 124959 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09407-04 |
| phenotype ID: | 124983 |
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME09407-04 |
| phenotype ID: | 124984 |
| assay: | Soil Gross Morphology: 6 rosette leaves 1 mm in length |
| phenotype: | ROSETTE LEAVES - Glossy |
| notes: | NONE |
| unique F1 plant ID: | R1 PLANT:ME09407-04 |
| phenotype ID: | 124985 |
| assay: | Soil Gross Morphology: 6 rosette leaves 1 mm in length |
| phenotype: | WHOLE PLANT - Small |
| notes: | 50 pct wt |
| unique F1 plant ID: | R1 PLANT:ME09407-04 |
| phenotype ID: | 124986 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09407-05 |
| phenotype ID: | 125002 |
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME09407-05 |
| phenotype ID: | 125003 |
| assay: | Soil Gross Morphology: 6 rosette leaves 1 mm in length |
| phenotype: | ROSETTE LEAVES - Glossy |
| notes: | NONE |
| unique F1 plant ID: | R1 PLANT:ME09407-05 |
| phenotype ID: | 125004 |
| assay: | Soil Gross Morphology: 6 rosette leaves 1 mm in length |
| phenotype: | WHOLE PLANT - Small |
| notes: | 50 pct wt |
| unique F1 plant ID: | R1 PLANT:ME09407-05 |
| phenotype ID: | 125005 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09407-06 |
| phenotype ID: | 125027 |
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME09407-06 |
| phenotype ID: | 125028 |
| assay: | Soil Gross Morphology: 6 rosette leaves 1 mm in length |
| phenotype: | ROSETTE LEAVES - Glossy |
| notes: | NONE |
| unique F1 plant ID: | R1 PLANT:ME09407-06 |
| phenotype ID: | 125029 |
| assay: | Soil Gross Morphology: 6 rosette leaves 1 mm in length |
| phenotype: | WHOLE PLANT - Small |
| notes: | 50 pct wt |
| unique F1 plant ID: | R1 PLANT:ME09407-06 |
| phenotype ID: | 125030 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09407-07 |

TABLE 1-continued

| | |
|---|---|
| phenotype ID: | 125053 |
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME09407-07 |
| phenotype ID: | 125054 |
| assay: | Soil Gross Morphology: 6 rosette leaves 1 mm in length |
| phenotype: | ROSETTE LEAVES - Glossy |
| notes: | NONE |
| unique F1 plant ID: | R1 PLANT:ME09407-07 |
| phenotype ID: | 125055 |
| assay: | Soil Gross Morphology: 6 rosette leaves 1 mm in length |
| phenotype: | WHOLE PLANT - Small |
| notes: | 50 pct wt |
| unique F1 plant ID: | R1 PLANT:ME09407-07 |
| phenotype ID: | 125056 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09407-08 |
| phenotype ID: | 125071 |
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME09407-08 |
| phenotype ID: | 125072 |
| assay: | Soil Gross Morphology: 6 rosette leaves 1 mm in length |
| phenotype: | ROSETTE LEAVES - Glossy |
| notes: | NONE |
| unique F1 plant ID: | R1 PLANT:ME09407-08 |
| phenotype ID: | 125073 |
| assay: | Soil Gross Morphology: 6 rosette leaves 1 mm in length |
| phenotype: | WHOLE PLANT - Small |
| notes: | 50 pct wt |
| unique F1 plant ID: | R1 PLANT:ME09407-08 |
| phenotype ID: | 125074 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09407-09 |
| phenotype ID: | 125087 |
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME09407-09 |
| phenotype ID: | 125088 |
| assay: | Soil Gross Morphology: 6 rosette leaves 1 mm in length |
| phenotype: | ROSETTE LEAVES - Glossy |
| notes: | NONE |
| unique F1 plant ID: | R1 PLANT:ME09407-09 |
| phenotype ID: | 125089 |
| assay: | Soil Gross Morphology: 6 rosette leaves 1 mm in length |
| phenotype: | WHOLE PLANT - Small |
| notes: | 50 pct wt |
| unique F1 plant ID: | R1 PLANT:ME09407-09 |
| phenotype ID: | 125090 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09407-10 |
| phenotype ID: | 125123 |
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME09407-10 |
| phenotype ID: | 125124 |
| assay: | Soil Gross Morphology: 6 rosette leaves 1 mm in length |
| phenotype: | ROSETTE LEAVES - Glossy |
| notes: | NONE |
| unique F1 plant ID: | R1 PLANT:ME09407-10 |
| phenotype ID: | 125125 |
| assay: | Soil Gross Morphology: 6 rosette leaves 1 mm in length |
| phenotype: | WHOLE PLANT - Small |
| notes: | 50 pct wt |
| unique F1 plant ID: | R1 PLANT:ME09407-10 |
| phenotype ID: | 125126 |
| assay: | Soil Gross Morphology: 30% of flowers to be produced have opened |
| phenotype: | INFLORESCENCE - Late Flowering |
| notes: | NONE |

TABLE 1-continued

| | |
|---|---|
| unique F1 plant ID: | R1 PLANT:ME09421-01 |
| phenotype ID: | 124918 |
| assay: | Soil Gross Morphology: 10 rosette leaves 1 mm in length |
| phenotype: | INFLORESCENCE - Late Flowering |
| notes: | NONE |
| unique F1 plant ID: | R1 PLANT:ME09421-01 |
| phenotype ID: | 124919 |
| assay: | Soil Gross Morphology: 10 rosette leaves 1 mm in length |
| phenotype: | INFLORESCENCE - Late Flowering |
| notes: | NONE |
| unique F1 plant ID: | R1 PLANT:ME09421-02 |
| phenotype ID: | 124942 |
| assay: | Soil Gross Morphology: First flower buds visible |
| phenotype: | INFLORESCENCE - No Branching |
| notes: | NONE |
| unique F1 plant ID: | R1 PLANT:ME09421-02 |
| phenotype ID: | 124943 |
| assay: | Soil Gross Morphology: First flower buds visible |
| phenotype: | WHOLE PLANT - Small |
| notes: | 5 pct wt |
| unique F1 plant ID: | R1 PLANT:ME09421-03 |
| phenotype ID: | 124963 |
| assay: | Soil Gross Morphology: 10 rosette leaves 1 mm in length |
| phenotype: | INFLORESCENCE - Late Flowering |
| notes: | NONE |
| unique F1 plant ID: | R1 PLANT:ME09421-03 |
| phenotype ID: | 124964 |
| assay: | Soil Gross Morphology: 10 rosette leaves 1 mm in length |
| phenotype: | INFLORESCENCE - Late Flowering |
| notes: | NONE |
| unique F1 plant ID: | R1 PLANT:ME09421-04 |
| phenotype ID: | 124991 |
| assay: | Soil Gross Morphology: First flower buds visible |
| phenotype: | ROSETTE LEAVES - Disorganized Rosette |
| notes: | NONE |
| unique F1 plant ID: | R1 PLANT:ME09421-05 |
| phenotype ID: | 125007 |
| assay: | Soil Gross Morphology: First flower buds visible |
| phenotype: | ROSETTE LEAVES - Disorganized Rosette |
| notes: | NONE |
| unique F1 plant ID: | R1 PLANT:ME09421-06 |
| phenotype ID: | 125034 |
| assay: | Soil Gross Morphology: 14 rosette leaves 1 mm in length |
| phenotype: | ROSETTE LEAVES - Oval Shaped |
| notes: | NONE |
| unique F1 plant ID: | R1 PLANT:ME09421-06 |
| phenotype ID: | 125035 |
| assay: | Soil Gross Morphology: 14 rosette leaves 1 mm in length |
| phenotype: | ROSETTE LEAVES - Long Petioles |
| notes: | NONE |
| unique F1 plant ID: | R1 PLANT:ME09421-06 |
| phenotype ID: | 125036 |
| assay: | Soil Gross Morphology: 14 rosette leaves 1 mm in length |
| phenotype: | WHOLE PLANT - Small |
| notes: | 50 pct wt |
| unique F1 plant ID: | R1 PLANT:ME09421-06 |
| phenotype ID: | 125037 |
| assay: | Soil Gross Morphology: 13 rosette leaves 1 mm in length |
| phenotype: | INFLORESCENCE - Late Flowering |
| notes: | NONE |
| unique F1 plant ID: | R1 PLANT:ME09421-09 |
| phenotype ID: | 125101 |
| assay: | Soil Gross Morphology: 8 rosette leaves 1 mm in length |
| phenotype: | ROSETTE LEAVES - Oval Shaped |
| notes: | NONE |
| unique F1 plant ID: | R1 PLANT:ME09421-09 |
| phenotype ID: | 125102 |
| assay: | Soil Gross Morphology: 8 rosette leaves 1 mm in length |
| phenotype: | ROSETTE LEAVES - Long Petioles |
| notes: | NONE |
| unique F1 plant ID: | R1 PLANT:ME09421-09 |
| phenotype ID: | 125103 |
| assay: | Soil Gross Morphology: 8 rosette leaves 1 mm in length |
| phenotype: | WHOLE PLANT - Small |
| notes: | 50 pct wt |
| unique F1 plant ID: | R1 PLANT:ME09421-09 |
| phenotype ID: | 125104 |
| assay: | Soil Gross Morphology: 10 rosette leaves 1 mm in length |
| phenotype: | INFLORESCENCE - Late Flowering |

TABLE 1-continued

| | |
|---|---|
| notes: | NONE |
| unique F1 plant ID: | R1 PLANT:ME09421-10 |
| phenotype ID: | 125131 |
| assay: | Soil Gross Morphology: 7 rosette leaves 1 mm in length |
| phenotype: | ROSETTE LEAVES - Oval Shaped |
| notes: | NONE |
| unique F1 plant ID: | R1 PLANT:ME09421-10 |
| phenotype ID: | 125132 |
| assay: | Soil Gross Morphology: 7 rosette leaves 1 mm in length |
| phenotype: | ROSETTE LEAVES - Long Petioles |
| notes: | NONE |
| unique F1 plant ID: | R1 PLANT:ME09421-10 |
| phenotype ID: | 125133 |
| assay: | Soil Gross Morphology: 7 rosette leaves 1 mm in length |
| phenotype: | WHOLE PLANT - Small |
| notes: | 50 pct wt |
| unique F1 plant ID: | R1 PLANT:ME09421-10 |
| phenotype ID: | 125134 |
| assay: | Soil Gross Morphology: 10 rosette leaves 1 mm in length |
| phenotype: | INFLORESCENCE - Late Flowering |
| notes: | NONE |
| unique F1 plant ID: | R1 PLANT:ME09427-03 |
| phenotype ID: | 124854 |
| assay: | Soil Gross Morphology: 7 rosette leaves 1 mm in length |
| phenotype: | WHOLE PLANT - Small |
| notes: | 50 pct wt |
| unique F1 plant ID: | R1 PLANT:ME09427-03 |
| phenotype ID: | 124855 |
| assay: | Soil Gross Morphology: 7 rosette leaves 1 mm in length |
| phenotype: | ROSETTE LEAVES - Glossy |
| notes: | NONE |
| unique F1 plant ID: | R1 PLANT:ME09427-03 |
| phenotype ID: | 124856 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09427-06 |
| phenotype ID: | 124864 |
| assay: | Soil Gross Morphology: 7 rosette leaves 1 mm in length |
| phenotype: | WHOLE PLANT - Small |
| notes: | 50 pct wt |
| unique F1 plant ID: | R1 PLANT:ME09427-06 |
| phenotype ID: | 124865 |
| assay: | Soil Gross Morphology: 7 rosette leaves 1 mm in length |
| phenotype: | ROSETTE LEAVES - Glossy |
| notes: | NONE |
| unique F1 plant ID: | R1 PLANT:ME09427-06 |
| phenotype ID: | 124866 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09439-01 |
| phenotype ID: | 124815 |
| assay: | Soil Gross Morphology: 4 rosette leaves 1 mm in length |
| phenotype: | ROSETTE LEAVES - Long Petioles |
| notes: | NONE |
| unique F1 plant ID: | R1 PLANT:ME09439-01 |
| phenotype ID: | 124816 |
| assay: | Soil Gross Morphology: 4 rosette leaves 1 mm in length |
| phenotype: | ROSETTE LEAVES - Glossy |
| notes: | NONE |
| unique F1 plant ID: | R1 PLANT:ME09439-01 |
| phenotype ID: | 124817 |
| assay: | Soil Gross Morphology: 4 rosette leaves 1 mm in length |
| phenotype: | ROSETTE LEAVES - Oval Shaped |
| notes: | NONE |
| unique F1 plant ID: | R1 PLANT:ME09439-01 |
| phenotype ID: | 124818 |
| assay: | Soil Gross Morphology: 4 rosette leaves 1 mm in length |
| phenotype: | WHOLE PLANT - Small |
| notes: | 50 pct wt |
| unique F1 plant ID: | R1 PLANT:ME09439-03 |
| phenotype ID: | 124820 |
| assay: | Soil Gross Morphology: 5 rosette leaves 1 mm in length |
| phenotype: | ROSETTE LEAVES - Long Petioles |
| notes: | NONE |
| unique F1 plant ID: | R1 PLANT:ME09439-03 |
| phenotype ID: | 124821 |
| assay: | Soil Gross Morphology: 5 rosette leaves 1 mm in length |

TABLE 1-continued

| | |
|---|---|
| phenotype: | ROSETTE LEAVES - Glossy |
| notes: | NONE |
| unique F1 plant ID: | R1 PLANT:ME09439-03 |
| phenotype ID: | 124822 |
| assay: | Soil Gross Morphology: 5 rosette leaves 1 mm in length |
| phenotype: | ROSETTE LEAVES - Oval Shaped |
| notes: | NONE |
| unique F1 plant ID: | R1 PLANT:ME09439-03 |
| phenotype ID: | 124823 |
| assay: | Soil Gross Morphology: 5 rosette leaves 1 mm in length |
| phenotype: | WHOLE PLANT - Small |
| notes: | 50 pct wt |
| unique F1 plant ID: | R1 PLANT:ME09439-04 |
| phenotype ID: | 124825 |
| assay: | Soil Gross Morphology: 6 rosette leaves 1 mm in length |
| phenotype: | ROSETTE LEAVES - Long Petioles |
| notes: | NONE |
| unique F1 plant ID: | R1 PLANT:ME09439-04 |
| phenotype ID: | 124826 |
| assay: | Soil Gross Morphology: 6 rosette leaves 1 mm in length |
| phenotype: | ROSETTE LEAVES - Glossy |
| notes: | NONE |
| unique F1 plant ID: | R1 PLANT:ME09439-04 |
| phenotype ID: | 124827 |
| assay: | Soil Gross Morphology: 6 rosette leaves 1 mm in length |
| phenotype: | ROSETTE LEAVES - Oval Shaped |
| notes: | NONE |
| unique F1 plant ID: | R1 PLANT:ME09439-04 |
| phenotype ID: | 124828 |
| assay: | Soil Gross Morphology: 6 rosette leaves 1 mm in length |
| phenotype: | WHOLE PLANT - Small |
| notes: | 50 pct wt |
| unique F1 plant ID: | R1 PLANT:ME09373-01 |
| phenotype ID: | 124909 |
| assay: | Soil Gross Morphology: 6 rosette leaves 1 mm in length |
| phenotype: | ROSETTE LEAVES - Glossy |
| notes: | NONE |
| unique F1 plant ID: | R1 PLANT:ME09373-01 |
| phenotype ID: | 124910 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09373-02 |
| phenotype ID: | 124934 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09373-03 |
| phenotype ID: | 124952 |
| assay: | Soil Gross Morphology: 6 rosette leaves 1 mm in length |
| phenotype: | ROSETTE LEAVES - Glossy |
| notes: | NONE |
| unique F1 plant ID: | R1 PLANT:ME09373-03 |
| phenotype ID: | 124953 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09373-04 |
| phenotype ID: | 124977 |
| assay: | Soil Gross Morphology: 6 rosette leaves 1 mm in length |
| phenotype: | ROSETTE LEAVES - Glossy |
| notes: | NONE |
| unique F1 plant ID: | R1 PLANT:ME09373-04 |
| phenotype ID: | 124978 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09373-05 |
| phenotype ID: | 124998 |
| assay: | Soil Gross Morphology: 6 rosette leaves 1 mm in length |
| phenotype: | ROSETTE LEAVES - Glossy |
| notes: | NONE |
| unique F1 plant ID: | R1 PLANT:ME09373-05 |
| phenotype ID: | 124999 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09373-06 |
| phenotype ID: | 125025 |

TABLE 1-continued

| | |
|---|---|
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09373-07 |
| phenotype ID: | 125047 |
| assay: | Soil Gross Morphology: 6 rosette leaves 1 mm in length |
| phenotype: | ROSETTE LEAVES - Glossy |
| notes: | NONE |
| unique F1 plant ID: | R1 PLANT:ME09373-07 |
| phenotype ID: | 125048 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09373-08 |
| phenotype ID: | 125069 |
| assay: | Soil Gross Morphology: 6 rosette leaves 1 mm in length |
| phenotype: | ROSETTE LEAVES - Glossy |
| notes: | NONE |
| unique F1 plant ID: | R1 PLANT:ME09373-08 |
| phenotype ID: | 125070 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09373-09 |
| phenotype ID: | 125083 |
| assay: | Soil Gross Morphology: 6 rosette leaves 1 mm in length |
| phenotype: | ROSETTE LEAVES - Glossy |
| notes: | NONE |
| unique F1 plant ID: | R1 PLANT:ME09373-09 |
| phenotype ID: | 125084 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME09373-10 |
| phenotype ID: | 125113 |
| assay: | Soil Gross Morphology: 6 rosette leaves 1 mm in length |
| phenotype: | ROSETTE LEAVES - Glossy |
| notes: | NONE |
| unique F1 plant ID: | R1 PLANT:ME09373-10 |
| phenotype ID: | 125114 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME03188-01 |
| phenotype ID: | 71412 |
| assay: | Soil Gross Morphology: 50% of flowers to be produced have opened |
| phenotype: | ROSETTE LEAVES - Glossy |
| notes: | NONE |
| unique F1 plant ID: | R1 PLANT:ME03188-02 |
| phenotype ID: | 71427 |
| assay: | Soil Gross Morphology: First flower buds visible |
| phenotype: | INFLORESCENCE - Late Flowering |
| notes: | NONE |
| unique F1 plant ID: | R1 PLANT:ME03188-02 |
| phenotype ID: | 71428 |
| assay: | Soil Gross Morphology: First flower buds visible |
| phenotype: | ROSETTE LEAVES - Glossy |
| notes: | NONE |
| unique F1 plant ID: | R1 PLANT:ME03188-04 |
| phenotype ID: | 71479 |
| assay: | Soil Gross Morphology: First flower buds visible |
| phenotype: | ROSETTE LEAVES - Glossy |
| notes: | NONE |
| unique F1 plant ID: | R1 PLANT:ME03188-04 |
| phenotype ID: | 71480 |
| assay: | Soil Gross Morphology: First flower buds visible |
| phenotype: | INFLORESCENCE - Late Flowering |
| notes: | NONE |
| unique F1 plant ID: | R1 PLANT:ME03188-06 |
| phenotype ID: | 71508 |
| assay: | Soil Gross Morphology: 50% of flowers to be produced have opened |
| phenotype: | ROSETTE LEAVES - Glossy |
| notes: | NONE |
| unique F1 plant ID: | R1 PLANT:ME03188-06 |
| phenotype ID: | 71509 |
| assay: | Soil Gross Morphology: 50% of flowers to be produced have opened |
| phenotype: | WHOLE PLANT - Small |
| notes: | 25pct. of wt |
| unique F1 plant ID: | R1 PLANT:ME03188-07 |

TABLE 1-continued

| | |
|---|---|
| phenotype ID: | 71514 |
| assay: | Soil Gross Morphology: First flower buds visible |
| phenotype: | INFLORESCENCE - Late Flowering |
| notes: | NONE |
| unique F1 plant ID: | R1 PLANT:ME03188-07 |
| phenotype ID: | 71515 |
| assay: | Soil Gross Morphology: First flower buds visible |
| phenotype: | ROSETTE LEAVES - Glossy |
| notes: | NONE |
| unique F1 plant ID: | R1 PLANT:ME03188-08 |
| phenotype ID: | 71525 |
| assay: | Soil Gross Morphology: 50% of flowers to be produced have opened |
| phenotype: | ROSETTE LEAVES - Glossy |
| notes: | NONE |
| unique F1 plant ID: | R1 PLANT:ME03188-08 |
| phenotype ID: | 71526 |
| assay: | Soil Gross Morphology: 50% of flowers to be produced have opened |
| phenotype: | INFLORESCENCE - Late Flowering |
| notes: | NONE |
| unique F1 plant ID: | R1 PLANT:ME03188-09 |
| phenotype ID: | 71536 |
| assay: | Soil Gross Morphology: 30% of flowers to be produced have opened |
| phenotype: | ROSETTE LEAVES - Glossy |
| notes: | NONE |
| unique F1 plant ID: | R1 PLANT:ME03188-09 |
| phenotype ID: | 71537 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME03188-10 |
| phenotype ID: | 71567 |
| assay: | Soil Gross Morphology: First flower buds visible |
| phenotype: | ROSETTE LEAVES - Glossy |
| notes: | NONE |
| unique F1 plant ID: | R1 PLANT:ME03188-10 |
| phenotype ID: | 71568 |
| assay: | Soil Gross Morphology: First flower buds visible |
| phenotype: | INFLORESCENCE - Late Flowering |
| notes: | NONE |
| unique F1 plant ID: | R1 PLANT:ME05058-01 |
| phenotype ID: | 89113 |
| assay: | Soil Gross Morphology: 50% of flowers to be produced have opened |
| phenotype: | WHOLE PLANT - Dark Green |
| notes: | NONE |
| unique F1 plant ID: | R1 PLANT:ME05058-02 |
| phenotype ID: | 89147 |
| assay: | Soil Gross Morphology: 50% of flowers to be produced have opened |
| phenotype: | WHOLE PLANT - Dark Green |
| notes: | NONE |
| unique F1 plant ID: | R1 PLANT:ME05058-03 |
| phenotype ID: | 89188 |
| assay: | Soil Gross Morphology: 50% of flowers to be produced have opened |
| phenotype: | WHOLE PLANT - Dark Green |
| notes: | NONE |
| unique F1 plant ID: | R1 PLANT:ME05058-04 |
| phenotype ID: | 89237 |
| assay: | Soil Gross Morphology: 50% of flowers to be produced have opened |
| phenotype: | WHOLE PLANT - Dark Green |
| notes: | NONE |
| unique F1 plant ID: | R1 PLANT:ME05058-05 |
| phenotype ID: | 89273 |
| assay: | Soil Gross Morphology: 50% of flowers to be produced have opened |
| phenotype: | WHOLE PLANT - Dark Green |
| notes: | NONE |
| unique F1 plant ID: | R1 PLANT:ME05058-06 |
| phenotype ID: | 89312 |
| assay: | Soil Gross Morphology: 50% of flowers to be produced have opened |
| phenotype: | WHOLE PLANT - Dark Green |
| notes: | NONE |
| unique F1 plant ID: | R1 PLANT:ME05058-07 |
| phenotype ID: | 89340 |
| assay: | Soil Gross Morphology: 50% of flowers to be produced have opened |
| phenotype: | WHOLE PLANT - Dark Green |
| notes: | NONE |
| unique F1 plant ID: | R1 PLANT:ME05058-08 |
| phenotype ID: | 89369 |
| assay: | Soil Gross Morphology: 50% of flowers to be produced have opened |
| phenotype: | WHOLE PLANT - Dark Green |
| notes: | NONE |

TABLE 1-continued

| | |
|---|---|
| unique F1 plant ID: | R1 PLANT:ME05058-09 |
| phenotype ID: | 89414 |
| assay: | Soil Gross Morphology: 50% of flowers to be produced have opened |
| phenotype: | WHOLE PLANT - Dark Green |
| notes: | NONE |

Knock-in phenotype in gene(cDNA_id): 12466530

| | |
|---|---|
| clone ID: | 14583 |
| Promoter: | 326D |
| unique F1 plant ID: | R1 PLANT:ME09240-01 |
| phenotype ID: | 124846 |
| assay: | Soil Gross Morphology: 4 rosette leaves 1 mm in length |
| phenotype: | ROSETTE LEAVES - Glossy |
| notes: | glossy |
| unique F1 plant ID: | R1 PLANT:ME09240-01 |
| phenotype ID: | 124847 |
| assay: | Soil Gross Morphology: 10% of flowers to be produced have opened |
| phenotype: | INFLORESCENCE - Late Flowering |
| notes: | NONE |
| unique F1 plant ID: | R1 PLANT:ME09240-02 |
| phenotype ID: | 124849 |
| assay: | Soil Gross Morphology: 8 rosette leaves 1 mm in length |
| phenotype: | ROSETTE LEAVES - Glossy |
| notes: | glossy |
| unique F1 plant ID: | R1 PLANT:ME09240-03 |
| phenotype ID: | 124852 |
| assay: | Soil Gross Morphology: 10% of flowers to be produced have opened |
| phenotype: | INFLORESCENCE - Late Flowering |
| notes: | NONE |
| unique F1 plant ID: | R1 PLANT:ME09240-04 |
| phenotype ID: | 124858 |
| assay: | Soil Gross Morphology: 10% of flowers to be produced have opened |
| phenotype: | INFLORESCENCE - Late Flowering |
| notes: | NONE |
| unique F1 plant ID: | R1 PLANT:ME09240-05 |
| phenotype ID: | 124861 |
| assay: | Soil Gross Morphology: 10% of flowers to be produced have opened |
| phenotype: | INFLORESCENCE - Late Flowering |
| notes: | NONE |
| unique F1 plant ID: | R1 PLANT:ME09240-06 |
| phenotype ID: | 124863 |
| assay: | Soil Gross Morphology: 13 rosette leaves 1 mm in length |
| phenotype: | ROSETTE LEAVES - Glossy |
| notes: | glossy |
| unique F1 plant ID: | R1 PLANT:ME05444-01 |
| phenotype ID: | 89535 |
| assay: | Soil Gross Morphology: 50% of flowers to be produced have opened |
| phenotype: | FLOWER - Reduced fertility |
| notes: | NONE |
| unique F1 plant ID: | R1 PLANT:ME05444-01 |
| phenotype ID: | 89536 |
| assay: | Soil Gross Morphology: 30% of flowers to be produced have opened |
| phenotype: | WHOLE PLANT - Dark Green |
| notes: | NONE |
| unique F1 plant ID: | R1 PLANT:ME05444-01 |
| phenotype ID: | 89537 |
| assay: | Soil Gross Morphology: 30% of flowers to be produced have opened |
| phenotype: | ROSETTE LEAVES - Short Petioles |
| notes: | NONE |
| unique F1 plant ID: | R1 PLANT:ME05444-01 |
| phenotype ID: | 89538 |
| assay: | Soil Gross Morphology: 30% of flowers to be produced have opened |
| phenotype: | ROSETTE LEAVES - Glossy |
| notes: | NONE |
| unique F1 plant ID: | R1 PLANT:ME05444-01 |
| phenotype ID: | 89539 |
| assay: | Soil Gross Morphology: 30% of flowers to be produced have opened |
| phenotype: | INFLORESCENCE - Short Internode |
| notes: | NONE |
| unique F1 plant ID: | R1 PLANT:ME05444-01 |
| phenotype ID: | 89540 |
| assay: | Soil Gross Morphology: 30% of flowers to be produced have opened |
| phenotype: | INFLORESCENCE - Short |
| notes: | 60 pct size |
| unique F1 plant ID: | R1 PLANT:ME05444-01 |
| phenotype ID: | 89541 |
| assay: | Soil Gross Morphology: 30% of flowers to be produced have opened |
| phenotype: | FLOWER - Other |
| notes: | increased number of flowers |

TABLE 1-continued

| | |
|---|---|
| unique F1 plant ID: | R1 PLANT:ME05444-01 |
| phenotype ID: | 89542 |
| assay: | Soil Gross Morphology: 30% of flowers to be produced have opened |
| phenotype: | FLOWER - Other |
| notes: | many flowers open but delayed silique formation |
| unique F1 plant ID: | R1 PLANT:ME05444-02 |
| phenotype ID: | 89555 |
| assay: | Soil Gross Morphology: 50% of flowers to be produced have opened |
| phenotype: | FLOWER - Reduced fertility |
| notes: | NONE |
| unique F1 plant ID: | R1 PLANT:ME05444-02 |
| phenotype ID: | 89556 |
| assay: | Soil Gross Morphology: 30% of flowers to be produced have opened |
| phenotype: | WHOLE PLANT - Dark Green |
| notes: | NONE |
| unique F1 plant ID: | R1 PLANT:ME05444-02 |
| phenotype ID: | 89557 |
| assay: | Soil Gross Morphology: 30% of flowers to be produced have opened |
| phenotype: | ROSETTE LEAVES - Short Petioles |
| notes: | NONE |
| unique F1 plant ID: | R1 PLANT:ME05444-02 |
| phenotype ID: | 89558 |
| assay: | Soil Gross Morphology: 30% of flowers to be produced have opened |
| phenotype: | ROSETTE LEAVES - Glossy |
| notes: | NONE |
| unique F1 plant ID: | R1 PLANT:ME05444-02 |
| phenotype ID: | 89559 |
| assay: | Soil Gross Morphology: 30% of flowers to be produced have opened |
| phenotype: | INFLORESCENCE - Short Internode |
| notes: | NONE |
| unique F1 plant ID: | R1 PLANT:ME05444-02 |
| phenotype ID: | 89560 |
| assay: | Soil Gross Morphology: 30% of flowers to be produced have opened |
| phenotype: | INFLORESCENCE - Short |
| notes: | 75 pct size |
| unique F1 plant ID: | R1 PLANT:ME05444-02 |
| phenotype ID: | 89561 |
| assay: | Soil Gross Morphology: 30% of flowers to be produced have opened |
| phenotype: | FLOWER - Other |
| notes: | increased number of flowers |
| unique F1 plant ID: | R1 PLANT:ME05444-02 |
| phenotype ID: | 89562 |
| assay: | Soil Gross Morphology: 30% of flowers to be produced have opened |
| phenotype: | FLOWER - Other |
| notes: | many flowers open but delayed silique formation |
| unique F1 plant ID: | R1 PLANT:ME05444-03 |
| phenotype ID: | 89582 |
| assay: | Soil Gross Morphology: 50% of flowers to be produced have opened |
| phenotype: | FLOWER - Reduced fertility |
| notes: | NONE |
| unique F1 plant ID: | R1 PLANT:ME05444-03 |
| phenotype ID: | 89583 |
| assay: | Soil Gross Morphology: 30% of flowers to be produced have opened |
| phenotype: | WHOLE PLANT - Dark Green |
| notes: | NONE |
| unique F1 plant ID: | R1 PLANT:ME05444-03 |
| phenotype ID: | 89584 |
| assay: | Soil Gross Morphology: 30% of flowers to be produced have opened |
| phenotype: | ROSETTE LEAVES - Short Petioles |
| notes: | NONE |
| unique F1 plant ID: | R1 PLANT:ME05444-03 |
| phenotype ID: | 89585 |
| assay: | Soil Gross Morphology: 30% of flowers to be produced have opened |
| phenotype: | ROSETTE LEAVES - Glossy |
| notes: | NONE |
| unique F1 plant ID: | R1 PLANT:ME05444-03 |
| phenotype ID: | 89586 |
| assay: | Soil Gross Morphology: 30% of flowers to be produced have opened |
| phenotype: | INFLORESCENCE - Short Internode |
| notes: | NONE |
| unique F1 plant ID: | R1 PLANT:ME05444-03 |
| phenotype ID: | 89587 |
| assay: | Soil Gross Morphology: 30% of flowers to be produced have opened |
| phenotype: | INFLORESCENCE - Short |
| notes: | 75 pct size |
| unique F1 plant ID: | R1 PLANT:ME05444-03 |
| phenotype ID: | 89588 |
| assay: | Soil Gross Morphology: 30% of flowers to be produced have opened |
| phenotype: | FLOWER - Other |

TABLE 1-continued

| | |
|---|---|
| notes: | increased number of flowers |
| unique F1 plant ID: | R1 PLANT:ME05444-03 |
| phenotype ID: | 89589 |
| assay: | Soil Gross Morphology: 30% of flowers to be produced have opened |
| phenotype: | FLOWER - Other |
| notes: | many flowers open but delayed silique formation |
| unique F1 plant ID: | R1 PLANT:ME05444-04 |
| phenotype ID: | 89614 |
| assay: | Soil Gross Morphology: 50% of flowers to be produced have opened |
| phenotype: | SILIQUES - Short |
| notes: | NONE |
| unique F1 plant ID: | R1 PLANT:ME05444-04 |
| phenotype ID: | 89615 |
| assay: | Soil Gross Morphology: 30% of flowers to be produced have opened |
| phenotype: | WHOLE PLANT - Dark Green |
| notes: | NONE |
| unique F1 plant ID: | R1 PLANT:ME05444-04 |
| phenotype ID: | 89616 |
| assay: | Soil Gross Morphology: 30% of flowers to be produced have opened |
| phenotype: | ROSETTE LEAVES - Short Petioles |
| notes: | NONE |
| unique F1 plant ID: | R1 PLANT:ME05444-04 |
| phenotype ID: | 89617 |
| assay: | Soil Gross Morphology: 30% of flowers to be produced have opened |
| phenotype: | ROSETTE LEAVES - Glossy |
| notes: | NONE |
| unique F1 plant ID: | R1 PLANT:ME05444-04 |
| phenotype ID: | 89618 |
| assay: | Soil Gross Morphology: 30% of flowers to be produced have opened |
| phenotype: | INFLORESCENCE - Short Internode |
| notes: | NONE |
| unique F1 plant ID: | R1 PLANT:ME05444-04 |
| phenotype ID: | 89619 |
| assay: | Soil Gross Morphology: 30% of flowers to be produced have opened |
| phenotype: | INFLORESCENCE - Short |
| notes: | 75 pct size |
| unique F1 plant ID: | R1 PLANT:ME05444-04 |
| phenotype ID: | 89620 |
| assay: | Soil Gross Morphology: 30% of flowers to be produced have opened |
| phenotype: | FLOWER - Other |
| notes: | increased number of flowers |
| unique F1 plant ID: | R1 PLANT:ME05444-04 |
| phenotype ID: | 89621 |
| assay: | Soil Gross Morphology: 30% of flowers to be produced have opened |
| phenotype: | FLOWER - Other |
| notes: | many flowers open but delayed silique formation |
| unique F1 plant ID: | R1 PLANT:ME05444-06 |
| phenotype ID: | 89652 |
| assay: | Soil Gross Morphology: 50% of flowers to be produced have opened |
| phenotype: | FLOWER - Reduced fertility |
| notes: | NONE |
| unique F1 plant ID: | R1 PLANT:ME05444-06 |
| phenotype ID: | 89653 |
| assay: | Soil Gross Morphology: 30% of flowers to be produced have opened |
| phenotype: | WHOLE PLANT - Dark Green |
| notes: | NONE |
| unique F1 plant ID: | R1 PLANT:ME05444-06 |
| phenotype ID: | 89654 |
| assay: | Soil Gross Morphology: 30% of flowers to be produced have opened |
| phenotype: | ROSETTE LEAVES - Short Petioles |
| notes: | NONE |
| unique F1 plant ID: | R1 PLANT:ME05444-06 |
| phenotype ID: | 89655 |
| assay: | Soil Gross Morphology: 30% of flowers to be produced have opened |
| phenotype: | ROSETTE LEAVES - Glossy |
| notes: | NONE |
| unique F1 plant ID: | R1 PLANT:ME05444-06 |
| phenotype ID: | 89656 |
| assay: | Soil Gross Morphology: 30% of flowers to be produced have opened |
| phenotype: | INFLORESCENCE - Short Internode |
| notes: | NONE |
| unique F1 plant ID: | R1 PLANT:ME05444-06 |
| phenotype ID: | 89657 |
| assay: | Soil Gross Morphology: 30% of flowers to be produced have opened |
| phenotype: | INFLORESCENCE - Short |
| notes: | 75 pct size |
| unique F1 plant ID: | R1 PLANT:ME05444-06 |
| phenotype ID: | 89658 |
| assay: | Soil Gross Morphology: 30% of flowers to be produced have opened |

TABLE 1-continued

| | |
|---|---|
| phenotype: | FLOWER - Other |
| notes: | increased number of flowers |
| unique F1 plant ID: | R1 PLANT:ME05444-06 |
| phenotype ID: | 89659 |
| assay: | Soil Gross Morphology: 30% of flowers to be produced have opened |
| phenotype: | FLOWER - Other |
| notes: | many flowers open but delayed silique formation |
| unique F1 plant ID: | R1 PLANT:ME05444-07 |
| phenotype ID: | 89681 |
| assay: | Soil Gross Morphology: 50% of flowers to be produced have opened |
| phenotype: | SILIQUES - Short |
| notes: | NONE |
| unique F1 plant ID: | R1 PLANT:ME05444-07 |
| phenotype ID: | 89682 |
| assay: | Soil Gross Morphology: 30% of flowers to be produced have opened |
| phenotype: | WHOLE PLANT - Dark Green |
| notes: | NONE |
| unique F1 plant ID: | R1 PLANT:ME05444-07 |
| phenotype ID: | 89683 |
| assay: | Soil Gross Morphology: 30% of flowers to be produced have opened |
| phenotype: | ROSETTE LEAVES - Short Petioles |
| notes: | NONE |
| unique F1 plant ID: | R1 PLANT:ME05444-07 |
| phenotype ID: | 89684 |
| assay: | Soil Gross Morphology: 30% of flowers to be produced have opened |
| phenotype: | ROSETTE LEAVES - Glossy |
| notes: | NONE |
| unique F1 plant ID: | R1 PLANT:ME05444-07 |
| phenotype ID: | 89685 |
| assay: | Soil Gross Morphology: 30% of flowers to be produced have opened |
| phenotype: | INFLORESCENCE - Short Internode |
| notes: | NONE |
| unique F1 plant ID: | R1 PLANT:ME05444-07 |
| phenotype ID: | 89686 |
| assay: | Soil Gross Morphology: 30% of flowers to be produced have opened |
| phenotype: | INFLORESCENCE - Short |
| notes: | 75 pct size |
| unique F1 plant ID: | R1 PLANT:ME05444-07 |
| phenotype ID: | 89687 |
| assay: | Soil Gross Morphology: 30% of flowers to be produced have opened |
| phenotype: | FLOWER - Other |
| notes: | increased number of flowers |
| unique F1 plant ID: | R1 PLANT:ME05444-07 |
| phenotype ID: | 89688 |
| assay: | Soil Gross Morphology: 30% of flowers to be produced have opened |
| phenotype: | FLOWER - Other |
| notes: | many flowers open but delayed silique formation |
| unique F1 plant ID: | R1 PLANT:ME05444-09 |
| phenotype ID: | 89715 |
| assay: | Soil Gross Morphology: 50% of flowers to be produced have opened |
| phenotype: | FLOWER - Reduced fertility |
| notes: | NONE |
| unique F1 plant ID: | R1 PLANT:ME05444-09 |
| phenotype ID: | 89716 |
| assay: | Soil Gross Morphology: 30% of flowers to be produced have opened |
| phenotype: | WHOLE PLANT - Dark Green |
| notes: | NONE |
| unique F1 plant ID: | R1 PLANT:ME05444-09 |
| phenotype ID: | 89717 |
| assay: | Soil Gross Morphology: 30% of flowers to be produced have opened |
| phenotype: | ROSETTE LEAVES - Short Petioles |
| notes: | NONE |
| unique F1 plant ID: | R1 PLANT:ME05444-09 |
| phenotype ID: | 89718 |
| assay: | Soil Gross Morphology: 30% of flowers to be produced have opened |
| phenotype: | ROSETTE LEAVES - Glossy |
| notes: | NONE |
| unique F1 plant ID: | R1 PLANT:ME05444-09 |
| phenotype ID: | 89719 |
| assay: | Soil Gross Morphology: 30% of flowers to be produced have opened |
| phenotype: | INFLORESCENCE - Short Internode |
| notes: | NONE |
| unique F1 plant ID: | R1 PLANT:ME05444-09 |
| phenotype ID: | 89720 |
| assay: | Soil Gross Morphology: 30% of flowers to be produced have opened |
| phenotype: | INFLORESCENCE - Short |
| notes: | 75 pct size |
| unique F1 plant ID: | R1 PLANT:ME05444-09 |
| phenotype ID: | 89721 |

TABLE 1-continued

```
assay:              Soil Gross Morphology: 30% of flowers to be produced have opened
phenotype:          FLOWER - Other
notes:              increased number of flowers
unique F1 plant ID: R1 PLANT:ME05444-09
phenotype ID:       89722
assay:              Soil Gross Morphology: 30% of flowers to be produced have opened
phenotype:          FLOWER - Other
notes:              many flowers open but delayed silique formation
unique F1 plant ID: R1 PLANT:ME05444-10
phenotype ID:       89731
assay:              Soil Gross Morphology: 50% of flowers to be produced have opened
phenotype:          FLOWER - Reduced fertility
notes:              NONE
unique F1 plant ID: R1 PLANT:ME05444-10
phenotype ID:       89732
assay:              Soil Gross Morphology: 30% of flowers to be produced have opened
phenotype:          WHOLE PLANT - Dark Green
notes:              NONE
unique F1 plant ID: R1 PLANT:ME05444-10
phenotype ID:       89733
assay:              Soil Gross Morphology: 30% of flowers to be produced have opened
phenotype:          ROSETTE LEAVES - Short Petioles
notes:              NONE
unique F1 plant ID: R1 PLANT:ME05444-10
phenotype ID:       89734
assay:              Soil Gross Morphology: 30% of flowers to be produced have opened
phenotype:          ROSETTE LEAVES - Glossy
notes:              NONE
unique F1 plant ID: R1 PLANT:ME05444-10
phenotype ID:       89735
assay:              Soil Gross Morphology: 30% of flowers to be produced have opened
phenotype:          INFLORESCENCE - Short Internode
notes:              NONE
unique F1 plant ID: R1 PLANT:ME05444-10
phenotype ID:       89736
assay:              Soil Gross Morphology: 30% of flowers to be produced have opened
phenotype:          INFLORESCENCE - Short
notes:              75 pct size
unique F1 plant ID: R1 PLANT:ME05444-10
phenotype ID:       89737
assay:              Soil Gross Morphology: 30% of flowers to be produced have opened
phenotype:          FLOWER - Other
notes:              increased number of flowers
unique F1 plant ID: R1 PLANT:ME05444-10
phenotype ID:       89738
assay:              Soil Gross Morphology: 30% of flowers to be produced have opened
phenotype:          FLOWER - Other
notes:              many flowers open but delayed silique formation
                        Knock-in phenotype in gene(cDNA__id): 12472013 clone ID:           969750
Promoter:           35S
unique F1 plant ID: R1 PLANT:ME08454-02
phenotype ID:       124560
assay:              Soil Gross Morphology: 30% of flowers to be produced have opened
phenotype:          WHOLE PLANT - Large
notes:              125 pct wt
unique F1 plant ID: R1 PLANT:ME08454-02
phenotype ID:       124561
assay:              Soil Gross Morphology: 30% of flowers to be produced have opened
phenotype:          INFLORESCENCE - Late Flowering
notes:              NONE
unique F1 plant ID: R1 PLANT:ME08454-03
phenotype ID:       124569
assay:              Soil Gross Morphology: 30% of flowers to be produced have opened
phenotype:          WHOLE PLANT - Large
notes:              125 pct wt
unique F1 plant ID: R1 PLANT:ME08454-03
phenotype ID:       124570
assay:              Soil Gross Morphology: 30% of flowers to be produced have opened
phenotype:          INFLORESCENCE - Late Flowering
notes:              NONE
unique F1 plant ID: R1 PLANT:ME08454-04
phenotype ID:       124575
assay:              Soil Gross Morphology: 30% of flowers to be produced have opened
phenotype:          WHOLE PLANT - Large
notes:              125 pct wt
unique F1 plant ID: R1 PLANT:ME08454-04
phenotype ID:       124576
```

TABLE 1-continued

| | |
|---|---|
| assay: | Soil Gross Morphology: 30% of flowers to be produced have opened |
| phenotype: | INFLORESCENCE - Late Flowering |
| notes: | NONE |

Knock-in phenotype in gene(cDNA_id): 12482146

| | |
|---|---|
| clone ID: | 2036 |
| Promoter: | 35S |
| unique F1 plant ID: | R1 PLANT:ME01932-01 |
| phenotype ID: | 54474 |
| assay: | Soil Gross Morphology: 50% of flowers to be produced have opened |
| phenotype: | FLOWER - Reduced fertility |
| notes: | NONE |
| unique F1 plant ID: | R1 PLANT:ME01932-01 |
| phenotype ID: | 54475 |
| assay: | Soil Gross Morphology: 50% of flowers to be produced have opened |
| phenotype: | WHOLE PLANT - Large |
| notes: | NONE |
| unique F1 plant ID: | R1 PLANT:ME01932-01 |
| phenotype ID: | 54476 |
| assay: | Soil Gross Morphology: 50% of flowers to be produced have opened |
| phenotype: | FLOWER - Other |
| notes: | extra flowers |
| unique F1 plant ID: | R1 PLANT:ME01932-05 |
| phenotype ID: | 54485 |
| assay: | Soil Gross Morphology: 50% of flowers to be produced have opened |
| phenotype: | FLOWER - Other |
| notes: | extra flowers |
| unique F1 plant ID: | R1 PLANT:ME01932-05 |
| phenotype ID: | 54486 |
| assay: | Soil Gross Morphology: 50% of flowers to be produced have opened |
| phenotype: | FLOWER - Reduced fertility |
| notes: | NONE |
| unique F1 plant ID: | R1 PLANT:ME01932-06 |
| phenotype ID: | 54489 |
| assay: | Soil Gross Morphology: 50% of flowers to be produced have opened |
| phenotype: | FLOWER - Reduced fertility |
| notes: | NONE |
| unique F1 plant ID: | R1 PLANT:ME01932-07 |
| phenotype ID: | 54493 |
| assay: | Soil Gross Morphology: 50% of flowers to be produced have opened |
| phenotype: | FLOWER - Reduced fertility |
| notes: | NONE |
| unique F1 plant ID: | R1 PLANT:ME01932-07 |
| phenotype ID: | 54494 |
| assay: | Soil Gross Morphology: 50% of flowers to be produced have opened |
| phenotype: | FLOWER - Other |
| notes: | extra flowers |

Knock-in phenotype in gene(cDNA_id): 12482922

| | |
|---|---|
| clone ID: | 39286 |
| Promoter: | 35S |
| unique F1 plant ID: | R1 PLANT:ME02587-02 |
| phenotype ID: | 56314 |
| assay: | Soil Gross Morphology: 30% of flowers to be produced have opened |
| phenotype: | FLOWER - Reduced fertility |
| notes: | NONE |
| unique F1 plant ID: | R1 PLANT:ME02587-04 |
| phenotype ID: | 56315 |
| assay: | Soil Gross Morphology: 10 rosette leaves 1 mm in length |
| phenotype: | INFLORESCENCE - Late Flowering |
| notes: | NONE |
| unique F1 plant ID: | R1 PLANT:ME02587-04 |
| phenotype ID: | 56316 |
| assay: | Soil Gross Morphology: 10 rosette leaves 1 mm in length |
| phenotype: | WHOLE PLANT - Small |
| notes: | NONE |
| unique F1 plant ID: | R1 PLANT:ME02587-04 |
| phenotype ID: | 56317 |
| assay: | Soil Gross Morphology: 10 rosette leaves 1 mm in length |
| phenotype: | ROSETTE LEAVES - Serrate Margins |
| notes: | NONE |
| unique F1 plant ID: | R1 PLANT:ME02587-04 |
| phenotype ID: | 56318 |
| assay: | Soil Gross Morphology: 10 rosette leaves 1 mm in length |
| phenotype: | ROSETTE LEAVES - Other |
| notes: | pointed |
| unique F1 plant ID: | R1 PLANT:ME02587-04 |
| phenotype ID: | 56319 |
| assay: | Soil Gross Morphology: 10 rosette leaves 1 mm in length |

TABLE 1-continued

| | |
|---|---|
| phenotype: | WHOLE PLANT - Dark Green |
| notes: | NONE |
| unique F1 plant ID: | R1 PLANT:ME02587-05 |
| phenotype ID: | 56320 |
| assay: | Soil Gross Morphology: 8 rosette leaves 1 mm in length |
| phenotype: | INFLORESCENCE - Late Flowering |
| notes: | NONE |
| unique F1 plant ID: | R1 PLANT:ME02587-05 |
| phenotype ID: | 56321 |
| assay: | Soil Gross Morphology: 8 rosette leaves 1 mm in length |
| phenotype: | WHOLE PLANT - Small |
| notes: | NONE |
| unique F1 plant ID: | R1 PLANT:ME02587-05 |
| phenotype ID: | 56322 |
| assay: | Soil Gross Morphology: 8 rosette leaves 1 mm in length |
| phenotype: | WHOLE PLANT - Dark Green |
| notes: | NONE |
| unique F1 plant ID: | R1 PLANT:ME02587-05 |
| phenotype ID: | 56323 |
| assay: | Soil Gross Morphology: 8 rosette leaves 1 mm in length |
| phenotype: | ROSETTE LEAVES - Other |
| notes: | pointed |
| unique F1 plant ID: | R1 PLANT:ME02587-05 |
| phenotype ID: | 56324 |
| assay: | Soil Gross Morphology: 8 rosette leaves 1 mm in length |
| phenotype: | ROSETTE LEAVES - Serrate Margins |
| notes: | NONE |
| unique F1 plant ID: | R1 PLANT:ME02587-06 |
| phenotype ID: | 56325 |
| assay: | Soil Gross Morphology: 30% of flowers to be produced have opened |
| phenotype: | FLOWER - Reduced fertility |
| notes: | NONE |
| unique F1 plant ID: | R1 PLANT:ME02587-07 |
| phenotype ID: | 56328 |
| assay: | Soil Gross Morphology: 30% of flowers to be produced have opened |
| phenotype: | FLOWER - Reduced fertility |
| notes: | NONE |
| | Knock-in phenotype in gene(cDNA__id): 12579688 |
| clone ID: | 110454 |
| Promoter: | 35S |
| unique F1 plant ID: | R1 PLANT:ME04517-02 |
| phenotype ID: | 83590 |
| assay: | Soil Gross Morphology: 10% of flowers to be produced have opened |
| phenotype: | WHOLE PLANT - Small |
| notes: | 10 pct wt |
| unique F1 plant ID: | R1 PLANT:ME04517-02 |
| phenotype ID: | 83591 |
| assay: | Soil Gross Morphology: 10% of flowers to be produced have opened |
| phenotype: | WHOLE PLANT - Dark Green |
| notes: | NONE |
| unique F1 plant ID: | R1 PLANT:ME04517-02 |
| phenotype ID: | 83592 |
| assay: | Soil Gross Morphology: 10% of flowers to be produced have opened |
| phenotype: | WHOLE PLANT - High Anthocyanin |
| notes: | NONE |
| unique F1 plant ID: | R1 PLANT:ME04517-03 |
| phenotype ID: | 83598 |
| assay: | Soil Gross Morphology: 10% of flowers to be produced have opened |
| phenotype: | WHOLE PLANT - Dark Green |
| notes: | NONE |
| unique F1 plant ID: | R1 PLANT:ME04517-03 |
| phenotype ID: | 83599 |
| assay: | Soil Gross Morphology: 10% of flowers to be produced have opened |
| phenotype: | WHOLE PLANT - Small |
| notes: | 30 pct wt |
| unique F1 plant ID: | R1 PLANT:ME04517-04 |
| phenotype ID: | 83605 |
| assay: | Soil Gross Morphology: 10 rosette leaves 1 mm in length |
| phenotype: | ROSETTE LEAVES - Oval Shaped |
| notes: | NONE |
| unique F1 plant ID: | R1 PLANT:ME04517-04 |
| phenotype ID: | 83606 |
| assay: | Soil Gross Morphology: 10 rosette leaves 1 mm in length |
| phenotype: | WHOLE PLANT - Small |
| notes: | NONE |
| unique F1 plant ID: | R1 PLANT:ME04517-04 |
| phenotype ID: | 83607 |
| assay: | Soil Gross Morphology: 10 rosette leaves 1 mm in length |

TABLE 1-continued

| | |
|---|---|
| phenotype: | INFLORESCENCE - Late Flowering |
| notes: | NONE |
| unique F1 plant ID: | R1 PLANT:ME04517-09 |
| phenotype ID: | 83653 |
| assay: | Soil Gross Morphology: First flower open |
| phenotype: | WHOLE PLANT - Dark Green |
| notes: | NONE |
| unique F1 plant ID: | R1 PLANT:ME04517-09 |
| phenotype ID: | 83654 |
| assay: | Soil Gross Morphology: First flower open |
| phenotype: | WHOLE PLANT - High Anthocyanin |
| notes: | NONE |
| unique F1 plant ID: | R1 PLANT:ME04517-09 |
| phenotype ID: | 83655 |
| assay: | Soil Gross Morphology: First flower open |
| phenotype: | WHOLE PLANT - Small |
| notes: | 10 pct wt |

Knock-in phenotype in gene(cDNA_id): 12653898

| | |
|---|---|
| clone ID: | 32548 |
| Promoter: | 35S |
| unique F1 plant ID: | R1 PLANT:ME04257-01 |
| phenotype ID: | 82625 |
| assay: | Soil Gross Morphology: 50% of flowers to be produced have opened |
| phenotype: | FLOWER - Reduced fertility |
| notes: | NONE |
| unique F1 plant ID: | R1 PLANT:ME04257-01 |
| phenotype ID: | 82626 |
| assay: | Soil Gross Morphology: 10% of flowers to be produced have opened |
| phenotype: | INFLORESCENCE - Short |
| notes: | NONE |
| unique F1 plant ID: | R1 PLANT:ME04257-01 |
| phenotype ID: | 82627 |
| assay: | Soil Gross Morphology: 10% of flowers to be produced have opened |
| phenotype: | WHOLE PLANT - Small |
| notes: | NONE |
| unique F1 plant ID: | R1 PLANT:ME04257-01 |
| phenotype ID: | 82628 |
| assay: | Soil Gross Morphology: 50% of flowers to be produced have opened |
| phenotype: | WHOLE PLANT - Small |
| notes: | 25 percent weight |
| unique F1 plant ID: | R1 PLANT:ME04257-01 |
| phenotype ID: | 82629 |
| assay: | Soil Gross Morphology: 10% of flowers to be produced have opened |
| phenotype: | ROSETTE LEAVES - Curled 2 |
| notes: | NONE |
| unique F1 plant ID: | R1 PLANT:ME04257-02 |
| phenotype ID: | 82688 |
| assay: | Soil Gross Morphology: First flower buds visible |
| phenotype: | ROSETTE LEAVES - Other |
| notes: | NONE |
| unique F1 plant ID: | R1 PLANT:ME04257-02 |
| phenotype ID: | 82689 |
| assay: | Soil Gross Morphology: First flower buds visible |
| phenotype: | WHOLE PLANT - Small |
| notes: | 10 percent weight |
| unique F1 plant ID: | R1 PLANT:ME04257-02 |
| phenotype ID: | 82690 |
| assay: | Soil Gross Morphology: First flower buds visible |
| phenotype: | INFLORESCENCE - Short |
| notes: | NONE |
| unique F1 plant ID: | R1 PLANT:ME04257-02 |
| phenotype ID: | 82691 |
| assay: | Soil Gross Morphology: 50% of flowers to be produced have opened |
| phenotype: | FLOWER - Sterile |
| notes: | NONE |
| unique F1 plant ID: | R1 PLANT:ME04257-02 |
| phenotype ID: | 82692 |
| assay: | Soil Gross Morphology: First flower buds visible |
| phenotype: | ROSETTE LEAVES - Corkscrew |
| notes: | NONE |
| unique F1 plant ID: | R1 PLANT:ME04257-02 |
| phenotype ID: | 82693 |
| assay: | Soil Gross Morphology: 50% of flowers to be produced have opened |
| phenotype: | WHOLE PLANT - Small |
| notes: | 10 percent weight |
| unique F1 plant ID: | R1 PLANT:ME04257-02 |
| phenotype ID: | 82694 |
| assay: | Soil Gross Morphology: 50% of flowers to be produced have opened |

TABLE 1-continued

| | |
|---|---|
| phenotype: | CAULINE LEAVES - Curled 2 |
| notes: | NONE |
| unique F1 plant ID: | R1 PLANT:ME04257-02 |
| phenotype ID: | 82695 |
| assay: | Soil Gross Morphology: First flower buds visible |
| phenotype: | INFLORESCENCE - Late Flowering |
| notes: | NONE |
| unique F1 plant ID: | R1 PLANT:ME04257-06 |
| phenotype ID: | 82912 |
| assay: | Soil Gross Morphology: First flower buds visible |
| phenotype: | INFLORESCENCE - Late Flowering |
| notes: | NONE |
| unique F1 plant ID: | R1 PLANT:ME04257-06 |
| phenotype ID: | 82913 |
| assay: | Soil Gross Morphology: First flower buds visible |
| phenotype: | ROSETTE LEAVES - Serrate Margins |
| notes: | NONE |
| unique F1 plant ID: | R1 PLANT:ME04257-06 |
| phenotype ID: | 82914 |
| assay: | Soil Gross Morphology: 30% of flowers to be produced have opened |
| phenotype: | FLOWER - Sterile |
| notes: | NONE |
| unique F1 plant ID: | R1 PLANT:ME04257-06 |
| phenotype ID: | 82915 |
| assay: | Soil Gross Morphology: First flower buds visible |
| phenotype: | WHOLE PLANT - Dark Green |
| notes: | NONE |
| unique F1 plant ID: | R1 PLANT:ME04257-06 |
| phenotype ID: | 82916 |
| assay: | Soil Gross Morphology: 30% of flowers to be produced have opened |
| phenotype: | WHOLE PLANT - Small |
| notes: | 10 percent weight |
| unique F1 plant ID: | R1 PLANT:ME04257-06 |
| phenotype ID: | 82917 |
| assay: | Soil Gross Morphology: First flower buds visible |
| phenotype: | INFLORESCENCE - Short |
| notes: | NONE |
| unique F1 plant ID: | R1 PLANT:ME04257-06 |
| phenotype ID: | 82918 |
| assay: | Soil Gross Morphology: 30% of flowers to be produced have opened |
| phenotype: | WHOLE PLANT - Dark Green |
| notes: | NONE |
| unique F1 plant ID: | R1 PLANT:ME04257-06 |
| phenotype ID: | 82919 |
| assay: | Soil Gross Morphology: First flower buds visible |
| phenotype: | WHOLE PLANT - Small |
| notes: | 10 percent weight |
| unique F1 plant ID: | R1 PLANT:ME04257-06 |
| phenotype ID: | 82920 |
| assay: | Soil Gross Morphology: First flower buds visible |
| phenotype: | ROSETTE LEAVES - Curled 2 |
| notes: | NONE |
| unique F1 plant ID: | R1 PLANT:ME04257-06 |
| phenotype ID: | 82921 |
| assay: | Soil Gross Morphology: 30% of flowers to be produced have opened |
| phenotype: | ROSETTE LEAVES - Other |
| notes: | misshapen leaves |
| | Knock-in phenotype in gene(cDNA_id): 12661399 |
| clone ID: | 42533 |
| Promoter: | 35S |
| unique F1 plant ID: | R1 PLANT:ME05979-02 |
| phenotype ID: | 99052 |
| assay: | Soil Gross Morphology: 4 rosette leaves 1 mm in length |
| phenotype: | WHOLE PLANT - Dark Green |
| notes: | NONE |
| unique F1 plant ID: | R1 PLANT:ME05979-03 |
| phenotype ID: | 99084 |
| assay: | Soil Gross Morphology: 6 rosette leaves 1 mm in length |
| phenotype: | ROSETTE LEAVES - Lanceolate Shaped |
| notes: | NONE |
| unique F1 plant ID: | R1 PLANT:ME05979-03 |
| phenotype ID: | 99085 |
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME05979-04 |
| phenotype ID: | 99100 |
| assay: | Soil Gross Morphology: 6 rosette leaves 1 mm in length |

TABLE 1-continued

| | |
|---|---|
| phenotype: | ROSETTE LEAVES - Lanceolate Shaped |
| notes: | NONE |
| unique F1 plant ID: | R1 PLANT:ME05979-04 |
| phenotype ID: | 99101 |
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME05979-05 |
| phenotype ID: | 99134 |
| assay: | Soil Gross Morphology: 6 rosette leaves 1 mm in length |
| phenotype: | ROSETTE LEAVES - Lanceolate Shaped |
| notes: | NONE |
| unique F1 plant ID: | R1 PLANT:ME05979-05 |
| phenotype ID: | 99135 |
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME05979-06 |
| phenotype ID: | 99159 |
| assay: | Soil Gross Morphology: 6 rosette leaves 1 mm in length |
| phenotype: | ROSETTE LEAVES - Lanceolate Shaped |
| notes: | NONE |
| unique F1 plant ID: | R1 PLANT:ME05979-06 |
| phenotype ID: | 99160 |
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME05979-08 |
| phenotype ID: | 99202 |
| assay: | Soil Gross Morphology: 7 rosette leaves 1 mm in length |
| phenotype: | ROSETTE LEAVES - Lanceolate Shaped |
| notes: | NONE |
| unique F1 plant ID: | R1 PLANT:ME05979-08 |
| phenotype ID: | 99203 |
| assay: | Soil Gross Morphology: 7 rosette leaves 1 mm in length |
| phenotype: | WHOLE PLANT - Dark Green |
| notes: | NONE |
| unique F1 plant ID: | R1 PLANT:ME05979-09 |
| phenotype ID: | 99230 |
| assay: | Soil Gross Morphology: 6 rosette leaves 1 mm in length |
| phenotype: | ROSETTE LEAVES - Lanceolate Shaped |
| notes: | NONE |
| unique F1 plant ID: | R1 PLANT:ME05979-09 |
| phenotype ID: | 99231 |
| assay: | Soil Gross Morphology: 6 rosette leaves 1 mm in length |
| phenotype: | WHOLE PLANT - Dark Green |
| notes: | NONE |
| | Knock-in phenotype in gene(cDNA__id): 13486708 |
| clone ID: | 31044 |
| Promoter: | 35S |
| unique F1 plant ID: | R1 PLANT:ME04339-02 |
| phenotype ID: | 83360 |
| assay: | Soil Gross Morphology: 30% of flowers to be produced have opened |
| phenotype: | ROSETTE LEAVES - Other |
| notes: | fewer leaves |
| unique F1 plant ID: | R1 PLANT:ME04339-02 |
| phenotype ID: | 83361 |
| assay: | Soil Gross Morphology: 30% of flowers to be produced have opened |
| phenotype: | WHOLE PLANT - Small |
| notes: | 25 percent weight |
| unique F1 plant ID: | R1 PLANT:ME04339-04 |
| phenotype ID: | 83364 |
| assay: | Soil Gross Morphology: 30% of flowers to be produced have opened |
| phenotype: | ROSETTE LEAVES - Other |
| notes: | fewer leaves |
| unique F1 plant ID: | R1 PLANT:ME04339-04 |
| phenotype ID: | 83365 |
| assay: | Soil Gross Morphology: 30% of flowers to be produced have opened |
| phenotype: | WHOLE PLANT - Small |
| notes: | 25 percent weight |
| unique F1 plant ID: | R1 PLANT:ME04339-05 |
| phenotype ID: | 83373 |
| assay: | Soil Gross Morphology: 30% of flowers to be produced have opened |
| phenotype: | ROSETTE LEAVES - Other |
| notes: | fewer leaves |
| unique F1 plant ID: | R1 PLANT:ME04339-05 |
| phenotype ID: | 83374 |
| assay: | Soil Gross Morphology: 30% of flowers to be produced have opened |

TABLE 1-continued

| | |
|---|---|
| phenotype: | WHOLE PLANT - Small |
| notes: | 25 percent weight |
| unique F1 plant ID: | R1 PLANT:ME04339-08 |
| phenotype ID: | 83390 |
| assay: | Soil Gross Morphology: 30% of flowers to be produced have opened |
| phenotype: | ROSETTE LEAVES - Other |
| notes: | fewer leaves |
| unique F1 plant ID: | R1 PLANT:ME04339-08 |
| phenotype ID: | 83391 |
| assay: | Soil Gross Morphology: 30% of flowers to be produced have opened |
| phenotype: | WHOLE PLANT - Small |
| notes: | 25 percent weight |
| unique F1 plant ID: | R1 PLANT:ME04339-09 |
| phenotype ID: | 83392 |
| assay: | Soil Gross Morphology: 30% of flowers to be produced have opened |
| phenotype: | ROSETTE LEAVES - Other |
| notes: | fewer leaves |
| unique F1 plant ID: | R1 PLANT:ME04339-09 |
| phenotype ID: | 83393 |
| assay: | Soil Gross Morphology: 30% of flowers to be produced have opened |
| phenotype: | WHOLE PLANT - Small |
| notes: | 25 percent weight |

<div align="center">Knock-in phenotype in gene(cDNA_id): 13487771</div>

| | |
|---|---|
| clone ID: | 38635 |
| Promoter: | 35S |
| unique F1 plant ID: | R1 PLANT:ME04917-02 |
| phenotype ID: | 88860 |
| assay: | Soil Gross Morphology: 10% of flowers to be produced have opened |
| phenotype: | ROSETTE LEAVES - Other |
| notes: | misshapen |
| unique F1 plant ID: | R1 PLANT:ME04917-02 |
| phenotype ID: | 88861 |
| assay: | Soil Gross Morphology: 10% of flowers to be produced have opened |
| phenotype: | ROSETTE LEAVES - Curled 4 |
| notes: | NONE |
| unique F1 plant ID: | R1 PLANT:ME04917-06 |
| phenotype ID: | 88933 |
| assay: | Soil Gross Morphology: 10% of flowers to be produced have opened |
| phenotype: | ROSETTE LEAVES - Other |
| notes: | NONE |
| unique F1 plant ID: | R1 PLANT:ME04917-06 |
| phenotype ID: | 88934 |
| assay: | Soil Gross Morphology: 10% of flowers to be produced have opened |
| phenotype: | ROSETTE LEAVES - Curled 4 |
| notes: | NONE |
| unique F1 plant ID: | R1 PLANT:ME04917-08 |
| phenotype ID: | 88965 |
| assay: | Soil Gross Morphology: First flower buds visible |
| phenotype: | ROSETTE LEAVES - Other |
| notes: | NONE |
| unique F1 plant ID: | R1 PLANT:ME04917-08 |
| phenotype ID: | 88966 |
| assay: | Soil Gross Morphology: First flower buds visible |
| phenotype: | ROSETTE LEAVES - Curled 4 |
| notes: | NONE |
| unique F1 plant ID: | R1 PLANT:ME04917-09 |
| phenotype ID: | 88986 |
| assay: | Soil Gross Morphology: First flower buds visible |
| phenotype: | ROSETTE LEAVES - Other |
| notes: | NONE |
| unique F1 plant ID: | R1 PLANT:ME04917-09 |
| phenotype ID: | 88987 |
| assay: | Soil Gross Morphology: First flower buds visible |
| phenotype: | ROSETTE LEAVES - Curled 4 |
| notes: | NONE |
| unique F1 plant ID: | R1 PLANT:ME04917-10 |
| phenotype ID: | 89004 |
| assay: | Soil Gross Morphology: First flower buds visible |
| phenotype: | ROSETTE LEAVES - Other |
| notes: | NONE |
| unique F1 plant ID: | R1 PLANT:ME04917-10 |
| phenotype ID: | 89005 |
| assay: | Soil Gross Morphology: First flower buds visible |
| phenotype: | ROSETTE LEAVES - Curled 4 |
| notes: | NONE |

<div align="center">Knock-in phenotype in gene(cDNA_id): 13490208</div>

| | |
|---|---|
| clone ID: | 28528 |

TABLE 1-continued

| | |
|---|---|
| Promoter: | 35S |
| unique F1 plant ID: | R1 PLANT:ME02659-01 |
| phenotype ID: | 55453 |
| assay: | Soil Gross Morphology: 30% of flowers to be produced have opened |
| phenotype: | WHOLE PLANT - Small |
| notes: | 50pct. of wt |
| unique F1 plant ID: | R1 PLANT:ME02659-01 |
| phenotype ID: | 55454 |
| assay: | Soil Gross Morphology: 30% of flowers to be produced have opened |
| phenotype: | SILIQUES - Sickle |
| notes: | NONE |
| unique F1 plant ID: | R1 PLANT:ME02659-06 |
| phenotype ID: | 55829 |
| assay: | Soil Gross Morphology: 30% of flowers to be produced have opened |
| phenotype: | WHOLE PLANT - Small |
| notes: | NONE |
| unique F1 plant ID: | R1 PLANT:ME02659-08 |
| phenotype ID: | 55970 |
| assay: | Soil Gross Morphology: 30% of flowers to be produced have opened |
| phenotype: | WHOLE PLANT - Small |
| notes: | NONE |
| unique F1 plant ID: | R1 PLANT:ME02659-09 |
| phenotype ID: | 56031 |
| assay: | Soil Gross Morphology: 30% of flowers to be produced have opened |
| phenotype: | WHOLE PLANT - Small |
| notes: | NONE |

Knock-in phenotype in gene(cDNA_id): 13492937

| | |
|---|---|
| clone ID: | 41439 |
| Promoter: | 326D |
| unique F1 plant ID: | R1 PLANT:ME09199-01 |
| phenotype ID: | 124095 |
| assay: | Soil Gross Morphology: 7 rosette leaves 1 mm in length |
| phenotype: | ROSETTE LEAVES - Cup-shaped |
| notes: | NONE |
| unique F1 plant ID: | R1 PLANT:ME09199-04 |
| phenotype ID: | 124096 |
| assay: | Soil Gross Morphology: 7 rosette leaves 1 mm in length |
| phenotype: | ROSETTE LEAVES - Cup-shaped |
| notes: | NONE |
| unique F1 plant ID: | R1 PLANT:ME09357-01 |
| phenotype ID: | 124906 |
| assay: | Soil Gross Morphology: 13 rosette leaves 1 mm in length |
| phenotype: | INFLORESCENCE - Late Flowering |
| notes: | NONE |
| unique F1 plant ID: | R1 PLANT:ME09357-02 |
| phenotype ID: | 124927 |
| assay: | Soil Gross Morphology: 8 rosette leaves 1 mm in length |
| phenotype: | WHOLE PLANT - Small |
| notes: | 10 pct wt |
| unique F1 plant ID: | R1 PLANT:ME09357-02 |
| phenotype ID: | 124928 |
| assay: | Soil Gross Morphology: 8 rosette leaves 1 mm in length |
| phenotype: | WHOLE PLANT - Dark Green |
| notes: | NONE |
| unique F1 plant ID: | R1 PLANT:ME09357-02 |
| phenotype ID: | 124929 |
| assay: | Soil Gross Morphology: 8 rosette leaves 1 mm in length |
| phenotype: | ROSETTE LEAVES - Oval Shaped |
| notes: | NONE |
| unique F1 plant ID: | R1 PLANT:ME09357-02 |
| phenotype ID: | 124930 |
| assay: | Soil Gross Morphology: 8 rosette leaves 1 mm in length |
| phenotype: | ROSETTE LEAVES - Short Petioles |
| notes: | NONE |
| unique F1 plant ID: | R1 PLANT:ME09357-02 |
| phenotype ID: | 124931 |
| assay: | Soil Gross Morphology: 8 rosette leaves 1 mm in length |
| phenotype: | INFLORESCENCE - Late Flowering |
| notes: | NONE |
| unique F1 plant ID: | R1 PLANT:ME09357-03 |
| phenotype ID: | 124948 |
| assay: | Soil Gross Morphology: 11 rosette leaves 1 mm in length |
| phenotype: | INFLORESCENCE - Late Flowering |
| notes: | NONE |
| unique F1 plant ID: | R1 PLANT:ME09357-06 |
| phenotype ID: | 125022 |
| assay: | Soil Gross Morphology: 10 rosette leaves 1 mm in length |
| phenotype: | INFLORESCENCE - Late Flowering |

TABLE 1-continued

| | |
|---|---|
| notes: | NONE |
| unique F1 plant ID: | R1 PLANT:ME09357-10 |
| phenotype ID: | 125107 |
| assay: | Soil Gross Morphology: 11 rosette leaves 1 mm in length |
| phenotype: | WHOLE PLANT - Small |
| notes: | NONE |
| unique F1 plant ID: | R1 PLANT:ME09357-10 |
| phenotype ID: | 125108 |
| assay: | Soil Gross Morphology: 11 rosette leaves 1 mm in length |
| phenotype: | WHOLE PLANT - Dark Green |
| notes: | NONE |
| unique F1 plant ID: | R1 PLANT:ME09357-10 |
| phenotype ID: | 125109 |
| assay: | Soil Gross Morphology: 11 rosette leaves 1 mm in length |
| phenotype: | INFLORESCENCE - Late Flowering |
| notes: | NONE |
| unique F1 plant ID: | R1 PLANT:ME01731-01 |
| phenotype ID: | 54217 |
| assay: | Soil Gross Morphology: First flower buds visible |
| phenotype: | WHOLE PLANT - Small |
| notes: | NONE |
| unique F1 plant ID: | R1 PLANT:ME01731-01 |
| phenotype ID: | 54218 |
| assay: | Soil Gross Morphology: 50% of flowers to be produced have opened |
| phenotype: | WHOLE PLANT - Other |
| notes: | NONE |
| unique F1 plant ID: | R1 PLANT:ME01731-03 |
| phenotype ID: | 54267 |
| assay: | Soil Gross Morphology: First flower buds visible |
| phenotype: | WHOLE PLANT - Small |
| notes: | NONE |
| unique F1 plant ID: | R1 PLANT:ME01731-03 |
| phenotype ID: | 54268 |
| assay: | Soil Gross Morphology: 50% of flowers to be produced have opened |
| phenotype: | WHOLE PLANT - Other |
| notes: | NONE |
| unique F1 plant ID: | R1 PLANT:ME01731-05 |
| phenotype ID: | 54305 |
| assay: | Soil Gross Morphology: First flower buds visible |
| phenotype: | WHOLE PLANT - Small |
| notes: | NONE |
| unique F1 plant ID: | R1 PLANT:ME01731-05 |
| phenotype ID: | 54306 |
| assay: | Soil Gross Morphology: 50% of flowers to be produced have opened |
| phenotype: | WHOLE PLANT - Other |
| notes: | silver |
| | Knock-in phenotype in gene(cDNA_id): 13497014 |
| clone ID: | 4309 |
| Promoter: | 35S |
| unique F1 plant ID: | R1 PLANT:ME05418-01 |
| phenotype ID: | 89532 |
| assay: | Soil Gross Morphology: 50% of flowers to be produced have opened |
| phenotype: | WHOLE PLANT - Small |
| notes: | 25 pct wt |
| unique F1 plant ID: | R1 PLANT:ME05418-03 |
| phenotype ID: | 89581 |
| assay: | Soil Gross Morphology: 50% of flowers to be produced have opened |
| phenotype: | WHOLE PLANT - Small |
| notes: | 25 pct wt |
| unique F1 plant ID: | R1 PLANT:ME05418-04 |
| phenotype ID: | 89602 |
| assay: | Soil Gross Morphology: 50% of flowers to be produced have opened |
| phenotype: | WHOLE PLANT - Small |
| notes: | 25 pct wt |
| unique F1 plant ID: | R1 PLANT:ME05418-05 |
| phenotype ID: | 89630 |
| assay: | Soil Gross Morphology: 50% of flowers to be produced have opened |
| phenotype: | WHOLE PLANT - Small |
| notes: | 25 pct wt |
| unique F1 plant ID: | R1 PLANT:ME05418-06 |
| phenotype ID: | 89639 |
| assay: | Soil Gross Morphology: 50% of flowers to be produced have opened |
| phenotype: | WHOLE PLANT - Small |
| notes: | 25 pct wt |
| | Knock-in phenotype in gene(cDNA_id): 13497142 |
| clone ID: | 34480 |
| Promoter: | 35S |

TABLE 1-continued

| | |
|---|---|
| unique F1 plant ID: | R1 PLANT:ME05721-01 |
| phenotype ID: | 98428 |
| assay: | Soil Gross Morphology: First flower buds visible |
| phenotype: | WHOLE PLANT - Small |
| notes: | 25 pct wt |
| unique F1 plant ID: | R1 PLANT:ME05721-01 |
| phenotype ID: | 98429 |
| assay: | Soil Gross Morphology: First flower buds visible |
| phenotype: | WHOLE PLANT - Yellow-Green Viable 1 |
| notes: | NONE |
| unique F1 plant ID: | R1 PLANT:ME05721-03 |
| phenotype ID: | 98507 |
| assay: | Soil Gross Morphology: First flower buds visible |
| phenotype: | WHOLE PLANT - Small |
| notes: | 25 pct wt |
| unique F1 plant ID: | R1 PLANT:ME05721-03 |
| phenotype ID: | 98508 |
| assay: | Soil Gross Morphology: First flower buds visible |
| phenotype: | WHOLE PLANT - Yellow-Green Viable 1 |
| notes: | NONE |
| unique F1 plant ID: | R1 PLANT:ME05721-04 |
| phenotype ID: | 98551 |
| assay: | Soil Gross Morphology: First flower buds visible |
| phenotype: | WHOLE PLANT - Small |
| notes: | 25 pct wt |
| unique F1 plant ID: | R1 PLANT:ME05721-04 |
| phenotype ID: | 98552 |
| assay: | Soil Gross Morphology: First flower buds visible |
| phenotype: | WHOLE PLANT - Yellow-Green Viable 1 |
| notes: | NONE |
| unique F1 plant ID: | R1 PLANT:ME05721-05 |
| phenotype ID: | 98578 |
| assay: | Soil Gross Morphology: First flower buds visible |
| phenotype: | WHOLE PLANT - Small |
| notes: | 25 pct wt |
| unique F1 plant ID: | R1 PLANT:ME05721-05 |
| phenotype ID: | 98579 |
| assay: | Soil Gross Morphology: First flower buds visible |
| phenotype: | WHOLE PLANT - Yellow-Green Viable 1 |
| notes: | NONE |
| unique F1 plant ID: | R1 PLANT:ME05721-07 |
| phenotype ID: | 98675 |
| assay: | Soil Gross Morphology: First flower buds visible |
| phenotype: | WHOLE PLANT - Small |
| notes: | 25 pct wt |
| unique F1 plant ID: | R1 PLANT:ME05721-07 |
| phenotype ID: | 98676 |
| assay: | Soil Gross Morphology: First flower buds visible |
| phenotype: | WHOLE PLANT - Yellow-Green Viable 1 |
| notes: | NONE |
| unique F1 plant ID: | R1 PLANT:ME05721-08 |
| phenotype ID: | 98729 |
| assay: | Soil Gross Morphology: First flower buds visible |
| phenotype: | WHOLE PLANT - Small |
| notes: | 25 pct wt |
| unique F1 plant ID: | R1 PLANT:ME05721-08 |
| phenotype ID: | 98730 |
| assay: | Soil Gross Morphology: First flower buds visible |
| phenotype: | WHOLE PLANT - Yellow-Green Viable 1 |
| notes: | NONE |
| unique F1 plant ID: | R1 PLANT:ME05721-10 |
| phenotype ID: | 98808 |
| assay: | Soil Gross Morphology: 30% of flowers to be produced have opened |
| phenotype: | INFLORESCENCE - Short |
| notes: | NONE |
| unique F1 plant ID: | R1 PLANT:ME05721-10 |
| phenotype ID: | 98809 |
| assay: | Soil Gross Morphology: First flower buds visible |
| phenotype: | WHOLE PLANT - Small |
| notes: | 25 pct wt |
| unique F1 plant ID: | R1 PLANT:ME05721-10 |
| phenotype ID: | 98810 |
| assay: | Soil Gross Morphology: First flower buds visible |
| phenotype: | WHOLE PLANT - Yellow-Green Viable 1 |
| notes: | NONE |
| | Knock-in phenotype in gene(cDNA_id): 13497443 |
| clone ID: | 34167 |
| Promoter: | 35S |

TABLE 1-continued

| | |
|---|---|
| unique F1 plant ID: | R1 PLANT:ME03036-01 |
| phenotype ID: | 71177 |
| assay: | Soil Gross Morphology: 10% of flowers to be produced have opened |
| phenotype: | WHOLE PLANT - Small |
| notes: | 40pct |
| unique F1 plant ID: | R1 PLANT:ME03036-01 |
| phenotype ID: | 71178 |
| assay: | Soil Gross Morphology: 10% of flowers to be produced have opened |
| phenotype: | WHOLE PLANT - Yellow-Green Viable 1 |
| notes: | NONE |
| unique F1 plant ID: | R1 PLANT:ME03036-03 |
| phenotype ID: | 71209 |
| assay: | Soil Gross Morphology: 50% of flowers to be produced have opened |
| phenotype: | WHOLE PLANT - Yellow-Green Viable 1 |
| notes: | NONE |
| unique F1 plant ID: | R1 PLANT:ME03036-03 |
| phenotype ID: | 71210 |
| assay: | Soil Gross Morphology: 50% of flowers to be produced have opened |
| phenotype: | ROSETTE LEAVES - Other |
| notes: | fewer leaves |
| unique F1 plant ID: | R1 PLANT:ME03036-10 |
| phenotype ID: | 71282 |
| assay: | Soil Gross Morphology: First flower open |
| phenotype: | INFLORESCENCE - Late Flowering |
| notes: | NONE |
| unique F1 plant ID: | R1 PLANT:ME03036-10 |
| phenotype ID: | 71283 |
| assay: | Soil Gross Morphology: First flower open |
| phenotype: | WHOLE PLANT - Dark Green |
| notes: | NONE |

Knock-in phenotype in gene(cDNA_id): 13500819

| | |
|---|---|
| clone ID: | 464504 |
| Promoter: | 35S |
| unique F1 plant ID: | R1 PLANT:ME05780-06 |
| phenotype ID: | 98939 |
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME05780-09 |
| phenotype ID: | 98988 |
| assay: | Soil Gross Morphology: 5 rosette leaves 1 mm in length |
| phenotype: | WHOLE PLANT - Dark Green |
| notes: | NONE |
| unique F1 plant ID: | R1 PLANT:ME05780-09 |
| phenotype ID: | 98989 |
| assay: | Soil Gross Morphology: Flowering complete |
| phenotype: | WHOLE PLANT - Small |
| notes: | 50 pct wt |
| unique F1 plant ID: | R1 PLANT:ME05780-09 |
| phenotype ID: | 98990 |
| assay: | Soil Gross Morphology: Flowering complete |
| phenotype: | INFLORESCENCE - Short Internode |
| notes: | NONE |
| unique F1 plant ID: | R1 PLANT:ME05780-10 |
| phenotype ID: | 99016 |
| assay: | Soil Gross Morphology: 4 rosette leaves 1 mm in length |
| phenotype: | WHOLE PLANT - Dark Green |
| notes: | NONE |
| unique F1 plant ID: | R1 PLANT:ME05780-10 |
| phenotype ID: | 99017 |
| assay: | Soil Gross Morphology: 4 rosette leaves 1 mm in length |
| phenotype: | WHOLE PLANT - Small |
| notes: | 10 pct wt |

Knock-in phenotype in gene(cDNA_id): 13530629

| | |
|---|---|
| clone ID: | 681222 |
| Promoter: | 35S |
| unique F1 plant ID: | R1 PLANT:ME05056-05 |
| phenotype ID: | 89266 |
| assay: | Soil Gross Morphology: 30% of flowers to be produced have opened |
| phenotype: | ROSETTE LEAVES - Lanceolate Shaped |
| notes: | NONE |
| unique F1 plant ID: | R1 PLANT:ME05056-05 |
| phenotype ID: | 89267 |
| assay: | Soil Gross Morphology: 30% of flowers to be produced have opened |
| phenotype: | ROSETTE LEAVES - Curled 4 |
| notes: | NONE |
| unique F1 plant ID: | R1 PLANT:ME05056-08 |

TABLE 1-continued

| | |
|---|---|
| phenotype ID: | 89362 |
| assay: | Soil Gross Morphology: 30% of flowers to be produced have opened |
| phenotype: | ROSETTE LEAVES - Lanceolate Shaped |
| notes: | NONE |
| unique F1 plant ID: | R1 PLANT:ME05056-08 |
| phenotype ID: | 89363 |
| assay: | Soil Gross Morphology: 30% of flowers to be produced have opened |
| phenotype: | ROSETTE LEAVES - Curled 2 |
| notes: | NONE |
| unique F1 plant ID: | R1 PLANT:ME05056-09 |
| phenotype ID: | 89407 |
| assay: | Soil Gross Morphology: 30% of flowers to be produced have opened |
| phenotype: | ROSETTE LEAVES - Lanceolate Shaped |
| notes: | NONE |
| unique F1 plant ID: | R1 PLANT:ME05056-09 |
| phenotype ID: | 89408 |
| assay: | Soil Gross Morphology: 30% of flowers to be produced have opened |
| phenotype: | ROSETTE LEAVES - Curled 2 |
| notes: | NONE |

Knock-in phenotype in gene(cDNA_id): 13592698

| | |
|---|---|
| clone ID: | 32753 |
| Promoter: | 35S |
| unique F1 plant ID: | R1 PLANT:ME01518-04 |
| phenotype ID: | 54126 |
| assay: | Soil Gross Morphology: 8 rosette leaves 1 mm in length |
| phenotype: | WHOLE PLANT - Dark Green |
| notes: | NONE |
| unique F1 plant ID: | R1 PLANT:ME01518-04 |
| phenotype ID: | 54127 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME01518-04 |
| phenotype ID: | 54128 |
| assay: | Soil Gross Morphology: 30% of flowers to be produced have opened |
| phenotype: | FLOWER - Reduced fertility |
| notes: | NONE |
| unique F1 plant ID: | R1 PLANT:ME01518-04 |
| phenotype ID: | 54129 |
| assay: | Soil Gross Morphology: 30% of flowers to be produced have opened |
| phenotype: | WHOLE PLANT - Misc. Dwarf |
| notes: | NONE |
| unique F1 plant ID: | R1 PLANT:ME01518-05 |
| phenotype ID: | 54137 |
| assay: | Soil Gross Morphology: 50% of flowers to be produced have opened |
| phenotype: | WHOLE PLANT - Small |
| notes: | NONE |
| unique F1 plant ID: | R1 PLANT:ME01518-06 |
| phenotype ID: | 54146 |
| assay: | Soil Gross Morphology: 30% of flowers to be produced have opened |
| phenotype: | INFLORESCENCE - Late Flowering |
| notes: | NONE |
| unique F1 plant ID: | R1 PLANT:ME01518-06 |
| phenotype ID: | 54147 |
| assay: | Soil Gross Morphology: 30% of flowers to be produced have opened |
| phenotype: | WHOLE PLANT - Other |
| notes: | pale green |
| unique F1 plant ID: | R1 PLANT:ME01518-12 |
| phenotype ID: | 99059 |
| assay: | Soil Gross Morphology: 5 rosette leaves 1 mm in length |
| phenotype: | WHOLE PLANT - Small |
| notes: | 25 pct wt |
| unique F1 plant ID: | R1 PLANT:ME01518-12 |
| phenotype ID: | 99060 |
| assay: | Soil Gross Morphology: 5 rosette leaves 1 mm in length |
| phenotype: | WHOLE PLANT - Dark Green |
| notes: | NONE |

Knock-in phenotype in gene(cDNA_id): 13621980

| | |
|---|---|
| clone ID: | 25886 |
| Promoter: | 35S |
| unique F1 plant ID: | R1 PLANT:ME02879-01 |
| phenotype ID: | 55488 |
| assay: | Soil Gross Morphology: 30% of flowers to be produced have opened |
| phenotype: | INFLORESCENCE - Other |
| notes: | slightly wavy |
| unique F1 plant ID: | R1 PLANT:ME02879-01 |
| phenotype ID: | 55489 |

TABLE 1-continued

| | |
|---|---|
| assay: | Soil Gross Morphology: 30% of flowers to be produced have opened |
| phenotype: | WHOLE PLANT - Dark Green |
| notes: | NONE |
| unique F1 plant ID: | R1 PLANT:ME02879-01 |
| phenotype ID: | 55490 |
| assay: | Soil Gross Morphology: 30% of flowers to be produced have opened |
| phenotype: | INFLORESCENCE - Strong |
| notes: | NONE |
| unique F1 plant ID: | R1 PLANT:ME02879-01 |
| phenotype ID: | 55491 |
| assay: | Soil Gross Morphology: 30% of flowers to be produced have opened |
| phenotype: | FLOWER - Reduced fertility |
| notes: | NONE |
| unique F1 plant ID: | R1 PLANT:ME02879-01 |
| phenotype ID: | 55492 |
| assay: | Soil Gross Morphology: 30% of flowers to be produced have opened |
| phenotype: | WHOLE PLANT - Small |
| notes: | 50pct. of wt |
| unique F1 plant ID: | R1 PLANT:ME02879-03 |
| phenotype ID: | 55623 |
| assay: | Soil Gross Morphology: 30% of flowers to be produced have opened |
| phenotype: | FLOWER - Reduced fertility |
| notes: | NONE |
| unique F1 plant ID: | R1 PLANT:ME02879-03 |
| phenotype ID: | 55624 |
| assay: | Soil Gross Morphology: 30% of flowers to be produced have opened |
| phenotype: | WHOLE PLANT - Dark Green |
| notes: | NONE |
| unique F1 plant ID: | R1 PLANT:ME02879-03 |
| phenotype ID: | 55625 |
| assay: | Soil Gross Morphology: 30% of flowers to be produced have opened |
| phenotype: | INFLORESCENCE - Other |
| notes: | slightly wavy |
| unique F1 plant ID: | R1 PLANT:ME02879-03 |
| phenotype ID: | 55626 |
| assay: | Soil Gross Morphology: 30% of flowers to be produced have opened |
| phenotype: | WHOLE PLANT - Small |
| notes: | 50pct. of wt |
| unique F1 plant ID: | R1 PLANT:ME02879-03 |
| phenotype ID: | 55627 |
| assay: | Soil Gross Morphology: 30% of flowers to be produced have opened |
| phenotype: | INFLORESCENCE - Strong |
| notes: | NONE |
| unique F1 plant ID: | R1 PLANT:ME02879-04 |
| phenotype ID: | 55708 |
| assay: | Soil Gross Morphology: 30% of flowers to be produced have opened |
| phenotype: | WHOLE PLANT - Small |
| notes: | 50pct. of wt |
| unique F1 plant ID: | R1 PLANT:ME02879-04 |
| phenotype ID: | 55709 |
| assay: | Soil Gross Morphology: 30% of flowers to be produced have opened |
| phenotype: | INFLORESCENCE - Other |
| notes: | slightly wavy |
| unique F1 plant ID: | R1 PLANT:ME02879-04 |
| phenotype ID: | 55710 |
| assay: | Soil Gross Morphology: 30% of flowers to be produced have opened |
| phenotype: | WHOLE PLANT - Dark Green |
| notes: | NONE |
| unique F1 plant ID: | R1 PLANT:ME02879-04 |
| phenotype ID: | 55711 |
| assay: | Soil Gross Morphology: 30% of flowers to be produced have opened |
| phenotype: | INFLORESCENCE - Strong |
| notes: | NONE |
| unique F1 plant ID: | R1 PLANT:ME02879-04 |
| phenotype ID: | 55712 |
| assay: | Soil Gross Morphology: 30% of flowers to be produced have opened |
| phenotype: | FLOWER - Reduced fertility |
| notes: | NONE |
| unique F1 plant ID: | R1 PLANT:ME02879-09 |
| phenotype ID: | 56062 |
| assay: | Soil Gross Morphology: 30% of flowers to be produced have opened |
| phenotype: | INFLORESCENCE - Strong |
| notes: | NONE |
| unique F1 plant ID: | R1 PLANT:ME02879-09 |
| phenotype ID: | 56063 |
| assay: | Soil Gross Morphology: 30% of flowers to be produced have opened |
| phenotype: | WHOLE PLANT - Dark Green |
| notes: | NONE |
| unique F1 plant ID: | R1 PLANT:ME02879-09 |

TABLE 1-continued

```
phenotype ID:       56064
assay:              Soil Gross Morphology: 30% of flowers to be produced have opened
phenotype:          INFLORESCENCE - Other
notes:              slightly wavy
unique F1 plant ID: R1 PLANT:ME02879-09
phenotype ID:       56065
assay:              Soil Gross Morphology: 30% of flowers to be produced have opened
phenotype:          WHOLE PLANT - Small
notes:              50pct. of wt
unique F1 plant ID: R1 PLANT:ME02879-09
phenotype ID:       56066
assay:              Soil Gross Morphology: 30% of flowers to be produced have opened
phenotype:          FLOWER - Reduced fertility
notes:              NONE
                Knock-in phenotype in gene(cDNA_id): 15170337 clone ID:           708342
Promoter:           326D
unique F1 plant ID: R1 PLANT:ME09237-03
phenotype ID:       124946
assay:              Soil Gross Morphology: 10 rosette leaves 1 mm in length
phenotype:          INFLORESCENCE - Late Flowering
notes:              NONE
unique F1 plant ID: R1 PLANT:ME09237-03
phenotype ID:       124947
assay:              Soil Gross Morphology: 9 rosette leaves 1 mm in length
phenotype:          INFLORESCENCE - Late Flowering
notes:              NONE
unique F1 plant ID: R1 PLANT:ME09237-05
phenotype ID:       124997
assay:              Soil Gross Morphology: 9 rosette leaves 1 mm in length
phenotype:          INFLORESCENCE - Late Flowering
notes:              NONE
unique F1 plant ID: R1 PLANT:ME09237-06
phenotype ID:       125021
assay:              Soil Gross Morphology: 8 rosette leaves 1 mm in length
phenotype:          INFLORESCENCE - Late Flowering
notes:              NONE
unique F1 plant ID: R1 PLANT:ME09237-08
phenotype ID:       125066
assay:              Soil Gross Morphology: 7 rosette leaves 1 mm in length
phenotype:          INFLORESCENCE - Late Flowering
notes:              NONE
unique F1 plant ID: R1 PLANT:ME09237-09
phenotype ID:       125081
assay:              Soil Gross Morphology: 10 rosette leaves 1 mm in length
phenotype:          INFLORESCENCE - Late Flowering
notes:              NONE
unique F1 plant ID: R1 PLANT:ME09237-10
phenotype ID:       125106
assay:              Soil Gross Morphology: 10 rosette leaves 1 mm in length
phenotype:          INFLORESCENCE - Late Flowering
notes:              NONE
unique F1 plant ID: R1 PLANT:ME05214-01
phenotype ID:       89120
assay:              Soil Gross Morphology: 30% of flowers to be produced have opened
phenotype:          WHOLE PLANT - Small
notes:              20 pct wt
unique F1 plant ID: R1 PLANT:ME05214-01
phenotype ID:       89121
assay:              Soil Gross Morphology: 30% of flowers to be produced have opened
phenotype:          ROSETTE LEAVES - Short Petioles
notes:              NONE
unique F1 plant ID: R1 PLANT:ME05214-01
phenotype ID:       89122
assay:              Soil Gross Morphology: 30% of flowers to be produced have opened
phenotype:          FLOWER - Reduced fertility
notes:              NONE
unique F1 plant ID: R1 PLANT:ME05214-01
phenotype ID:       89123
assay:              Soil Gross Morphology: 30% of flowers to be produced have opened
phenotype:          ROSETTE LEAVES - Oval Shaped
notes:              NONE
unique F1 plant ID: R1 PLANT:ME05214-02
phenotype ID:       89162
assay:              Soil Gross Morphology: 30% of flowers to be produced have opened
phenotype:          WHOLE PLANT - Small
notes:              40 pct wt
unique F1 plant ID: R1 PLANT:ME05214-02
```

TABLE 1-continued

| | |
|---|---|
| phenotype ID: | 89163 |
| assay: | Soil Gross Morphology: 30% of flowers to be produced have opened |
| phenotype: | ROSETTE LEAVES - Short Petioles |
| notes: | NONE |
| unique F1 plant ID: | R1 PLANT:ME05214-02 |
| phenotype ID: | 89164 |
| assay: | Soil Gross Morphology: 30% of flowers to be produced have opened |
| phenotype: | ROSETTE LEAVES - Oval Shaped |
| notes: | NONE |
| unique F1 plant ID: | R1 PLANT:ME05214-03 |
| phenotype ID: | 89209 |
| assay: | Soil Gross Morphology: 30% of flowers to be produced have opened |
| phenotype: | WHOLE PLANT - Small |
| notes: | 40 pct wt |
| unique F1 plant ID: | R1 PLANT:ME05214-03 |
| phenotype ID: | 89210 |
| assay: | Soil Gross Morphology: 30% of flowers to be produced have opened |
| phenotype: | ROSETTE LEAVES - Short Petioles |
| notes: | NONE |
| unique F1 plant ID: | R1 PLANT:ME05214-03 |
| phenotype ID: | 89211 |
| assay: | Soil Gross Morphology: 30% of flowers to be produced have opened |
| phenotype: | ROSETTE LEAVES - Oval Shaped |
| notes: | NONE |
| unique F1 plant ID: | R1 PLANT:ME05214-04 |
| phenotype ID: | 89252 |
| assay: | Soil Gross Morphology: 30% of flowers to be produced have opened |
| phenotype: | WHOLE PLANT - Small |
| notes: | 40 pct wt |
| unique F1 plant ID: | R1 PLANT:ME05214-04 |
| phenotype ID: | 89253 |
| assay: | Soil Gross Morphology: 30% of flowers to be produced have opened |
| phenotype: | ROSETTE LEAVES - Short Petioles |
| notes: | NONE |
| unique F1 plant ID: | R1 PLANT:ME05214-04 |
| phenotype ID: | 89254 |
| assay: | Soil Gross Morphology: 30% of flowers to be produced have opened |
| phenotype: | ROSETTE LEAVES - Oval Shaped |
| notes: | NONE |
| unique F1 plant ID: | R1 PLANT:ME05214-05 |
| phenotype ID: | 89287 |
| assay: | Soil Gross Morphology: 30% of flowers to be produced have opened |
| phenotype: | WHOLE PLANT - Small |
| notes: | 40 pct wt |
| unique F1 plant ID: | R1 PLANT:ME05214-05 |
| phenotype ID: | 89288 |
| assay: | Soil Gross Morphology: 30% of flowers to be produced have opened |
| phenotype: | ROSETTE LEAVES - Short Petioles |
| notes: | NONE |
| unique F1 plant ID: | R1 PLANT:ME05214-05 |
| phenotype ID: | 89289 |
| assay: | Soil Gross Morphology: 30% of flowers to be produced have opened |
| phenotype: | ROSETTE LEAVES - Oval Shaped |
| notes: | NONE |
| unique F1 plant ID: | R1 PLANT:ME05214-06 |
| phenotype ID: | 89320 |
| assay: | Soil Gross Morphology: 30% of flowers to be produced have opened |
| phenotype: | WHOLE PLANT - Small |
| notes: | 40 pct wt |
| unique F1 plant ID: | R1 PLANT:ME05214-06 |
| phenotype ID: | 89321 |
| assay: | Soil Gross Morphology: 30% of flowers to be produced have opened |
| phenotype: | ROSETTE LEAVES - Short Petioles |
| notes: | NONE |
| unique F1 plant ID: | R1 PLANT:ME05214-06 |
| phenotype ID: | 89322 |
| assay: | Soil Gross Morphology: 30% of flowers to be produced have opened |
| phenotype: | ROSETTE LEAVES - Oval Shaped |
| notes: | NONE |
| unique F1 plant ID: | R1 PLANT:ME05214-07 |
| phenotype ID: | 89346 |
| assay: | Soil Gross Morphology: 30% of flowers to be produced have opened |
| phenotype: | WHOLE PLANT - Small |
| notes: | 40 pct wt |
| unique F1 plant ID: | R1 PLANT:ME05214-07 |
| phenotype ID: | 89347 |
| assay: | Soil Gross Morphology: 30% of flowers to be produced have opened |
| phenotype: | ROSETTE LEAVES - Short Petioles |
| notes: | NONE |

TABLE 1-continued

| | |
|---|---|
| unique F1 plant ID: | R1 PLANT:ME05214-07 |
| phenotype ID: | 89348 |
| assay: | Soil Gross Morphology: 30% of flowers to be produced have opened |
| phenotype: | ROSETTE LEAVES - Oval Shaped |
| notes: | NONE |
| unique F1 plant ID: | R1 PLANT:ME05214-08 |
| phenotype ID: | 89390 |
| assay: | Soil Gross Morphology: 30% of flowers to be produced have opened |
| phenotype: | WHOLE PLANT - Small |
| notes: | 40 pct wt |
| unique F1 plant ID: | R1 PLANT:ME05214-08 |
| phenotype ID: | 89391 |
| assay: | Soil Gross Morphology: 30% of flowers to be produced have opened |
| phenotype: | ROSETTE LEAVES - Short Petioles |
| notes: | NONE |
| unique F1 plant ID: | R1 PLANT:ME05214-08 |
| phenotype ID: | 89392 |
| assay: | Soil Gross Morphology: 30% of flowers to be produced have opened |
| phenotype: | ROSETTE LEAVES - Oval Shaped |
| notes: | NONE |
| unique F1 plant ID: | R1 PLANT:ME05214-09 |
| phenotype ID: | 89424 |
| assay: | Soil Gross Morphology: 30% of flowers to be produced have opened |
| phenotype: | WHOLE PLANT - Small |
| notes: | 40 pct wt |
| unique F1 plant ID: | R1 PLANT:ME05214-09 |
| phenotype ID: | 89425 |
| assay: | Soil Gross Morphology: 30% of flowers to be produced have opened |
| phenotype: | ROSETTE LEAVES - Short Petioles |
| notes: | NONE |
| unique F1 plant ID: | R1 PLANT:ME05214-09 |
| phenotype ID: | 89426 |
| assay: | Soil Gross Morphology: 30% of flowers to be produced have opened |
| phenotype: | ROSETTE LEAVES - Oval Shaped |
| notes: | NONE |
| unique F1 plant ID: | R1 PLANT:ME05214-10 |
| phenotype ID: | 89449 |
| assay: | Soil Gross Morphology: 30% of flowers to be produced have opened |
| phenotype: | WHOLE PLANT - Small |
| notes: | 40 pct wt |
| unique F1 plant ID: | R1 PLANT:ME05214-10 |
| phenotype ID: | 89450 |
| assay: | Soil Gross Morphology: 30% of flowers to be produced have opened |
| phenotype: | ROSETTE LEAVES - Short Petioles |
| notes: | NONE |
| unique F1 plant ID: | R1 PLANT:ME05214-10 |
| phenotype ID: | 89451 |
| assay: | Soil Gross Morphology: 30% of flowers to be produced have opened |
| phenotype: | ROSETTE LEAVES - Oval Shaped |
| notes: | NONE |
| | Knock-in phenotype in gene(cDNA__id): 12343570 |
| clone ID: | 38214 |
| Promoter: | 35S |
| unique F1 plant ID: | R1 PLANT:ME04223-03 |
| phenotype ID: | 81980 |
| assay: | Soil Gross Morphology: First flower open |
| phenotype: | WHOLE PLANT - Dark Green |
| notes: | NONE |
| unique F1 plant ID: | R1 PLANT:ME04223-03 |
| phenotype ID: | 81981 |
| assay: | Soil Gross Morphology: 50% of flowers to be produced have opened |
| phenotype: | INFLORESCENCE - Other |
| notes: | reduced branching |
| unique F1 plant ID: | R1 PLANT:ME04223-03 |
| phenotype ID: | 81982 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04223-03 |
| phenotype ID: | 81983 |
| assay: | Soil Gross Morphology: First flower open |
| phenotype: | INFLORESCENCE - Short |
| notes: | NONE |
| unique F1 plant ID: | R1 PLANT:ME04223-03 |
| phenotype ID: | 81984 |
| assay: | Soil Gross Morphology: 50% of flowers to be produced have opened |
| phenotype: | FLOWER - Sterile |
| notes: | NONE |

TABLE 1-continued

| | |
|---|---|
| unique F1 plant ID: | R1 PLANT:ME04223-04 |
| phenotype ID: | 82367 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04223-04 |
| phenotype ID: | 82368 |
| assay: | Soil Gross Morphology: First flower open |
| phenotype: | WHOLE PLANT - Dark Green |
| notes: | NONE |
| unique F1 plant ID: | R1 PLANT:ME04223-04 |
| phenotype ID: | 82369 |
| assay: | Soil Gross Morphology: First flower open |
| phenotype: | INFLORESCENCE - Short |
| notes: | NONE |
| unique F1 plant ID: | R1 PLANT:ME04223-04 |
| phenotype ID: | 82370 |
| assay: | Soil Gross Morphology: 50% of flowers to be produced have opened |
| phenotype: | FLOWER - Sterile |
| notes: | NONE |
| unique F1 plant ID: | R1 PLANT:ME04223-04 |
| phenotype ID: | 82371 |
| assay: | Soil Gross Morphology: 50% of flowers to be produced have opened |
| phenotype: | INFLORESCENCE - Other |
| notes: | reduced branching |
| | Knock-in phenotype in gene(cDNA_id): 13492937 |
| clone ID: | 41439 |
| Promoter: | 326D |
| unique F1 plant ID: | R1 PLANT:ME09199-01 |
| phenotype ID: | 124095 |
| assay: | Soil Gross Morphology: 7 rosette leaves 1 mm in length |
| phenotype: | ROSETTE LEAVES - Cup-shaped |
| notes: | NONE |
| unique F1 plant ID: | R1 PLANT:ME09199-04 |
| phenotype ID: | 124096 |
| assay: | Soil Gross Morphology: 7 rosette leaves 1 mm in length |
| phenotype: | ROSETTE LEAVES - Cup-shaped |
| notes: | NONE |
| | Knock-in phenotype in gene(cDNA_id): 13493832 |
| clone ID: | 141805 |
| Promoter: | 35S |
| unique F1 plant ID: | R1 PLANT:ME03659-02 |
| phenotype ID: | 71878 |
| assay: | Soil Gross Morphology: First flower buds visible |
| phenotype: | INFLORESCENCE - Late Flowering |
| notes: | very late |
| unique F1 plant ID: | R1 PLANT:ME03659-03 |
| phenotype ID: | 71879 |
| assay: | Soil Gross Morphology: First flower buds visible |
| phenotype: | INFLORESCENCE - Late Flowering |
| notes: | NONE |
| | Knock-in phenotype in gene(cDNA_id): 13606025 |
| clone ID: | NULL |
| Promoter: | 35S |
| unique F1 plant ID: | R1 PLANT:ME10830-01 |
| phenotype ID: | 146048 |
| assay: | Soil Gross Morphology: 9 rosette leaves 1 mm in length |
| phenotype: | ROSETTE LEAVES - Lanceolate Shaped |
| notes: | NONE |
| unique F1 plant ID: | R1 PLANT:ME10830-02 |
| phenotype ID: | 146050 |
| assay: | Soil Gross Morphology: 7 rosette leaves 1 mm in length |
| phenotype: | ROSETTE LEAVES - Lanceolate Shaped |
| notes: | NONE |
| unique F1 plant ID: | R1 PLANT:ME10830-02 |
| phenotype ID: | 146051 |
| assay: | Soil Gross Morphology: 7 rosette leaves 1 mm in length |
| phenotype: | INFLORESCENCE - Late Flowering |
| notes: | NONE |
| unique F1 plant ID: | R1 PLANT:ME10830-03 |
| phenotype ID: | 146053 |
| assay: | Soil Gross Morphology: 6 rosette leaves 1 mm in length |
| phenotype: | ROSETTE LEAVES - Lanceolate Shaped |
| notes: | NONE |
| unique F1 plant ID: | R1 PLANT:ME10830-04 |
| phenotype ID: | 146054 |

TABLE 1-continued

| | |
|---|---|
| assay: | Soil Gross Morphology: 6 rosette leaves 1 mm in length |
| phenotype: | ROSETTE LEAVES - Lanceolate Shaped |
| notes: | NONE |
| unique F1 plant ID: | R1 PLANT:ME10830-05 |
| phenotype ID: | 146055 |
| assay: | Soil Gross Morphology: 3 rosette leaves 1 mm in length |
| phenotype: | ROSETTE LEAVES - Lanceolate Shaped |
| notes: | NONE |

Knock-in phenotype in gene(cDNA__id): 12327921

| | |
|---|---|
| clone ID: | 113719 |
| Promoter: | 35S |
| unique F1 plant ID: | R1 PLANT:ME04940-03 |
| phenotype ID: | 88884 |
| assay: | Soil Gross Morphology: 14 rosette leaves 1 mm in length |
| phenotype: | WHOLE PLANT - Other |
| notes: | grayish |
| unique F1 plant ID: | R1 PLANT:ME04940-03 |
| phenotype ID: | 88885 |
| assay: | Soil Gross Morphology: 14 rosette leaves 1 mm in length |
| phenotype: | ROSETTE LEAVES - Oval Shaped |
| notes: | NONE |
| unique F1 plant ID: | R1 PLANT:ME04940-03 |
| phenotype ID: | 88886 |
| assay: | Soil Gross Morphology: 14 rosette leaves 1 mm in length |
| phenotype: | WHOLE PLANT - Small |
| notes: | 25 percent wt |
| unique F1 plant ID: | R1 PLANT:ME04940-06 |
| phenotype ID: | 88935 |
| assay: | Soil Gross Morphology: First flower buds visible |
| phenotype: | WHOLE PLANT - Yellow-Green Viable 1 |
| notes: | NONE |
| unique F1 plant ID: | R1 PLANT:ME04940-06 |
| phenotype ID: | 88936 |
| assay: | Soil Gross Morphology: First flower buds visible |
| phenotype: | ROSETTE LEAVES - Oval Shaped |
| notes: | NONE |
| unique F1 plant ID: | R1 PLANT:ME04940-06 |
| phenotype ID: | 88937 |
| assay: | Soil Gross Morphology: First flower buds visible |
| phenotype: | WHOLE PLANT - Small |
| notes: | 25 percent wt |
| unique F1 plant ID: | R1 PLANT:ME04940-10 |
| phenotype ID: | 89006 |
| assay: | Soil Gross Morphology: 14 rosette leaves 1 mm in length |
| phenotype: | ROSETTE LEAVES - Oval Shaped |
| notes: | NONE |
| unique F1 plant ID: | R1 PLANT:ME04940-10 |
| phenotype ID: | 89007 |
| assay: | Soil Gross Morphology: 14 rosette leaves 1 mm in length |
| phenotype: | WHOLE PLANT - Small |
| notes: | 25 percent wt |

Knock-in phenotype in gene(cDNA__id): 12335159

| | |
|---|---|
| clone ID: | 25758 |
| Promoter: | 35S |
| unique F1 plant ID: | R1 PLANT:ME06526-01 |
| phenotype ID: | 99468 |
| assay: | Soil Gross Morphology: 50% of flowers to be produced have opened |
| phenotype: | INFLORESCENCE - Short Internode |
| notes: | NONE |
| unique F1 plant ID: | R1 PLANT:ME06526-01 |
| phenotype ID: | 99469 |
| assay: | Soil Gross Morphology: 50% of flowers to be produced have opened |
| phenotype: | INFLORESCENCE - Short |
| notes: | 15 pct wt |
| unique F1 plant ID: | R1 PLANT:ME06526-01 |
| phenotype ID: | 99470 |
| assay: | Soil Gross Morphology: 50% of flowers to be produced have opened |
| phenotype: | INFLORESCENCE - Other |
| notes: | all flowers at top of inflorescence |
| unique F1 plant ID: | R1 PLANT:ME06526-01 |
| phenotype ID: | 99471 |
| assay: | Soil Gross Morphology: 10% of flowers to be produced have opened |
| phenotype: | WHOLE PLANT - Dark Green |
| notes: | NONE |
| unique F1 plant ID: | R1 PLANT:ME06526-02 |
| phenotype ID: | 99486 |
| assay: | Soil Gross Morphology: 10% of flowers to be produced have opened |

TABLE 1-continued

| | |
|---|---|
| phenotype: | WHOLE PLANT - Dark Green |
| notes: | NONE |
| unique F1 plant ID: | R1 PLANT:ME06526-06 |
| phenotype ID: | 99550 |
| assay: | Soil Gross Morphology: 50% of flowers to be produced have opened |
| phenotype: | INFLORESCENCE - Short Internode |
| notes: | NONE |
| unique F1 plant ID: | R1 PLANT:ME06526-06 |
| phenotype ID: | 99551 |
| assay: | Soil Gross Morphology: 50% of flowers to be produced have opened |
| phenotype: | INFLORESCENCE - Short |
| notes: | 25 pct wt |
| unique F1 plant ID: | R1 PLANT:ME06526-06 |
| phenotype ID: | 99552 |
| assay: | Soil Gross Morphology: 50% of flowers to be produced have opened |
| phenotype: | INFLORESCENCE - Other |
| notes: | all flowers at top of inflorescence |
| unique F1 plant ID: | R1 PLANT:ME06526-07 |
| phenotype ID: | 99576 |
| assay: | Soil Gross Morphology: 50% of flowers to be produced have opened |
| phenotype: | INFLORESCENCE - Short Internode |
| notes: | NONE |
| unique F1 plant ID: | R1 PLANT:ME06526-07 |
| phenotype ID: | 99577 |
| assay: | Soil Gross Morphology: 50% of flowers to be produced have opened |
| phenotype: | INFLORESCENCE - Short |
| notes: | 40 pct wt |
| unique F1 plant ID: | R1 PLANT:ME06526-07 |
| phenotype ID: | 99578 |
| assay: | Soil Gross Morphology: 50% of flowers to be produced have opened |
| phenotype: | INFLORESCENCE - Other |
| notes: | all flowers at top of inflorescence |
| unique F1 plant ID: | R1 PLANT:ME06526-08 |
| phenotype ID: | 99590 |
| assay: | Soil Gross Morphology: 50% of flowers to be produced have opened |
| phenotype: | INFLORESCENCE - Short Internode |
| notes: | NONE |
| unique F1 plant ID: | R1 PLANT:ME06526-08 |
| phenotype ID: | 99591 |
| assay: | Soil Gross Morphology: 50% of flowers to be produced have opened |
| phenotype: | INFLORESCENCE - Short |
| notes: | 40 pct wt |
| unique F1 plant ID: | R1 PLANT:ME06526-08 |
| phenotype ID: | 99592 |
| assay: | Soil Gross Morphology: 50% of flowers to be produced have opened |
| phenotype: | INFLORESCENCE - Other |
| notes: | all flowers at top of inflorescence |
| unique F1 plant ID: | R1 PLANT:ME06526-08 |
| phenotype ID: | 99593 |
| assay: | Soil Gross Morphology: 10% of flowers to be produced have opened |
| phenotype: | WHOLE PLANT - Dark Green |
| notes: | NONE |
| unique F1 plant ID: | R1 PLANT:ME06526-10 |
| phenotype ID: | 99616 |
| assay: | Soil Gross Morphology: 50% of flowers to be produced have opened |
| phenotype: | INFLORESCENCE - Short Internode |
| notes: | NONE |
| unique F1 plant ID: | R1 PLANT:ME06526-10 |
| phenotype ID: | 99617 |
| assay: | Soil Gross Morphology: 50% of flowers to be produced have opened |
| phenotype: | INFLORESCENCE - Short |
| notes: | 25 pct wt |
| unique F1 plant ID: | R1 PLANT:ME06526-10 |
| phenotype ID: | 99618 |
| assay: | Soil Gross Morphology: 50% of flowers to be produced have opened |
| phenotype: | INFLORESCENCE - Other |
| notes: | all flowers at top of inflorescence |

Knock-in phenotype in gene(cDNA_id): 12336276

| | |
|---|---|
| clone ID: | 158108 |
| Promoter: | null |
| unique F1 plant ID: | R1 PLANT:ME07624-02 |
| phenotype ID: | 125221 |
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME07624-03 |
| phenotype ID: | 125223 |
| assay: | Soil Gross Morphology: 4 rosette leaves 1 mm in length |

TABLE 1-continued

| | |
|---|---|
| phenotype: | WHOLE PLANT - Dark Green |
| notes: | NONE |
| unique F1 plant ID: | R1 PLANT:ME07624-04 |
| phenotype ID: | 125225 |
| assay: | Soil Gross Morphology: 6 rosette leaves 1 mm in length |
| phenotype: | WHOLE PLANT - Dark Green |
| notes: | NONE |

Knock-in phenotype in gene(cDNA_id): 12338463

| | |
|---|---|
| clone ID: | 38625 |
| Promoter: | 35S |
| unique F1 plant ID: | R1 PLANT:ME06291-01 |
| phenotype ID: | 99372 |
| assay: | Soil Gross Morphology: 5 rosette leaves 1 mm in length |
| phenotype: | WHOLE PLANT - Yellow-Green Viable 1 |
| notes: | NONE |
| unique F1 plant ID: | R1 PLANT:ME06291-02 |
| phenotype ID: | 99378 |
| assay: | Soil Gross Morphology: 5 rosette leaves 1 mm in length |
| phenotype: | WHOLE PLANT - Yellow-Green Viable 1 |
| notes: | NONE |
| unique F1 plant ID: | R1 PLANT:ME06291-03 |
| phenotype ID: | 99380 |
| assay: | Soil Gross Morphology: 5 rosette leaves 1 mm in length |
| phenotype: | WHOLE PLANT - Yellow-Green Viable 1 |
| notes: | NONE |
| unique F1 plant ID: | R1 PLANT:ME06291-04 |
| phenotype ID: | 99388 |
| assay: | Soil Gross Morphology: 5 rosette leaves 1 mm in length |
| phenotype: | WHOLE PLANT - Yellow-Green Viable 1 |
| notes: | NONE |
| unique F1 plant ID: | R1 PLANT:ME06291-05 |
| phenotype ID: | 99394 |
| assay: | Soil Gross Morphology: 5 rosette leaves 1 mm in length |
| phenotype: | WHOLE PLANT - Yellow-Green Viable 1 |
| notes: | NONE |
| unique F1 plant ID: | R1 PLANT:ME06291-06 |
| phenotype ID: | 99408 |
| assay: | Soil Gross Morphology: 4 rosette leaves 1 mm in length |
| phenotype: | WHOLE PLANT - Yellow-Green Viable 1 |
| notes: | NONE |
| unique F1 plant ID: | R1 PLANT:ME06291-07 |
| phenotype ID: | 99412 |
| assay: | Soil Gross Morphology: 6 rosette leaves 1 mm in length |
| phenotype: | WHOLE PLANT - Yellow-Green Viable 1 |
| notes: | NONE |
| unique F1 plant ID: | R1 PLANT:ME06291-08 |
| phenotype ID: | 99429 |
| assay: | Soil Gross Morphology: 4 rosette leaves 1 mm in length |
| phenotype: | WHOLE PLANT - Yellow-Green Viable 1 |
| notes: | NONE |
| unique F1 plant ID: | R1 PLANT:ME06291-09 |
| phenotype ID: | 99435 |
| assay: | Soil Gross Morphology: 4 rosette leaves 1 mm in length |
| phenotype: | WHOLE PLANT - Yellow-Green Viable 1 |
| notes: | NONE |
| unique F1 plant ID: | R1 PLANT:ME06291-10 |
| phenotype ID: | 99445 |
| assay: | Soil Gross Morphology: 4 rosette leaves 1 mm in length |
| phenotype: | WHOLE PLANT - Yellow-Green Viable 1 |
| notes: | NONE |

Knock-in phenotype in gene(cDNA_id): 12338681

| | |
|---|---|
| clone ID: | 7191 |
| Promoter: | 35S |
| unique F1 plant ID: | R1 PLANT:ME06712-02 |
| phenotype ID: | 99559 |
| assay: | Soil Gross Morphology: 5 rosette leaves 1 mm in length |
| phenotype: | WHOLE PLANT - Dark Green |
| notes: | NONE |
| unique F1 plant ID: | R1 PLANT:ME06712-02 |
| phenotype ID: | 99560 |
| assay: | Soil Gross Morphology: 5 rosette leaves 1 mm in length |
| phenotype: | WHOLE PLANT - Small |
| notes: | 10 pct wt |
| unique F1 plant ID: | R1 PLANT:ME06712-06 |
| phenotype ID: | 99703 |
| assay: | Soil Gross Morphology: 5 rosette leaves 1 mm in length |
| phenotype: | WHOLE PLANT - Dark Green |

TABLE 1-continued

| | |
|---|---|
| notes: | NONE |
| unique F1 plant ID: | R1 PLANT:ME06712-06 |
| phenotype ID: | 99704 |
| assay: | Soil Gross Morphology: 5 rosette leaves 1 mm in length |
| phenotype: | WHOLE PLANT - Small |
| notes: | 15 pct wt |
| unique F1 plant ID: | R1 PLANT:ME06712-10 |
| phenotype ID: | 99787 |
| assay: | Soil Gross Morphology: 5 rosette leaves 1 mm in length |
| phenotype: | WHOLE PLANT - Dark Green |
| notes: | NONE |
| unique F1 plant ID: | R1 PLANT:ME06712-10 |
| phenotype ID: | 99788 |
| assay: | Soil Gross Morphology: 5 rosette leaves 1 mm in length |
| phenotype: | WHOLE PLANT - Small |
| notes: | 15 pct wt |

Knock-in phenotype in gene(cDNA__id): 12365221

| | |
|---|---|
| clone ID: | 241131 |
| Promoter: | 35S |
| unique F1 plant ID: | R1 PLANT:ME08460-01 |
| phenotype ID: | 124548 |
| assay: | Soil Gross Morphology: First flower open |
| phenotype: | ROSETTE LEAVES - Cup-shaped |
| notes: | NONE |
| unique F1 plant ID: | R1 PLANT:ME08460-01 |
| phenotype ID: | 124549 |
| assay: | Soil Gross Morphology: First flower open |
| phenotype: | INFLORESCENCE - Late Flowering |
| notes: | NONE |
| unique F1 plant ID: | R1 PLANT:ME08460-02 |
| phenotype ID: | 124562 |
| assay: | Soil Gross Morphology: First flower open |
| phenotype: | ROSETTE LEAVES - Cup-shaped |
| notes: | NONE |
| unique F1 plant ID: | R1 PLANT:ME08460-02 |
| phenotype ID: | 124563 |
| assay: | Soil Gross Morphology: First flower open |
| phenotype: | INFLORESCENCE - Late Flowering |
| notes: | NONE |
| unique F1 plant ID: | R1 PLANT:ME08460-04 |
| phenotype ID: | 124577 |
| assay: | Soil Gross Morphology: First flower open |
| phenotype: | ROSETTE LEAVES - Cup-shaped |
| notes: | NONE |
| unique F1 plant ID: | R1 PLANT:ME08460-04 |
| phenotype ID: | 124578 |
| assay: | Soil Gross Morphology: First flower open |
| phenotype: | INFLORESCENCE - Late Flowering |
| notes: | NONE |
| unique F1 plant ID: | R1 PLANT:ME08460-05 |
| phenotype ID: | 124588 |
| assay: | Soil Gross Morphology: First flower open |
| phenotype: | ROSETTE LEAVES - Cup-shaped |
| notes: | NONE |
| unique F1 plant ID: | R1 PLANT:ME08460-05 |
| phenotype ID: | 124589 |
| assay: | Soil Gross Morphology: First flower open |
| phenotype: | INFLORESCENCE - Late Flowering |
| notes: | NONE |
| unique F1 plant ID: | R1 PLANT:ME08460-07 |
| phenotype ID: | 124602 |
| assay: | Soil Gross Morphology: First flower open |
| phenotype: | ROSETTE LEAVES - Cup-shaped |
| notes: | NONE |
| unique F1 plant ID: | R1 PLANT:ME08460-07 |
| phenotype ID: | 124603 |
| assay: | Soil Gross Morphology: First flower open |
| phenotype: | INFLORESCENCE - Late Flowering |
| notes: | NONE |
| unique F1 plant ID: | R1 PLANT:ME08460-09 |
| phenotype ID: | 124607 |
| assay: | Soil Gross Morphology: First flower open |
| phenotype: | ROSETTE LEAVES - Cup-shaped |
| notes: | NONE |
| unique F1 plant ID: | R1 PLANT:ME08460-09 |
| phenotype ID: | 124608 |
| assay: | Soil Gross Morphology: First flower open |
| phenotype: | INFLORESCENCE - Late Flowering |

TABLE 1-continued

| | |
|---|---|
| notes: | NONE |
| unique F1 plant ID: | R1 PLANT:ME08460-09 |
| phenotype ID: | 124609 |
| assay: | Soil Gross Morphology: 11 rosette leaves 1 mm in length |
| phenotype: | WHOLE PLANT - Small |
| notes: | 50 pct wt |
| unique F1 plant ID: | R1 PLANT:ME08460-09 |
| phenotype ID: | 124610 |
| assay: | Soil Gross Morphology: 11 rosette leaves 1 mm in length |
| phenotype: | ROSETTE LEAVES - Short Petioles |
| notes: | NONE |

Knock-in phenotype in gene(cDNA_id): 12370296

| | |
|---|---|
| clone ID: | 150798 |
| Promoter: | 35S |
| unique F1 plant ID: | R1 PLANT:ME07592-01 |
| phenotype ID: | 100493 |
| assay: | Soil Gross Morphology: 5 rosette leaves 1 mm in length |
| phenotype: | WHOLE PLANT - Other |
| notes: | Pale Green |
| unique F1 plant ID: | R1 PLANT:ME07592-03 |
| phenotype ID: | 100497 |
| assay: | Soil Gross Morphology: 6 rosette leaves 1 mm in length |
| phenotype: | WHOLE PLANT - Other |
| notes: | Pale Green |
| unique F1 plant ID: | R1 PLANT:ME07592-04 |
| phenotype ID: | 100498 |
| assay: | Soil Gross Morphology: 5 rosette leaves 1 mm in length |
| phenotype: | WHOLE PLANT - Other |
| notes: | Pale Green |
| unique F1 plant ID: | R1 PLANT:ME07592-05 |
| phenotype ID: | 100500 |
| assay: | Soil Gross Morphology: 8 rosette leaves 1 mm in length |
| phenotype: | WHOLE PLANT - Other |
| notes: | Pale Green |

Knock-in phenotype in gene(cDNA_id): 12394681

| | |
|---|---|
| clone ID: | 157547 |
| Promoter: | 35S |
| unique F1 plant ID: | R1 PLANT:ME04159-01 |
| phenotype ID: | 82584 |
| assay: | Soil Gross Morphology: First flower buds visible |
| phenotype: | INFLORESCENCE - Short |
| notes: | NONE |
| unique F1 plant ID: | R1 PLANT:ME04159-01 |
| phenotype ID: | 82585 |
| assay: | Soil Gross Morphology: First flower buds visible |
| phenotype: | ROSETTE LEAVES - Other |
| notes: | fewer rosette leaves |
| unique F1 plant ID: | R1 PLANT:ME04159-01 |
| phenotype ID: | 82586 |
| assay: | Soil Gross Morphology: 50% of flowers to be produced have opened |
| phenotype: | FLOWER - Sterile |
| notes: | NONE |
| unique F1 plant ID: | R1 PLANT:ME04159-01 |
| phenotype ID: | 82587 |
| assay: | Soil Gross Morphology: 50% of flowers to be produced have opened |
| phenotype: | WHOLE PLANT - Small |
| notes: | 10 percent weight |
| unique F1 plant ID: | R1 PLANT:ME04159-01 |
| phenotype ID: | 82588 |
| assay: | Soil Gross Morphology: First flower buds visible |
| phenotype: | WHOLE PLANT - Small |
| notes: | 10 percent weight |
| unique F1 plant ID: | R1 PLANT:ME04159-03 |
| phenotype ID: | 82702 |
| assay: | Soil Gross Morphology: 10% of flowers to be produced have opened |
| phenotype: | ROSETTE LEAVES - Serrate Margins |
| notes: | NONE |
| unique F1 plant ID: | R1 PLANT:ME04159-03 |
| phenotype ID: | 82703 |
| assay: | Soil Gross Morphology: 10% of flowers to be produced have opened |
| phenotype: | ROSETTE LEAVES - Other |
| notes: | misshapen leaves |
| unique F1 plant ID: | R1 PLANT:ME04159-07 |
| phenotype ID: | 82937 |
| assay: | Soil Gross Morphology: 10% of flowers to be produced have opened |
| phenotype: | ROSETTE LEAVES - Serrate Margins |
| notes: | NONE |

TABLE 1-continued

| | |
|---|---|
| unique F1 plant ID: | R1 PLANT:ME04159-07 |
| phenotype ID: | 82938 |
| assay: | Soil Gross Morphology: 10% of flowers to be produced have opened |
| phenotype: | ROSETTE LEAVES - Other |
| notes: | misshapen leaves |
| unique F1 plant ID: | R1 PLANT:ME04159-09 |
| phenotype ID: | 83060 |
| assay: | Soil Gross Morphology: First flower open |
| phenotype: | ROSETTE LEAVES - Disorganized Rosette |
| notes: | NONE |
| unique F1 plant ID: | R1 PLANT:ME04159-09 |
| phenotype ID: | 83061 |
| assay: | Soil Gross Morphology: First flower open |
| phenotype: | INFLORESCENCE - Late Flowering |
| notes: | NONE |
| unique F1 plant ID: | R1 PLANT:ME04159-09 |
| phenotype ID: | 83062 |
| assay: | Soil Gross Morphology: First flower open |
| phenotype: | INFLORESCENCE - Short |
| notes: | NONE |
| unique F1 plant ID: | R1 PLANT:ME04159-09 |
| phenotype ID: | 83063 |
| assay: | Soil Gross Morphology: 50% of flowers to be produced have opened |
| phenotype: | FLOWER - Sterile |
| notes: | NONE |
| unique F1 plant ID: | R1 PLANT:ME04159-09 |
| phenotype ID: | 83064 |
| assay: | Soil Gross Morphology: First flower open |
| phenotype: | ROSETTE LEAVES - Other |
| notes: | misshapen leaves |
| unique F1 plant ID: | R1 PLANT:ME04159-10 |
| phenotype ID: | 83123 |
| assay: | Soil Gross Morphology: 50% of flowers to be produced have opened |
| phenotype: | INFLORESCENCE - Other |
| notes: | reduced branching |
| unique F1 plant ID: | R1 PLANT:ME04159-10 |
| phenotype ID: | 83124 |
| assay: | Soil Gross Morphology: 50% of flowers to be produced have opened |
| phenotype: | FLOWER - Sterile |
| notes: | NONE |
| | Knock-in phenotype in gene(cDNA_id): 12394980 |
| clone ID: | 6082 |
| Promoter: | 35S |
| unique F1 plant ID: | R1 PLANT:ME04999-05 |
| phenotype ID: | 88931 |
| assay: | Soil Gross Morphology: First flower buds visible |
| phenotype: | ROSETTE LEAVES - Curled 2 |
| notes: | NONE |
| unique F1 plant ID: | R1 PLANT:ME04999-05 |
| phenotype ID: | 88932 |
| assay: | Soil Gross Morphology: First flower buds visible |
| phenotype: | WHOLE PLANT - Small |
| notes: | 25 percent wt |
| unique F1 plant ID: | R1 PLANT:ME04999-06 |
| phenotype ID: | 88940 |
| assay: | Soil Gross Morphology: 6 rosette leaves 1 mm in length |
| phenotype: | WHOLE PLANT - High Anthocyanin |
| notes: | NONE |
| unique F1 plant ID: | R1 PLANT:ME04999-06 |
| phenotype ID: | 88941 |
| assay: | Soil Gross Morphology: 6 rosette leaves 1 mm in length |
| phenotype: | ROSETTE LEAVES - Oval Shaped |
| notes: | NONE |
| unique F1 plant ID: | R1 PLANT:ME04999-06 |
| phenotype ID: | 88942 |
| assay: | Soil Gross Morphology: 6 rosette leaves 1 mm in length |
| phenotype: | WHOLE PLANT - Small |
| notes: | 10 percent wt |
| unique F1 plant ID: | R1 PLANT:ME04999-07 |
| phenotype ID: | 88957 |
| assay: | Soil Gross Morphology: 4 rosette leaves 1 mm in length |
| phenotype: | WHOLE PLANT - Misc. Dwarf |
| notes: | NONE |
| unique F1 plant ID: | R1 PLANT:ME04999-08 |
| phenotype ID: | 88978 |
| assay: | Soil Gross Morphology: 10% of flowers to be produced have opened |
| phenotype: | WHOLE PLANT - Misc. Dwarf |
| notes: | NONE |

TABLE 1-continued

| | |
|---|---|
| unique F1 plant ID: | R1 PLANT:ME04999-08 |
| phenotype ID: | 88979 |
| assay: | Soil Gross Morphology: 10% of flowers to be produced have opened |
| phenotype: | WHOLE PLANT - High Anthocyanin |
| notes: | NONE |
| unique F1 plant ID: | R1 PLANT:ME04999-09 |
| phenotype ID: | 88997 |
| assay: | Soil Gross Morphology: 10% of flowers to be produced have opened |
| phenotype: | WHOLE PLANT - Misc. Dwarf |
| notes: | NONE |
| unique F1 plant ID: | R1 PLANT:ME04999-09 |
| phenotype ID: | 88998 |
| assay: | Soil Gross Morphology: 10% of flowers to be produced have opened |
| phenotype: | WHOLE PLANT - High Anthocyanin |
| notes: | NONE |
| unique F1 plant ID: | R1 PLANT:ME04999-10 |
| phenotype ID: | 89015 |
| assay: | Soil Gross Morphology: 4 rosette leaves 1 mm in length |
| phenotype: | WHOLE PLANT - Misc. Dwarf |
| notes: | NONE |

Knock-in phenotype in gene(cDNA_id): 12396516

| | |
|---|---|
| clone ID: | 98340 |
| Promoter: | 35S |
| unique F1 plant ID: | R1 PLANT:ME02479-05 |
| phenotype ID: | 54779 |
| assay: | Soil Gross Morphology: 50% of flowers to be produced have opened |
| phenotype: | WHOLE PLANT - Small |
| notes: | NONE |
| unique F1 plant ID: | R1 PLANT:ME02479-05 |
| phenotype ID: | 54780 |
| assay: | Soil Gross Morphology: 50% of flowers to be produced have opened |
| phenotype: | SILIQUES - Other |
| notes: | thick siliques, questionable phenotype, needs closer examination |
| unique F1 plant ID: | R1 PLANT:ME02479-05 |
| phenotype ID: | 54781 |
| assay: | Soil Gross Morphology: 30% of flowers to be produced have opened |
| phenotype: | WHOLE PLANT - Dark Green |
| notes: | NONE |
| unique F1 plant ID: | R1 PLANT:ME02479-05 |
| phenotype ID: | 54782 |
| assay: | Soil Gross Morphology: 30% of flowers to be produced have opened |
| phenotype: | WHOLE PLANT - Small |
| notes: | NONE |
| unique F1 plant ID: | R1 PLANT:ME02479-06 |
| phenotype ID: | 54783 |
| assay: | Soil Gross Morphology: 30% of flowers to be produced have opened |
| phenotype: | WHOLE PLANT - Small |
| notes: | NONE |
| unique F1 plant ID: | R1 PLANT:ME02479-06 |
| phenotype ID: | 54784 |
| assay: | Soil Gross Morphology: 30% of flowers to be produced have opened |
| phenotype: | WHOLE PLANT - Dark Green |
| notes: | NONE |
| unique F1 plant ID: | R1 PLANT:ME02479-06 |
| phenotype ID: | 54785 |
| assay: | Soil Gross Morphology: 50% of flowers to be produced have opened |
| phenotype: | SILIQUES - Other |
| notes: | thick siliques, questionable phenotype, needs closer examination |
| unique F1 plant ID: | R1 PLANT:ME02479-06 |
| phenotype ID: | 54786 |
| assay: | Soil Gross Morphology: 50% of flowers to be produced have opened |
| phenotype: | WHOLE PLANT - Small |
| notes: | NONE |
| unique F1 plant ID: | R1 PLANT:ME02479-07 |
| phenotype ID: | 54787 |
| assay: | Soil Gross Morphology: 30% of flowers to be produced have opened |
| phenotype: | WHOLE PLANT - Dark Green |
| notes: | NONE |
| unique F1 plant ID: | R1 PLANT:ME02479-07 |
| phenotype ID: | 54788 |
| assay: | Soil Gross Morphology: 50% of flowers to be produced have opened |
| phenotype: | WHOLE PLANT - Small |
| notes: | NONE |
| unique F1 plant ID: | R1 PLANT:ME02479-07 |
| phenotype ID: | 54789 |
| assay: | Soil Gross Morphology: 30% of flowers to be produced have opened |
| phenotype: | WHOLE PLANT - Small |
| notes: | NONE |

TABLE 1-continued

| | |
|---|---|
| unique F1 plant ID: | R1 PLANT:ME02479-07 |
| phenotype ID: | 54790 |
| assay: | Soil Gross Morphology: 50% of flowers to be produced have opened |
| phenotype: | SILIQUES - Other |
| notes: | thick siliques, questionable phenotype, needs closer examination |

Knock-in phenotype in gene(cDNA_id): 12396791

| | |
|---|---|
| clone ID: | 18820 |
| Promoter: | 35S |
| unique F1 plant ID: | R1 PLANT:ME04887-01 |
| phenotype ID: | 87808 |
| assay: | Soil Gross Morphology: 6 rosette leaves 1 mm in length |
| phenotype: | WHOLE PLANT - Standing Rosette Shaped |
| notes: | NONE |
| unique F1 plant ID: | R1 PLANT:ME04887-01 |
| phenotype ID: | 87809 |
| assay: | Soil Gross Morphology: 6 rosette leaves 1 mm in length |
| phenotype: | ROSETTE LEAVES - Curled 4 |
| notes: | curled downward |
| unique F1 plant ID: | R1 PLANT:ME04887-01 |
| phenotype ID: | 87810 |
| assay: | Soil Gross Morphology: 6 rosette leaves 1 mm in length |
| phenotype: | ROSETTE LEAVES - Other |
| notes: | small rosette leaves |
| unique F1 plant ID: | R1 PLANT:ME04887-01 |
| phenotype ID: | 87811 |
| assay: | Soil Gross Morphology: 6 rosette leaves 1 mm in length |
| phenotype: | WHOLE PLANT - Small |
| notes: | 10 pct wt |
| unique F1 plant ID: | R1 PLANT:ME04887-01 |
| phenotype ID: | 87812 |
| assay: | Soil Gross Morphology: 14 rosette leaves 1 mm in length |
| phenotype: | INFLORESCENCE - Late Flowering |
| notes: | NONE |
| unique F1 plant ID: | R1 PLANT:ME04887-01 |
| phenotype ID: | 87813 |
| assay: | Soil Gross Morphology: 14 rosette leaves 1 mm in length |
| phenotype: | ROSETTE LEAVES - Long Petioles |
| notes: | NONE |
| unique F1 plant ID: | R1 PLANT:ME04887-01 |
| phenotype ID: | 87814 |
| assay: | Soil Gross Morphology: 14 rosette leaves 1 mm in length |
| phenotype: | WHOLE PLANT - Small |
| notes: | 25 percent wt |
| unique F1 plant ID: | R1 PLANT:ME04887-01 |
| phenotype ID: | 87815 |
| assay: | Soil Gross Morphology: 14 rosette leaves 1 mm in length |
| phenotype: | ROSETTE LEAVES - Curled 4 |
| notes: | NONE |
| unique F1 plant ID: | R1 PLANT:ME04887-02 |
| phenotype ID: | 87939 |
| assay: | Soil Gross Morphology: 6 rosette leaves 1 mm in length |
| phenotype: | WHOLE PLANT - Standing Rosette Shaped |
| notes: | NONE |
| unique F1 plant ID: | R1 PLANT:ME04887-02 |
| phenotype ID: | 87940 |
| assay: | Soil Gross Morphology: 6 rosette leaves 1 mm in length |
| phenotype: | ROSETTE LEAVES - Curled 4 |
| notes: | curled downward |
| unique F1 plant ID: | R1 PLANT:ME04887-02 |
| phenotype ID: | 87941 |
| assay: | Soil Gross Morphology: 6 rosette leaves 1 mm in length |
| phenotype: | ROSETTE LEAVES - Other |
| notes: | small rosette leaves |
| unique F1 plant ID: | R1 PLANT:ME04887-02 |
| phenotype ID: | 87942 |
| assay: | Soil Gross Morphology: 6 rosette leaves 1 mm in length |
| phenotype: | WHOLE PLANT - Small |
| notes: | 10 pct wt |
| unique F1 plant ID: | R1 PLANT:ME04887-02 |
| phenotype ID: | 87943 |
| assay: | Soil Gross Morphology: First flower buds visible |
| phenotype: | INFLORESCENCE - Short |
| notes: | NONE |
| unique F1 plant ID: | R1 PLANT:ME04887-02 |
| phenotype ID: | 87944 |
| assay: | Soil Gross Morphology: First flower buds visible |
| phenotype: | INFLORESCENCE - Late Flowering |
| notes: | NONE |

TABLE 1-continued

| | |
|---|---|
| unique F1 plant ID: | R1 PLANT:ME04887-02 |
| phenotype ID: | 87945 |
| assay: | Soil Gross Morphology: First flower buds visible |
| phenotype: | ROSETTE LEAVES - Oval Shaped |
| notes: | NONE |
| unique F1 plant ID: | R1 PLANT:ME04887-02 |
| phenotype ID: | 87946 |
| assay: | Soil Gross Morphology: First flower buds visible |
| phenotype: | ROSETTE LEAVES - Cup-shaped |
| notes: | NONE |
| unique F1 plant ID: | R1 PLANT:ME04887-03 |
| phenotype ID: | 88053 |
| assay: | Soil Gross Morphology: 10 rosette leaves 1 mm in length |
| phenotype: | WHOLE PLANT - Standing Rosette Shaped |
| notes: | NONE |
| unique F1 plant ID: | R1 PLANT:ME04887-03 |
| phenotype ID: | 88054 |
| assay: | Soil Gross Morphology: 10 rosette leaves 1 mm in length |
| phenotype: | ROSETTE LEAVES - Curled 4 |
| notes: | curled downward |
| unique F1 plant ID: | R1 PLANT:ME04887-03 |
| phenotype ID: | 88055 |
| assay: | Soil Gross Morphology: 10 rosette leaves 1 mm in length |
| phenotype: | ROSETTE LEAVES - Other |
| notes: | small rosette leaves |
| unique F1 plant ID: | R1 PLANT:ME04887-03 |
| phenotype ID: | 88056 |
| assay: | Soil Gross Morphology: 14 rosette leaves 1 mm in length |
| phenotype: | ROSETTE LEAVES - Curled 5 |
| notes: | NONE |
| unique F1 plant ID: | R1 PLANT:ME04887-03 |
| phenotype ID: | 88057 |
| assay: | Soil Gross Morphology: 14 rosette leaves 1 mm in length |
| phenotype: | INFLORESCENCE - Late Flowering |
| notes: | NONE |
| unique F1 plant ID: | R1 PLANT:ME04887-03 |
| phenotype ID: | 88058 |
| assay: | Soil Gross Morphology: 14 rosette leaves 1 mm in length |
| phenotype: | ROSETTE LEAVES - Long Petioles |
| notes: | NONE |
| unique F1 plant ID: | R1 PLANT:ME04887-04 |
| phenotype ID: | 88144 |
| assay: | Soil Gross Morphology: 10% of flowers to be produced have opened |
| phenotype: | INFLORESCENCE - Short |
| notes: | NONE |
| unique F1 plant ID: | R1 PLANT:ME04887-04 |
| phenotype ID: | 88145 |
| assay: | Soil Gross Morphology: 10% of flowers to be produced have opened |
| phenotype: | INFLORESCENCE - Late Flowering |
| notes: | NONE |
| unique F1 plant ID: | R1 PLANT:ME04887-04 |
| phenotype ID: | 88146 |
| assay: | Soil Gross Morphology: 10% of flowers to be produced have opened |
| phenotype: | ROSETTE LEAVES - Oval Shaped |
| notes: | NONE |
| unique F1 plant ID: | R1 PLANT:ME04887-05 |
| phenotype ID: | 88243 |
| assay: | Soil Gross Morphology: 6 rosette leaves 1 mm in length |
| phenotype: | WHOLE PLANT - Standing Rosette Shaped |
| notes: | NONE |
| unique F1 plant ID: | R1 PLANT:ME04887-05 |
| phenotype ID: | 88244 |
| assay: | Soil Gross Morphology: 6 rosette leaves 1 mm in length |
| phenotype: | ROSETTE LEAVES - Curled 3 |
| notes: | curled downward |
| unique F1 plant ID: | R1 PLANT:ME04887-05 |
| phenotype ID: | 88245 |
| assay: | Soil Gross Morphology: 6 rosette leaves 1 mm in length |
| phenotype: | ROSETTE LEAVES - Other |
| notes: | small rosette leaves |
| unique F1 plant ID: | R1 PLANT:ME04887-05 |
| phenotype ID: | 88246 |
| assay: | Soil Gross Morphology: 10% of flowers to be produced have opened |
| phenotype: | ROSETTE LEAVES - Cup-shaped |
| notes: | NONE |
| unique F1 plant ID: | R1 PLANT:ME04887-06 |
| phenotype ID: | 88352 |
| assay: | Soil Gross Morphology: 7 rosette leaves 1 mm in length |
| phenotype: | WHOLE PLANT - Standing Rosette Shaped |

TABLE 1-continued

| | |
|---|---|
| notes: | NONE |
| unique F1 plant ID: | R1 PLANT:ME04887-06 |
| phenotype ID: | 88353 |
| assay: | Soil Gross Morphology: 7 rosette leaves 1 mm in length |
| phenotype: | ROSETTE LEAVES - Curled 4 |
| notes: | curled downward |
| unique F1 plant ID: | R1 PLANT:ME04887-06 |
| phenotype ID: | 88354 |
| assay: | Soil Gross Morphology: 7 rosette leaves 1 mm in length |
| phenotype: | ROSETTE LEAVES - Other |
| notes: | small rosette leaves |
| unique F1 plant ID: | R1 PLANT:ME04887-06 |
| phenotype ID: | 88355 |
| assay: | Soil Gross Morphology: 7 rosette leaves 1 mm in length |
| phenotype: | WHOLE PLANT - Small |
| notes: | 10 pct wt |
| unique F1 plant ID: | R1 PLANT:ME04887-06 |
| phenotype ID: | 88356 |
| assay: | Soil Gross Morphology: 14 rosette leaves 1 mm in length |
| phenotype: | WHOLE PLANT - Small |
| notes: | 10 percent wt |
| unique F1 plant ID: | R1 PLANT:ME04887-06 |
| phenotype ID: | 88357 |
| assay: | Soil Gross Morphology: 14 rosette leaves 1 mm in length |
| phenotype: | ROSETTE LEAVES - Oval Shaped |
| notes: | NONE |
| unique F1 plant ID: | R1 PLANT:ME04887-06 |
| phenotype ID: | 88358 |
| assay: | Soil Gross Morphology: 14 rosette leaves 1 mm in length |
| phenotype: | INFLORESCENCE - Late Flowering |
| notes: | NONE |
| unique F1 plant ID: | R1 PLANT:ME04887-07 |
| phenotype ID: | 88460 |
| assay: | Soil Gross Morphology: 6 rosette leaves 1 mm in length |
| phenotype: | WHOLE PLANT - Standing Rosette Shaped |
| notes: | NONE |
| unique F1 plant ID: | R1 PLANT:ME04887-07 |
| phenotype ID: | 88461 |
| assay: | Soil Gross Morphology: 6 rosette leaves 1 mm in length |
| phenotype: | ROSETTE LEAVES - Curled 4 |
| notes: | curled downward |
| unique F1 plant ID: | R1 PLANT:ME04887-07 |
| phenotype ID: | 88462 |
| assay: | Soil Gross Morphology: 6 rosette leaves 1 mm in length |
| phenotype: | ROSETTE LEAVES - Other |
| notes: | small rosette leaves |
| unique F1 plant ID: | R1 PLANT:ME04887-07 |
| phenotype ID: | 88463 |
| assay: | Soil Gross Morphology: 6 rosette leaves 1 mm in length |
| phenotype: | WHOLE PLANT - Small |
| notes: | 10 pct wt |
| unique F1 plant ID: | R1 PLANT:ME04887-07 |
| phenotype ID: | 88464 |
| assay: | Soil Gross Morphology: 14 rosette leaves 1 mm in length |
| phenotype: | WHOLE PLANT - Small |
| notes: | 10 percent wt |
| unique F1 plant ID: | R1 PLANT:ME04887-07 |
| phenotype ID: | 88465 |
| assay: | Soil Gross Morphology: 14 rosette leaves 1 mm in length |
| phenotype: | ROSETTE LEAVES - Oval Shaped |
| notes: | NONE |
| unique F1 plant ID: | R1 PLANT:ME04887-07 |
| phenotype ID: | 88466 |
| assay: | Soil Gross Morphology: 14 rosette leaves 1 mm in length |
| phenotype: | INFLORESCENCE - Late Flowering |
| notes: | NONE |
| unique F1 plant ID: | R1 PLANT:ME04887-08 |
| phenotype ID: | 88613 |
| assay: | Soil Gross Morphology: 10% of flowers to be produced have opened |
| phenotype: | WHOLE PLANT - Small |
| notes: | 25 percent wt |
| unique F1 plant ID: | R1 PLANT:ME04887-08 |
| phenotype ID: | 88614 |
| assay: | Soil Gross Morphology: 10% of flowers to be produced have opened |
| phenotype: | ROSETTE LEAVES - Curled 1 |
| notes: | NONE |
| unique F1 plant ID: | R1 PLANT:ME04887-08 |
| phenotype ID: | 88615 |
| assay: | Soil Gross Morphology: 10% of flowers to be produced have opened |

TABLE 1-continued

| | |
|---|---|
| phenotype: | ROSETTE LEAVES - Glossy |
| notes: | NONE |
| unique F1 plant ID: | R1 PLANT:ME04887-10 |
| phenotype ID: | 88813 |
| assay: | Soil Gross Morphology: 6 rosette leaves 1 mm in length |
| phenotype: | WHOLE PLANT - Standing Rosette Shaped |
| notes: | NONE |
| unique F1 plant ID: | R1 PLANT:ME04887-10 |
| phenotype ID: | 88814 |
| assay: | Soil Gross Morphology: 6 rosette leaves 1 mm in length |
| phenotype: | ROSETTE LEAVES - Curled 4 |
| notes: | curled downward |
| unique F1 plant ID: | R1 PLANT:ME04887-10 |
| phenotype ID: | 88815 |
| assay: | Soil Gross Morphology: 6 rosette leaves 1 mm in length |
| phenotype: | ROSETTE LEAVES - Other |
| notes: | small rosette leaves |
| unique F1 plant ID: | R1 PLANT:ME04887-10 |
| phenotype ID: | 88816 |
| assay: | Soil Gross Morphology: 6 rosette leaves 1 mm in length |
| phenotype: | WHOLE PLANT - Small |
| notes: | 20 pct wt |
| unique F1 plant ID: | R1 PLANT:ME04887-10 |
| phenotype ID: | 88817 |
| assay: | Soil Gross Morphology: First flower buds visible |
| phenotype: | INFLORESCENCE - Short |
| notes: | NONE |
| unique F1 plant ID: | R1 PLANT:ME04887-10 |
| phenotype ID: | 88818 |
| assay: | Soil Gross Morphology: First flower buds visible |
| phenotype: | INFLORESCENCE - Late Flowering |
| notes: | NONE |
| unique F1 plant ID: | R1 PLANT:ME04887-10 |
| phenotype ID: | 88819 |
| assay: | Soil Gross Morphology: First flower buds visible |
| phenotype: | ROSETTE LEAVES - Oval Shaped |
| notes: | NONE |
| unique F1 plant ID: | R1 PLANT:ME04887-10 |
| phenotype ID: | 88820 |
| assay: | Soil Gross Morphology: First flower buds visible |
| phenotype: | WHOLE PLANT - Small |
| notes: | 25 percent wt |
| | Knock-in phenotype in gene(cDNA_id): 12398609 |
| | |
| clone ID: | 536457 |
| Promoter: | 35S |
| unique F1 plant ID: | R1 PLANT:ME08827-05 |
| phenotype ID: | 124992 |
| assay: | Soil Gross Morphology: 7 rosette leaves 1 mm in length |
| phenotype: | INFLORESCENCE - Late Flowering |
| notes: | NONE |
| unique F1 plant ID: | R1 PLANT:ME08827-05 |
| phenotype ID: | 124993 |
| assay: | Soil Gross Morphology: 7 rosette leaves 1 mm in length |
| phenotype: | WHOLE PLANT - Small |
| notes: | 50 pct wt |
| unique F1 plant ID: | R1 PLANT:ME08827-06 |
| phenotype ID: | 125015 |
| assay: | Soil Gross Morphology: 9 rosette leaves 1 mm in length |
| phenotype: | INFLORESCENCE - Late Flowering |
| notes: | NONE |
| unique F1 plant ID: | R1 PLANT:ME08827-06 |
| phenotype ID: | 125016 |
| assay: | Soil Gross Morphology: 10% of flowers to be produced have opened |
| phenotype: | INFLORESCENCE - Late Flowering |
| notes: | NONE |
| unique F1 plant ID: | R1 PLANT:ME08827-06 |
| phenotype ID: | 125017 |
| assay: | Soil Gross Morphology: 10% of flowers to be produced have opened |
| phenotype: | WHOLE PLANT - Large |
| notes: | 125 pct wt |
| unique F1 plant ID: | R1 PLANT:ME08827-08 |
| phenotype ID: | 125061 |
| assay: | Soil Gross Morphology: 10% of flowers to be produced have opened |
| phenotype: | WHOLE PLANT - Large |
| notes: | 125 pct wt |
| | Knock-in phenotype in gene(cDNA_id): 12421224 |
| | |
| clone ID: | 41337 |

TABLE 1-continued

| | |
|---|---|
| Promoter: | 35S |
| unique F1 plant ID: | R1 PLANT:ME06282-02 |
| phenotype ID: | 99375 |
| assay: | Soil Gross Morphology: Flowering complete |
| phenotype: | WHOLE PLANT - Dark Green |
| notes: | NONE |
| unique F1 plant ID: | R1 PLANT:ME06282-02 |
| phenotype ID: | 99376 |
| assay: | Soil Gross Morphology: Flowering complete |
| phenotype: | INFLORESCENCE - Early Flowering |
| notes: | possible |
| unique F1 plant ID: | R1 PLANT:ME06282-02 |
| phenotype ID: | 99377 |
| assay: | Soil Gross Morphology: Flowering complete |
| phenotype: | FLOWER - Other |
| notes: | flowers bunched at top of bolt |
| unique F1 plant ID: | R1 PLANT:ME06282-04 |
| phenotype ID: | 99387 |
| assay: | Soil Gross Morphology: 30% of flowers to be produced have opened |
| phenotype: | INFLORESCENCE - Short |
| notes: | 10 pct wt |
| unique F1 plant ID: | R1 PLANT:ME06282-06 |
| phenotype ID: | 99406 |
| assay: | Soil Gross Morphology: 50% of flowers to be produced have opened |
| phenotype: | INFLORESCENCE - Other |
| notes: | varying internode length |
| unique F1 plant ID: | R1 PLANT:ME06282-06 |
| phenotype ID: | 99407 |
| assay: | Soil Gross Morphology: 50% of flowers to be produced have opened |
| phenotype: | INFLORESCENCE - Other |
| notes: | more siliques at flower base |
| unique F1 plant ID: | R1 PLANT:ME06282-08 |
| phenotype ID: | 99422 |
| assay: | Soil Gross Morphology: 10% of flowers to be produced have opened |
| phenotype: | WHOLE PLANT - Dark Green |
| notes: | NONE |
| unique F1 plant ID: | R1 PLANT:ME06282-08 |
| phenotype ID: | 99423 |
| assay: | Soil Gross Morphology: 10% of flowers to be produced have opened |
| phenotype: | INFLORESCENCE - Short |
| notes: | 50 pct wt |
| unique F1 plant ID: | R1 PLANT:ME06282-08 |
| phenotype ID: | 99424 |
| assay: | Soil Gross Morphology: 10% of flowers to be produced have opened |
| phenotype: | INFLORESCENCE - Early Flowering |
| notes: | questionable phenotype |
| unique F1 plant ID: | R1 PLANT:ME06282-08 |
| phenotype ID: | 99425 |
| assay: | Soil Gross Morphology: 10% of flowers to be produced have opened |
| phenotype: | FLOWER - Other |
| notes: | flowers bunched at top of bolt |
| unique F1 plant ID: | R1 PLANT:ME06282-08 |
| phenotype ID: | 99426 |
| assay: | Soil Gross Morphology: 30% of flowers to be produced have opened |
| phenotype: | INFLORESCENCE - Other |
| notes: | varying internode length |
| unique F1 plant ID: | R1 PLANT:ME06282-08 |
| phenotype ID: | 99427 |
| assay: | Soil Gross Morphology: 30% of flowers to be produced have opened |
| phenotype: | INFLORESCENCE - Other |
| notes: | more siliques at flower base |
| unique F1 plant ID: | R1 PLANT:ME06282-08 |
| phenotype ID: | 99428 |
| assay: | Soil Gross Morphology: 30% of flowers to be produced have opened |
| phenotype: | INFLORESCENCE - Short |
| notes: | 15 pct wt |
| | Knock-in phenotype in gene(cDNA_id): 12442501 |
| | |
| clone ID: | 608818 |
| Promoter: | 35S |
| unique F1 plant ID: | R1 PLANT:ME05206-03 |
| phenotype ID: | 89201 |
| assay: | Soil Gross Morphology: 10% of flowers to be produced have opened |
| phenotype: | WHOLE PLANT - Small |
| notes: | 30 pct wt |
| unique F1 plant ID: | R1 PLANT:ME05206-03 |
| phenotype ID: | 89202 |
| assay: | Soil Gross Morphology: 10% of flowers to be produced have opened |
| phenotype: | ROSETTE LEAVES - Curled 4 |

TABLE 1-continued

| | |
|---|---|
| notes: | NONE |
| unique F1 plant ID: | R1 PLANT:ME05206-07 |
| phenotype ID: | 89342 |
| assay: | Soil Gross Morphology: 10% of flowers to be produced have opened |
| phenotype: | WHOLE PLANT - Small |
| notes: | 30 pct wt |
| unique F1 plant ID: | R1 PLANT:ME05206-08 |
| phenotype ID: | 89378 |
| assay: | Soil Gross Morphology: 10% of flowers to be produced have opened |
| phenotype: | WHOLE PLANT - Small |
| notes: | 40 pct wt |
| unique F1 plant ID: | R1 PLANT:ME05206-08 |
| phenotype ID: | 89379 |
| assay: | Soil Gross Morphology: 10% of flowers to be produced have opened |
| phenotype: | ROSETTE LEAVES - Curled 5 |
| notes: | NONE |
| unique F1 plant ID: | R1 PLANT:ME05206-10 |
| phenotype ID: | 89448 |
| assay: | Soil Gross Morphology: 10% of flowers to be produced have opened |
| phenotype: | WHOLE PLANT - Small |
| notes: | 40 pct wt |

Knock-in phenotype in gene(cDNA_id): 12447172

| | |
|---|---|
| clone ID: | 681088 |
| Promoter: | 35S |
| unique F1 plant ID: | R1 PLANT:ME03190-01 |
| phenotype ID: | 71413 |
| assay: | Soil Gross Morphology: 50% of flowers to be produced have opened |
| phenotype: | ROSETTE LEAVES - Curled 1 |
| notes: | NONE |
| unique F1 plant ID: | R1 PLANT:ME03190-01 |
| phenotype ID: | 71414 |
| assay: | Soil Gross Morphology: 50% of flowers to be produced have opened |
| phenotype: | WHOLE PLANT - Small |
| notes: | 25pct. of wt |
| unique F1 plant ID: | R1 PLANT:ME03190-02 |
| phenotype ID: | 71429 |
| assay: | Soil Gross Morphology: 50% of flowers to be produced have opened |
| phenotype: | ROSETTE LEAVES - Curled 1 |
| notes: | NONE |
| unique F1 plant ID: | R1 PLANT:ME03190-02 |
| phenotype ID: | 71430 |
| assay: | Soil Gross Morphology: 50% of flowers to be produced have opened |
| phenotype: | WHOLE PLANT - Small |
| notes: | 50pct. of wt |
| unique F1 plant ID: | R1 PLANT:ME03190-03 |
| phenotype ID: | 71455 |
| assay: | Soil Gross Morphology: 10% of flowers to be produced have opened |
| phenotype: | WHOLE PLANT - Small |
| notes: | 70pct.of wt |
| unique F1 plant ID: | R1 PLANT:ME03190-03 |
| phenotype ID: | 71456 |
| assay: | Soil Gross Morphology: 10% of flowers to be produced have opened |
| phenotype: | ROSETTE LEAVES - Curled 1 |
| notes: | less so |
| unique F1 plant ID: | R1 PLANT:ME03190-04 |
| phenotype ID: | 71482 |
| assay: | Soil Gross Morphology: 10% of flowers to be produced have opened |
| phenotype: | ROSETTE LEAVES - Curled 1 |
| notes: | NONE |
| unique F1 plant ID: | R1 PLANT:ME03190-04 |
| phenotype ID: | 71483 |
| assay: | Soil Gross Morphology: 10% of flowers to be produced have opened |
| phenotype: | WHOLE PLANT - Small |
| notes: | 10pct. of wt |
| unique F1 plant ID: | R1 PLANT:ME03190-09 |
| phenotype ID: | 71538 |
| assay: | Soil Gross Morphology: 50% of flowers to be produced have opened |
| phenotype: | WHOLE PLANT - Small |
| notes: | 50pct. of wt |
| unique F1 plant ID: | R1 PLANT:ME03190-09 |
| phenotype ID: | 71539 |
| assay: | Soil Gross Morphology: 50% of flowers to be produced have opened |
| phenotype: | ROSETTE LEAVES - Lanceolate Shaped |
| notes: | NONE |

Knock-in phenotype in gene(cDNA_id): 12452925

| | |
|---|---|
| clone ID: | 691319 |
| Promoter: | 35S |

TABLE 1-continued

| | |
|---|---|
| unique F1 plant ID: | R1 PLANT:ME05057-01 |
| phenotype ID: | 89108 |
| assay: | Soil Gross Morphology: 50% of flowers to be produced have opened |
| phenotype: | ROSETTE LEAVES - Disorganized Rosette |
| notes: | NONE |
| unique F1 plant ID: | R1 PLANT:ME05057-01 |
| phenotype ID: | 89109 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME05057-01 |
| phenotype ID: | 89110 |
| assay: | Soil Gross Morphology: 50% of flowers to be produced have opened |
| phenotype: | ROSETTE LEAVES - Other |
| notes: | extra rosette leaves |
| unique F1 plant ID: | R1 PLANT:ME05057-01 |
| phenotype ID: | 89111 |
| assay: | Soil Gross Morphology: 50% of flowers to be produced have opened |
| phenotype: | WHOLE PLANT - Small |
| notes: | 50 pct wt |
| unique F1 plant ID: | R1 PLANT:ME05057-01 |
| phenotype ID: | 89112 |
| assay: | Soil Gross Morphology: 50% of flowers to be produced have opened |
| phenotype: | INFLORESCENCE - Short |
| notes: | 40 pct wt |
| unique F1 plant ID: | R1 PLANT:ME05057-02 |
| phenotype ID: | 89142 |
| assay: | Soil Gross Morphology: 50% of flowers to be produced have opened |
| phenotype: | ROSETTE LEAVES - Disorganized Rosette |
| notes: | NONE |
| unique F1 plant ID: | R1 PLANT:ME05057-02 |
| phenotype ID: | 89143 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME05057-02 |
| phenotype ID: | 89144 |
| assay: | Soil Gross Morphology: 50% of flowers to be produced have opened |
| phenotype: | ROSETTE LEAVES - Other |
| notes: | extra rosette leaves |
| unique F1 plant ID: | R1 PLANT:ME05057-02 |
| phenotype ID: | 89145 |
| assay: | Soil Gross Morphology: 50% of flowers to be produced have opened |
| phenotype: | WHOLE PLANT - Small |
| notes: | 20 pct wt |
| unique F1 plant ID: | R1 PLANT:ME05057-02 |
| phenotype ID: | 89146 |
| assay: | Soil Gross Morphology: 50% of flowers to be produced have opened |
| phenotype: | INFLORESCENCE - Short |
| notes: | 10 pct wt |
| unique F1 plant ID: | R1 PLANT:ME05057-03 |
| phenotype ID: | 89183 |
| assay: | Soil Gross Morphology: 50% of flowers to be produced have opened |
| phenotype: | ROSETTE LEAVES - Disorganized Rosette |
| notes: | NONE |
| unique F1 plant ID: | R1 PLANT:ME05057-03 |
| phenotype ID: | 89184 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME05057-03 |
| phenotype ID: | 89185 |
| assay: | Soil Gross Morphology: 50% of flowers to be produced have opened |
| phenotype: | ROSETTE LEAVES - Other |
| notes: | extra rosette leaves |
| unique F1 plant ID: | R1 PLANT:ME05057-03 |
| phenotype ID: | 89186 |
| assay: | Soil Gross Morphology: 50% of flowers to be produced have opened |
| phenotype: | WHOLE PLANT - Small |
| notes: | 20 pct wt |
| unique F1 plant ID: | R1 PLANT:ME05057-03 |
| phenotype ID: | 89187 |
| assay: | Soil Gross Morphology: 50% of flowers to be produced have opened |
| phenotype: | INFLORESCENCE - Short |
| notes: | 10 pct wt |
| unique F1 plant ID: | R1 PLANT:ME05057-04 |
| phenotype ID: | 89232 |
| assay: | Soil Gross Morphology: 50% of flowers to be produced have opened |
| phenotype: | ROSETTE LEAVES - Disorganized Rosette |

TABLE 1-continued

| | |
|---|---|
| notes: | NONE |
| unique F1 plant ID: | R1 PLANT:ME05057-04 |
| phenotype ID: | 89233 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME05057-04 |
| phenotype ID: | 89234 |
| assay: | Soil Gross Morphology: 50% of flowers to be produced have opened |
| phenotype: | ROSETTE LEAVES - Other |
| notes: | extra rosette leaves |
| unique F1 plant ID: | R1 PLANT:ME05057-04 |
| phenotype ID: | 89235 |
| assay: | Soil Gross Morphology: 50% of flowers to be produced have opened |
| phenotype: | WHOLE PLANT - Small |
| notes: | 20 pct wt |
| unique F1 plant ID: | R1 PLANT:ME05057-04 |
| phenotype ID: | 89236 |
| assay: | Soil Gross Morphology: 50% of flowers to be produced have opened |
| phenotype: | INFLORESCENCE - Short |
| notes: | 10 pct wt |
| unique F1 plant ID: | R1 PLANT:ME05057-05 |
| phenotype ID: | 89268 |
| assay: | Soil Gross Morphology: 50% of flowers to be produced have opened |
| phenotype: | ROSETTE LEAVES - Disorganized Rosette |
| notes: | NONE |
| unique F1 plant ID: | R1 PLANT:ME05057-05 |
| phenotype ID: | 89269 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME05057-05 |
| phenotype ID: | 89270 |
| assay: | Soil Gross Morphology: 50% of flowers to be produced have opened |
| phenotype: | ROSETTE LEAVES - Other |
| notes: | extra rosette leaves |
| unique F1 plant ID: | R1 PLANT:ME05057-05 |
| phenotype ID: | 89271 |
| assay: | Soil Gross Morphology: 50% of flowers to be produced have opened |
| phenotype: | WHOLE PLANT - Small |
| notes: | 50 pct wt |
| unique F1 plant ID: | R1 PLANT:ME05057-05 |
| phenotype ID: | 89272 |
| assay: | Soil Gross Morphology: 50% of flowers to be produced have opened |
| phenotype: | INFLORESCENCE - Short |
| notes: | 40 pct wt |
| unique F1 plant ID: | R1 PLANT:ME05057-06 |
| phenotype ID: | 89307 |
| assay: | Soil Gross Morphology: 50% of flowers to be produced have opened |
| phenotype: | ROSETTE LEAVES - Disorganized Rosette |
| notes: | NONE |
| unique F1 plant ID: | R1 PLANT:ME05057-06 |
| phenotype ID: | 89308 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME05057-06 |
| phenotype ID: | 89309 |
| assay: | Soil Gross Morphology: 50% of flowers to be produced have opened |
| phenotype: | ROSETTE LEAVES - Other |
| notes: | extra rosette leaves |
| unique F1 plant ID: | R1 PLANT:ME05057-06 |
| phenotype ID: | 89310 |
| assay: | Soil Gross Morphology: 50% of flowers to be produced have opened |
| phenotype: | WHOLE PLANT - Small |
| notes: | 50 pct wt |
| unique F1 plant ID: | R1 PLANT:ME05057-06 |
| phenotype ID: | 89311 |
| assay: | Soil Gross Morphology: 50% of flowers to be produced have opened |
| phenotype: | INFLORESCENCE - Short |
| notes: | 40 pct wt |
| unique F1 plant ID: | R1 PLANT:ME05057-07 |
| phenotype ID: | 89335 |
| assay: | Soil Gross Morphology: 50% of flowers to be produced have opened |
| phenotype: | ROSETTE LEAVES - Disorganized Rosette |
| notes: | NONE |
| unique F1 plant ID: | R1 PLANT:ME05057-07 |
| phenotype ID: | 89336 |
| assay: | Soil Gross Morphology: 50% of flowers to be produced have opened |

TABLE 1-continued

| | |
|---|---|
| phenotype: | ROSETTE LEAVES - Lanceolate Shaped |
| notes: | NONE |
| unique F1 plant ID: | R1 PLANT:ME05057-07 |
| phenotype ID: | 89337 |
| assay: | Soil Gross Morphology: 50% of flowers to be produced have opened |
| phenotype: | ROSETTE LEAVES - Other |
| notes: | extra rosette leaves |
| unique F1 plant ID: | R1 PLANT:ME05057-07 |
| phenotype ID: | 89338 |
| assay: | Soil Gross Morphology: 50% of flowers to be produced have opened |
| phenotype: | WHOLE PLANT - Small |
| notes: | 50 pct wt |
| unique F1 plant ID: | R1 PLANT:ME05057-07 |
| phenotype ID: | 89339 |
| assay: | Soil Gross Morphology: 50% of flowers to be produced have opened |
| phenotype: | INFLORESCENCE - Short |
| notes: | 40 pct wt |
| unique F1 plant ID: | R1 PLANT:ME05057-08 |
| phenotype ID: | 89364 |
| assay: | Soil Gross Morphology: 50% of flowers to be produced have opened |
| phenotype: | ROSETTE LEAVES - Disorganized Rosette |
| notes: | NONE |
| unique F1 plant ID: | R1 PLANT:ME05057-08 |
| phenotype ID: | 89365 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME05057-08 |
| phenotype ID: | 89366 |
| assay: | Soil Gross Morphology: 50% of flowers to be produced have opened |
| phenotype: | ROSETTE LEAVES - Other |
| notes: | extra rosette leaves |
| unique F1 plant ID: | R1 PLANT:ME05057-08 |
| phenotype ID: | 89367 |
| assay: | Soil Gross Morphology: 50% of flowers to be produced have opened |
| phenotype: | WHOLE PLANT - Small |
| notes: | 50 pct wt |
| unique F1 plant ID: | R1 PLANT:ME05057-08 |
| phenotype ID: | 89368 |
| assay: | Soil Gross Morphology: 50% of flowers to be produced have opened |
| phenotype: | INFLORESCENCE - Short |
| notes: | 40 pct wt |
| unique F1 plant ID: | R1 PLANT:ME05057-09 |
| phenotype ID: | 89409 |
| assay: | Soil Gross Morphology: 50% of flowers to be produced have opened |
| phenotype: | ROSETTE LEAVES - Disorganized Rosette |
| notes: | NONE |
| unique F1 plant ID: | R1 PLANT:ME05057-09 |
| phenotype ID: | 89410 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME05057-09 |
| phenotype ID: | 89411 |
| assay: | Soil Gross Morphology: 50% of flowers to be produced have opened |
| phenotype: | ROSETTE LEAVES - Other |
| notes: | extra rosette leaves |
| unique F1 plant ID: | R1 PLANT:ME05057-09 |
| phenotype ID: | 89412 |
| assay: | Soil Gross Morphology: 50% of flowers to be produced have opened |
| phenotype: | WHOLE PLANT - Small |
| notes: | 20 pct wt |
| unique F1 plant ID: | R1 PLANT:ME05057-09 |
| phenotype ID: | 89413 |
| assay: | Soil Gross Morphology: 50% of flowers to be produced have opened |
| phenotype: | INFLORESCENCE - Short |
| notes: | 10 pct wt |
| unique F1 plant ID: | R1 PLANT:ME05057-10 |
| phenotype ID: | 89442 |
| assay: | Soil Gross Morphology: 50% of flowers to be produced have opened |
| phenotype: | ROSETTE LEAVES - Disorganized Rosette |
| notes: | NONE |
| unique F1 plant ID: | R1 PLANT:ME05057-10 |
| phenotype ID: | 89443 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME05057-10 |
| phenotype ID: | 89444 |

TABLE 1-continued

| | |
|---|---|
| assay: | Soil Gross Morphology: 50% of flowers to be produced have opened |
| phenotype: | ROSETTE LEAVES - Other |
| notes: | extra rosette leaves |
| unique F1 plant ID: | R1 PLANT:ME05057-10 |
| phenotype ID: | 89445 |
| assay: | Soil Gross Morphology: 50% of flowers to be produced have opened |
| phenotype: | WHOLE PLANT - Small |
| notes: | 50 pct wt |
| unique F1 plant ID: | R1 PLANT:ME05057-10 |
| phenotype ID: | 89446 |
| assay: | Soil Gross Morphology: 50% of flowers to be produced have opened |
| phenotype: | INFLORESCENCE - Short |
| notes: | 40 pct wt |

Knock-in phenotype in gene(cDNA_id): 12562634

| | |
|---|---|
| clone ID: | 123905 |
| Promoter: | 13879F |
| unique F1 plant ID: | R1 PLANT:ME04689-01 |
| phenotype ID: | 100648 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04689-01 |
| phenotype ID: | 100649 |
| assay: | Soil Gross Morphology: 50% of flowers to be produced have opened |
| phenotype: | ROSETTE LEAVES - Other |
| notes: | increased leaf number |
| unique F1 plant ID: | R1 PLANT:ME04689-01 |
| phenotype ID: | 100650 |
| assay: | Soil Gross Morphology: 50% of flowers to be produced have opened |
| phenotype: | INFLORESCENCE - Short |
| notes: | 75 pct. wt |
| unique F1 plant ID: | R1 PLANT:ME04689-01 |
| phenotype ID: | 100651 |
| assay: | Soil Gross Morphology: 50% of flowers to be produced have opened |
| phenotype: | INFLORESCENCE - Other |
| notes: | extra inflorescence |
| unique F1 plant ID: | R1 PLANT:ME04689-02 |
| phenotype ID: | 100771 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04689-02 |
| phenotype ID: | 100772 |
| assay: | Soil Gross Morphology: 50% of flowers to be produced have opened |
| phenotype: | ROSETTE LEAVES - Other |
| notes: | increased leaf number |
| unique F1 plant ID: | R1 PLANT:ME04689-02 |
| phenotype ID: | 100773 |
| assay: | Soil Gross Morphology: 50% of flowers to be produced have opened |
| phenotype: | INFLORESCENCE - Short |
| notes: | 75 pct. wt |
| unique F1 plant ID: | R1 PLANT:ME04689-02 |
| phenotype ID: | 100774 |
| assay: | Soil Gross Morphology: 50% of flowers to be produced have opened |
| phenotype: | INFLORESCENCE - Other |
| notes: | extra inflorescence |
| unique F1 plant ID: | R1 PLANT:ME04689-03 |
| phenotype ID: | 100899 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04689-03 |
| phenotype ID: | 100900 |
| assay: | Soil Gross Morphology: 50% of flowers to be produced have opened |
| phenotype: | ROSETTE LEAVES - Other |
| notes: | increased leaf number |
| unique F1 plant ID: | R1 PLANT:ME04689-03 |
| phenotype ID: | 100901 |
| assay: | Soil Gross Morphology: 50% of flowers to be produced have opened |
| phenotype: | INFLORESCENCE - Short |
| notes: | 75 pct. wt |
| unique F1 plant ID: | R1 PLANT:ME04689-03 |
| phenotype ID: | 100902 |
| assay: | Soil Gross Morphology: 50% of flowers to be produced have opened |
| phenotype: | INFLORESCENCE - Other |
| notes: | extra inflorescence |
| unique F1 plant ID: | R1 PLANT:ME04689-03 |
| phenotype ID: | 100903 |

TABLE 1-continued

| | |
|---|---|
| assay: | Soil Gross Morphology: 50% of flowers to be produced have opened |
| phenotype: | FLOWER - Reduced fertility |
| notes: | NONE |
| unique F1 plant ID: | R1 PLANT:ME04689-04 |
| phenotype ID: | 101035 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04689-04 |
| phenotype ID: | 101036 |
| assay: | Soil Gross Morphology: 50% of flowers to be produced have opened |
| phenotype: | ROSETTE LEAVES - Other |
| notes: | increased leaf number |
| unique F1 plant ID: | R1 PLANT:ME04689-04 |
| phenotype ID: | 101037 |
| assay: | Soil Gross Morphology: 50% of flowers to be produced have opened |
| phenotype: | INFLORESCENCE - Short |
| notes: | 75 pct. wt |
| unique F1 plant ID: | R1 PLANT:ME04689-04 |
| phenotype ID: | 101038 |
| assay: | Soil Gross Morphology: 50% of flowers to be produced have opened |
| phenotype: | INFLORESCENCE - Other |
| notes: | extra inflorescence |
| unique F1 plant ID: | R1 PLANT:ME04689-05 |
| phenotype ID: | 101168 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04689-05 |
| phenotype ID: | 101169 |
| assay: | Soil Gross Morphology: 50% of flowers to be produced have opened |
| phenotype: | ROSETTE LEAVES - Other |
| notes: | increased leaf number |
| unique F1 plant ID: | R1 PLANT:ME04689-05 |
| phenotype ID: | 101170 |
| assay: | Soil Gross Morphology: 50% of flowers to be produced have opened |
| phenotype: | INFLORESCENCE - Short |
| notes: | 75 pct. wt |
| unique F1 plant ID: | R1 PLANT:ME04689-05 |
| phenotype ID: | 101171 |
| assay: | Soil Gross Morphology: 50% of flowers to be produced have opened |
| phenotype: | INFLORESCENCE - Other |
| notes: | extra inflorescence |
| unique F1 plant ID: | R1 PLANT:ME04689-06 |
| phenotype ID: | 101296 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04689-06 |
| phenotype ID: | 101297 |
| assay: | Soil Gross Morphology: 50% of flowers to be produced have opened |
| phenotype: | ROSETTE LEAVES - Other |
| notes: | increased leaf number |
| unique F1 plant ID: | R1 PLANT:ME04689-06 |
| phenotype ID: | 101298 |
| assay: | Soil Gross Morphology: 50% of flowers to be produced have opened |
| phenotype: | INFLORESCENCE - Short |
| notes: | 75 pct. wt |
| unique F1 plant ID: | R1 PLANT:ME04689-06 |
| phenotype ID: | 101299 |
| assay: | Soil Gross Morphology: 50% of flowers to be produced have opened |
| phenotype: | INFLORESCENCE - Other |
| notes: | extra inflorescence |
| unique F1 plant ID: | R1 PLANT:ME04689-06 |
| phenotype ID: | 101300 |
| assay: | Soil Gross Morphology: 50% of flowers to be produced have opened |
| phenotype: | FLOWER - Reduced fertility |
| notes: | NONE |
| unique F1 plant ID: | R1 PLANT:ME04689-07 |
| phenotype ID: | 101421 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04689-07 |
| phenotype ID: | 101422 |
| assay: | Soil Gross Morphology: 50% of flowers to be produced have opened |
| phenotype: | ROSETTE LEAVES - Other |
| notes: | increased leaf number |
| unique F1 plant ID: | R1 PLANT:ME04689-07 |

TABLE 1-continued

| | |
|---|---|
| phenotype ID: | 101423 |
| assay: | Soil Gross Morphology: 50% of flowers to be produced have opened |
| phenotype: | INFLORESCENCE - Short |
| notes: | 75 pct. wt |
| unique F1 plant ID: | R1 PLANT:ME04689-07 |
| phenotype ID: | 101424 |
| assay: | Soil Gross Morphology: 50% of flowers to be produced have opened |
| phenotype: | INFLORESCENCE - Other |
| notes: | extra inflorescence |
| unique F1 plant ID: | R1 PLANT:ME04689-08 |
| phenotype ID: | 101544 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04689-08 |
| phenotype ID: | 101545 |
| assay: | Soil Gross Morphology: 50% of flowers to be produced have opened |
| phenotype: | ROSETTE LEAVES - Other |
| notes: | increased leaf number |
| unique F1 plant ID: | R1 PLANT:ME04689-08 |
| phenotype ID: | 101546 |
| assay: | Soil Gross Morphology: 50% of flowers to be produced have opened |
| phenotype: | INFLORESCENCE - Short |
| notes: | 25 pct wt |
| unique F1 plant ID: | R1 PLANT:ME04689-08 |
| phenotype ID: | 101547 |
| assay: | Soil Gross Morphology: 50% of flowers to be produced have opened |
| phenotype: | INFLORESCENCE - Other |
| notes: | extra inflorescence |
| unique F1 plant ID: | R1 PLANT:ME04689-08 |
| phenotype ID: | 101548 |
| assay: | Soil Gross Morphology: 50% of flowers to be produced have opened |
| phenotype: | FLOWER - Reduced fertility |
| notes: | NONE |
| unique F1 plant ID: | R1 PLANT:ME04689-09 |
| phenotype ID: | 101681 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04689-09 |
| phenotype ID: | 101682 |
| assay: | Soil Gross Morphology: 50% of flowers to be produced have opened |
| phenotype: | ROSETTE LEAVES - Other |
| notes: | increased leaf number |
| unique F1 plant ID: | R1 PLANT:ME04689-09 |
| phenotype ID: | 101683 |
| assay: | Soil Gross Morphology: 50% of flowers to be produced have opened |
| phenotype: | INFLORESCENCE - Short |
| notes: | 75 pct. wt |
| unique F1 plant ID: | R1 PLANT:ME04689-09 |
| phenotype ID: | 101684 |
| assay: | Soil Gross Morphology: 50% of flowers to be produced have opened |
| phenotype: | INFLORESCENCE - Other |
| notes: | extra inflorescence |
| unique F1 plant ID: | R1 PLANT:ME04689-10 |
| phenotype ID: | 101807 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04689-10 |
| phenotype ID: | 101808 |
| assay: | Soil Gross Morphology: 50% of flowers to be produced have opened |
| phenotype: | ROSETTE LEAVES - Other |
| notes: | increased leaf number |
| unique F1 plant ID: | R1 PLANT:ME04689-10 |
| phenotype ID: | 101809 |
| assay: | Soil Gross Morphology: 50% of flowers to be produced have opened |
| phenotype: | INFLORESCENCE - Short |
| notes: | 75 pct. wt |
| unique F1 plant ID: | R1 PLANT:ME04689-10 |
| phenotype ID: | 101810 |
| assay: | Soil Gross Morphology: 50% of flowers to be produced have opened |
| phenotype: | INFLORESCENCE - Other |
| notes: | extra inflorescence |
| unique F1 plant ID: | R1 PLANT:ME05073-01 |
| phenotype ID: | 101914 |
| assay: | Soil Gross Morphology: 10% of flowers to be produced have opened |
| phenotype: | WHOLE PLANT - Dark Green |
| notes: | NONE |

TABLE 1-continued

```
unique F1 plant ID:   R1 PLANT:ME05073-01
phenotype ID:         101915
assay:                Soil Gross Morphology: 10% of flowers to be produced have opened
phenotype:            INFLORESCENCE - Late Flowering
notes:                NONE
unique F1 plant ID:   R1 PLANT:ME05073-01
phenotype ID:         101916
assay:                Soil Gross Morphology: 10% of flowers to be produced have opened
phenotype:            ROSETTE LEAVES - Lanceolate Shaped
notes:                NONE
unique F1 plant ID:   R1 PLANT:ME05073-01
phenotype ID:         101917
assay:                Soil Gross Morphology: 10% of flowers to be produced have opened
phenotype:            ROSETTE LEAVES - Serrate Margins
notes:                NONE
unique F1 plant ID:   R1 PLANT:ME05073-01
phenotype ID:         101918
assay:                Soil Gross Morphology: 10% of flowers to be produced have opened
phenotype:            ROSETTE LEAVES - Other
notes:                extra rosette leaves
unique F1 plant ID:   R1 PLANT:ME05073-02
phenotype ID:         101952
assay:                Soil Gross Morphology: 30% of flowers to be produced have opened
phenotype:            ROSETTE LEAVES - Lanceolate Shaped
notes:                NONE
unique F1 plant ID:   R1 PLANT:ME05073-02
phenotype ID:         101953
assay:                Soil Gross Morphology: 30% of flowers to be produced have opened
phenotype:            ROSETTE LEAVES - Other
notes:                extra rosette leaves
unique F1 plant ID:   R1 PLANT:ME05073-02
phenotype ID:         101954
assay:                Soil Gross Morphology: 30% of flowers to be produced have opened
phenotype:            WHOLE PLANT - Dark Green
notes:                NONE
unique F1 plant ID:   R1 PLANT:ME05073-02
phenotype ID:         101955
assay:                Soil Gross Morphology: 30% of flowers to be produced have opened
phenotype:            INFLORESCENCE - Short
notes:                75 pct wt
unique F1 plant ID:   R1 PLANT:ME05073-03
phenotype ID:         101977
assay:                Soil Gross Morphology: 30% of flowers to be produced have opened
phenotype:            ROSETTE LEAVES - Lanceolate Shaped
notes:                NONE
unique F1 plant ID:   R1 PLANT:ME05073-03
phenotype ID:         101978
assay:                Soil Gross Morphology: 30% of flowers to be produced have opened
phenotype:            ROSETTE LEAVES - Other
notes:                extra rosette leaves
unique F1 plant ID:   R1 PLANT:ME05073-03
phenotype ID:         101979
assay:                Soil Gross Morphology: 30% of flowers to be produced have opened
phenotype:            WHOLE PLANT - Dark Green
notes:                NONE
unique F1 plant ID:   R1 PLANT:ME05073-03
phenotype ID:         101980
assay:                Soil Gross Morphology: 30% of flowers to be produced have opened
phenotype:            INFLORESCENCE - Short
notes:                75 pct wt
unique F1 plant ID:   R1 PLANT:ME05073-04
phenotype ID:         102005
assay:                Soil Gross Morphology: 30% of flowers to be produced have opened
phenotype:            ROSETTE LEAVES - Lanceolate Shaped
notes:                NONE
unique F1 plant ID:   R1 PLANT:ME05073-04
phenotype ID:         102006
assay:                Soil Gross Morphology: 30% of flowers to be produced have opened
phenotype:            ROSETTE LEAVES - Other
notes:                extra rosette leaves
unique F1 plant ID:   R1 PLANT:ME05073-04
phenotype ID:         102007
assay:                Soil Gross Morphology: 30% of flowers to be produced have opened
phenotype:            WHOLE PLANT - Dark Green
notes:                NONE
unique F1 plant ID:   R1 PLANT:ME05073-04
phenotype ID:         102008
assay:                Soil Gross Morphology: 30% of flowers to be produced have opened
phenotype:            INFLORESCENCE - Short
```

TABLE 1-continued

| | |
|---|---|
| notes: | 75 pct wt |
| unique F1 plant ID: | R1 PLANT:ME05073-05 |
| phenotype ID: | 102029 |
| assay: | Soil Gross Morphology: 30% of flowers to be produced have opened |
| phenotype: | ROSETTE LEAVES - Lanceolate Shaped |
| notes: | NONE |
| unique F1 plant ID: | R1 PLANT:ME05073-05 |
| phenotype ID: | 102030 |
| assay: | Soil Gross Morphology: 30% of flowers to be produced have opened |
| phenotype: | ROSETTE LEAVES - Other |
| notes: | extra rosette leaves |
| unique F1 plant ID: | R1 PLANT:ME05073-05 |
| phenotype ID: | 102031 |
| assay: | Soil Gross Morphology: 30% of flowers to be produced have opened |
| phenotype: | WHOLE PLANT - Dark Green |
| notes: | NONE |
| unique F1 plant ID: | R1 PLANT:ME05073-05 |
| phenotype ID: | 102032 |
| assay: | Soil Gross Morphology: 30% of flowers to be produced have opened |
| phenotype: | INFLORESCENCE - Short |
| notes: | 75 pct wt |
| unique F1 plant ID: | R1 PLANT:ME05073-08 |
| phenotype ID: | 102094 |
| assay: | Soil Gross Morphology: 30% of flowers to be produced have opened |
| phenotype: | ROSETTE LEAVES - Lanceolate Shaped |
| notes: | NONE |
| unique F1 plant ID: | R1 PLANT:ME05073-08 |
| phenotype ID: | 102095 |
| assay: | Soil Gross Morphology: 30% of flowers to be produced have opened |
| phenotype: | ROSETTE LEAVES - Other |
| notes: | extra rosette leaves |
| unique F1 plant ID: | R1 PLANT:ME05073-08 |
| phenotype ID: | 102096 |
| assay: | Soil Gross Morphology: 30% of flowers to be produced have opened |
| phenotype: | WHOLE PLANT - Dark Green |
| notes: | NONE |
| unique F1 plant ID: | R1 PLANT:ME05073-08 |
| phenotype ID: | 102097 |
| assay: | Soil Gross Morphology: 30% of flowers to be produced have opened |
| phenotype: | INFLORESCENCE - Short |
| notes: | 75 pct wt |
| unique F1 plant ID: | R1 PLANT:ME04735-01 |
| phenotype ID: | 100726 |
| assay: | Soil Gross Morphology: 50% of flowers to be produced have opened |
| phenotype: | ROSETTE LEAVES - Disorganized Rosette |
| notes: | NONE |
| unique F1 plant ID: | R1 PLANT:ME04735-01 |
| phenotype ID: | 100727 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04735-01 |
| phenotype ID: | 100728 |
| assay: | Soil Gross Morphology: 50% of flowers to be produced have opened |
| phenotype: | ROSETTE LEAVES - Other |
| notes: | extra leaves |
| unique F1 plant ID: | R1 PLANT:ME04735-01 |
| phenotype ID: | 100729 |
| assay: | Soil Gross Morphology: 50% of flowers to be produced have opened |
| phenotype: | WHOLE PLANT - Small |
| notes: | 10 pct wt |
| unique F1 plant ID: | R1 PLANT:ME04735-01 |
| phenotype ID: | 100730 |
| assay: | Soil Gross Morphology: 50% of flowers to be produced have opened |
| phenotype: | INFLORESCENCE - Reduced Apical Dominance |
| notes: | NONE |
| unique F1 plant ID: | R1 PLANT:ME04735-01 |
| phenotype ID: | 100731 |
| assay: | Soil Gross Morphology: 50% of flowers to be produced have opened |
| phenotype: | INFLORESCENCE - Short |
| notes: | 10 pct wt |
| unique F1 plant ID: | R1 PLANT:ME04735-01 |
| phenotype ID: | 100732 |
| assay: | Soil Gross Morphology: 50% of flowers to be produced have opened |
| phenotype: | INFLORESCENCE - Other |
| notes: | extra inflorescence |
| unique F1 plant ID: | R1 PLANT:ME04735-01 |
| phenotype ID: | 100733 |
| assay: | Soil Gross Morphology: 50% of flowers to be produced have opened |

TABLE 1-continued

| | |
|---|---|
| phenotype: | FLOWER - Reduced fertility |
| notes: | NONE |
| unique F1 plant ID: | R1 PLANT:ME04735-02 |
| phenotype ID: | 100863 |
| assay: | Soil Gross Morphology: 50% of flowers to be produced have opened |
| phenotype: | ROSETTE LEAVES - Disorganized Rosette |
| notes: | NONE |
| unique F1 plant ID: | R1 PLANT:ME04735-02 |
| phenotype ID: | 100864 |
| assay: | Soil Gross Morphology: 50% of flowers to be produced have opened |
| phenotype: | ROSETTE LEAVES - Other |
| notes: | extra rosette leaves |
| unique F1 plant ID: | R1 PLANT:ME04735-02 |
| phenotype ID: | 100865 |
| assay: | Soil Gross Morphology: 50% of flowers to be produced have opened |
| phenotype: | WHOLE PLANT - Small |
| notes: | 10 pct wt |
| unique F1 plant ID: | R1 PLANT:ME04735-02 |
| phenotype ID: | 100866 |
| assay: | Soil Gross Morphology: 50% of flowers to be produced have opened |
| phenotype: | INFLORESCENCE - Late Flowering |
| notes: | NONE |
| unique F1 plant ID: | R1 PLANT:ME04735-02 |
| phenotype ID: | 100867 |
| assay: | Soil Gross Morphology: 50% of flowers to be produced have opened |
| phenotype: | INFLORESCENCE - Short |
| notes: | 10 pct wt |
| unique F1 plant ID: | R1 PLANT:ME04735-03 |
| phenotype ID: | 100987 |
| assay: | Soil Gross Morphology: 50% of flowers to be produced have opened |
| phenotype: | ROSETTE LEAVES - Disorganized Rosette |
| notes: | NONE |
| unique F1 plant ID: | R1 PLANT:ME04735-03 |
| phenotype ID: | 100988 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04735-03 |
| phenotype ID: | 100989 |
| assay: | Soil Gross Morphology: 50% of flowers to be produced have opened |
| phenotype: | ROSETTE LEAVES - Other |
| notes: | extra leaves |
| unique F1 plant ID: | R1 PLANT:ME04735-03 |
| phenotype ID: | 100990 |
| assay: | Soil Gross Morphology: 50% of flowers to be produced have opened |
| phenotype: | WHOLE PLANT - Small |
| notes: | 10 pct wt |
| unique F1 plant ID: | R1 PLANT:ME04735-03 |
| phenotype ID: | 100991 |
| assay: | Soil Gross Morphology: 50% of flowers to be produced have opened |
| phenotype: | INFLORESCENCE - Reduced Apical Dominance |
| notes: | NONE |
| unique F1 plant ID: | R1 PLANT:ME04735-03 |
| phenotype ID: | 100992 |
| assay: | Soil Gross Morphology: 50% of flowers to be produced have opened |
| phenotype: | INFLORESCENCE - Short |
| notes: | 10 pct wt |
| unique F1 plant ID: | R1 PLANT:ME04735-03 |
| phenotype ID: | 100993 |
| assay: | Soil Gross Morphology: 50% of flowers to be produced have opened |
| phenotype: | INFLORESCENCE - Other |
| notes: | extra inflorescence |
| unique F1 plant ID: | R1 PLANT:ME04735-03 |
| phenotype ID: | 100994 |
| assay: | Soil Gross Morphology: 50% of flowers to be produced have opened |
| phenotype: | FLOWER - Reduced fertility |
| notes: | NONE |
| unique F1 plant ID: | R1 PLANT:ME04735-04 |
| phenotype ID: | 101118 |
| assay: | Soil Gross Morphology: 50% of flowers to be produced have opened |
| phenotype: | ROSETTE LEAVES - Disorganized Rosette |
| notes: | NONE |
| unique F1 plant ID: | R1 PLANT:ME04735-04 |
| phenotype ID: | 101119 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04735-04 |
| phenotype ID: | 101120 |

TABLE 1-continued

| | |
|---|---|
| assay: | Soil Gross Morphology: 50% of flowers to be produced have opened |
| phenotype: | ROSETTE LEAVES - Other |
| notes: | extra leaves |
| unique F1 plant ID: | R1 PLANT:ME04735-04 |
| phenotype ID: | 101121 |
| assay: | Soil Gross Morphology: 50% of flowers to be produced have opened |
| phenotype: | WHOLE PLANT - Small |
| notes: | 10 pct wt |
| unique F1 plant ID: | R1 PLANT:ME04735-04 |
| phenotype ID: | 101122 |
| assay: | Soil Gross Morphology: 50% of flowers to be produced have opened |
| phenotype: | INFLORESCENCE - Reduced Apical Dominance |
| notes: | NONE |
| unique F1 plant ID: | R1 PLANT:ME04735-04 |
| phenotype ID: | 101123 |
| assay: | Soil Gross Morphology: 50% of flowers to be produced have opened |
| phenotype: | INFLORESCENCE - Short |
| notes: | 10 pct wt |
| unique F1 plant ID: | R1 PLANT:ME04735-04 |
| phenotype ID: | 101124 |
| assay: | Soil Gross Morphology: 50% of flowers to be produced have opened |
| phenotype: | INFLORESCENCE - Other |
| notes: | extra inflorescence |
| unique F1 plant ID: | R1 PLANT:ME04735-04 |
| phenotype ID: | 101125 |
| assay: | Soil Gross Morphology: 50% of flowers to be produced have opened |
| phenotype: | FLOWER - Reduced fertility |
| notes: | NONE |
| unique F1 plant ID: | R1 PLANT:ME04735-05 |
| phenotype ID: | 101253 |
| assay: | Soil Gross Morphology: 50% of flowers to be produced have opened |
| phenotype: | ROSETTE LEAVES - Disorganized Rosette |
| notes: | NONE |
| unique F1 plant ID: | R1 PLANT:ME04735-05 |
| phenotype ID: | 101254 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04735-05 |
| phenotype ID: | 101255 |
| assay: | Soil Gross Morphology: 50% of flowers to be produced have opened |
| phenotype: | ROSETTE LEAVES - Other |
| notes: | extra leaves |
| unique F1 plant ID: | R1 PLANT:ME04735-05 |
| phenotype ID: | 101256 |
| assay: | Soil Gross Morphology: 50% of flowers to be produced have opened |
| phenotype: | INFLORESCENCE - Reduced Apical Dominance |
| notes: | NONE |
| unique F1 plant ID: | R1 PLANT:ME04735-05 |
| phenotype ID: | 101257 |
| assay: | Soil Gross Morphology: 50% of flowers to be produced have opened |
| phenotype: | INFLORESCENCE - Short |
| notes: | 50 pct wt |
| unique F1 plant ID: | R1 PLANT:ME04735-05 |
| phenotype ID: | 101258 |
| assay: | Soil Gross Morphology: 50% of flowers to be produced have opened |
| phenotype: | INFLORESCENCE - Other |
| notes: | extra inflorescence |
| unique F1 plant ID: | R1 PLANT:ME04735-06 |
| phenotype ID: | 101377 |
| assay: | Soil Gross Morphology: 50% of flowers to be produced have opened |
| phenotype: | ROSETTE LEAVES - Disorganized Rosette |
| notes: | NONE |
| unique F1 plant ID: | R1 PLANT:ME04735-06 |
| phenotype ID: | 101378 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04735-06 |
| phenotype ID: | 101379 |
| assay: | Soil Gross Morphology: 50% of flowers to be produced have opened |
| phenotype: | ROSETTE LEAVES - Other |
| notes: | extra leaves |
| unique F1 plant ID: | R1 PLANT:ME04735-06 |
| phenotype ID: | 101380 |
| assay: | Soil Gross Morphology: 50% of flowers to be produced have opened |
| phenotype: | INFLORESCENCE - Reduced Apical Dominance |
| notes: | NONE |
| unique F1 plant ID: | R1 PLANT:ME04735-06 |

TABLE 1-continued

| | |
|---|---|
| phenotype ID: | 101381 |
| assay: | Soil Gross Morphology: 50% of flowers to be produced have opened |
| phenotype: | INFLORESCENCE - Short |
| notes: | 50 pct wt |
| unique F1 plant ID: | R1 PLANT:ME04735-06 |
| phenotype ID: | 101382 |
| assay: | Soil Gross Morphology: 50% of flowers to be produced have opened |
| phenotype: | INFLORESCENCE - Other |
| notes: | extra inflorescence |
| unique F1 plant ID: | R1 PLANT:ME04735-06 |
| phenotype ID: | 101383 |
| assay: | Soil Gross Morphology: 50% of flowers to be produced have opened |
| phenotype: | FLOWER - Reduced fertility |
| notes: | NONE |
| unique F1 plant ID: | R1 PLANT:ME04735-08 |
| phenotype ID: | 101629 |
| assay: | Soil Gross Morphology: 50% of flowers to be produced have opened |
| phenotype: | ROSETTE LEAVES - Disorganized Rosette |
| notes: | NONE |
| unique F1 plant ID: | R1 PLANT:ME04735-08 |
| phenotype ID: | 101630 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04735-08 |
| phenotype ID: | 101631 |
| assay: | Soil Gross Morphology: 50% of flowers to be produced have opened |
| phenotype: | ROSETTE LEAVES - Other |
| notes: | extra leaves |
| unique F1 plant ID: | R1 PLANT:ME04735-08 |
| phenotype ID: | 101632 |
| assay: | Soil Gross Morphology: 50% of flowers to be produced have opened |
| phenotype: | WHOLE PLANT - Small |
| notes: | 10 pct wt |
| unique F1 plant ID: | R1 PLANT:ME04735-08 |
| phenotype ID: | 101633 |
| assay: | Soil Gross Morphology: 50% of flowers to be produced have opened |
| phenotype: | INFLORESCENCE - Reduced Apical Dominance |
| notes: | NONE |
| unique F1 plant ID: | R1 PLANT:ME04735-08 |
| phenotype ID: | 101634 |
| assay: | Soil Gross Morphology: 50% of flowers to be produced have opened |
| phenotype: | INFLORESCENCE - Short |
| notes: | 10 pct wt |
| unique F1 plant ID: | R1 PLANT:ME04735-08 |
| phenotype ID: | 101635 |
| assay: | Soil Gross Morphology: 50% of flowers to be produced have opened |
| phenotype: | INFLORESCENCE - Other |
| notes: | extra inflorescence |
| unique F1 plant ID: | R1 PLANT:ME04735-08 |
| phenotype ID: | 101636 |
| assay: | Soil Gross Morphology: 50% of flowers to be produced have opened |
| phenotype: | FLOWER - Reduced fertility |
| notes: | NONE |
| unique F1 plant ID: | R1 PLANT:ME04735-09 |
| phenotype ID: | 101764 |
| assay: | Soil Gross Morphology: 50% of flowers to be produced have opened |
| phenotype: | ROSETTE LEAVES - Disorganized Rosette |
| notes: | NONE |
| unique F1 plant ID: | R1 PLANT:ME04735-09 |
| phenotype ID: | 101765 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04735-09 |
| phenotype ID: | 101766 |
| assay: | Soil Gross Morphology: 50% of flowers to be produced have opened |
| phenotype: | ROSETTE LEAVES - Other |
| notes: | extra leaves |
| unique F1 plant ID: | R1 PLANT:ME04735-09 |
| phenotype ID: | 101767 |
| assay: | Soil Gross Morphology: 50% of flowers to be produced have opened |
| phenotype: | INFLORESCENCE - Reduced Apical Dominance |
| notes: | NONE |
| unique F1 plant ID: | R1 PLANT:ME04735-09 |
| phenotype ID: | 101768 |
| assay: | Soil Gross Morphology: 50% of flowers to be produced have opened |
| phenotype: | INFLORESCENCE - Short |
| notes: | 50 pct wt |

TABLE 1-continued

| | |
|---|---|
| unique F1 plant ID: | R1 PLANT:ME04735-09 |
| phenotype ID: | 101769 |
| assay: | Soil Gross Morphology: 50% of flowers to be produced have opened |
| phenotype: | INFLORESCENCE - Other |
| notes: | extra inflorescence |
| unique F1 plant ID: | R1 PLANT:ME04735-10 |
| phenotype ID: | 101890 |
| assay: | Soil Gross Morphology: 50% of flowers to be produced have opened |
| phenotype: | ROSETTE LEAVES - Disorganized Rosette |
| notes: | NONE |
| unique F1 plant ID: | R1 PLANT:ME04735-10 |
| phenotype ID: | 101891 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04735-10 |
| phenotype ID: | 101892 |
| assay: | Soil Gross Morphology: 50% of flowers to be produced have opened |
| phenotype: | ROSETTE LEAVES - Other |
| notes: | extra leaves |
| unique F1 plant ID: | R1 PLANT:ME04735-10 |
| phenotype ID: | 101893 |
| assay: | Soil Gross Morphology: 50% of flowers to be produced have opened |
| phenotype: | INFLORESCENCE - Reduced Apical Dominance |
| notes: | NONE |
| unique F1 plant ID: | R1 PLANT:ME04735-10 |
| phenotype ID: | 101894 |
| assay: | Soil Gross Morphology: 50% of flowers to be produced have opened |
| phenotype: | INFLORESCENCE - Short |
| notes: | 50 pct wt |
| unique F1 plant ID: | R1 PLANT:ME04735-10 |
| phenotype ID: | 101895 |
| assay: | Soil Gross Morphology: 50% of flowers to be produced have opened |
| phenotype: | INFLORESCENCE - Other |
| notes: | extra inflorescence |
| unique F1 plant ID: | R1 PLANT:ME04735-10 |
| phenotype ID: | 101896 |
| assay: | Soil Gross Morphology: 50% of flowers to be produced have opened |
| phenotype: | FLOWER - Reduced fertility |
| notes: | NONE |
| unique F1 plant ID: | R1 PLANT:ME04717-02 |
| phenotype ID: | 100837 |
| assay: | Soil Gross Morphology: 50% of flowers to be produced have opened |
| phenotype: | ROSETTE LEAVES - Disorganized Rosette |
| notes: | NONE |
| unique F1 plant ID: | R1 PLANT:ME04717-02 |
| phenotype ID: | 100838 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04717-02 |
| phenotype ID: | 100839 |
| assay: | Soil Gross Morphology: 50% of flowers to be produced have opened |
| phenotype: | ROSETTE LEAVES - Other |
| notes: | extra leaves |
| unique F1 plant ID: | R1 PLANT:ME04717-02 |
| phenotype ID: | 100840 |
| assay: | Soil Gross Morphology: 50% of flowers to be produced have opened |
| phenotype: | INFLORESCENCE - Reduced Apical Dominance |
| notes: | NONE |
| unique F1 plant ID: | R1 PLANT:ME04717-02 |
| phenotype ID: | 100841 |
| assay: | Soil Gross Morphology: 50% of flowers to be produced have opened |
| phenotype: | INFLORESCENCE - Short |
| notes: | 75 pct wt |
| unique F1 plant ID: | R1 PLANT:ME04717-02 |
| phenotype ID: | 100842 |
| assay: | Soil Gross Morphology: 50% of flowers to be produced have opened |
| phenotype: | INFLORESCENCE - Other |
| notes: | extra inflorescence |
| unique F1 plant ID: | R1 PLANT:ME04717-02 |
| phenotype ID: | 100843 |
| assay: | Soil Gross Morphology: 50% of flowers to be produced have opened |
| phenotype: | FLOWER - Reduced fertility |
| notes: | NONE |
| unique F1 plant ID: | R1 PLANT:ME04717-03 |
| phenotype ID: | 100962 |
| assay: | Soil Gross Morphology: Flowering complete |
| phenotype: | ROSETTE LEAVES - Disorganized Rosette |

TABLE 1-continued

| | |
|---|---|
| notes: | NONE |
| unique F1 plant ID: | R1 PLANT:ME04717-03 |
| phenotype ID: | 100963 |
| assay: | Soil Gross Morphology: Flowering complete |
| phenotype: | ROSETTE LEAVES - Lanceolate Shaped |
| notes: | NONE |
| unique F1 plant ID: | R1 PLANT:ME04717-03 |
| phenotype ID: | 100964 |
| assay: | Soil Gross Morphology: Flowering complete |
| phenotype: | ROSETTE LEAVES - Other |
| notes: | extra leaves |
| unique F1 plant ID: | R1 PLANT:ME04717-03 |
| phenotype ID: | 100965 |
| assay: | Soil Gross Morphology: Flowering complete |
| phenotype: | INFLORESCENCE - Reduced Apical Dominance |
| notes: | NONE |
| unique F1 plant ID: | R1 PLANT:ME04717-03 |
| phenotype ID: | 100966 |
| assay: | Soil Gross Morphology: Flowering complete |
| phenotype: | INFLORESCENCE - Short |
| notes: | 75 pct wt |
| unique F1 plant ID: | R1 PLANT:ME04717-03 |
| phenotype ID: | 100967 |
| assay: | Soil Gross Morphology: Flowering complete |
| phenotype: | INFLORESCENCE - Other |
| notes: | extra inflorescence |
| unique F1 plant ID: | R1 PLANT:ME04717-04 |
| phenotype ID: | 101097 |
| assay: | Soil Gross Morphology: Flowering complete |
| phenotype: | ROSETTE LEAVES - Disorganized Rosette |
| notes: | NONE |
| unique F1 plant ID: | R1 PLANT:ME04717-04 |
| phenotype ID: | 101098 |
| assay: | Soil Gross Morphology: Flowering complete |
| phenotype: | ROSETTE LEAVES - Lanceolate Shaped |
| notes: | NONE |
| unique F1 plant ID: | R1 PLANT:ME04717-04 |
| phenotype ID: | 101099 |
| assay: | Soil Gross Morphology: Flowering complete |
| phenotype: | ROSETTE LEAVES - Other |
| notes: | extra leaves |
| unique F1 plant ID: | R1 PLANT:ME04717-04 |
| phenotype ID: | 101100 |
| assay: | Soil Gross Morphology: Flowering complete |
| phenotype: | INFLORESCENCE - Reduced Apical Dominance |
| notes: | NONE |
| unique F1 plant ID: | R1 PLANT:ME04717-04 |
| phenotype ID: | 101101 |
| assay: | Soil Gross Morphology: Flowering complete |
| phenotype: | INFLORESCENCE - Other |
| notes: | extra inflorescence |
| unique F1 plant ID: | R1 PLANT:ME04717-05 |
| phenotype ID: | 101225 |
| assay: | Soil Gross Morphology: Flowering complete |
| phenotype: | ROSETTE LEAVES - Disorganized Rosette |
| notes: | NONE |
| unique F1 plant ID: | R1 PLANT:ME04717-05 |
| phenotype ID: | 101226 |
| assay: | Soil Gross Morphology: Flowering complete |
| phenotype: | ROSETTE LEAVES - Lanceolate Shaped |
| notes: | NONE |
| unique F1 plant ID: | R1 PLANT:ME04717-05 |
| phenotype ID: | 101227 |
| assay: | Soil Gross Morphology: Flowering complete |
| phenotype: | ROSETTE LEAVES - Other |
| notes: | extra leaves |
| unique F1 plant ID: | R1 PLANT:ME04717-05 |
| phenotype ID: | 101228 |
| assay: | Soil Gross Morphology: Flowering complete |
| phenotype: | INFLORESCENCE - Reduced Apical Dominance |
| notes: | NONE |
| unique F1 plant ID: | R1 PLANT:ME04717-05 |
| phenotype ID: | 101229 |
| assay: | Soil Gross Morphology: Flowering complete |
| phenotype: | INFLORESCENCE - Short |
| notes: | 75 pct wt |
| unique F1 plant ID: | R1 PLANT:ME04717-05 |
| phenotype ID: | 101230 |
| assay: | Soil Gross Morphology: Flowering complete |

TABLE 1-continued

| | |
|---|---|
| phenotype: | INFLORESCENCE - Other |
| notes: | extra inflorescence |
| unique F1 plant ID: | R1 PLANT:ME04717-06 |
| phenotype ID: | 101351 |
| assay: | Soil Gross Morphology: Flowering complete |
| phenotype: | ROSETTE LEAVES - Disorganized Rosette |
| notes: | NONE |
| unique F1 plant ID: | R1 PLANT:ME04717-06 |
| phenotype ID: | 101352 |
| assay: | Soil Gross Morphology: Flowering complete |
| phenotype: | ROSETTE LEAVES - Lanceolate Shaped |
| notes: | NONE |
| unique F1 plant ID: | R1 PLANT:ME04717-06 |
| phenotype ID: | 101353 |
| assay: | Soil Gross Morphology: Flowering complete |
| phenotype: | ROSETTE LEAVES - Other |
| notes: | extra leaves |
| unique F1 plant ID: | R1 PLANT:ME04717-06 |
| phenotype ID: | 101354 |
| assay: | Soil Gross Morphology: Flowering complete |
| phenotype: | INFLORESCENCE - Reduced Apical Dominance |
| notes: | NONE |
| unique F1 plant ID: | R1 PLANT:ME04717-06 |
| phenotype ID: | 101355 |
| assay: | Soil Gross Morphology: Flowering complete |
| phenotype: | INFLORESCENCE - Short |
| notes: | 75 pct wt |
| unique F1 plant ID: | R1 PLANT:ME04717-06 |
| phenotype ID: | 101356 |
| assay: | Soil Gross Morphology: Flowering complete |
| phenotype: | INFLORESCENCE - Other |
| notes: | extra inflorescence |
| unique F1 plant ID: | R1 PLANT:ME04717-07 |
| phenotype ID: | 101481 |
| assay: | Soil Gross Morphology: Flowering complete |
| phenotype: | ROSETTE LEAVES - Disorganized Rosette |
| notes: | NONE |
| unique F1 plant ID: | R1 PLANT:ME04717-07 |
| phenotype ID: | 101482 |
| assay: | Soil Gross Morphology: Flowering complete |
| phenotype: | ROSETTE LEAVES - Lanceolate Shaped |
| notes: | NONE |
| unique F1 plant ID: | R1 PLANT:ME04717-07 |
| phenotype ID: | 101483 |
| assay: | Soil Gross Morphology: Flowering complete |
| phenotype: | ROSETTE LEAVES - Other |
| notes: | extra leaves |
| unique F1 plant ID: | R1 PLANT:ME04717-07 |
| phenotype ID: | 101484 |
| assay: | Soil Gross Morphology: Flowering complete |
| phenotype: | INFLORESCENCE - Reduced Apical Dominance |
| notes: | NONE |
| unique F1 plant ID: | R1 PLANT:ME04717-07 |
| phenotype ID: | 101485 |
| assay: | Soil Gross Morphology: Flowering complete |
| phenotype: | INFLORESCENCE - Short |
| notes: | 75 pct wt |
| unique F1 plant ID: | R1 PLANT:ME04717-07 |
| phenotype ID: | 101486 |
| assay: | Soil Gross Morphology: Flowering complete |
| phenotype: | INFLORESCENCE - Other |
| notes: | extra inflorescence |
| unique F1 plant ID: | R1 PLANT:ME04717-08 |
| phenotype ID: | 101603 |
| assay: | Soil Gross Morphology: Flowering complete |
| phenotype: | ROSETTE LEAVES - Disorganized Rosette |
| notes: | NONE |
| unique F1 plant ID: | R1 PLANT:ME04717-08 |
| phenotype ID: | 101604 |
| assay: | Soil Gross Morphology: Flowering complete |
| phenotype: | ROSETTE LEAVES - Lanceolate Shaped |
| notes: | NONE |
| unique F1 plant ID: | R1 PLANT:ME04717-08 |
| phenotype ID: | 101605 |
| assay: | Soil Gross Morphology: Flowering complete |
| phenotype: | ROSETTE LEAVES - Other |
| notes: | extra leaves |
| unique F1 plant ID: | R1 PLANT:ME04717-08 |
| phenotype ID: | 101606 |

TABLE 1-continued

| | |
|---|---|
| assay: | Soil Gross Morphology: Flowering complete |
| phenotype: | INFLORESCENCE - Reduced Apical Dominance |
| notes: | NONE |
| unique F1 plant ID: | R1 PLANT:ME04717-08 |
| phenotype ID: | 101607 |
| assay: | Soil Gross Morphology: Flowering complete |
| phenotype: | INFLORESCENCE - Short |
| notes: | 75 pct wt |
| unique F1 plant ID: | R1 PLANT:ME04717-08 |
| phenotype ID: | 101608 |
| assay: | Soil Gross Morphology: Flowering complete |
| phenotype: | INFLORESCENCE - Other |
| notes: | extra inflorescence |
| unique F1 plant ID: | R1 PLANT:ME04717-09 |
| phenotype ID: | 101737 |
| assay: | Soil Gross Morphology: Flowering complete |
| phenotype: | ROSETTE LEAVES - Disorganized Rosette |
| notes: | NONE |
| unique F1 plant ID: | R1 PLANT:ME04717-09 |
| phenotype ID: | 101738 |
| assay: | Soil Gross Morphology: Flowering complete |
| phenotype: | ROSETTE LEAVES - Lanceolate Shaped |
| notes: | NONE |
| unique F1 plant ID: | R1 PLANT:ME04717-09 |
| phenotype ID: | 101739 |
| assay: | Soil Gross Morphology: Flowering complete |
| phenotype: | ROSETTE LEAVES - Other |
| notes: | extra leaves |
| unique F1 plant ID: | R1 PLANT:ME04717-09 |
| phenotype ID: | 101740 |
| assay: | Soil Gross Morphology: Flowering complete |
| phenotype: | INFLORESCENCE - Reduced Apical Dominance |
| notes: | NONE |
| unique F1 plant ID: | R1 PLANT:ME04717-09 |
| phenotype ID: | 101741 |
| assay: | Soil Gross Morphology: Flowering complete |
| phenotype: | INFLORESCENCE - Short |
| notes: | 75 pct wt |
| unique F1 plant ID: | R1 PLANT:ME04717-09 |
| phenotype ID: | 101742 |
| assay: | Soil Gross Morphology: Flowering complete |
| phenotype: | INFLORESCENCE - Other |
| notes: | extra inflorescence |
| unique F1 plant ID: | R1 PLANT:ME04717-10 |
| phenotype ID: | 101863 |
| assay: | Soil Gross Morphology: Flowering complete |
| phenotype: | ROSETTE LEAVES - Disorganized Rosette |
| notes: | NONE |
| unique F1 plant ID: | R1 PLANT:ME04717-10 |
| phenotype ID: | 101864 |
| assay: | Soil Gross Morphology: Flowering complete |
| phenotype: | ROSETTE LEAVES - Lanceolate Shaped |
| notes: | NONE |
| unique F1 plant ID: | R1 PLANT:ME04717-10 |
| phenotype ID: | 101865 |
| assay: | Soil Gross Morphology: Flowering complete |
| phenotype: | ROSETTE LEAVES - Other |
| notes: | extra leaves |
| unique F1 plant ID: | R1 PLANT:ME04717-10 |
| phenotype ID: | 101866 |
| assay: | Soil Gross Morphology: Flowering complete |
| phenotype: | INFLORESCENCE - Reduced Apical Dominance |
| notes: | NONE |
| unique F1 plant ID: | R1 PLANT:ME04717-10 |
| phenotype ID: | 101867 |
| assay: | Soil Gross Morphology: Flowering complete |
| phenotype: | INFLORESCENCE - Short |
| notes: | 75 pct wt |
| unique F1 plant ID: | R1 PLANT:ME04717-10 |
| phenotype ID: | 101868 |
| assay: | Soil Gross Morphology: Flowering complete |
| phenotype: | INFLORESCENCE - Other |
| notes: | extra inflorescence |
| unique F1 plant ID: | R1 PLANT:ME04709-01 |
| phenotype ID: | 100700 |
| assay: | Soil Gross Morphology: 50% of flowers to be produced have opened |
| phenotype: | ROSETTE LEAVES - Disorganized Rosette |
| notes: | NONE |
| unique F1 plant ID: | R1 PLANT:ME04709-01 |

TABLE 1-continued

| | |
|---|---|
| phenotype ID: | 100701 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04709-01 |
| phenotype ID: | 100702 |
| assay: | Soil Gross Morphology: 50% of flowers to be produced have opened |
| phenotype: | ROSETTE LEAVES - Other |
| notes: | extra leaves |
| unique F1 plant ID: | R1 PLANT:ME04709-01 |
| phenotype ID: | 100703 |
| assay: | Soil Gross Morphology: 50% of flowers to be produced have opened |
| phenotype: | INFLORESCENCE - Reduced Apical Dominance |
| notes: | NONE |
| unique F1 plant ID: | R1 PLANT:ME04709-01 |
| phenotype ID: | 100704 |
| assay: | Soil Gross Morphology: 50% of flowers to be produced have opened |
| phenotype: | INFLORESCENCE - Short |
| notes: | 75 pct wt |
| unique F1 plant ID: | R1 PLANT:ME04709-01 |
| phenotype ID: | 100705 |
| assay: | Soil Gross Morphology: 50% of flowers to be produced have opened |
| phenotype: | INFLORESCENCE - Other |
| notes: | extra inflorescence |
| unique F1 plant ID: | R1 PLANT:ME04709-02 |
| phenotype ID: | 100825 |
| assay: | Soil Gross Morphology: 50% of flowers to be produced have opened |
| phenotype: | ROSETTE LEAVES - Disorganized Rosette |
| notes: | NONE |
| unique F1 plant ID: | R1 PLANT:ME04709-02 |
| phenotype ID: | 100826 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04709-02 |
| phenotype ID: | 100827 |
| assay: | Soil Gross Morphology: 50% of flowers to be produced have opened |
| phenotype: | ROSETTE LEAVES - Other |
| notes: | extra leaves |
| unique F1 plant ID: | R1 PLANT:ME04709-02 |
| phenotype ID: | 100828 |
| assay: | Soil Gross Morphology: 50% of flowers to be produced have opened |
| phenotype: | INFLORESCENCE - Reduced Apical Dominance |
| notes: | NONE |
| unique F1 plant ID: | R1 PLANT:ME04709-02 |
| phenotype ID: | 100829 |
| assay: | Soil Gross Morphology: 50% of flowers to be produced have opened |
| phenotype: | INFLORESCENCE - Short |
| notes: | 75 pct wt |
| unique F1 plant ID: | R1 PLANT:ME04709-02 |
| phenotype ID: | 100830 |
| assay: | Soil Gross Morphology: 50% of flowers to be produced have opened |
| phenotype: | INFLORESCENCE - Other |
| notes: | extra inflorescence |
| unique F1 plant ID: | R1 PLANT:ME04709-02 |
| phenotype ID: | 100831 |
| assay: | Soil Gross Morphology: 50% of flowers to be produced have opened |
| phenotype: | FLOWER - Reduced fertility |
| notes: | NONE |
| unique F1 plant ID: | R1 PLANT:ME04709-03 |
| phenotype ID: | 100951 |
| assay: | Soil Gross Morphology: 50% of flowers to be produced have opened |
| phenotype: | ROSETTE LEAVES - Disorganized Rosette |
| notes: | NONE |
| unique F1 plant ID: | R1 PLANT:ME04709-03 |
| phenotype ID: | 100952 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04709-03 |
| phenotype ID: | 100953 |
| assay: | Soil Gross Morphology: 50% of flowers to be produced have opened |
| phenotype: | ROSETTE LEAVES - Other |
| notes: | extra leaves |
| unique F1 plant ID: | R1 PLANT:ME04709-03 |
| phenotype ID: | 100954 |
| assay: | Soil Gross Morphology: 50% of flowers to be produced have opened |
| phenotype: | INFLORESCENCE - Reduced Apical Dominance |
| notes: | NONE |

TABLE 1-continued

```
unique F1 plant ID:  R1 PLANT:ME04709-03
phenotype ID:        100955
assay:               Soil Gross Morphology: 50% of flowers to be produced have opened
phenotype:           INFLORESCENCE - Short
notes:               75 pct wt
unique F1 plant ID:  R1 PLANT:ME04709-03
phenotype ID:        100956
assay:               Soil Gross Morphology: 50% of flowers to be produced have opened
phenotype:           INFLORESCENCE - Other
notes:               extra inflorescence
unique F1 plant ID:  R1 PLANT:ME04709-03
phenotype ID:        100957
assay:               Soil Gross Morphology: 50% of flowers to be produced have opened
phenotype:           FLOWER - Reduced fertility
notes:               NONE
unique F1 plant ID:  R1 PLANT:ME04709-04
phenotype ID:        101089
assay:               Soil Gross Morphology: 50% of flowers to be produced have opened
phenotype:           ROSETTE LEAVES - Disorganized Rosette
notes:               NONE
unique F1 plant ID:  R1 PLANT:ME04709-04
phenotype ID:        101090
assay:               Soil Gross Morphology: 50% of flowers to be produced have opened
phenotype:           ROSETTE LEAVES - Lanceolate Shaped
notes:               NONE
unique F1 plant ID:  R1 PLANT:ME04709-04
phenotype ID:        101091
assay:               Soil Gross Morphology: 50% of flowers to be produced have opened
phenotype:           ROSETTE LEAVES - Other
notes:               extra leaves
unique F1 plant ID:  R1 PLANT:ME04709-04
phenotype ID:        101092
assay:               Soil Gross Morphology: 50% of flowers to be produced have opened
phenotype:           INFLORESCENCE - Reduced Apical Dominance
notes:               NONE
unique F1 plant ID:  R1 PLANT:ME04709-04
phenotype ID:        101093
assay:               Soil Gross Morphology: 50% of flowers to be produced have opened
phenotype:           INFLORESCENCE - Other
notes:               extra inflorescence
unique F1 plant ID:  R1 PLANT:ME04709-04
phenotype ID:        101094
assay:               Soil Gross Morphology: 50% of flowers to be produced have opened
phenotype:           FLOWER - Reduced fertility
notes:               NONE
unique F1 plant ID:  R1 PLANT:ME04709-05
phenotype ID:        101215
assay:               Soil Gross Morphology: 50% of flowers to be produced have opened
phenotype:           ROSETTE LEAVES - Disorganized Rosette
notes:               NONE
unique F1 plant ID:  R1 PLANT:ME04709-05
phenotype ID:        101216
assay:               Soil Gross Morphology: 50% of flowers to be produced have opened
phenotype:           ROSETTE LEAVES - Lanceolate Shaped
notes:               NONE
unique F1 plant ID:  R1 PLANT:ME04709-05
phenotype ID:        101217
assay:               Soil Gross Morphology: 50% of flowers to be produced have opened
phenotype:           ROSETTE LEAVES - Other
notes:               extra leaves
unique F1 plant ID:  R1 PLANT:ME04709-05
phenotype ID:        101218
assay:               Soil Gross Morphology: 50% of flowers to be produced have opened
phenotype:           INFLORESCENCE - Reduced Apical Dominance
notes:               NONE
unique F1 plant ID:  R1 PLANT:ME04709-05
phenotype ID:        101219
assay:               Soil Gross Morphology: 50% of flowers to be produced have opened
phenotype:           INFLORESCENCE - Short
notes:               50 pct wt
unique F1 plant ID:  R1 PLANT:ME04709-05
phenotype ID:        101220
assay:               Soil Gross Morphology: 50% of flowers to be produced have opened
phenotype:           INFLORESCENCE - Other
notes:               extra inflorescence
unique F1 plant ID:  R1 PLANT:ME04709-07
phenotype ID:        101471
assay:               Soil Gross Morphology: 50% of flowers to be produced have opened
phenotype:           ROSETTE LEAVES - Disorganized Rosette
```

TABLE 1-continued

| | |
|---|---|
| notes: | NONE |
| unique F1 plant ID: | R1 PLANT:ME04709-07 |
| phenotype ID: | 101472 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04709-07 |
| phenotype ID: | 101473 |
| assay: | Soil Gross Morphology: 50% of flowers to be produced have opened |
| phenotype: | ROSETTE LEAVES - Other |
| notes: | extra leaves |
| unique F1 plant ID: | R1 PLANT:ME04709-07 |
| phenotype ID: | 101474 |
| assay: | Soil Gross Morphology: 50% of flowers to be produced have opened |
| phenotype: | INFLORESCENCE - Reduced Apical Dominance |
| notes: | NONE |
| unique F1 plant ID: | R1 PLANT:ME04709-07 |
| phenotype ID: | 101475 |
| assay: | Soil Gross Morphology: 50% of flowers to be produced have opened |
| phenotype: | INFLORESCENCE - Short |
| notes: | 50 pct wt |
| unique F1 plant ID: | R1 PLANT:ME04709-07 |
| phenotype ID: | 101476 |
| assay: | Soil Gross Morphology: 50% of flowers to be produced have opened |
| phenotype: | INFLORESCENCE - Other |
| notes: | extra inflorescence |
| unique F1 plant ID: | R1 PLANT:ME04709-08 |
| phenotype ID: | 101592 |
| assay: | Soil Gross Morphology: 50% of flowers to be produced have opened |
| phenotype: | ROSETTE LEAVES - Disorganized Rosette |
| notes: | NONE |
| unique F1 plant ID: | R1 PLANT:ME04709-08 |
| phenotype ID: | 101593 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04709-08 |
| phenotype ID: | 101594 |
| assay: | Soil Gross Morphology: 50% of flowers to be produced have opened |
| phenotype: | ROSETTE LEAVES - Other |
| notes: | extra leaves |
| unique F1 plant ID: | R1 PLANT:ME04709-08 |
| phenotype ID: | 101595 |
| assay: | Soil Gross Morphology: 50% of flowers to be produced have opened |
| phenotype: | INFLORESCENCE - Reduced Apical Dominance |
| notes: | NONE |
| unique F1 plant ID: | R1 PLANT:ME04709-08 |
| phenotype ID: | 101596 |
| assay: | Soil Gross Morphology: 50% of flowers to be produced have opened |
| phenotype: | INFLORESCENCE - Short |
| notes: | 50 pct wt |
| unique F1 plant ID: | R1 PLANT:ME04709-08 |
| phenotype ID: | 101597 |
| assay: | Soil Gross Morphology: 50% of flowers to be produced have opened |
| phenotype: | INFLORESCENCE - Other |
| notes: | extra inflorescence |
| unique F1 plant ID: | R1 PLANT:ME04709-08 |
| phenotype ID: | 101598 |
| assay: | Soil Gross Morphology: 50% of flowers to be produced have opened |
| phenotype: | FLOWER - Reduced fertility |
| notes: | NONE |
| unique F1 plant ID: | R1 PLANT:ME04709-09 |
| phenotype ID: | 101727 |
| assay: | Soil Gross Morphology: 50% of flowers to be produced have opened |
| phenotype: | ROSETTE LEAVES - Disorganized Rosette |
| notes: | NONE |
| unique F1 plant ID: | R1 PLANT:ME04709-09 |
| phenotype ID: | 101728 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04709-09 |
| phenotype ID: | 101729 |
| assay: | Soil Gross Morphology: 50% of flowers to be produced have opened |
| phenotype: | ROSETTE LEAVES - Other |
| notes: | extra leaves |
| unique F1 plant ID: | R1 PLANT:ME04709-09 |
| phenotype ID: | 101730 |
| assay: | Soil Gross Morphology: 50% of flowers to be produced have opened |

TABLE 1-continued

| | |
|---|---|
| phenotype: | INFLORESCENCE - Reduced Apical Dominance |
| notes: | NONE |
| unique F1 plant ID: | R1 PLANT:ME04709-09 |
| phenotype ID: | 101731 |
| assay: | Soil Gross Morphology: 50% of flowers to be produced have opened |
| phenotype: | INFLORESCENCE - Short |
| notes: | 75 pct wt |
| unique F1 plant ID: | R1 PLANT:ME04709-09 |
| phenotype ID: | 101732 |
| assay: | Soil Gross Morphology: 50% of flowers to be produced have opened |
| phenotype: | INFLORESCENCE - Other |
| notes: | extra inflorescence |
| unique F1 plant ID: | R1 PLANT:ME04709-10 |
| phenotype ID: | 101852 |
| assay: | Soil Gross Morphology: 50% of flowers to be produced have opened |
| phenotype: | ROSETTE LEAVES - Disorganized Rosette |
| notes: | NONE |
| unique F1 plant ID: | R1 PLANT:ME04709-10 |
| phenotype ID: | 101853 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04709-10 |
| phenotype ID: | 101854 |
| assay: | Soil Gross Morphology: 50% of flowers to be produced have opened |
| phenotype: | ROSETTE LEAVES - Other |
| notes: | extra leaves |
| unique F1 plant ID: | R1 PLANT:ME04709-10 |
| phenotype ID: | 101855 |
| assay: | Soil Gross Morphology: 50% of flowers to be produced have opened |
| phenotype: | INFLORESCENCE - Reduced Apical Dominance |
| notes: | NONE |
| unique F1 plant ID: | R1 PLANT:ME04709-10 |
| phenotype ID: | 101856 |
| assay: | Soil Gross Morphology: 50% of flowers to be produced have opened |
| phenotype: | INFLORESCENCE - Short |
| notes: | 50 pct wt |
| unique F1 plant ID: | R1 PLANT:ME04709-10 |
| phenotype ID: | 101857 |
| assay: | Soil Gross Morphology: 50% of flowers to be produced have opened |
| phenotype: | INFLORESCENCE - Other |
| notes: | extra inflorescence |
| unique F1 plant ID: | R1 PLANT:ME04709-10 |
| phenotype ID: | 101858 |
| assay: | Soil Gross Morphology: 50% of flowers to be produced have opened |
| phenotype: | FLOWER - Reduced fertility |
| notes: | NONE |
| unique F1 plant ID: | R1 PLANT:ME02543-01 |
| phenotype ID: | 54899 |
| assay: | Soil Gross Morphology: First flower buds visible |
| phenotype: | ROSETTE LEAVES - Disorganized Rosette |
| notes: | NONE |
| unique F1 plant ID: | R1 PLANT:ME02543-01 |
| phenotype ID: | 54900 |
| assay: | Soil Gross Morphology: 30% of flowers to be produced have opened |
| phenotype: | INFLORESCENCE - Short |
| notes: | 40pct height wt |
| unique F1 plant ID: | R1 PLANT:ME02543-01 |
| phenotype ID: | 54901 |
| assay: | Soil Gross Morphology: First flower buds visible |
| phenotype: | ROSETTE LEAVES - Lanceolate Shaped |
| notes: | NONE |
| unique F1 plant ID: | R1 PLANT:ME02543-01 |
| phenotype ID: | 54902 |
| assay: | Soil Gross Morphology: 30% of flowers to be produced have opened |
| phenotype: | WHOLE PLANT - Other |
| notes: | many extra leaves |
| unique F1 plant ID: | R1 PLANT:ME02543-01 |
| phenotype ID: | 54903 |
| assay: | Soil Gross Morphology: First flower buds visible |
| phenotype: | ROSETTE LEAVES - Serrate Margins |
| notes: | NONE |
| unique F1 plant ID: | R1 PLANT:ME02543-01 |
| phenotype ID: | 54904 |
| assay: | Soil Gross Morphology: First flower buds visible |
| phenotype: | ROSETTE LEAVES - Curled 1 |
| notes: | NONE |
| unique F1 plant ID: | R1 PLANT:ME02543-01 |
| phenotype ID: | 54905 |

TABLE 1-continued

| | |
|---|---|
| assay: | Soil Gross Morphology: 30% of flowers to be produced have opened |
| phenotype: | INFLORESCENCE - Short |
| notes: | 40pct height wt |
| unique F1 plant ID: | R1 PLANT:ME02543-01 |
| phenotype ID: | 54906 |
| assay: | Soil Gross Morphology: 30% of flowers to be produced have opened |
| phenotype: | INFLORESCENCE - Reduced Apical Dominance |
| notes: | NONE |
| unique F1 plant ID: | R1 PLANT:ME02543-01 |
| phenotype ID: | 54907 |
| assay: | Soil Gross Morphology: First flower buds visible |
| phenotype: | ROSETTE LEAVES - Other |
| notes: | extra rosette leaves |
| unique F1 plant ID: | R1 PLANT:ME02543-01 |
| phenotype ID: | 54908 |
| assay: | Soil Gross Morphology: First flower buds visible |
| phenotype: | CAULINE LEAVES - Other |
| notes: | long cauline leaves |
| unique F1 plant ID: | R1 PLANT:ME02543-02 |
| phenotype ID: | 54948 |
| assay: | Soil Gross Morphology: 30% of flowers to be produced have opened |
| phenotype: | WHOLE PLANT - Small |
| notes: | 70pct size wt |
| unique F1 plant ID: | R1 PLANT:ME02543-02 |
| phenotype ID: | 54949 |
| assay: | Soil Gross Morphology: 30% of flowers to be produced have opened |
| phenotype: | ROSETTE LEAVES - Disorganized Rosette |
| notes: | strong pheno |
| unique F1 plant ID: | R1 PLANT:ME02543-02 |
| phenotype ID: | 54950 |
| assay: | Soil Gross Morphology: 30% of flowers to be produced have opened |
| phenotype: | ROSETTE LEAVES - Serrate Margins |
| notes: | NONE |
| unique F1 plant ID: | R1 PLANT:ME02543-02 |
| phenotype ID: | 54951 |
| assay: | Soil Gross Morphology: 30% of flowers to be produced have opened |
| phenotype: | ROSETTE LEAVES - Lanceolate Shaped |
| notes: | NONE |
| unique F1 plant ID: | R1 PLANT:ME02543-02 |
| phenotype ID: | 54952 |
| assay: | Soil Gross Morphology: 30% of flowers to be produced have opened |
| phenotype: | FLOWER - Sterile |
| notes: | NONE |
| unique F1 plant ID: | R1 PLANT:ME02543-02 |
| phenotype ID: | 54953 |
| assay: | Soil Gross Morphology: 30% of flowers to be produced have opened |
| phenotype: | ROSETTE LEAVES - Curled 1 |
| notes: | NONE |
| unique F1 plant ID: | R1 PLANT:ME02543-02 |
| phenotype ID: | 54954 |
| assay: | Soil Gross Morphology: 30% of flowers to be produced have opened |
| phenotype: | ROSETTE LEAVES - Other |
| notes: | extra rosette leaves |
| unique F1 plant ID: | R1 PLANT:ME02543-02 |
| phenotype ID: | 54955 |
| assay: | Soil Gross Morphology: 30% of flowers to be produced have opened |
| phenotype: | CAULINE LEAVES - Other |
| notes: | long cauline leaves |
| unique F1 plant ID: | R1 PLANT:ME02543-03 |
| phenotype ID: | 54979 |
| assay: | Soil Gross Morphology: 30% of flowers to be produced have opened |
| phenotype: | ROSETTE LEAVES - Other |
| notes: | extra rosette leaves |
| unique F1 plant ID: | R1 PLANT:ME02543-03 |
| phenotype ID: | 54980 |
| assay: | Soil Gross Morphology: 30% of flowers to be produced have opened |
| phenotype: | ROSETTE LEAVES - Serrate Margins |
| notes: | NONE |
| unique F1 plant ID: | R1 PLANT:ME02543-03 |
| phenotype ID: | 54981 |
| assay: | Soil Gross Morphology: 30% of flowers to be produced have opened |
| phenotype: | ROSETTE LEAVES - Curled 1 |
| notes: | NONE |
| unique F1 plant ID: | R1 PLANT:ME02543-03 |
| phenotype ID: | 54982 |
| assay: | Soil Gross Morphology: 30% of flowers to be produced have opened |
| phenotype: | WHOLE PLANT - Small |
| notes: | 70pct size wt |
| unique F1 plant ID: | R1 PLANT:ME02543-03 |

TABLE 1-continued

| | |
|---|---|
| phenotype ID: | 54983 |
| assay: | Soil Gross Morphology: 30% of flowers to be produced have opened |
| phenotype: | INFLORESCENCE - Reduced Apical Dominance |
| notes: | NONE |
| unique F1 plant ID: | R1 PLANT:ME02543-03 |
| phenotype ID: | 54984 |
| assay: | Soil Gross Morphology: 30% of flowers to be produced have opened |
| phenotype: | ROSETTE LEAVES - Lanceolate Shaped |
| notes: | NONE |
| unique F1 plant ID: | R1 PLANT:ME02543-03 |
| phenotype ID: | 54985 |
| assay: | Soil Gross Morphology: 30% of flowers to be produced have opened |
| phenotype: | CAULINE LEAVES - Other |
| notes: | long cauline leaves |
| unique F1 plant ID: | R1 PLANT:ME02543-04 |
| phenotype ID: | 55025 |
| assay: | Soil Gross Morphology: 30% of flowers to be produced have opened |
| phenotype: | WHOLE PLANT - Other |
| notes: | many extra leaves |
| unique F1 plant ID: | R1 PLANT:ME02543-04 |
| phenotype ID: | 55026 |
| assay: | Soil Gross Morphology: 30% of flowers to be produced have opened |
| phenotype: | ROSETTE LEAVES - Other |
| notes: | extra rosette leaves |
| unique F1 plant ID: | R1 PLANT:ME02543-04 |
| phenotype ID: | 55027 |
| assay: | Soil Gross Morphology: 30% of flowers to be produced have opened |
| phenotype: | INFLORESCENCE - Reduced Apical Dominance |
| notes: | NONE |
| unique F1 plant ID: | R1 PLANT:ME02543-04 |
| phenotype ID: | 55028 |
| assay: | Soil Gross Morphology: 30% of flowers to be produced have opened |
| phenotype: | INFLORESCENCE - Short |
| notes: | 70pct height wt |
| unique F1 plant ID: | R1 PLANT:ME02543-04 |
| phenotype ID: | 55029 |
| assay: | Soil Gross Morphology: 30% of flowers to be produced have opened |
| phenotype: | ROSETTE LEAVES - Lanceolate Shaped |
| notes: | NONE |
| unique F1 plant ID: | R1 PLANT:ME02543-04 |
| phenotype ID: | 55030 |
| assay: | Soil Gross Morphology: 30% of flowers to be produced have opened |
| phenotype: | CAULINE LEAVES - Other |
| notes: | long cauline leaves |
| unique F1 plant ID: | R1 PLANT:ME02543-04 |
| phenotype ID: | 55031 |
| assay: | Soil Gross Morphology: 30% of flowers to be produced have opened |
| phenotype: | ROSETTE LEAVES - Serrate Margins |
| notes: | NONE |
| unique F1 plant ID: | R1 PLANT:ME02543-04 |
| phenotype ID: | 55032 |
| assay: | Soil Gross Morphology: 30% of flowers to be produced have opened |
| phenotype: | ROSETTE LEAVES - Curled 1 |
| notes: | NONE |
| unique F1 plant ID: | R1 PLANT:ME02543-05 |
| phenotype ID: | 55069 |
| assay: | Soil Gross Morphology: 30% of flowers to be produced have opened |
| phenotype: | CAULINE LEAVES - Other |
| notes: | long cauline leaves |
| unique F1 plant ID: | R1 PLANT:ME02543-05 |
| phenotype ID: | 55070 |
| assay: | Soil Gross Morphology: 30% of flowers to be produced have opened |
| phenotype: | INFLORESCENCE - Short |
| notes: | 70pct height wt |
| unique F1 plant ID: | R1 PLANT:ME02543-05 |
| phenotype ID: | 55071 |
| assay: | Soil Gross Morphology: 30% of flowers to be produced have opened |
| phenotype: | WHOLE PLANT - Other |
| notes: | many extra leaves |
| unique F1 plant ID: | R1 PLANT:ME02543-05 |
| phenotype ID: | 55072 |
| assay: | Soil Gross Morphology: 30% of flowers to be produced have opened |
| phenotype: | ROSETTE LEAVES - Other |
| notes: | extra rosette leaves |
| unique F1 plant ID: | R1 PLANT:ME02543-05 |
| phenotype ID: | 55073 |
| assay: | Soil Gross Morphology: 30% of flowers to be produced have opened |
| phenotype: | ROSETTE LEAVES - Curled 1 |
| notes: | NONE |

TABLE 1-continued

```
unique F1 plant ID:  R1 PLANT:ME02543-05
phenotype ID:        55074
assay:               Soil Gross Morphology: 30% of flowers to be produced have opened
phenotype:           INFLORESCENCE - Reduced Apical Dominance
notes:               NONE
unique F1 plant ID:  R1 PLANT:ME02543-05
phenotype ID:        55075
assay:               Soil Gross Morphology: 30% of flowers to be produced have opened
phenotype:           ROSETTE LEAVES - Lanceolate Shaped
notes:               NONE
unique F1 plant ID:  R1 PLANT:ME02543-05
phenotype ID:        55076
assay:               Soil Gross Morphology: 30% of flowers to be produced have opened
phenotype:           ROSETTE LEAVES - Serrate Margins
notes:               NONE
unique F1 plant ID:  R1 PLANT:ME02543-06
phenotype ID:        55104
assay:               Soil Gross Morphology: 30% of flowers to be produced have opened
phenotype:           INFLORESCENCE - Short
notes:               40pct height wt
unique F1 plant ID:  R1 PLANT:ME02543-06
phenotype ID:        55105
assay:               Soil Gross Morphology: 30% of flowers to be produced have opened
phenotype:           INFLORESCENCE - Reduced Apical Dominance
notes:               NONE
unique F1 plant ID:  R1 PLANT:ME02543-06
phenotype ID:        55106
assay:               Soil Gross Morphology: 30% of flowers to be produced have opened
phenotype:           WHOLE PLANT - Other
notes:               many extra leaves
unique F1 plant ID:  R1 PLANT:ME02543-06
phenotype ID:        55107
assay:               Soil Gross Morphology: 30% of flowers to be produced have opened
phenotype:           FLOWER - Sterile
notes:               NONE
unique F1 plant ID:  R1 PLANT:ME02543-06
phenotype ID:        55108
assay:               Soil Gross Morphology: 14 rosette leaves 1 mm in length
phenotype:           ROSETTE LEAVES - Serrate Margins
notes:               NONE
unique F1 plant ID:  R1 PLANT:ME02543-06
phenotype ID:        55109
assay:               Soil Gross Morphology: 30% of flowers to be produced have opened
phenotype:           WHOLE PLANT - Other
notes:               many extra leaves
unique F1 plant ID:  R1 PLANT:ME02543-06
phenotype ID:        55110
assay:               Soil Gross Morphology: 14 rosette leaves 1 mm in length
phenotype:           ROSETTE LEAVES - Other
notes:               extra rosette leaves
unique F1 plant ID:  R1 PLANT:ME02543-06
phenotype ID:        55111
assay:               Soil Gross Morphology: 14 rosette leaves 1 mm in length
phenotype:           ROSETTE LEAVES - Curled 1
notes:               NONE
unique F1 plant ID:  R1 PLANT:ME02543-06
phenotype ID:        55112
assay:               Soil Gross Morphology: 14 rosette leaves 1 mm in length
phenotype:           ROSETTE LEAVES - Lanceolate Shaped
notes:               NONE
unique F1 plant ID:  R1 PLANT:ME02543-06
phenotype ID:        55113
assay:               Soil Gross Morphology: 14 rosette leaves 1 mm in length
phenotype:           INFLORESCENCE - Late Flowering
notes:               NONE
unique F1 plant ID:  R1 PLANT:ME02543-07
phenotype ID:        55143
assay:               Soil Gross Morphology: 30% of flowers to be produced have opened
phenotype:           FLOWER - Reduced fertility
notes:               NONE
unique F1 plant ID:  R1 PLANT:ME02543-07
phenotype ID:        55144
assay:               Soil Gross Morphology: 30% of flowers to be produced have opened
phenotype:           WHOLE PLANT - Other
notes:               many extra leaves
unique F1 plant ID:  R1 PLANT:ME02543-07
phenotype ID:        55145
assay:               Soil Gross Morphology: 14 rosette leaves 1 mm in length
phenotype:           ROSETTE LEAVES - Lanceolate Shaped
```

TABLE 1-continued

| | |
|---|---|
| notes: | NONE |
| unique F1 plant ID: | R1 PLANT:ME02543-07 |
| phenotype ID: | 55146 |
| assay: | Soil Gross Morphology: 14 rosette leaves 1 mm in length |
| phenotype: | ROSETTE LEAVES - Serrate Margins |
| notes: | NONE |
| unique F1 plant ID: | R1 PLANT:ME02543-07 |
| phenotype ID: | 55147 |
| assay: | Soil Gross Morphology: 30% of flowers to be produced have opened |
| phenotype: | INFLORESCENCE - Reduced Apical Dominance |
| notes: | NONE |
| unique F1 plant ID: | R1 PLANT:ME02543-07 |
| phenotype ID: | 55148 |
| assay: | Soil Gross Morphology: 30% of flowers to be produced have opened |
| phenotype: | INFLORESCENCE - Short |
| notes: | 60pct height wt |
| unique F1 plant ID: | R1 PLANT:ME02543-07 |
| phenotype ID: | 55149 |
| assay: | Soil Gross Morphology: 14 rosette leaves 1 mm in length |
| phenotype: | INFLORESCENCE - Late Flowering |
| notes: | NONE |
| unique F1 plant ID: | R1 PLANT:ME02543-07 |
| phenotype ID: | 55150 |
| assay: | Soil Gross Morphology: 14 rosette leaves 1 mm in length |
| phenotype: | ROSETTE LEAVES - Other |
| notes: | extra rosette leaves |
| unique F1 plant ID: | R1 PLANT:ME02543-07 |
| phenotype ID: | 55151 |
| assay: | Soil Gross Morphology: 14 rosette leaves 1 mm in length |
| phenotype: | ROSETTE LEAVES - Curled 1 |
| notes: | NONE |
| unique F1 plant ID: | R1 PLANT:ME02543-07 |
| phenotype ID: | 55152 |
| assay: | Soil Gross Morphology: 30% of flowers to be produced have opened |
| phenotype: | WHOLE PLANT - Other |
| notes: | many extra leaves |
| unique F1 plant ID: | R1 PLANT:ME02543-09 |
| phenotype ID: | 55227 |
| assay: | Soil Gross Morphology: 30% of flowers to be produced have opened |
| phenotype: | INFLORESCENCE - Short |
| notes: | 40pct height wt |
| unique F1 plant ID: | R1 PLANT:ME02543-09 |
| phenotype ID: | 55228 |
| assay: | Soil Gross Morphology: 30% of flowers to be produced have opened |
| phenotype: | FLOWER - Sterile |
| notes: | NONE |
| unique F1 plant ID: | R1 PLANT:ME02543-09 |
| phenotype ID: | 55229 |
| assay: | Soil Gross Morphology: 30% of flowers to be produced have opened |
| phenotype: | INFLORESCENCE - Reduced Apical Dominance |
| notes: | NONE |
| unique F1 plant ID: | R1 PLANT:ME02543-09 |
| phenotype ID: | 55230 |
| assay: | Soil Gross Morphology: 14 rosette leaves 1 mm in length |
| phenotype: | ROSETTE LEAVES - Serrate Margins |
| notes: | NONE |
| unique F1 plant ID: | R1 PLANT:ME02543-09 |
| phenotype ID: | 55231 |
| assay: | Soil Gross Morphology: 14 rosette leaves 1 mm in length |
| phenotype: | ROSETTE LEAVES - Lanceolate Shaped |
| notes: | NONE |
| unique F1 plant ID: | R1 PLANT:ME02543-09 |
| phenotype ID: | 55232 |
| assay: | Soil Gross Morphology: 30% of flowers to be produced have opened |
| phenotype: | WHOLE PLANT - Other |
| notes: | many extra leaves |
| unique F1 plant ID: | R1 PLANT:ME02543-09 |
| phenotype ID: | 55233 |
| assay: | Soil Gross Morphology: 14 rosette leaves 1 mm in length |
| phenotype: | ROSETTE LEAVES - Other |
| notes: | extra rosette leaves |
| unique F1 plant ID: | R1 PLANT:ME02543-09 |
| phenotype ID: | 55234 |
| assay: | Soil Gross Morphology: 14 rosette leaves 1 mm in length |
| phenotype: | ROSETTE LEAVES - Curled 1 |
| notes: | NONE |
| unique F1 plant ID: | R1 PLANT:ME02543-09 |
| phenotype ID: | 55235 |
| assay: | Soil Gross Morphology: 14 rosette leaves 1 mm in length |

TABLE 1-continued

| | |
|---|---|
| phenotype: | INFLORESCENCE - Late Flowering |
| notes: | NONE |
| unique F1 plant ID: | R1 PLANT:ME02543-10 |
| phenotype ID: | 55255 |
| assay: | Soil Gross Morphology: 30% of flowers to be produced have opened |
| phenotype: | INFLORESCENCE - Reduced Apical Dominance |
| notes: | NONE |
| unique F1 plant ID: | R1 PLANT:ME02543-10 |
| phenotype ID: | 55256 |
| assay: | Soil Gross Morphology: 14 rosette leaves 1 mm in length |
| phenotype: | ROSETTE LEAVES - Other |
| notes: | extra rosette leaves |
| unique F1 plant ID: | R1 PLANT:ME02543-10 |
| phenotype ID: | 55257 |
| assay: | Soil Gross Morphology: 30% of flowers to be produced have opened |
| phenotype: | WHOLE PLANT - Other |
| notes: | many extra leaves |
| unique F1 plant ID: | R1 PLANT:ME02543-10 |
| phenotype ID: | 55258 |
| assay: | Soil Gross Morphology: 30% of flowers to be produced have opened |
| phenotype: | WHOLE PLANT - Other |
| notes: | many extra leaves |
| unique F1 plant ID: | R1 PLANT:ME02543-10 |
| phenotype ID: | 55259 |
| assay: | Soil Gross Morphology: 30% of flowers to be produced have opened |
| phenotype: | INFLORESCENCE - Short |
| notes: | 40pct height wt |
| unique F1 plant ID: | R1 PLANT:ME02543-10 |
| phenotype ID: | 55260 |
| assay: | Soil Gross Morphology: 30% of flowers to be produced have opened |
| phenotype: | FLOWER - Reduced fertility |
| notes: | NONE |
| unique F1 plant ID: | R1 PLANT:ME02543-10 |
| phenotype ID: | 55261 |
| assay: | Soil Gross Morphology: 14 rosette leaves 1 mm in length |
| phenotype: | ROSETTE LEAVES - Lanceolate Shaped |
| notes: | NONE |
| unique F1 plant ID: | R1 PLANT:ME02543-10 |
| phenotype ID: | 55262 |
| assay: | Soil Gross Morphology: 14 rosette leaves 1 mm in length |
| phenotype: | ROSETTE LEAVES - Serrate Margins |
| notes: | NONE |
| unique F1 plant ID: | R1 PLANT:ME02543-10 |
| phenotype ID: | 55263 |
| assay: | Soil Gross Morphology: 14 rosette leaves 1 mm in length |
| phenotype: | INFLORESCENCE - Late Flowering |
| notes: | NONE |
| unique F1 plant ID: | R1 PLANT:ME02543-10 |
| phenotype ID: | 55264 |
| assay: | Soil Gross Morphology: 14 rosette leaves 1 mm in length |
| phenotype: | ROSETTE LEAVES - Curled 1 |
| notes: | NONE |
| | Knock-in phenotype in gene(cDNA_id): 12575176 |
| clone ID: | 1207749 |
| Promoter: | 35S |
| unique F1 plant ID: | R1 PLANT:ME04632-03 |
| phenotype ID: | 119609 |
| assay: | Soil Gross Morphology: First flower buds visible |
| phenotype: | WHOLE PLANT - Small |
| notes: | 5 percent wt |
| unique F1 plant ID: | R1 PLANT:ME04632-03 |
| phenotype ID: | 119610 |
| assay: | Soil Gross Morphology: First flower buds visible |
| phenotype: | INFLORESCENCE - Short |
| notes: | NONE |
| unique F1 plant ID: | R1 PLANT:ME04632-03 |
| phenotype ID: | 119611 |
| assay: | Soil Gross Morphology: First flower buds visible |
| phenotype: | INFLORESCENCE - Late Flowering |
| notes: | NONE |
| unique F1 plant ID: | R1 PLANT:ME04632-03 |
| phenotype ID: | 119612 |
| assay: | Soil Gross Morphology: First flower buds visible |
| phenotype: | ROSETTE LEAVES - Long Petioles |
| notes: | NONE |
| unique F1 plant ID: | R1 PLANT:ME04632-03 |
| phenotype ID: | 119613 |
| assay: | Soil Gross Morphology: First flower buds visible |

TABLE 1-continued

| | |
|---|---|
| phenotype: | ROSETTE LEAVES - Other |
| notes: | fewer |
| unique F1 plant ID: | R1 PLANT:ME04632-03 |
| phenotype ID: | 119614 |
| assay: | Soil Gross Morphology: First flower buds visible |
| phenotype: | ROSETTE LEAVES - Other |
| notes: | standing |
| unique F1 plant ID: | R1 PLANT:ME04632-05 |
| phenotype ID: | 119710 |
| assay: | Soil Gross Morphology: First flower buds visible |
| phenotype: | INFLORESCENCE - Short |
| notes: | NONE |
| unique F1 plant ID: | R1 PLANT:ME04632-05 |
| phenotype ID: | 119711 |
| assay: | Soil Gross Morphology: First flower buds visible |
| phenotype: | INFLORESCENCE - Late Flowering |
| notes: | NONE |
| unique F1 plant ID: | R1 PLANT:ME04632-05 |
| phenotype ID: | 119712 |
| assay: | Soil Gross Morphology: First flower buds visible |
| phenotype: | ROSETTE LEAVES - Disorganized Rosette |
| notes: | NONE |
| unique F1 plant ID: | R1 PLANT:ME04632-07 |
| phenotype ID: | 119805 |
| assay: | Soil Gross Morphology: First flower buds visible |
| phenotype: | INFLORESCENCE - Short |
| notes: | NONE |
| unique F1 plant ID: | R1 PLANT:ME04632-07 |
| phenotype ID: | 119806 |
| assay: | Soil Gross Morphology: First flower buds visible |
| phenotype: | INFLORESCENCE - Late Flowering |
| notes: | NONE |
| unique F1 plant ID: | R1 PLANT:ME04632-08 |
| phenotype ID: | 119857 |
| assay: | Soil Gross Morphology: First flower buds visible |
| phenotype: | INFLORESCENCE - Short |
| notes: | NONE |
| unique F1 plant ID: | R1 PLANT:ME04632-08 |
| phenotype ID: | 119858 |
| assay: | Soil Gross Morphology: First flower buds visible |
| phenotype: | INFLORESCENCE - Late Flowering |
| notes: | NONE |
| | Knock-in phenotype in gene(cDNA_id): 12595094 |
| clone ID: | 292789 |
| Promoter: | 35S |
| unique F1 plant ID: | R1 PLANT:ME05153-03 |
| phenotype ID: | 89193 |
| assay: | Soil Gross Morphology: 10% of flowers to be produced have opened |
| phenotype: | WHOLE PLANT - Small |
| notes: | 20 pct wt |
| unique F1 plant ID: | R1 PLANT:ME05153-03 |
| phenotype ID: | 89194 |
| assay: | Soil Gross Morphology: 10% of flowers to be produced have opened |
| phenotype: | ROSETTE LEAVES - Disorganized Rosette |
| notes: | NONE |
| unique F1 plant ID: | R1 PLANT:ME05153-03 |
| phenotype ID: | 89195 |
| assay: | Soil Gross Morphology: 10% of flowers to be produced have opened |
| phenotype: | ROSETTE LEAVES - Other |
| notes: | misshapen |
| unique F1 plant ID: | R1 PLANT:ME05153-03 |
| phenotype ID: | 89196 |
| assay: | Soil Gross Morphology: 10% of flowers to be produced have opened |
| phenotype: | FLOWER - Reduced fertility |
| notes: | NONE |
| unique F1 plant ID: | R1 PLANT:ME05153-03 |
| phenotype ID: | 89197 |
| assay: | Soil Gross Morphology: 10% of flowers to be produced have opened |
| phenotype: | SILIQUES - Other |
| notes: | curled downward, resembles brevipedicellus |
| unique F1 plant ID: | R1 PLANT:ME05153-04 |
| phenotype ID: | 89245 |
| assay: | Soil Gross Morphology: 10% of flowers to be produced have opened |
| phenotype: | WHOLE PLANT - Small |
| notes: | 20 pct wt |
| unique F1 plant ID: | R1 PLANT:ME05153-04 |
| phenotype ID: | 89246 |
| assay: | Soil Gross Morphology: 10% of flowers to be produced have opened |

TABLE 1-continued

| | |
|---|---|
| phenotype: | SILIQUES - Other |
| notes: | curled downward, resembles brevipedicellus |
| unique F1 plant ID: | R1 PLANT:ME05153-05 |
| phenotype ID: | 89281 |
| assay: | Soil Gross Morphology: 10% of flowers to be produced have opened |
| phenotype: | WHOLE PLANT - Small |
| notes: | 40 pct wt |
| unique F1 plant ID: | R1 PLANT:ME05153-05 |
| phenotype ID: | 89282 |
| assay: | Soil Gross Morphology: 10% of flowers to be produced have opened |
| phenotype: | INFLORESCENCE - Other |
| notes: | wavy |
| unique F1 plant ID: | R1 PLANT:ME05153-08 |
| phenotype ID: | 89377 |
| assay: | Soil Gross Morphology: 10% of flowers to be produced have opened |
| phenotype: | SILIQUES - Other |
| notes: | curled downward, resembles brevipedicellus |

Knock-in phenotype in gene(cDNA_id): 12605081

| | |
|---|---|
| clone ID: | 1339493 |
| Promoter: | 35S |
| unique F1 plant ID: | R1 PLANT:ME04652-01 |
| phenotype ID: | 119539 |
| assay: | Soil Gross Morphology: 10% of flowers to be produced have opened |
| phenotype: | INFLORESCENCE - Short |
| notes: | NONE |
| unique F1 plant ID: | R1 PLANT:ME04652-01 |
| phenotype ID: | 119540 |
| assay: | Soil Gross Morphology: 10% of flowers to be produced have opened |
| phenotype: | INFLORESCENCE - Late Flowering |
| notes: | NONE |
| unique F1 plant ID: | R1 PLANT:ME04652-01 |
| phenotype ID: | 119541 |
| assay: | Soil Gross Morphology: 10% of flowers to be produced have opened |
| phenotype: | ROSETTE LEAVES - Curled 3 |
| notes: | NONE |
| unique F1 plant ID: | R1 PLANT:ME04652-01 |
| phenotype ID: | 119542 |
| assay: | Soil Gross Morphology: 10% of flowers to be produced have opened |
| phenotype: | WHOLE PLANT - Dark Green |
| notes: | NONE |
| unique F1 plant ID: | R1 PLANT:ME04652-01 |
| phenotype ID: | 119543 |
| assay: | Soil Gross Morphology: 10% of flowers to be produced have opened |
| phenotype: | ROSETTE LEAVES - Other |
| notes: | fewer |
| unique F1 plant ID: | R1 PLANT:ME04652-01 |
| phenotype ID: | 119544 |
| assay: | Soil Gross Morphology: 10% of flowers to be produced have opened |
| phenotype: | WHOLE PLANT - Small |
| notes: | 25 percent wt |
| unique F1 plant ID: | R1 PLANT:ME04652-05 |
| phenotype ID: | 119722 |
| assay: | Soil Gross Morphology: First flower buds visible |
| phenotype: | INFLORESCENCE - Late Flowering |
| notes: | NONE |
| unique F1 plant ID: | R1 PLANT:ME04652-05 |
| phenotype ID: | 119723 |
| assay: | Soil Gross Morphology: First flower buds visible |
| phenotype: | INFLORESCENCE - Short |
| notes: | NONE |
| unique F1 plant ID: | R1 PLANT:ME04652-05 |
| phenotype ID: | 119724 |
| assay: | Soil Gross Morphology: First flower buds visible |
| phenotype: | WHOLE PLANT - Dark Green |
| notes: | NONE |
| unique F1 plant ID: | R1 PLANT:ME04652-05 |
| phenotype ID: | 119725 |
| assay: | Soil Gross Morphology: First flower buds visible |
| phenotype: | WHOLE PLANT - Small |
| notes: | 25 percent wt |
| unique F1 plant ID: | R1 PLANT:ME04652-05 |
| phenotype ID: | 119726 |
| assay: | Soil Gross Morphology: First flower buds visible |
| phenotype: | ROSETTE LEAVES - Serrate Margins |
| notes: | NONE |
| unique F1 plant ID: | R1 PLANT:ME04652-10 |
| phenotype ID: | 119951 |
| assay: | Soil Gross Morphology: First flower buds visible |

TABLE 1-continued

| | |
|---|---|
| phenotype: | WHOLE PLANT - Other |
| notes: | pale |
| unique F1 plant ID: | R1 PLANT:ME04652-10 |
| phenotype ID: | 119952 |
| assay: | Soil Gross Morphology: First flower buds visible |
| phenotype: | WHOLE PLANT - Small |
| notes: | 5 percent wt |
| unique F1 plant ID: | R1 PLANT:ME04652-10 |
| phenotype ID: | 119953 |
| assay: | Soil Gross Morphology: First flower buds visible |
| phenotype: | ROSETTE LEAVES - Oval Shaped |
| notes: | NONE |
| unique F1 plant ID: | R1 PLANT:ME04652-10 |
| phenotype ID: | 119954 |
| assay: | Soil Gross Morphology: First flower buds visible |
| phenotype: | INFLORESCENCE - Late Flowering |
| notes: | NONE |
| unique F1 plant ID: | R1 PLANT:ME04652-10 |
| phenotype ID: | 119955 |
| assay: | Soil Gross Morphology: First flower buds visible |
| phenotype: | INFLORESCENCE - Short |
| notes: | NONE |

Knock-in phenotype in gene(cDNA_id): 12670870

| | |
|---|---|
| clone ID: | NULL |
| Promoter: | 35S |
| unique F1 plant ID: | R1 PLANT:ME11241-01 |
| phenotype ID: | 146181 |
| assay: | Soil Gross Morphology: 10% of flowers to be produced have opened |
| phenotype: | ROSETTE LEAVES - Undulate Shaped |
| notes: | NONE |
| unique F1 plant ID: | R1 PLANT:ME11241-01 |
| phenotype ID: | 146182 |
| assay: | Soil Gross Morphology: 10% of flowers to be produced have opened |
| phenotype: | WHOLE PLANT - Small |
| notes: | 50 pct size of wt |
| unique F1 plant ID: | R1 PLANT:ME11241-01 |
| phenotype ID: | 146183 |
| assay: | Soil Gross Morphology: 10% of flowers to be produced have opened |
| phenotype: | ROSETTE LEAVES - Serrate Margins |
| notes: | NONE |
| unique F1 plant ID: | R1 PLANT:ME11241-02 |
| phenotype ID: | 146184 |
| assay: | Soil Gross Morphology: 10% of flowers to be produced have opened |
| phenotype: | ROSETTE LEAVES - Serrate Margins |
| notes: | NONE |
| unique F1 plant ID: | R1 PLANT:ME11241-02 |
| phenotype ID: | 146185 |
| assay: | Soil Gross Morphology: 10% of flowers to be produced have opened |
| phenotype: | ROSETTE LEAVES - Undulate Shaped |
| notes: | NONE |
| unique F1 plant ID: | R1 PLANT:ME11241-07 |
| phenotype ID: | 146186 |
| assay: | Soil Gross Morphology: 10% of flowers to be produced have opened |
| phenotype: | ROSETTE LEAVES - Serrate Margins |
| notes: | NONE |
| unique F1 plant ID: | R1 PLANT:ME11241-07 |
| phenotype ID: | 146187 |
| assay: | Soil Gross Morphology: 10% of flowers to be produced have opened |
| phenotype: | ROSETTE LEAVES - Undulate Shaped |
| notes: | NONE |
| unique F1 plant ID: | R1 PLANT:ME11241-08 |
| phenotype ID: | 146188 |
| assay: | Soil Gross Morphology: 10% of flowers to be produced have opened |
| phenotype: | ROSETTE LEAVES - Serrate Margins |
| notes: | NONE |
| unique F1 plant ID: | R1 PLANT:ME11241-08 |
| phenotype ID: | 146189 |
| assay: | Soil Gross Morphology: 10% of flowers to be produced have opened |
| phenotype: | ROSETTE LEAVES - Undulate Shaped |
| notes: | NONE |
| unique F1 plant ID: | R1 PLANT:ME11241-09 |
| phenotype ID: | 146190 |
| assay: | Soil Gross Morphology: 10% of flowers to be produced have opened |
| phenotype: | ROSETTE LEAVES - Serrate Margins |
| notes: | NONE |
| unique F1 plant ID: | R1 PLANT:ME11241-09 |
| phenotype ID: | 146191 |
| assay: | Soil Gross Morphology: 10% of flowers to be produced have opened |

TABLE 1-continued

| | |
|---|---|
| phenotype: | ROSETTE LEAVES - Undulate Shaped |
| notes: | NONE |
| unique F1 plant ID: | R1 PLANT:ME11241-10 |
| phenotype ID: | 146192 |
| assay: | Soil Gross Morphology: 10% of flowers to be produced have opened |
| phenotype: | ROSETTE LEAVES - Serrate Margins |
| notes: | NONE |
| unique F1 plant ID: | R1 PLANT:ME11241-10 |
| phenotype ID: | 146193 |
| assay: | Soil Gross Morphology: 10% of flowers to be produced have opened |
| phenotype: | ROSETTE LEAVES - Undulate Shaped |
| notes: | NONE |
| unique F1 plant ID: | R1 PLANT:ME11241-10 |
| phenotype ID: | 146194 |
| assay: | Soil Gross Morphology: 10% of flowers to be produced have opened |
| phenotype: | WHOLE PLANT - Small |
| notes: | 40 pct size of wt |
| | Knock-in phenotype in gene(cDNA_id): 12718480 |
| | |
| clone ID: | NULL |
| Promoter: | 35S |
| unique F1 plant ID: | R1 PLANT:ME09546-01 |
| phenotype ID: | 139073 |
| assay: | Soil Gross Morphology: 5 rosette leaves 1 mm in length |
| phenotype: | ROSETTE LEAVES - Curled 4 |
| notes: | NONE |
| unique F1 plant ID: | R1 PLANT:ME09546-02 |
| phenotype ID: | 139075 |
| assay: | Soil Gross Morphology: 6 rosette leaves 1 mm in length |
| phenotype: | ROSETTE LEAVES - Curled 4 |
| notes: | NONE |
| unique F1 plant ID: | R1 PLANT:ME09546-02 |
| phenotype ID: | 139076 |
| assay: | Soil Gross Morphology: 6 rosette leaves 1 mm in length |
| phenotype: | WHOLE PLANT - Small |
| notes: | 25 pct wt |
| unique F1 plant ID: | R1 PLANT:ME09546-04 |
| phenotype ID: | 139077 |
| assay: | Soil Gross Morphology: 5 rosette leaves 1 mm in length |
| phenotype: | ROSETTE LEAVES - Curled 4 |
| notes: | NONE |
| unique F1 plant ID: | R1 PLANT:ME09546-04 |
| phenotype ID: | 139078 |
| assay: | Soil Gross Morphology: 5 rosette leaves 1 mm in length |
| phenotype: | WHOLE PLANT - Small |
| notes: | 25 pct wt |
| unique F1 plant ID: | R1 PLANT:ME09546-05 |
| phenotype ID: | 139082 |
| assay: | Soil Gross Morphology: 6 rosette leaves 1 mm in length |
| phenotype: | ROSETTE LEAVES - Curled 4 |
| notes: | NONE |
| unique F1 plant ID: | R1 PLANT:ME09546-05 |
| phenotype ID: | 139083 |
| assay: | Soil Gross Morphology: 6 rosette leaves 1 mm in length |
| phenotype: | WHOLE PLANT - Small |
| notes: | 25 pct wt |
| | Knock-in phenotype in gene(cDNA_id): 12722627 |
| | |
| clone ID: | 18857 |
| Promoter: | 35S |
| unique F1 plant ID: | R1 PLANT:ME08493-01 |
| phenotype ID: | 124552 |
| assay: | Soil Gross Morphology: 30% of flowers to be produced have opened |
| phenotype: | WHOLE PLANT - Large |
| notes: | 120 pct wt |
| unique F1 plant ID: | R1 PLANT:ME08493-03 |
| phenotype ID: | 124572 |
| assay: | Soil Gross Morphology: 30% of flowers to be produced have opened |
| phenotype: | WHOLE PLANT - Large |
| notes: | 120 pct wt |
| unique F1 plant ID: | R1 PLANT:ME08493-04 |
| phenotype ID: | 124580 |
| assay: | Soil Gross Morphology: 30% of flowers to be produced have opened |
| phenotype: | WHOLE PLANT - Large |
| notes: | 120 pct wt |
| unique F1 plant ID: | R1 PLANT:ME08493-05 |
| phenotype ID: | 124590 |
| assay: | Soil Gross Morphology: 30% of flowers to be produced have opened |
| phenotype: | WHOLE PLANT - Large |

TABLE 1-continued

| | |
|---|---|
| notes: | 120 pct wt |
| unique F1 plant ID: | R1 PLANT:ME08493-06 |
| phenotype ID: | 124599 |
| assay: | Soil Gross Morphology: 30% of flowers to be produced have opened |
| phenotype: | WHOLE PLANT - Large |
| notes: | 120 pct wt |
| unique F1 plant ID: | R1 PLANT:ME08493-08 |
| phenotype ID: | 124606 |
| assay: | Soil Gross Morphology: 30% of flowers to be produced have opened |
| phenotype: | WHOLE PLANT - Large |
| notes: | 120 pct wt |
| unique F1 plant ID: | R1 PLANT:ME08493-10 |
| phenotype ID: | 124613 |
| assay: | Soil Gross Morphology: 30% of flowers to be produced have opened |
| phenotype: | WHOLE PLANT - Large |
| notes: | 120 pct wt |

Knock-in phenotype in gene(cDNA_id): 12734583

| | |
|---|---|
| clone ID: | NULL |
| Promoter: | 35S |
| unique F1 plant ID: | R1 PLANT:ME09538-01 |
| phenotype ID: | 139091 |
| assay: | Soil Gross Morphology: 5 rosette leaves 1 mm in length |
| phenotype: | ROSETTE LEAVES - Long Petioles |
| notes: | NONE |
| unique F1 plant ID: | R1 PLANT:ME09538-02 |
| phenotype ID: | 139093 |
| assay: | Soil Gross Morphology: 6 rosette leaves 1 mm in length |
| phenotype: | ROSETTE LEAVES - Long Petioles |
| notes: | NONE |
| unique F1 plant ID: | R1 PLANT:ME09538-02 |
| phenotype ID: | 139094 |
| assay: | Soil Gross Morphology: 10% of flowers to be produced have opened |
| phenotype: | FLOWER - Reduced fertility |
| notes: | NONE |
| unique F1 plant ID: | R1 PLANT:ME09538-04 |
| phenotype ID: | 139099 |
| assay: | Soil Gross Morphology: 30% of flowers to be produced have opened |
| phenotype: | FLOWER - Reduced fertility |
| notes: | NONE |
| unique F1 plant ID: | R1 PLANT:ME09538-04 |
| phenotype ID: | 139100 |
| assay: | Soil Gross Morphology: 30% of flowers to be produced have opened |
| phenotype: | SILIQUES - Sickle |
| notes: | NONE |
| unique F1 plant ID: | R1 PLANT:ME09538-05 |
| phenotype ID: | 139102 |
| assay: | Soil Gross Morphology: 4 rosette leaves 1 mm in length |
| phenotype: | ROSETTE LEAVES - Long Petioles |
| notes: | NONE |
| unique F1 plant ID: | R1 PLANT:ME09538-06 |
| phenotype ID: | 139104 |
| assay: | Soil Gross Morphology: 4 rosette leaves 1 mm in length |
| phenotype: | ROSETTE LEAVES - Long Petioles |
| notes: | NONE |

Knock-in phenotype in gene(cDNA_id): 13486967

| | |
|---|---|
| clone ID: | 19486 |
| Promoter: | 35S |
| unique F1 plant ID: | R1 PLANT:ME02915-01 |
| phenotype ID: | 55495 |
| assay: | Soil Gross Morphology: 30% of flowers to be produced have opened |
| phenotype: | ROSETTE LEAVES - Other |
| notes: | few rosette leaves |
| unique F1 plant ID: | R1 PLANT:ME02915-01 |
| phenotype ID: | 55496 |
| assay: | Soil Gross Morphology: 30% of flowers to be produced have opened |
| phenotype: | WHOLE PLANT - Other |
| notes: | lt. green |
| unique F1 plant ID: | R1 PLANT:ME02915-01 |
| phenotype ID: | 55497 |
| assay: | Soil Gross Morphology: 30% of flowers to be produced have opened |
| phenotype: | ROSETTE LEAVES - Serrate Margins |
| notes: | NONE |
| unique F1 plant ID: | R1 PLANT:ME02915-04 |
| phenotype ID: | 55729 |
| assay: | Soil Gross Morphology: 30% of flowers to be produced have opened |
| phenotype: | ROSETTE LEAVES - Curled 1 |
| notes: | NONE |

TABLE 1-continued

| | |
|---|---|
| unique F1 plant ID: | R1 PLANT:ME02915-04 |
| phenotype ID: | 55730 |
| assay: | Soil Gross Morphology: 30% of flowers to be produced have opened |
| phenotype: | WHOLE PLANT - Other |
| notes: | lt. green |
| unique F1 plant ID: | R1 PLANT:ME02915-04 |
| phenotype ID: | 55731 |
| assay: | Soil Gross Morphology: 30% of flowers to be produced have opened |
| phenotype: | ROSETTE LEAVES - Serrate Margins |
| notes: | NONE |
| unique F1 plant ID: | R1 PLANT:ME02915-06 |
| phenotype ID: | 55868 |
| assay: | Soil Gross Morphology: 30% of flowers to be produced have opened |
| phenotype: | WHOLE PLANT - Other |
| notes: | lt.green |
| unique F1 plant ID: | R1 PLANT:ME02915-09 |
| phenotype ID: | 56402 |
| assay: | Soil Gross Morphology: 10% of flowers to be produced have opened |
| phenotype: | ROSETTE LEAVES - Oval Shaped |
| notes: | NONE |
| unique F1 plant ID: | R1 PLANT:ME02915-09 |
| phenotype ID: | 56403 |
| assay: | Soil Gross Morphology: 10% of flowers to be produced have opened |
| phenotype: | WHOLE PLANT - Small |
| notes: | NONE |
| unique F1 plant ID: | R1 PLANT:ME02915-09 |
| phenotype ID: | 56404 |
| assay: | Soil Gross Morphology: 10% of flowers to be produced have opened |
| phenotype: | WHOLE PLANT - Dark Green |
| notes: | NONE |

Knock-in phenotype in gene(cDNA_id): 13491243

| | |
|---|---|
| clone ID: | 11975 |
| Promoter: | 35S |
| unique F1 plant ID: | R1 PLANT:ME03249-01 |
| phenotype ID: | 71423 |
| assay: | Soil Gross Morphology: 50% of flowers to be produced have opened |
| phenotype: | ROSETTE LEAVES - Curled 3 |
| notes: | burning |
| unique F1 plant ID: | R1 PLANT:ME03249-02 |
| phenotype ID: | 71436 |
| assay: | Soil Gross Morphology: 50% of flowers to be produced have opened |
| phenotype: | ROSETTE LEAVES - Curled 3 |
| notes: | burning |
| unique F1 plant ID: | R1 PLANT:ME03249-03 |
| phenotype ID: | 71462 |
| assay: | Soil Gross Morphology: 50% of flowers to be produced have opened |
| phenotype: | ROSETTE LEAVES - Curled 3 |
| notes: | burning |
| unique F1 plant ID: | R1 PLANT:ME03249-03 |
| phenotype ID: | 71463 |
| assay: | Soil Gross Morphology: 50% of flowers to be produced have opened |
| phenotype: | WHOLE PLANT - Small |
| notes: | 75pct. of wt |
| unique F1 plant ID: | R1 PLANT:ME03249-04 |
| phenotype ID: | 71487 |
| assay: | Soil Gross Morphology: 50% of flowers to be produced have opened |
| phenotype: | ROSETTE LEAVES - Curled 3 |
| notes: | NONE |
| unique F1 plant ID: | R1 PLANT:ME03249-04 |
| phenotype ID: | 71488 |
| assay: | Soil Gross Morphology: 50% of flowers to be produced have opened |
| phenotype: | WHOLE PLANT - Small |
| notes: | 50pct. of wt |
| unique F1 plant ID: | R1 PLANT:ME03249-05 |
| phenotype ID: | 71499 |
| assay: | Soil Gross Morphology: 50% of flowers to be produced have opened |
| phenotype: | WHOLE PLANT - Small |
| notes: | 60pct. of wt |
| unique F1 plant ID: | R1 PLANT:ME03249-05 |
| phenotype ID: | 71500 |
| assay: | Soil Gross Morphology: 50% of flowers to be produced have opened |
| phenotype: | ROSETTE LEAVES - Curled 3 |
| notes: | burning |
| unique F1 plant ID: | R1 PLANT:ME03249-09 |
| phenotype ID: | 71547 |
| assay: | Soil Gross Morphology: 50% of flowers to be produced have opened |
| phenotype: | ROSETTE LEAVES - Curled 3 |
| notes: | burning |

TABLE 1-continued

| | |
|---|---|
| unique F1 plant ID: | R1 PLANT:ME03249-09 |
| phenotype ID: | 71548 |
| assay: | Soil Gross Morphology: 50% of flowers to be produced have opened |
| phenotype: | WHOLE PLANT - Small |
| notes: | 15pct. of wt |

Knock-in phenotype in gene(cDNA_id): 13491788

| | |
|---|---|
| clone ID: | 101798 |
| Promoter: | 35S |
| unique F1 plant ID: | R1 PLANT:ME04066-07 |
| phenotype ID: | 82203 |
| assay: | Soil Gross Morphology: 50% of flowers to be produced have opened |
| phenotype: | WHOLE PLANT - Late Senescence |
| notes: | NONE |
| unique F1 plant ID: | R1 PLANT:ME04066-07 |
| phenotype ID: | 82204 |
| assay: | Soil Gross Morphology: 50% of flowers to be produced have opened |
| phenotype: | FLOWER - Sterile |
| notes: | NONE |
| unique F1 plant ID: | R1 PLANT:ME04066-08 |
| phenotype ID: | 82257 |
| assay: | Soil Gross Morphology: 50% of flowers to be produced have opened |
| phenotype: | FLOWER - Reduced fertility |
| notes: | NONE |
| unique F1 plant ID: | R1 PLANT:ME04066-08 |
| phenotype ID: | 82258 |
| assay: | Soil Gross Morphology: 50% of flowers to be produced have opened |
| phenotype: | WHOLE PLANT - Late Senescence |
| notes: | NONE |
| unique F1 plant ID: | R1 PLANT:ME04066-10 |
| phenotype ID: | 82334 |
| assay: | Soil Gross Morphology: 30% of flowers to be produced have opened |
| phenotype: | WHOLE PLANT - Small |
| notes: | 10 percent weight |
| unique F1 plant ID: | R1 PLANT:ME04066-10 |
| phenotype ID: | 82335 |
| assay: | Soil Gross Morphology: 30% of flowers to be produced have opened |
| phenotype: | FLOWER - Sterile |
| notes: | NONE |

Knock-in phenotype in gene(cDNA_id): 13492937

| | |
|---|---|
| clone ID: | 41439 |
| Promoter: | 34414F |
| unique F1 plant ID: | R1 PLANT:ME09357-01 |
| phenotype ID: | 124906 |
| assay: | Soil Gross Morphology: 13 rosette leaves 1 mm in length |
| phenotype: | INFLORESCENCE - Late Flowering |
| notes: | NONE |
| unique F1 plant ID: | R1 PLANT:ME09357-02 |
| phenotype ID: | 124927 |
| assay: | Soil Gross Morphology: 8 rosette leaves 1 mm in length |
| phenotype: | WHOLE PLANT - Small |
| notes: | 10 pct wt |
| unique F1 plant ID: | R1 PLANT:ME09357-02 |
| phenotype ID: | 124928 |
| assay: | Soil Gross Morphology: 8 rosette leaves 1 mm in length |
| phenotype: | WHOLE PLANT - Dark Green |
| notes: | NONE |
| unique F1 plant ID: | R1 PLANT:ME09357-02 |
| phenotype ID: | 124929 |
| assay: | Soil Gross Morphology: 8 rosette leaves 1 mm in length |
| phenotype: | ROSETTE LEAVES - Oval Shaped |
| notes: | NONE |
| unique F1 plant ID: | R1 PLANT:ME09357-02 |
| phenotype ID: | 124930 |
| assay: | Soil Gross Morphology: 8 rosette leaves 1 mm in length |
| phenotype: | ROSETTE LEAVES - Short Petioles |
| notes: | NONE |
| unique F1 plant ID: | R1 PLANT:ME09357-02 |
| phenotype ID: | 124931 |
| assay: | Soil Gross Morphology: 8 rosette leaves 1 mm in length |
| phenotype: | INFLORESCENCE - Late Flowering |
| notes: | NONE |
| unique F1 plant ID: | R1 PLANT:ME09357-03 |
| phenotype ID: | 124948 |
| assay: | Soil Gross Morphology: 11 rosette leaves 1 mm in length |
| phenotype: | INFLORESCENCE - Late Flowering |
| notes: | NONE |
| unique F1 plant ID: | R1 PLANT:ME09357-06 |

TABLE 1-continued

```
phenotype ID:        125022
assay:               Soil Gross Morphology: 10 rosette leaves 1 mm in length
phenotype:           INFLORESCENCE - Late Flowering
notes:               NONE
unique F1 plant ID:  R1 PLANT:ME09357-10
phenotype ID:        125107
assay:               Soil Gross Morphology: 11 rosette leaves 1 mm in length
phenotype:           WHOLE PLANT - Small
notes:               NONE
unique F1 plant ID:  R1 PLANT:ME09357-10
phenotype ID:        125108
assay:               Soil Gross Morphology: 11 rosette leaves 1 mm in length
phenotype:           WHOLE PLANT - Dark Green
notes:               NONE
unique F1 plant ID:  R1 PLANT:ME09357-10
phenotype ID:        125109
assay:               Soil Gross Morphology: 11 rosette leaves 1 mm in length
phenotype:           INFLORESCENCE - Late Flowering
notes:               NONE
unique F1 plant ID:  R1 PLANT:ME01731-01
phenotype ID:        54217
assay:               Soil Gross Morphology: First flower buds visible
phenotype:           WHOLE PLANT - Small
notes:               NONE
unique F1 plant ID:  R1 PLANT:ME01731-01
phenotype ID:        54218
assay:               Soil Gross Morphology: 50% of flowers to be produced have opened
phenotype:           WHOLE PLANT - Other
notes:               NONE
unique F1 plant ID:  R1 PLANT:ME01731-03
phenotype ID:        54267
assay:               Soil Gross Morphology: First flower buds visible
phenotype:           WHOLE PLANT - Small
notes:               NONE
unique F1 plant ID:  R1 PLANT:ME01731-03
phenotype ID:        54268
assay:               Soil Gross Morphology: 50% of flowers to be produced have opened
phenotype:           WHOLE PLANT - Other
notes:               NONE
unique F1 plant ID:  R1 PLANT:ME01731-05
phenotype ID:        54305
assay:               Soil Gross Morphology: First flower buds visible
phenotype:           WHOLE PLANT - Small
notes:               NONE
unique F1 plant ID:  R1 PLANT:ME01731-05
phenotype ID:        54306
assay:               Soil Gross Morphology: 50% of flowers to be produced have opened
phenotype:           WHOLE PLANT - Other
notes:               silver
```

Knock-in phenotype in gene(cDNA__id): 13494229

```
clone ID:            38101
Promoter:            35S
unique F1 plant ID:  R1 PLANT:ME05650-04
phenotype ID:        98542
assay:               Soil Gross Morphology: First flower buds visible
phenotype:           WHOLE PLANT - Small
notes:               2 pct wt
unique F1 plant ID:  R1 PLANT:ME05650-04
phenotype ID:        98543
assay:               Soil Gross Morphology: First flower buds visible
phenotype:           ROSETTE LEAVES - Short Petioles
notes:               NONE
unique F1 plant ID:  R1 PLANT:ME05650-04
phenotype ID:        98544
assay:               Soil Gross Morphology: First flower buds visible
phenotype:           ROSETTE LEAVES - Disorganized Rosette
notes:               NONE
unique F1 plant ID:  R1 PLANT:ME05650-05
phenotype ID:        98566
assay:               Soil Gross Morphology: First flower buds visible
phenotype:           WHOLE PLANT - Small
notes:               50 pct wt
unique F1 plant ID:  R1 PLANT:ME05650-05
phenotype ID:        98567
assay:               Soil Gross Morphology: First flower buds visible
phenotype:           WHOLE PLANT - Dark Green
notes:               NONE
unique F1 plant ID:  R1 PLANT:ME05650-05
```

TABLE 1-continued

| | |
|---|---|
| phenotype ID: | 98568 |
| assay: | Soil Gross Morphology: First flower buds visible |
| phenotype: | ROSETTE LEAVES - Curled 2 |
| notes: | NONE |
| unique F1 plant ID: | R1 PLANT:ME05650-06 |
| phenotype ID: | 98605 |
| assay: | Soil Gross Morphology: 7 rosette leaves 1 mm in length |
| phenotype: | INFLORESCENCE - Late Flowering |
| notes: | NONE |
| unique F1 plant ID: | R1 PLANT:ME05650-06 |
| phenotype ID: | 98606 |
| assay: | Soil Gross Morphology: 7 rosette leaves 1 mm in length |
| phenotype: | ROSETTE LEAVES - Short Petioles |
| notes: | NONE |
| unique F1 plant ID: | R1 PLANT:ME05650-06 |
| phenotype ID: | 98607 |
| assay: | Soil Gross Morphology: 7 rosette leaves 1 mm in length |
| phenotype: | WHOLE PLANT - Misc. Dwarf |
| notes: | NONE |
| unique F1 plant ID: | R1 PLANT:ME05650-06 |
| phenotype ID: | 98608 |
| assay: | Soil Gross Morphology: 7 rosette leaves 1 mm in length |
| phenotype: | WHOLE PLANT - Small |
| notes: | 2 pct wt |
| unique F1 plant ID: | R1 PLANT:ME05650-07 |
| phenotype ID: | 98657 |
| assay: | Soil Gross Morphology: First flower buds visible |
| phenotype: | INFLORESCENCE - Late Flowering |
| notes: | NONE |
| unique F1 plant ID: | R1 PLANT:ME05650-07 |
| phenotype ID: | 98658 |
| assay: | Soil Gross Morphology: First flower buds visible |
| phenotype: | ROSETTE LEAVES - Short Petioles |
| notes: | NONE |
| unique F1 plant ID: | R1 PLANT:ME05650-07 |
| phenotype ID: | 98659 |
| assay: | Soil Gross Morphology: First flower buds visible |
| phenotype: | WHOLE PLANT - Misc. Dwarf |
| notes: | NONE |
| unique F1 plant ID: | R1 PLANT:ME05650-07 |
| phenotype ID: | 98660 |
| assay: | Soil Gross Morphology: First flower buds visible |
| phenotype: | WHOLE PLANT - Small |
| notes: | 5 pct wt |
| unique F1 plant ID: | R1 PLANT:ME05650-08 |
| phenotype ID: | 98711 |
| assay: | Soil Gross Morphology: 4 rosette leaves 1 mm in length |
| phenotype: | WHOLE PLANT - Small |
| notes: | very slow growing |
| unique F1 plant ID: | R1 PLANT:ME05650-08 |
| phenotype ID: | 98712 |
| assay: | Soil Gross Morphology: 4 rosette leaves 1 mm in length |
| phenotype: | INFLORESCENCE - Late Flowering |
| notes: | NONE |
| unique F1 plant ID: | R1 PLANT:ME05650-08 |
| phenotype ID: | 98713 |
| assay: | Soil Gross Morphology: First flower buds visible |
| phenotype: | WHOLE PLANT - Small |
| notes: | 50 pct wt |
| unique F1 plant ID: | R1 PLANT:ME05650-08 |
| phenotype ID: | 98714 |
| assay: | Soil Gross Morphology: First flower buds visible |
| phenotype: | WHOLE PLANT - Dark Green |
| notes: | NONE |
| unique F1 plant ID: | R1 PLANT:ME05650-08 |
| phenotype ID: | 98715 |
| assay: | Soil Gross Morphology: First flower buds visible |
| phenotype: | ROSETTE LEAVES - Curled 2 |
| notes: | NONE |
| unique F1 plant ID: | R1 PLANT:ME05650-09 |
| phenotype ID: | 98757 |
| assay: | Soil Gross Morphology: First flower buds visible |
| phenotype: | WHOLE PLANT - Small |
| notes: | 2 pct wt |
| unique F1 plant ID: | R1 PLANT:ME05650-09 |
| phenotype ID: | 98758 |
| assay: | Soil Gross Morphology: First flower buds visible |
| phenotype: | ROSETTE LEAVES - Short Petioles |
| notes: | NONE |

TABLE 1-continued

| | |
|---|---|
| unique F1 plant ID: | R1 PLANT:ME05650-09 |
| phenotype ID: | 98759 |
| assay: | Soil Gross Morphology: First flower buds visible |
| phenotype: | ROSETTE LEAVES - Disorganized Rosette |
| notes: | NONE |

Knock-in phenotype in gene(cDNA_id): 13495872

| | |
|---|---|
| clone ID: | 95453 |
| Promoter: | 35S |
| unique F1 plant ID: | R1 PLANT:ME04115-02 |
| phenotype ID: | 82079 |
| assay: | Soil Gross Morphology: 50% of flowers to be produced have opened |
| phenotype: | WHOLE PLANT - Dark Green |
| notes: | NONE |
| unique F1 plant ID: | R1 PLANT:ME04115-02 |
| phenotype ID: | 82080 |
| assay: | Soil Gross Morphology: 50% of flowers to be produced have opened |
| phenotype: | FLOWER - Reduced fertility |
| notes: | NONE |
| unique F1 plant ID: | R1 PLANT:ME04115-02 |
| phenotype ID: | 82081 |
| assay: | Soil Gross Morphology: 50% of flowers to be produced have opened |
| phenotype: | WHOLE PLANT - Dark Green |
| notes: | NONE |
| unique F1 plant ID: | R1 PLANT:ME04115-02 |
| phenotype ID: | 82082 |
| assay: | Soil Gross Morphology: 50% of flowers to be produced have opened |
| phenotype: | FLOWER - Other |
| notes: | clustered flowers |
| unique F1 plant ID: | R1 PLANT:ME04115-02 |
| phenotype ID: | 82083 |
| assay: | Soil Gross Morphology: 50% of flowers to be produced have opened |
| phenotype: | WHOLE PLANT - Dark Green |
| notes: | NONE |
| unique F1 plant ID: | R1 PLANT:ME04115-02 |
| phenotype ID: | 82084 |
| assay: | Soil Gross Morphology: 50% of flowers to be produced have opened |
| phenotype: | FLOWER - Reduced fertility |
| notes: | NONE |
| unique F1 plant ID: | R1 PLANT:ME04115-02 |
| phenotype ID: | 82085 |
| assay: | Soil Gross Morphology: 50% of flowers to be produced have opened |
| phenotype: | FLOWER - Other |
| notes: | clustered flowers |
| unique F1 plant ID: | R1 PLANT:ME04115-05 |
| phenotype ID: | 82159 |
| assay: | Soil Gross Morphology: 50% of flowers to be produced have opened |
| phenotype: | ROSETTE LEAVES - Lanceolate Shaped |
| notes: | NONE |
| unique F1 plant ID: | R1 PLANT:ME04115-05 |
| phenotype ID: | 82160 |
| assay: | Soil Gross Morphology: Flowering complete |
| phenotype: | INFLORESCENCE - Weak |
| notes: | NONE |
| unique F1 plant ID: | R1 PLANT:ME04115-05 |
| phenotype ID: | 82161 |
| assay: | Soil Gross Morphology: Flowering complete |
| phenotype: | WHOLE PLANT - Small |
| notes: | NONE |
| unique F1 plant ID: | R1 PLANT:ME04115-05 |
| phenotype ID: | 82162 |
| assay: | Soil Gross Morphology: Flowering complete |
| phenotype: | WHOLE PLANT - Small |
| notes: | NONE |
| unique F1 plant ID: | R1 PLANT:ME04115-05 |
| phenotype ID: | 82163 |
| assay: | Soil Gross Morphology: Flowering complete |
| phenotype: | WHOLE PLANT - Dark Green |
| notes: | 50 percent weight |
| unique F1 plant ID: | R1 PLANT:ME04115-05 |
| phenotype ID: | 82164 |
| assay: | Soil Gross Morphology: Flowering complete |
| phenotype: | WHOLE PLANT - Dark Green |
| notes: | 50 percent weight |
| unique F1 plant ID: | R1 PLANT:ME04115-05 |
| phenotype ID: | 82165 |
| assay: | Soil Gross Morphology: Flowering complete |
| phenotype: | INFLORESCENCE - Weak |
| notes: | NONE |

TABLE 1-continued

```
unique F1 plant ID:  R1 PLANT:ME04115-05
phenotype ID:        82166
assay:               Soil Gross Morphology: Flowering complete
phenotype:           FLOWER - Reduced fertility
notes:               NONE
unique F1 plant ID:  R1 PLANT:ME04115-05
phenotype ID:        82167
assay:               Soil Gross Morphology: 50% of flowers to be produced have opened
phenotype:           WHOLE PLANT - Dark Green
notes:               NONE
unique F1 plant ID:  R1 PLANT:ME04115-05
phenotype ID:        82168
assay:               Soil Gross Morphology: Flowering complete
phenotype:           FLOWER - Reduced fertility
notes:               NONE
unique F1 plant ID:  R1 PLANT:ME04115-06
phenotype ID:        82196
assay:               Soil Gross Morphology: 50% of flowers to be produced have opened
phenotype:           WHOLE PLANT - Dark Green
notes:               NONE
unique F1 plant ID:  R1 PLANT:ME04115-10
phenotype ID:        82364
assay:               Soil Gross Morphology: 50% of flowers to be produced have opened
phenotype:           WHOLE PLANT - Dark Green
notes:               NONE
unique F1 plant ID:  R1 PLANT:ME04115-10
phenotype ID:        82365
assay:               Soil Gross Morphology: Flowering complete
phenotype:           WHOLE PLANT - Small
notes:               50 percent weight
unique F1 plant ID:  R1 PLANT:ME04115-10
phenotype ID:        82366
assay:               Soil Gross Morphology: Flowering complete
phenotype:           WHOLE PLANT - Small
notes:               50 percent weight
                        Knock-in phenotype in gene(cDNA__id): 13497142 clone ID:            34480
Promoter:            35S
unique F1 plant ID:  R1 PLANT:ME05721-01
phenotype ID:        98428
assay:               Soil Gross Morphology: First flower buds visible
phenotype:           WHOLE PLANT - Small
notes:               25 pct wt
unique F1 plant ID:  R1 PLANT:ME05721-01
phenotype ID:        98429
assay:               Soil Gross Morphology: First flower buds visible
phenotype:           WHOLE PLANT - Yellow-Green Viable 1
notes:               NONE
unique F1 plant ID:  R1 PLANT:ME05721-03
phenotype ID:        98507
assay:               Soil Gross Morphology: First flower buds visible
phenotype:           WHOLE PLANT - Small
notes:               25 pct wt
unique F1 plant ID:  R1 PLANT:ME05721-03
phenotype ID:        98508
assay:               Soil Gross Morphology: First flower buds visible
phenotype:           WHOLE PLANT - Yellow-Green Viable 1
notes:               NONE
unique F1 plant ID:  R1 PLANT:ME05721-04
phenotype ID:        98551
assay:               Soil Gross Morphology: First flower buds visible
phenotype:           WHOLE PLANT - Small
notes:               25 pct wt
unique F1 plant ID:  R1 PLANT:ME05721-04
phenotype ID:        98552
assay:               Soil Gross Morphology: First flower buds visible
phenotype:           WHOLE PLANT - Yellow-Green Viable 1
notes:               NONE
unique F1 plant ID:  R1 PLANT:ME05721-05
phenotype ID:        98578
assay:               Soil Gross Morphology: First flower buds visible
phenotype:           WHOLE PLANT - Small
notes:               25 pct wt
unique F1 plant ID:  R1 PLANT:ME05721-05
phenotype ID:        98579
assay:               Soil Gross Morphology: First flower buds visible
phenotype:           WHOLE PLANT - Yellow-Green Viable 1
notes:               NONE
```

TABLE 1-continued

| | |
|---|---|
| unique F1 plant ID: | R1 PLANT:ME05721-07 |
| phenotype ID: | 98675 |
| assay: | Soil Gross Morphology: First flower buds visible |
| phenotype: | WHOLE PLANT - Small |
| notes: | 25 pct wt |
| unique F1 plant ID: | R1 PLANT:ME05721-07 |
| phenotype ID: | 98676 |
| assay: | Soil Gross Morphology: First flower buds visible |
| phenotype: | WHOLE PLANT - Yellow-Green Viable 1 |
| notes: | NONE |
| unique F1 plant ID: | R1 PLANT:ME05721-08 |
| phenotype ID: | 98729 |
| assay: | Soil Gross Morphology: First flower buds visible |
| phenotype: | WHOLE PLANT - Small |
| notes: | 25 pct wt |
| unique F1 plant ID: | R1 PLANT:ME05721-08 |
| phenotype ID: | 98730 |
| assay: | Soil Gross Morphology: First flower buds visible |
| phenotype: | WHOLE PLANT - Yellow-Green Viable 1 |
| notes: | NONE |
| unique F1 plant ID: | R1 PLANT:ME05721-10 |
| phenotype ID: | 98808 |
| assay: | Soil Gross Morphology: 30% of flowers to be produced have opened |
| phenotype: | INFLORESCENCE - Short |
| notes: | NONE |
| unique F1 plant ID: | R1 PLANT:ME05721-10 |
| phenotype ID: | 98809 |
| assay: | Soil Gross Morphology: First flower buds visible |
| phenotype: | WHOLE PLANT - Small |
| notes: | 25 pct wt |
| unique F1 plant ID: | R1 PLANT:ME05721-10 |
| phenotype ID: | 98810 |
| assay: | Soil Gross Morphology: First flower buds visible |
| phenotype: | WHOLE PLANT - Yellow-Green Viable 1 |
| notes: | NONE |
| | Knock-in phenotype in gene(cDNA__id): 13497451 |
| clone ID: | 27197 |
| Promoter: | 35S |
| unique F1 plant ID: | R1 PLANT:ME05396-03 |
| phenotype ID: | 89577 |
| assay: | Soil Gross Morphology: 50% of flowers to be produced have opened |
| phenotype: | WHOLE PLANT - Small |
| notes: | NONE |
| unique F1 plant ID: | R1 PLANT:ME05396-03 |
| phenotype ID: | 89578 |
| assay: | Soil Gross Morphology: 50% of flowers to be produced have opened |
| phenotype: | FLOWER - Reduced fertility |
| notes: | NONE |
| unique F1 plant ID: | R1 PLANT:ME05396-06 |
| phenotype ID: | 89637 |
| assay: | Soil Gross Morphology: 50% of flowers to be produced have opened |
| phenotype: | FLOWER - Reduced fertility |
| notes: | NONE |
| unique F1 plant ID: | R1 PLANT:ME05396-07 |
| phenotype ID: | 89668 |
| assay: | Soil Gross Morphology: 50% of flowers to be produced have opened |
| phenotype: | FLOWER - Reduced fertility |
| notes: | NONE |
| | Knock-in phenotype in gene(cDNA__id): 13499732 |
| clone ID: | 28602 |
| Promoter: | 35S |
| unique F1 plant ID: | R1 PLANT:ME02925-01 |
| phenotype ID: | 55498 |
| assay: | Soil Gross Morphology: First flower open |
| phenotype: | ROSETTE LEAVES - Other |
| notes: | few rosette leaves |
| unique F1 plant ID: | R1 PLANT:ME02925-01 |
| phenotype ID: | 55499 |
| assay: | Soil Gross Morphology: First flower open |
| phenotype: | ROSETTE LEAVES - Lanceolate Shaped |
| notes: | NONE |
| unique F1 plant ID: | R1 PLANT:ME02925-01 |
| phenotype ID: | 55500 |
| assay: | Soil Gross Morphology: First flower open |
| phenotype: | ROSETTE LEAVES - Curled 3 |
| notes: | NONE |
| unique F1 plant ID: | R1 PLANT:ME02925-07 |

TABLE 1-continued

| | |
|---|---|
| phenotype ID: | 55941 |
| assay: | Soil Gross Morphology: 30% of flowers to be produced have opened |
| phenotype: | ROSETTE LEAVES - Lanceolate Shaped |
| notes: | NONE |
| unique F1 plant ID: | R1 PLANT:ME02925-08 |
| phenotype ID: | 56007 |
| assay: | Soil Gross Morphology: 10% of flowers to be produced have opened |
| phenotype: | WHOLE PLANT - Small |
| notes: | very small |
| unique F1 plant ID: | R1 PLANT:ME02925-08 |
| phenotype ID: | 56008 |
| assay: | Soil Gross Morphology: 10% of flowers to be produced have opened |
| phenotype: | WHOLE PLANT - Dark Green |
| notes: | NONE |
| unique F1 plant ID: | R1 PLANT:ME02925-08 |
| phenotype ID: | 56009 |
| assay: | Soil Gross Morphology: 10% of flowers to be produced have opened |
| phenotype: | ROSETTE LEAVES - Oval Shaped |
| notes: | NONE |
| unique F1 plant ID: | R1 PLANT:ME02925-08 |
| phenotype ID: | 56010 |
| assay: | Soil Gross Morphology: 10% of flowers to be produced have opened |
| phenotype: | WHOLE PLANT - Standing Rosette Shaped |
| notes: | NONE |
| unique F1 plant ID: | R1 PLANT:ME02925-08 |
| phenotype ID: | 56011 |
| assay: | Soil Gross Morphology: 10% of flowers to be produced have opened |
| phenotype: | HYPOCOTYL - Long |
| notes: | NONE |

Knock-in phenotype in gene(cDNA_id): 13500819

| | |
|---|---|
| clone ID: | 464504 |
| Promoter: | 35S |
| unique F1 plant ID: | R1 PLANT:ME05780-06 |
| phenotype ID: | 98939 |
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME05780-09 |
| phenotype ID: | 98988 |
| assay: | Soil Gross Morphology: 5 rosette leaves 1 mm in length |
| phenotype: | WHOLE PLANT - Dark Green |
| notes: | NONE |
| unique F1 plant ID: | R1 PLANT:ME05780-09 |
| phenotype ID: | 98989 |
| assay: | Soil Gross Morphology: Flowering complete |
| phenotype: | WHOLE PLANT - Small |
| notes: | 50 pct wt |
| unique F1 plant ID: | R1 PLANT:ME05780-09 |
| phenotype ID: | 98990 |
| assay: | Soil Gross Morphology: Flowering complete |
| phenotype: | INFLORESCENCE - Short Internode |
| notes: | NONE |
| unique F1 plant ID: | R1 PLANT:ME05780-10 |
| phenotype ID: | 99016 |
| assay: | Soil Gross Morphology: 4 rosette leaves 1 mm in length |
| phenotype: | WHOLE PLANT - Dark Green |
| notes: | NONE |
| unique F1 plant ID: | R1 PLANT:ME05780-10 |
| phenotype ID: | 99017 |
| assay: | Soil Gross Morphology: 4 rosette leaves 1 mm in length |
| phenotype: | WHOLE PLANT - Small |
| notes: | 10 pct wt |

Knock-in phenotype in gene(cDNA_id): 13530629

| | |
|---|---|
| clone ID: | 681222 |
| Promoter: | 35S |
| unique F1 plant ID: | R1 PLANT:ME05056-05 |
| phenotype ID: | 89266 |
| assay: | Soil Gross Morphology: 30% of flowers to be produced have opened |
| phenotype: | ROSETTE LEAVES - Lanceolate Shaped |
| notes: | NONE |
| unique F1 plant ID: | R1 PLANT:ME05056-05 |
| phenotype ID: | 89267 |
| assay: | Soil Gross Morphology: 30% of flowers to be produced have opened |
| phenotype: | ROSETTE LEAVES - Curled 4 |
| notes: | NONE |
| unique F1 plant ID: | R1 PLANT:ME05056-08 |
| phenotype ID: | 89362 |

TABLE 1-continued

| | |
|---|---|
| assay: | Soil Gross Morphology: 30% of flowers to be produced have opened |
| phenotype: | ROSETTE LEAVES - Lanceolate Shaped |
| notes: | NONE |
| unique F1 plant ID: | R1 PLANT:ME05056-08 |
| phenotype ID: | 89363 |
| assay: | Soil Gross Morphology: 30% of flowers to be produced have opened |
| phenotype: | ROSETTE LEAVES - Curled 2 |
| notes: | NONE |
| unique F1 plant ID: | R1 PLANT:ME05056-09 |
| phenotype ID: | 89407 |
| assay: | Soil Gross Morphology: 30% of flowers to be produced have opened |
| phenotype: | ROSETTE LEAVES - Lanceolate Shaped |
| notes: | NONE |
| unique F1 plant ID: | R1 PLANT:ME05056-09 |
| phenotype ID: | 89408 |
| assay: | Soil Gross Morphology: 30% of flowers to be produced have opened |
| phenotype: | ROSETTE LEAVES - Curled 2 |
| notes: | NONE |

Knock-in phenotype in gene(cDNA_id): 13592165

| | |
|---|---|
| clone ID: | 1150844 |
| Promoter: | 35S |
| unique F1 plant ID: | R1 PLANT:ME10482-03 |
| phenotype ID: | 139332 |
| assay: | Soil Gross Morphology: First flower buds visible |
| phenotype: | ROSETTE LEAVES - Short Petioles |
| notes: | NONE |
| unique F1 plant ID: | R1 PLANT:ME10482-03 |
| phenotype ID: | 139333 |
| assay: | Soil Gross Morphology: First flower buds visible |
| phenotype: | ROSETTE LEAVES - Oval Shaped |
| notes: | NONE |
| unique F1 plant ID: | R1 PLANT:ME10482-04 |
| phenotype ID: | 139334 |
| assay: | Soil Gross Morphology: 30% of flowers to be produced have opened |
| phenotype: | FLOWER - Reduced fertility |
| notes: | NONE |
| unique F1 plant ID: | R1 PLANT:ME10482-05 |
| phenotype ID: | 139335 |
| assay: | Soil Gross Morphology: First flower buds visible |
| phenotype: | ROSETTE LEAVES - Short Petioles |
| notes: | NONE |
| unique F1 plant ID: | R1 PLANT:ME10482-05 |
| phenotype ID: | 139336 |
| assay: | Soil Gross Morphology: First flower buds visible |
| phenotype: | ROSETTE LEAVES - Oval Shaped |
| notes: | NONE |
| unique F1 plant ID: | R1 PLANT:ME10482-07 |
| phenotype ID: | 139337 |
| assay: | Soil Gross Morphology: First flower buds visible |
| phenotype: | ROSETTE LEAVES - Short Petioles |
| notes: | NONE |
| unique F1 plant ID: | R1 PLANT:ME10482-07 |
| phenotype ID: | 139338 |
| assay: | Soil Gross Morphology: First flower buds visible |
| phenotype: | ROSETTE LEAVES - Oval Shaped |
| notes: | NONE |
| unique F1 plant ID: | R1 PLANT:ME10482-08 |
| phenotype ID: | 139339 |
| assay: | Soil Gross Morphology: First flower buds visible |
| phenotype: | ROSETTE LEAVES - Short Petioles |
| notes: | NONE |
| unique F1 plant ID: | R1 PLANT:ME10482-08 |
| phenotype ID: | 139340 |
| assay: | Soil Gross Morphology: First flower buds visible |
| phenotype: | ROSETTE LEAVES - Oval Shaped |
| notes: | NONE |

Knock-in phenotype in gene(cDNA_id): 13622089

| | |
|---|---|
| clone ID: | 96020 |
| Promoter: | 35S |
| unique F1 plant ID: | R1 PLANT:ME07168-01 |
| phenotype ID: | 100118 |
| assay: | Soil Gross Morphology: 7 rosette leaves 1 mm in length |
| phenotype: | ROSETTE LEAVES - Curled 4 |
| notes: | NONE |
| unique F1 plant ID: | R1 PLANT:ME07168-01 |
| phenotype ID: | 100119 |
| assay: | Soil Gross Morphology: 7 rosette leaves 1 mm in length |

TABLE 1-continued

| | |
|---|---|
| phenotype: | ROSETTE LEAVES - Corkscrew |
| notes: | NONE |
| unique F1 plant ID: | R1 PLANT:ME07168-01 |
| phenotype ID: | 100120 |
| assay: | Soil Gross Morphology: 7 rosette leaves 1 mm in length |
| phenotype: | WHOLE PLANT - Other |
| notes: | green at tips yellow at petioles |
| unique F1 plant ID: | R1 PLANT:ME07168-01 |
| phenotype ID: | 100121 |
| assay: | Soil Gross Morphology: 7 rosette leaves 1 mm in length |
| phenotype: | WHOLE PLANT - Small |
| notes: | 5 pct wt |
| unique F1 plant ID: | R1 PLANT:ME07168-01 |
| phenotype ID: | 100122 |
| assay: | Soil Gross Morphology: 30% of flowers to be produced have opened |
| phenotype: | INFLORESCENCE - Short |
| notes: | 10 pct wt |
| unique F1 plant ID: | R1 PLANT:ME07168-01 |
| phenotype ID: | 100123 |
| assay: | Soil Gross Morphology: 30% of flowers to be produced have opened |
| phenotype: | INFLORESCENCE - Other |
| notes: | secondary inflorescence 5 pct wt |
| unique F1 plant ID: | R1 PLANT:ME07168-01 |
| phenotype ID: | 100124 |
| assay: | Soil Gross Morphology: 30% of flowers to be produced have opened |
| phenotype: | INFLORESCENCE - Short |
| notes: | 25 pct wt |
| unique F1 plant ID: | R1 PLANT:ME07168-04 |
| phenotype ID: | 100191 |
| assay: | Soil Gross Morphology: 4 rosette leaves 1 mm in length |
| phenotype: | WHOLE PLANT - Dark Green |
| notes: | NONE |
| unique F1 plant ID: | R1 PLANT:ME07168-04 |
| phenotype ID: | 100192 |
| assay: | Soil Gross Morphology: 4 rosette leaves 1 mm in length |
| phenotype: | ROSETTE LEAVES - Oval Shaped |
| notes: | NONE |
| unique F1 plant ID: | R1 PLANT:ME07168-04 |
| phenotype ID: | 100193 |
| assay: | Soil Gross Morphology: 4 rosette leaves 1 mm in length |
| phenotype: | WHOLE PLANT - Small |
| notes: | 10 pct wt |
| unique F1 plant ID: | R1 PLANT:ME07168-04 |
| phenotype ID: | 100194 |
| assay: | Soil Gross Morphology: 30% of flowers to be produced have opened |
| phenotype: | INFLORESCENCE - Other |
| notes: | secondary inflorescence 5 pct wt |
| unique F1 plant ID: | R1 PLANT:ME07168-05 |
| phenotype ID: | 100213 |
| assay: | Soil Gross Morphology: 30% of flowers to be produced have opened |
| phenotype: | INFLORESCENCE - Other |
| notes: | secondary inflorescence 5 pct wt |
| unique F1 plant ID: | R1 PLANT:ME07168-06 |
| phenotype ID: | 100229 |
| assay: | Soil Gross Morphology: 30% of flowers to be produced have opened |
| phenotype: | INFLORESCENCE - Reduced Apical Dominance |
| notes: | NONE |
| unique F1 plant ID: | R1 PLANT:ME07168-06 |
| phenotype ID: | 100230 |
| assay: | Soil Gross Morphology: 30% of flowers to be produced have opened |
| phenotype: | INFLORESCENCE - Short |
| notes: | 50 pct wt |
| unique F1 plant ID: | R1 PLANT:ME07168-06 |
| phenotype ID: | 100231 |
| assay: | Soil Gross Morphology: 30% of flowers to be produced have opened |
| phenotype: | ROSETTE LEAVES - Serrate Margins |
| notes: | NONE |
| unique F1 plant ID: | R1 PLANT:ME07168-06 |
| phenotype ID: | 100232 |
| assay: | Soil Gross Morphology: 50% of flowers to be produced have opened |
| phenotype: | FLOWER - Reduced fertility |
| notes: | NONE |
| unique F1 plant ID: | R1 PLANT:ME07168-08 |
| phenotype ID: | 100260 |
| assay: | Soil Gross Morphology: 6 rosette leaves 1 mm in length |
| phenotype: | WHOLE PLANT - Dark Green |
| notes: | NONE |
| unique F1 plant ID: | R1 PLANT:ME07168-08 |
| phenotype ID: | 100261 |

TABLE 1-continued

| | |
|---|---|
| assay: | Soil Gross Morphology: 6 rosette leaves 1 mm in length |
| phenotype: | ROSETTE LEAVES - Oval Shaped |
| notes: | NONE |
| unique F1 plant ID: | R1 PLANT:ME07168-08 |
| phenotype ID: | 100262 |
| assay: | Soil Gross Morphology: 6 rosette leaves 1 mm in length |
| phenotype: | WHOLE PLANT - Small |
| notes: | 10 pct wt |

Knock-in phenotype in gene(cDNA__id): 12654761

| | |
|---|---|
| clone ID: | 0 |
| Promoter: | 35S |
| unique F1 plant ID: | R1 PLANT:ME04665-01 |
| phenotype ID: | 119545 |
| assay: | Soil Gross Morphology: Soil Gross Morphology: First flower buds visible |
| phenotype: | WHOLE PLANT - Dark Green |
| notes: | NONE |
| unique F1 plant ID: | R1 PLANT:ME04665-01 |
| phenotype ID: | 119546 |
| assay: | Soil Gross Morphology: Soil Gross Morphology: First flower buds visible |
| phenotype: | WHOLE PLANT - Small |
| notes: | 10 percent wt |
| unique F1 plant ID: | R1 PLANT:ME04665-01 |
| phenotype ID: | 119547 |
| assay: | Soil Gross Morphology: Soil Gross Morphology: First flower buds visible |
| phenotype: | INFLORESCENCE - Late Flowering |
| notes: | NONE |
| unique F1 plant ID: | R1 PLANT:ME04665-01 |
| phenotype ID: | 119548 |
| assay: | Soil Gross Morphology: Soil Gross Morphology: First flower buds visible |
| phenotype: | ROSETTE LEAVES - Oval Shaped |
| notes: | NONE |
| unique F1 plant ID: | R1 PLANT:ME04665-01 |
| phenotype ID: | 119549 |
| assay: | Soil Gross Morphology: Soil Gross Morphology: First flower buds visible |
| phenotype: | ROSETTE LEAVES - Serrate Margins |
| notes: | NONE |
| unique F1 plant ID: | R1 PLANT:ME04665-02 |
| phenotype ID: | 119578 |
| assay: | Soil Gross Morphology: Soil Gross Morphology: First flower buds visible |
| phenotype: | WHOLE PLANT - Dark Green |
| notes: | NONE |
| unique F1 plant ID: | R1 PLANT:ME04665-02 |
| phenotype ID: | 119579 |
| assay: | Soil Gross Morphology: Soil Gross Morphology: First flower buds visible |
| phenotype: | WHOLE PLANT - Small |
| notes: | 10 percent wt |
| unique F1 plant ID: | R1 PLANT:ME04665-02 |
| phenotype ID: | 119580 |
| assay: | Soil Gross Morphology: Soil Gross Morphology: First flower buds visible |
| phenotype: | INFLORESCENCE - Late Flowering |
| notes: | NONE |
| unique F1 plant ID: | R1 PLANT:ME04665-02 |
| phenotype ID: | 119581 |
| assay: | Soil Gross Morphology: Soil Gross Morphology: First flower buds visible |
| phenotype: | ROSETTE LEAVES - Oval Shaped |
| notes: | NONE |
| unique F1 plant ID: | R1 PLANT:ME04665-02 |
| phenotype ID: | 119582 |
| assay: | Soil Gross Morphology: Soil Gross Morphology: First flower buds visible |
| phenotype: | ROSETTE LEAVES - Serrate Margins |
| notes: | NONE |
| unique F1 plant ID: | R1 PLANT:ME04665-03 |
| phenotype ID: | 119625 |
| assay: | Soil Gross Morphology: Soil Gross Morphology: First flower buds visible |
| phenotype: | ROSETTE LEAVES - Serrate Margins |
| notes: | NONE |
| unique F1 plant ID: | R1 PLANT:ME04665-03 |
| phenotype ID: | 119626 |
| assay: | Soil Gross Morphology: Soil Gross Morphology: First flower buds visible |
| phenotype: | WHOLE PLANT - Dark Green |
| notes: | NONE |
| unique F1 plant ID: | R1 PLANT:ME04665-03 |
| phenotype ID: | 119627 |
| assay: | Soil Gross Morphology: Soil Gross Morphology: First flower buds visible |
| phenotype: | WHOLE PLANT - Small |
| notes: | 10 percent wt |
| unique F1 plant ID: | R1 PLANT:ME04665-03 |
| phenotype ID: | 119628 |

TABLE 1-continued

| | |
|---|---|
| assay: | Soil Gross Morphology: Soil Gross Morphology: First flower buds visible |
| phenotype: | INFLORESCENCE - Late Flowering |
| notes: | NONE |
| unique F1 plant ID: | R1 PLANT:ME04665-03 |
| phenotype ID: | 119629 |
| assay: | Soil Gross Morphology: Soil Gross Morphology: First flower buds visible |
| phenotype: | ROSETTE LEAVES - Oval Shaped |
| notes: | NONE |
| unique F1 plant ID: | R1 PLANT:ME04665-04 |
| phenotype ID: | 119668 |
| assay: | Soil Gross Morphology: Soil Gross Morphology: First flower buds visible |
| phenotype: | WHOLE PLANT - Dark Green |
| notes: | NONE |
| unique F1 plant ID: | R1 PLANT:ME04665-04 |
| phenotype ID: | 119669 |
| assay: | Soil Gross Morphology: Soil Gross Morphology: First flower buds visible |
| phenotype: | WHOLE PLANT - Small |
| notes: | 10 percent wt |
| unique F1 plant ID: | R1 PLANT:ME04665-04 |
| phenotype ID: | 119670 |
| assay: | Soil Gross Morphology: Soil Gross Morphology: First flower buds visible |
| phenotype: | INFLORESCENCE - Late Flowering |
| notes: | NONE |
| unique F1 plant ID: | R1 PLANT:ME04665-04 |
| phenotype ID: | 119671 |
| assay: | Soil Gross Morphology: Soil Gross Morphology: First flower buds visible |
| phenotype: | ROSETTE LEAVES - Oval Shaped |
| notes: | NONE |
| unique F1 plant ID: | R1 PLANT:ME04665-04 |
| phenotype ID: | 119672 |
| assay: | Soil Gross Morphology: Soil Gross Morphology: First flower buds visible |
| phenotype: | ROSETTE LEAVES - Serrate Margins |
| notes: | NONE |
| unique F1 plant ID: | R1 PLANT:ME04665-05 |
| phenotype ID: | 119727 |
| assay: | Soil Gross Morphology: Soil Gross Morphology: First flower buds visible |
| phenotype: | WHOLE PLANT - Dark Green |
| notes: | NONE |
| unique F1 plant ID: | R1 PLANT:ME04665-05 |
| phenotype ID: | 119728 |
| assay: | Soil Gross Morphology: Soil Gross Morphology: First flower buds visible |
| phenotype: | WHOLE PLANT - Small |
| notes: | 10 percent wt |
| unique F1 plant ID: | R1 PLANT:ME04665-05 |
| phenotype ID: | 119729 |
| assay: | Soil Gross Morphology: Soil Gross Morphology: First flower buds visible |
| phenotype: | INFLORESCENCE - Late Flowering |
| notes: | NONE |
| unique F1 plant ID: | R1 PLANT:ME04665-05 |
| phenotype ID: | 119730 |
| assay: | Soil Gross Morphology: Soil Gross Morphology: First flower buds visible |
| phenotype: | ROSETTE LEAVES - Oval Shaped |
| notes: | NONE |
| unique F1 plant ID: | R1 PLANT:ME04665-05 |
| phenotype ID: | 119731 |
| assay: | Soil Gross Morphology: Soil Gross Morphology: First flower buds visible |
| phenotype: | ROSETTE LEAVES - Serrate Margins |
| notes: | NONE |
| unique F1 plant ID: | R1 PLANT:ME04665-06 |
| phenotype ID: | 119776 |
| assay: | Soil Gross Morphology: Soil Gross Morphology: First flower buds visible |
| phenotype: | WHOLE PLANT - Dark Green |
| notes: | NONE |
| unique F1 plant ID: | R1 PLANT:ME04665-06 |
| phenotype ID: | 119777 |
| assay: | Soil Gross Morphology: Soil Gross Morphology: First flower buds visible |
| phenotype: | WHOLE PLANT - Small |
| notes: | 10 percent wt |
| unique F1 plant ID: | R1 PLANT:ME04665-06 |
| phenotype ID: | 119778 |
| assay: | Soil Gross Morphology: Soil Gross Morphology: First flower buds visible |
| phenotype: | INFLORESCENCE - Late Flowering |
| notes: | NONE |
| unique F1 plant ID: | R1 PLANT:ME04665-06 |
| phenotype ID: | 119779 |
| assay: | Soil Gross Morphology: Soil Gross Morphology: First flower buds visible |
| phenotype: | ROSETTE LEAVES - Oval Shaped |
| notes: | NONE |
| unique F1 plant ID: | R1 PLANT:ME04665-06 |

TABLE 1-continued

| | |
|---|---|
| phenotype ID: | 119780 |
| assay: | Soil Gross Morphology: Soil Gross Morphology: First flower buds visible |
| phenotype: | ROSETTE LEAVES - Serrate Margins |
| notes: | NONE |
| unique F1 plant ID: | R1 PLANT:ME04665-07 |
| phenotype ID: | 119815 |
| assay: | Soil Gross Morphology: Soil Gross Morphology: First flower buds visible |
| phenotype: | WHOLE PLANT - Dark Green |
| notes: | NONE |
| unique F1 plant ID: | R1 PLANT:ME04665-07 |
| phenotype ID: | 119816 |
| assay: | Soil Gross Morphology: Soil Gross Morphology: First flower buds visible |
| phenotype: | WHOLE PLANT - Small |
| notes: | 10 percent wt |
| unique F1 plant ID: | R1 PLANT:ME04665-07 |
| phenotype ID: | 119817 |
| assay: | Soil Gross Morphology: Soil Gross Morphology: First flower buds visible |
| phenotype: | INFLORESCENCE - Late Flowering |
| notes: | NONE |
| unique F1 plant ID: | R1 PLANT:ME04665-07 |
| phenotype ID: | 119818 |
| assay: | Soil Gross Morphology: Soil Gross Morphology: First flower buds visible |
| phenotype: | ROSETTE LEAVES - Oval Shaped |
| notes: | NONE |
| unique F1 plant ID: | R1 PLANT:ME04665-07 |
| phenotype ID: | 119819 |
| assay: | Soil Gross Morphology: Soil Gross Morphology: First flower buds visible |
| phenotype: | ROSETTE LEAVES - Serrate Margins |
| notes: | NONE |
| unique F1 plant ID: | R1 PLANT:ME04665-08 |
| phenotype ID: | 119870 |
| assay: | Soil Gross Morphology: Soil Gross Morphology: First flower buds visible |
| phenotype: | WHOLE PLANT - Dark Green |
| notes: | NONE |
| unique F1 plant ID: | R1 PLANT:ME04665-08 |
| phenotype ID: | 119871 |
| assay: | Soil Gross Morphology: Soil Gross Morphology: First flower buds visible |
| phenotype: | WHOLE PLANT - Small |
| notes: | 10 percent wt |
| unique F1 plant ID: | R1 PLANT:ME04665-08 |
| phenotype ID: | 119872 |
| assay: | Soil Gross Morphology: Soil Gross Morphology: First flower buds visible |
| phenotype: | INFLORESCENCE - Late Flowering |
| notes: | NONE |
| unique F1 plant ID: | R1 PLANT:ME04665-08 |
| phenotype ID: | 119873 |
| assay: | Soil Gross Morphology: Soil Gross Morphology: First flower buds visible |
| phenotype: | ROSETTE LEAVES - Oval Shaped |
| notes: | NONE |
| unique F1 plant ID: | R1 PLANT:ME04665-08 |
| phenotype ID: | 119874 |
| assay: | Soil Gross Morphology: Soil Gross Morphology: First flower buds visible |
| phenotype: | ROSETTE LEAVES - Serrate Margins |
| notes: | NONE |
| unique F1 plant ID: | R1 PLANT:ME04665-10 |
| phenotype ID: | 119956 |
| assay: | Soil Gross Morphology: Soil Gross Morphology: First flower buds visible |
| phenotype: | WHOLE PLANT - Dark Green |
| notes: | NONE |
| unique F1 plant ID: | R1 PLANT:ME04665-10 |
| phenotype ID: | 119957 |
| assay: | Soil Gross Morphology: Soil Gross Morphology: First flower buds visible |
| phenotype: | WHOLE PLANT - Small |
| notes: | 10 percent wt |
| unique F1 plant ID: | R1 PLANT:ME04665-10 |
| phenotype ID: | 119958 |
| assay: | Soil Gross Morphology: Soil Gross Morphology: First flower buds visible |
| phenotype: | INFLORESCENCE - Late Flowering |
| notes: | NONE |
| unique F1 plant ID: | R1 PLANT:ME04665-10 |
| phenotype ID: | 119959 |
| assay: | Soil Gross Morphology: Soil Gross Morphology: First flower buds visible |
| phenotype: | ROSETTE LEAVES - Oval Shaped |
| notes: | NONE |
| unique F1 plant ID: | R1 PLANT:ME04665-10 |
| phenotype ID: | 119960 |
| assay: | Soil Gross Morphology: Soil Gross Morphology: First flower buds visible |
| phenotype: | ROSETTE LEAVES - Serrate Margins |
| notes: | NONE |

TABLE 1-continued

Knock-in phenotype in gene(cDNA__id): 12658399

| | |
|---|---|
| clone ID: | 0 |
| Promoter: | 35S |
| unique F1 plant ID: | R1 PLANT:ME04640-01 |
| phenotype ID: | 119524 |
| assay: | Soil Gross Morphology: Soil Gross Morphology: 50% of flowers to be produced have opened |
| phenotype: | WHOLE PLANT - Dark Green |
| notes: | NONE |
| unique F1 plant ID: | R1 PLANT:ME04640-01 |
| phenotype ID: | 119525 |
| assay: | Soil Gross Morphology: Soil Gross Morphology: 50% of flowers to be produced have opened |
| phenotype: | ROSETTE LEAVES - Other |
| notes: | extra rosette leaves |
| unique F1 plant ID: | R1 PLANT:ME04640-01 |
| phenotype ID: | 119526 |
| assay: | Soil Gross Morphology: Soil Gross Morphology: 50% of flowers to be produced have opened |
| phenotype: | INFLORESCENCE - Short |
| notes: | 10 pct wt |
| unique F1 plant ID: | R1 PLANT:ME04640-01 |
| phenotype ID: | 119527 |
| assay: | Soil Gross Morphology: Soil Gross Morphology: 50% of flowers to be produced have opened |
| phenotype: | FLOWER - Reduced fertility |
| notes: | NONE |
| unique F1 plant ID: | R1 PLANT:ME04640-01 |
| phenotype ID: | 119528 |
| assay: | Soil Gross Morphology: Soil Gross Morphology: 14 rosette leaves 1 mm in length |
| phenotype: | WHOLE PLANT - Dark Green |
| notes: | NONE |
| unique F1 plant ID: | R1 PLANT:ME04640-01 |
| phenotype ID: | 119529 |
| assay: | Soil Gross Morphology: Soil Gross Morphology: 14 rosette leaves 1 mm in length |
| phenotype: | WHOLE PLANT - Small |
| notes: | 10 percent wt |
| unique F1 plant ID: | R1 PLANT:ME04640-01 |
| phenotype ID: | 119530 |
| assay: | Soil Gross Morphology: Soil Gross Morphology: 14 rosette leaves 1 mm in length |
| phenotype: | INFLORESCENCE - Late Flowering |
| notes: | NONE |
| unique F1 plant ID: | R1 PLANT:ME04640-01 |
| phenotype ID: | 119531 |
| assay: | Soil Gross Morphology: Soil Gross Morphology: 14 rosette leaves 1 mm in length |
| phenotype: | ROSETTE LEAVES - Short Petioles |
| notes: | NONE |
| unique F1 plant ID: | R1 PLANT:ME04640-02 |
| phenotype ID: | 119561 |
| assay: | Soil Gross Morphology: Soil Gross Morphology: Flowering complete |
| phenotype: | ROSETTE LEAVES - Other |
| notes: | extra rosette leaves |
| unique F1 plant ID: | R1 PLANT:ME04640-02 |
| phenotype ID: | 119562 |
| assay: | Soil Gross Morphology: Soil Gross Morphology: Flowering complete |
| phenotype: | INFLORESCENCE - Short |
| notes: | 40 pct wt |
| unique F1 plant ID: | R1 PLANT:ME04640-02 |
| phenotype ID: | 119563 |
| assay: | Soil Gross Morphology: Soil Gross Morphology: Flowering complete |
| phenotype: | INFLORESCENCE - Other |
| notes: | extra inflorescence |
| unique F1 plant ID: | R1 PLANT:ME04640-02 |
| phenotype ID: | 119564 |
| assay: | Soil Gross Morphology: Soil Gross Morphology: First flower buds visible |
| phenotype: | WHOLE PLANT - Dark Green |
| notes: | NONE |
| unique F1 plant ID: | R1 PLANT:ME04640-02 |
| phenotype ID: | 119565 |
| assay: | Soil Gross Morphology: Soil Gross Morphology: First flower buds visible |
| phenotype: | INFLORESCENCE - Late Flowering |
| notes: | NONE |
| unique F1 plant ID: | R1 PLANT:ME04640-02 |
| phenotype ID: | 119566 |
| assay: | Soil Gross Morphology: Soil Gross Morphology: First flower buds visible |
| phenotype: | ROSETTE LEAVES - Serrate Margins |
| notes: | NONE |
| unique F1 plant ID: | R1 PLANT:ME04640-02 |

TABLE 1-continued

| | |
|---|---|
| phenotype ID: | 119567 |
| assay: | Soil Gross Morphology: Soil Gross Morphology: First flower buds visible |
| phenotype: | WHOLE PLANT - Small |
| notes: | 25 percent wt |
| unique F1 plant ID: | R1 PLANT:ME04640-03 |
| phenotype ID: | 119615 |
| assay: | Soil Gross Morphology: Soil Gross Morphology: Flowering complete |
| phenotype: | ROSETTE LEAVES - Other |
| notes: | extra rosette leaves |
| unique F1 plant ID: | R1 PLANT:ME04640-03 |
| phenotype ID: | 119616 |
| assay: | Soil Gross Morphology: Soil Gross Morphology: Flowering complete |
| phenotype: | INFLORESCENCE - Short |
| notes: | 40 pct wt |
| unique F1 plant ID: | R1 PLANT:ME04640-03 |
| phenotype ID: | 119617 |
| assay: | Soil Gross Morphology: Soil Gross Morphology: Flowering complete |
| phenotype: | INFLORESCENCE - Other |
| notes: | extra inflorescence |
| unique F1 plant ID: | R1 PLANT:ME04640-03 |
| phenotype ID: | 119618 |
| assay: | Soil Gross Morphology: Soil Gross Morphology: Flowering complete |
| phenotype: | SILIQUES - Other |
| notes: | possible increase in silique number |
| unique F1 plant ID: | R1 PLANT:ME04640-03 |
| phenotype ID: | 119619 |
| assay: | Soil Gross Morphology: Soil Gross Morphology: First flower open |
| phenotype: | WHOLE PLANT - Dark Green |
| notes: | NONE |
| unique F1 plant ID: | R1 PLANT:ME04640-03 |
| phenotype ID: | 119620 |
| assay: | Soil Gross Morphology: Soil Gross Morphology: First flower open |
| phenotype: | ROSETTE LEAVES - Serrate Margins |
| notes: | NONE |
| unique F1 plant ID: | R1 PLANT:ME04640-03 |
| phenotype ID: | 119621 |
| assay: | Soil Gross Morphology: Soil Gross Morphology: First flower open |
| phenotype: | INFLORESCENCE - Short |
| notes: | NONE |
| unique F1 plant ID: | R1 PLANT:ME04640-03 |
| phenotype ID: | 119622 |
| assay: | Soil Gross Morphology: Soil Gross Morphology: First flower open |
| phenotype: | INFLORESCENCE - Late Flowering |
| notes: | NONE |
| unique F1 plant ID: | R1 PLANT:ME04640-04 |
| phenotype ID: | 119657 |
| assay: | Soil Gross Morphology: Soil Gross Morphology: Flowering complete |
| phenotype: | ROSETTE LEAVES - Other |
| notes: | extra rosette leaves |
| unique F1 plant ID: | R1 PLANT:ME04640-04 |
| phenotype ID: | 119658 |
| assay: | Soil Gross Morphology: Soil Gross Morphology: Flowering complete |
| phenotype: | INFLORESCENCE - Short |
| notes: | 40 pct wt |
| unique F1 plant ID: | R1 PLANT:ME04640-04 |
| phenotype ID: | 119659 |
| assay: | Soil Gross Morphology: Soil Gross Morphology: First flower buds visible |
| phenotype: | WHOLE PLANT - Dark Green |
| notes: | NONE |
| unique F1 plant ID: | R1 PLANT:ME04640-04 |
| phenotype ID: | 119660 |
| assay: | Soil Gross Morphology: Soil Gross Morphology: First flower buds visible |
| phenotype: | INFLORESCENCE - Late Flowering |
| notes: | NONE |
| unique F1 plant ID: | R1 PLANT:ME04640-04 |
| phenotype ID: | 119661 |
| assay: | Soil Gross Morphology: Soil Gross Morphology: First flower buds visible |
| phenotype: | ROSETTE LEAVES - Other |
| notes: | fewer |
| unique F1 plant ID: | R1 PLANT:ME04640-05 |
| phenotype ID: | 119713 |
| assay: | Soil Gross Morphology: Soil Gross Morphology: Flowering complete |
| phenotype: | ROSETTE LEAVES - Other |
| notes: | extra rosette leaves |
| unique F1 plant ID: | R1 PLANT:ME04640-05 |
| phenotype ID: | 119714 |
| assay: | Soil Gross Morphology: Soil Gross Morphology: Flowering complete |
| phenotype: | INFLORESCENCE - Short |
| notes: | 40 pct wt |

TABLE 1-continued

| | |
|---|---|
| unique F1 plant ID: | R1 PLANT:ME04640-05 |
| phenotype ID: | 119715 |
| assay: | Soil Gross Morphology: Soil Gross Morphology: Flowering complete |
| phenotype: | INFLORESCENCE - Other |
| notes: | extra inflorescence |
| unique F1 plant ID: | R1 PLANT:ME04640-05 |
| phenotype ID: | 119716 |
| assay: | Soil Gross Morphology: Soil Gross Morphology: Flowering complete |
| phenotype: | FLOWER - Reduced fertility |
| notes: | NONE |
| unique F1 plant ID: | R1 PLANT:ME04640-05 |
| phenotype ID: | 119717 |
| assay: | Soil Gross Morphology: Soil Gross Morphology: First flower open |
| phenotype: | WHOLE PLANT - Dark Green |
| notes: | NONE |
| unique F1 plant ID: | R1 PLANT:ME04640-05 |
| phenotype ID: | 119718 |
| assay: | Soil Gross Morphology: Soil Gross Morphology: First flower open |
| phenotype: | WHOLE PLANT - Small |
| notes: | 25 percent wt |
| unique F1 plant ID: | R1 PLANT:ME04640-05 |
| phenotype ID: | 119719 |
| assay: | Soil Gross Morphology: Soil Gross Morphology: First flower open |
| phenotype: | INFLORESCENCE - Late Flowering |
| notes: | NONE |
| unique F1 plant ID: | R1 PLANT:ME04640-06 |
| phenotype ID: | 119767 |
| assay: | Soil Gross Morphology: Soil Gross Morphology: Flowering complete |
| phenotype: | ROSETTE LEAVES - Other |
| notes: | extra rosette leaves |
| unique F1 plant ID: | R1 PLANT:ME04640-06 |
| phenotype ID: | 119768 |
| assay: | Soil Gross Morphology: Soil Gross Morphology: Flowering complete |
| phenotype: | INFLORESCENCE - Short |
| notes: | 40 pct wt |
| unique F1 plant ID: | R1 PLANT:ME04640-06 |
| phenotype ID: | 119769 |
| assay: | Soil Gross Morphology: Soil Gross Morphology: Flowering complete |
| phenotype: | INFLORESCENCE - Other |
| notes: | extra inflorescence |
| unique F1 plant ID: | R1 PLANT:ME04640-06 |
| phenotype ID: | 119770 |
| assay: | Soil Gross Morphology: Soil Gross Morphology: Flowering complete |
| phenotype: | SILIQUES - Other |
| notes: | possible increase in silique number |
| unique F1 plant ID: | R1 PLANT:ME04640-06 |
| phenotype ID: | 119771 |
| assay: | Soil Gross Morphology: Soil Gross Morphology: 10% of flowers to be produced have opened |
| phenotype: | WHOLE PLANT - Dark Green |
| notes: | NONE |
| unique F1 plant ID: | R1 PLANT:ME04640-06 |
| phenotype ID: | 119772 |
| assay: | Soil Gross Morphology: Soil Gross Morphology: 10% of flowers to be produced have opened |
| phenotype: | INFLORESCENCE - Late Flowering |
| notes: | NONE |
| unique F1 plant ID: | R1 PLANT:ME04640-06 |
| phenotype ID: | 119773 |
| assay: | Soil Gross Morphology: Soil Gross Morphology: 10% of flowers to be produced have opened |
| phenotype: | INFLORESCENCE - Short |
| notes: | NONE |
| unique F1 plant ID: | R1 PLANT:ME04640-07 |
| phenotype ID: | 119807 |
| assay: | Soil Gross Morphology: Soil Gross Morphology: Flowering complete |
| phenotype: | ROSETTE LEAVES - Other |
| notes: | extra rosette leaves |
| unique F1 plant ID: | R1 PLANT:ME04640-07 |
| phenotype ID: | 119808 |
| assay: | Soil Gross Morphology: Soil Gross Morphology: Flowering complete |
| phenotype: | INFLORESCENCE - Short |
| notes: | 40 pct wt |
| unique F1 plant ID: | R1 PLANT:ME04640-07 |
| phenotype ID: | 119809 |
| assay: | Soil Gross Morphology: Soil Gross Morphology: Flowering complete |
| phenotype: | INFLORESCENCE - Other |
| notes: | extra inflorescence |
| unique F1 plant ID: | R1 PLANT:ME04640-07 |

TABLE 1-continued

| | |
|---|---|
| phenotype ID: | 119810 |
| assay: | Soil Gross Morphology: Soil Gross Morphology: Flowering complete |
| phenotype: | SILIQUES - Other |
| notes: | possible increase in silique number |
| unique F1 plant ID: | R1 PLANT:ME04640-07 |
| phenotype ID: | 119811 |
| assay: | Soil Gross Morphology: Soil Gross Morphology: Flowering complete |
| phenotype: | FLOWER - Reduced fertility |
| notes: | slightly reduced |
| unique F1 plant ID: | R1 PLANT:ME04640-07 |
| phenotype ID: | 119812 |
| assay: | Soil Gross Morphology: Soil Gross Morphology: First flower open |
| phenotype: | WHOLE PLANT - Dark Green |
| notes: | NONE |
| unique F1 plant ID: | R1 PLANT:ME04640-07 |
| phenotype ID: | 119813 |
| assay: | Soil Gross Morphology: Soil Gross Morphology: First flower open |
| phenotype: | INFLORESCENCE - Late Flowering |
| notes: | NONE |
| unique F1 plant ID: | R1 PLANT:ME04640-07 |
| phenotype ID: | 119814 |
| assay: | Soil Gross Morphology: Soil Gross Morphology: First flower open |
| phenotype: | INFLORESCENCE - Short |
| notes: | NONE |
| unique F1 plant ID: | R1 PLANT:ME04640-08 |
| phenotype ID: | 119862 |
| assay: | Soil Gross Morphology: Soil Gross Morphology: Flowering complete |
| phenotype: | ROSETTE LEAVES - Other |
| notes: | extra rosette leaves |
| unique F1 plant ID: | R1 PLANT:ME04640-08 |
| phenotype ID: | 119863 |
| assay: | Soil Gross Morphology: Soil Gross Morphology: Flowering complete |
| phenotype: | INFLORESCENCE - Short |
| notes: | 40 pct wt |
| unique F1 plant ID: | R1 PLANT:ME04640-08 |
| phenotype ID: | 119864 |
| assay: | Soil Gross Morphology: Soil Gross Morphology: Flowering complete |
| phenotype: | INFLORESCENCE - Other |
| notes: | extra inflorescence |
| unique F1 plant ID: | R1 PLANT:ME04640-08 |
| phenotype ID: | 119865 |
| assay: | Soil Gross Morphology: Soil Gross Morphology: 10% of flowers to be produced have opened |
| phenotype: | WHOLE PLANT - Dark Green |
| notes: | NONE |
| unique F1 plant ID: | R1 PLANT:ME04640-08 |
| phenotype ID: | 119866 |
| assay: | Soil Gross Morphology: Soil Gross Morphology: 10% of flowers to be produced have opened |
| phenotype: | INFLORESCENCE - Late Flowering |
| notes: | NONE |
| unique F1 plant ID: | R1 PLANT:ME04640-08 |
| phenotype ID: | 119867 |
| assay: | Soil Gross Morphology: Soil Gross Morphology: 10% of flowers to be produced have opened |
| phenotype: | INFLORESCENCE - Short |
| notes: | NONE |
| unique F1 plant ID: | R1 PLANT:ME04640-09 |
| phenotype ID: | 119903 |
| assay: | Soil Gross Morphology: Soil Gross Morphology: Flowering complete |
| phenotype: | ROSETTE LEAVES - Other |
| notes: | extra rosette leaves |
| unique F1 plant ID: | R1 PLANT:ME04640-09 |
| phenotype ID: | 119904 |
| assay: | Soil Gross Morphology: Soil Gross Morphology: Flowering complete |
| phenotype: | INFLORESCENCE - Short |
| notes: | 40 pct wt |
| unique F1 plant ID: | R1 PLANT:ME04640-09 |
| phenotype ID: | 119905 |
| assay: | Soil Gross Morphology: Soil Gross Morphology: Flowering complete |
| phenotype: | INFLORESCENCE - Other |
| notes: | extra inflorescence |
| unique F1 plant ID: | R1 PLANT:ME04640-09 |
| phenotype ID: | 119906 |
| assay: | Soil Gross Morphology: Soil Gross Morphology: Flowering complete |
| phenotype: | SILIQUES - Other |
| notes: | possible increase in silique number |
| unique F1 plant ID: | R1 PLANT:ME04640-09 |
| phenotype ID: | 119907 |

TABLE 1-continued

| | |
|---|---|
| assay: | Soil Gross Morphology: Soil Gross Morphology: 10% of flowers to be produced have opened |
| phenotype: | WHOLE PLANT - Dark Green |
| notes: | NONE |
| unique F1 plant ID: | R1 PLANT:ME04640-09 |
| phenotype ID: | 119908 |
| assay: | Soil Gross Morphology: Soil Gross Morphology: 10% of flowers to be produced have opened |
| phenotype: | INFLORESCENCE - Late Flowering |
| notes: | NONE |
| unique F1 plant ID: | R1 PLANT:ME04640-09 |
| phenotype ID: | 119909 |
| assay: | Soil Gross Morphology: Soil Gross Morphology: 10% of flowers to be produced have opened |
| phenotype: | INFLORESCENCE - Short |
| notes: | NONE |
| unique F1 plant ID: | R1 PLANT:ME04640-09 |
| phenotype ID: | 119910 |
| assay: | Soil Gross Morphology: Soil Gross Morphology: 10% of flowers to be produced have opened |
| phenotype: | ROSETTE LEAVES - Serrate Margins |
| notes: | NONE |
| unique F1 plant ID: | R1 PLANT:ME04640-10 |
| phenotype ID: | 119942 |
| assay: | Soil Gross Morphology: Soil Gross Morphology: Flowering complete |
| phenotype: | ROSETTE LEAVES - Other |
| notes: | extra rosette leaves |
| unique F1 plant ID: | R1 PLANT:ME04640-10 |
| phenotype ID: | 119943 |
| assay: | Soil Gross Morphology: Soil Gross Morphology: Flowering complete |
| phenotype: | INFLORESCENCE - Short |
| notes: | 40 pct wt |
| unique F1 plant ID: | R1 PLANT:ME04640-10 |
| phenotype ID: | 119944 |
| assay: | Soil Gross Morphology: Soil Gross Morphology: Flowering complete |
| phenotype: | INFLORESCENCE - Other |
| notes: | extra inflorescence |
| unique F1 plant ID: | R1 PLANT:ME04640-10 |
| phenotype ID: | 119945 |
| assay: | Soil Gross Morphology: Soil Gross Morphology: Flowering complete |
| phenotype: | SILIQUES - Other |
| notes: | possible increase in silique number |
| unique F1 plant ID: | R1 PLANT:ME04640-10 |
| phenotype ID: | 119946 |
| assay: | Soil Gross Morphology: Soil Gross Morphology: Flowering complete |
| phenotype: | FLOWER - Reduced fertility |
| notes: | NONE |
| unique F1 plant ID: | R1 PLANT:ME04640-10 |
| phenotype ID: | 119947 |
| assay: | Soil Gross Morphology: Soil Gross Morphology: 10% of flowers to be produced have opened |
| phenotype: | WHOLE PLANT - Dark Green |
| notes: | NONE |
| unique F1 plant ID: | R1 PLANT:ME04640-10 |
| phenotype ID: | 119948 |
| assay: | Soil Gross Morphology: Soil Gross Morphology: 10% of flowers to be produced have opened |
| phenotype: | INFLORESCENCE - Late Flowering |
| notes: | NONE |
| unique F1 plant ID: | R1 PLANT:ME04640-10 |
| phenotype ID: | 119949 |
| assay: | Soil Gross Morphology: Soil Gross Morphology: 10% of flowers to be produced have opened |
| phenotype: | INFLORESCENCE - Short |
| notes: | NONE |
| unique F1 plant ID: | R1 PLANT:ME04640-10 |
| phenotype ID: | 119950 |
| assay: | Soil Gross Morphology: Soil Gross Morphology: 10% of flowers to be produced have opened |
| phenotype: | ROSETTE LEAVES - Serrate Margins |
| notes: | NONE |
| | Knock-in phenotype in gene(cDNA_id): 12727290 |
| clone ID: | 0 |
| Promoter: | 35S |
| unique F1 plant ID: | R1 PLANT:ME11313-05 |
| phenotype ID: | 146195 |
| assay: | Soil Gross Morphology: Soil Gross Morphology: 10% of flowers to be produced have opened |
| phenotype: | INFLORESCENCE - Short |

TABLE 1-continued

| | |
|---|---|
| notes: | 90 pct wt |
| unique F1 plant ID: | R1 PLANT:ME11313-06 |
| phenotype ID: | 146197 |
| assay: | Soil Gross Morphology: Soil Gross Morphology: 10% of flowers to be produced have opened |
| phenotype: | INFLORESCENCE - Short |
| notes: | 30 pct wt |
| unique F1 plant ID: | R1 PLANT:ME11313-07 |
| phenotype ID: | 146199 |
| assay: | Soil Gross Morphology: Soil Gross Morphology: 10% of flowers to be produced have opened |
| phenotype: | INFLORESCENCE - Short |
| notes: | 90 pct wt |
| unique F1 plant ID: | R1 PLANT:ME11313-07 |
| phenotype ID: | 146200 |
| assay: | Soil Gross Morphology: Soil Gross Morphology: 10% of flowers to be produced have opened |
| phenotype: | FLOWER - Reduced fertility |
| notes: | NONE |
| unique F1 plant ID: | R1 PLANT:ME11313-08 |
| phenotype ID: | 146201 |
| assay: | Soil Gross Morphology: Soil Gross Morphology: 10% of flowers to be produced have opened |
| phenotype: | INFLORESCENCE - Short |
| notes: | 30 pct wt |

Knock-in phenotype in gene(cDNA_id): 12733452

| | |
|---|---|
| clone ID: | 0 |
| Promoter: | 35S |
| unique F1 plant ID: | R1 PLANT:ME09534-01 |
| phenotype ID: | 139072 |
| assay: | Soil Gross Morphology: Soil Gross Morphology: 10% of flowers to be produced have opened |
| phenotype: | INFLORESCENCE - Late Flowering |
| notes: | NONE |
| unique F1 plant ID: | R1 PLANT:ME09534-02 |
| phenotype ID: | 139074 |
| assay: | Soil Gross Morphology: Soil Gross Morphology: 10% of flowers to be produced have opened |
| phenotype: | INFLORESCENCE - Late Flowering |
| notes: | NONE |
| unique F1 plant ID: | R1 PLANT:ME09534-05 |
| phenotype ID: | 139081 |
| assay: | Soil Gross Morphology: Soil Gross Morphology: First flower buds visible |
| phenotype: | INFLORESCENCE - Late Flowering |
| notes: | NONE |
| unique F1 plant ID: | R1 PLANT:ME09534-07 |
| phenotype ID: | 139088 |
| assay: | Soil Gross Morphology: Soil Gross Morphology: First flower buds visible |
| phenotype: | INFLORESCENCE - Late Flowering |
| notes: | NONE |

Knock-in phenotype in gene(cDNA_id): 12395524

| | |
|---|---|
| clone ID: | 101250 |
| Promoter: | 35S |
| unique F1 plant ID: | R1 PLANT:ME03577-01 |
| phenotype ID: | 71735 |
| assay: | Soil Gross Morphology: 50% of flowers to be produced have opened |
| phenotype: | FLOWER - Aborted fertility |
| notes: | NONE |
| unique F1 plant ID: | R1 PLANT:ME03577-04 |
| phenotype ID: | 71775 |
| assay: | Soil Gross Morphology: 50% of flowers to be produced have opened |
| phenotype: | FLOWER - Aborted fertility |
| notes: | NONE |
| unique F1 plant ID: | R1 PLANT:ME03577-08 |
| phenotype ID: | 71842 |
| assay: | Soil Gross Morphology: 50% of flowers to be produced have opened |
| phenotype: | SILIQUES - Other |
| notes: | siliques short and reduced in size |

Knock-in phenotype in gene(cDNA_id): 12422009

| | |
|---|---|
| clone ID: | 100319 |
| Promoter: | 35S |
| unique F1 plant ID: | R1 PLANT:ME04078-02 |
| phenotype ID: | 82063 |
| assay: | Soil Gross Morphology: 50% of flowers to be produced have opened |
| phenotype: | FLOWER - Reduced fertility |
| notes: | NONE |

TABLE 1-continued

```
unique F1 plant ID:  R1 PLANT:ME04078-02
phenotype ID:        82064
assay:               Soil Gross Morphology: 50% of flowers to be produced have opened
phenotype:           FLOWER - Sterile
notes:               NONE
unique F1 plant ID:  R1 PLANT:ME04078-02
phenotype ID:        82065
assay:               Soil Gross Morphology: 50% of flowers to be produced have opened
phenotype:           INFLORESCENCE - Short
notes:               NONE
unique F1 plant ID:  R1 PLANT:ME04078-02
phenotype ID:        82066
assay:               Soil Gross Morphology: 50% of flowers to be produced have opened
phenotype:           INFLORESCENCE - Other
notes:               increased branches
unique F1 plant ID:  R1 PLANT:ME04078-02
phenotype ID:        82067
assay:               Soil Gross Morphology: 50% of flowers to be produced have opened
phenotype:           ROSETTE LEAVES - Lanceolate Shaped
notes:               NONE
unique F1 plant ID:  R1 PLANT:ME04078-03
phenotype ID:        82104
assay:               Soil Gross Morphology: 50% of flowers to be produced have opened
phenotype:           WHOLE PLANT - Small
notes:               25 percent weight
unique F1 plant ID:  R1 PLANT:ME04078-03
phenotype ID:        82105
assay:               Soil Gross Morphology: 50% of flowers to be produced have opened
phenotype:           FLOWER - Reduced fertility
notes:               NONE
unique F1 plant ID:  R1 PLANT:ME04078-03
phenotype ID:        82106
assay:               Soil Gross Morphology: 50% of flowers to be produced have opened
phenotype:           INFLORESCENCE - Tall
notes:               NONE
unique F1 plant ID:  R1 PLANT:ME04078-06
phenotype ID:        82182
assay:               Soil Gross Morphology: 50% of flowers to be produced have opened
phenotype:           SILIQUES - Short
notes:               NONE
unique F1 plant ID:  R1 PLANT:ME04078-06
phenotype ID:        82183
assay:               Soil Gross Morphology: 50% of flowers to be produced have opened
phenotype:           ROSETTE LEAVES - Lanceolate Shaped
notes:               NONE
unique F1 plant ID:  R1 PLANT:ME04078-06
phenotype ID:        82184
assay:               Soil Gross Morphology: 50% of flowers to be produced have opened
phenotype:           FLOWER - Reduced fertility
notes:               NONE
unique F1 plant ID:  R1 PLANT:ME04078-06
phenotype ID:        82185
assay:               Soil Gross Morphology: 50% of flowers to be produced have opened
phenotype:           INFLORESCENCE - Other
notes:               decreased branching
unique F1 plant ID:  R1 PLANT:ME04078-07
phenotype ID:        82219
assay:               Soil Gross Morphology: 50% of flowers to be produced have opened
phenotype:           FLOWER - Sterile
notes:               NONE
unique F1 plant ID:  R1 PLANT:ME04078-07
phenotype ID:        82220
assay:               Soil Gross Morphology: 50% of flowers to be produced have opened
phenotype:           ROSETTE LEAVES - Lanceolate Shaped
notes:               NONE
unique F1 plant ID:  R1 PLANT:ME04078-07
phenotype ID:        82221
assay:               Soil Gross Morphology: 50% of flowers to be produced have opened
phenotype:           FLOWER - Reduced fertility
notes:               NONE
unique F1 plant ID:  R1 PLANT:ME04078-07
phenotype ID:        82222
assay:               Soil Gross Morphology: 50% of flowers to be produced have opened
phenotype:           FLOWER - Other
notes:               short pedicel
unique F1 plant ID:  R1 PLANT:ME04078-07
phenotype ID:        82223
assay:               Soil Gross Morphology: 50% of flowers to be produced have opened
```

TABLE 1-continued

| | |
|---|---|
| phenotype: | FLOWER - Other |
| notes: | increased number |

Knock-in phenotype in gene(cDNA_id): 12602447

| | |
|---|---|
| clone ID: | 39351 |
| Promoter: | 35S |
| unique F1 plant ID: | R1 PLANT:ME05502-02 |
| phenotype ID: | 89567 |
| assay: | Soil Gross Morphology: 50% of flowers to be produced have opened |
| phenotype: | WHOLE PLANT - Yellow-Green Viable 1 |
| notes: | NONE |
| unique F1 plant ID: | R1 PLANT:ME05502-02 |
| phenotype ID: | 89568 |
| assay: | Soil Gross Morphology: 50% of flowers to be produced have opened |
| phenotype: | CAULINE LEAVES - Small |
| notes: | 50 pct wt |
| unique F1 plant ID: | R1 PLANT:ME05502-04 |
| phenotype ID: | 89623 |
| assay: | Soil Gross Morphology: 50% of flowers to be produced have opened |
| phenotype: | WHOLE PLANT - Yellow-Green Viable 1 |
| notes: | NONE |
| unique F1 plant ID: | R1 PLANT:ME05502-04 |
| phenotype ID: | 89624 |
| assay: | Soil Gross Morphology: 50% of flowers to be produced have opened |
| phenotype: | CAULINE LEAVES - Small |
| notes: | 50 pct wt |
| unique F1 plant ID: | R1 PLANT:ME05502-05 |
| phenotype ID: | 89632 |
| assay: | Soil Gross Morphology: 50% of flowers to be produced have opened |
| phenotype: | WHOLE PLANT - Yellow-Green Viable 1 |
| notes: | NONE |
| unique F1 plant ID: | R1 PLANT:ME05502-05 |
| phenotype ID: | 89633 |
| assay: | Soil Gross Morphology: 50% of flowers to be produced have opened |
| phenotype: | CAULINE LEAVES - Small |
| notes: | 10 pct wt |
| unique F1 plant ID: | R1 PLANT:ME05502-09 |
| phenotype ID: | 89725 |
| assay: | Soil Gross Morphology: 50% of flowers to be produced have opened |
| phenotype: | WHOLE PLANT - Yellow-Green Viable 1 |
| notes: | NONE |
| unique F1 plant ID: | R1 PLANT:ME05502-09 |
| phenotype ID: | 89726 |
| assay: | Soil Gross Morphology: 50% of flowers to be produced have opened |
| phenotype: | CAULINE LEAVES - Small |
| notes: | 10 pct wt |
| unique F1 plant ID: | R1 PLANT:ME05502-10 |
| phenotype ID: | 89741 |
| assay: | Soil Gross Morphology: 50% of flowers to be produced have opened |
| phenotype: | WHOLE PLANT - Yellow-Green Viable 1 |
| notes: | NONE |
| unique F1 plant ID: | R1 PLANT:ME05502-10 |
| phenotype ID: | 89742 |
| assay: | Soil Gross Morphology: 50% of flowers to be produced have opened |
| phenotype: | CAULINE LEAVES - Small |
| notes: | 30 pct wt |
| unique F1 plant ID: | R1 PLANT:ME05502-10 |
| phenotype ID: | 89743 |
| assay: | Soil Gross Morphology: 50% of flowers to be produced have opened |
| phenotype: | FLOWER - Reduced fertility |
| notes: | NONE |

Knock-in phenotype in gene(cDNA_id): 12727312

| | |
|---|---|
| clone ID: | 100245 |
| Promoter: | 35S |
| unique F1 plant ID: | R1 PLANT:ME04065-01 |
| phenotype ID: | 82033 |
| assay: | Soil Gross Morphology: 50% of flowers to be produced have opened |
| phenotype: | WHOLE PLANT - Small |
| notes: | 50 percent weight |
| unique F1 plant ID: | R1 PLANT:ME04065-01 |
| phenotype ID: | 82034 |
| assay: | Soil Gross Morphology: 50% of flowers to be produced have opened |
| phenotype: | WHOLE PLANT - Late Senescence |
| notes: | NONE |
| unique F1 plant ID: | R1 PLANT:ME04065-01 |
| phenotype ID: | 82035 |
| assay: | Soil Gross Morphology: 50% of flowers to be produced have opened |
| phenotype: | FLOWER - Sterile |

TABLE 1-continued

| | |
|---|---|
| notes: | NONE |
| unique F1 plant ID: | R1 PLANT:ME04065-03 |
| phenotype ID: | 82089 |
| assay: | Soil Gross Morphology: 50% of flowers to be produced have opened |
| phenotype: | WHOLE PLANT - Small |
| notes: | 10 percent weight |
| unique F1 plant ID: | R1 PLANT:ME04065-03 |
| phenotype ID: | 82090 |
| assay: | Soil Gross Morphology: 50% of flowers to be produced have opened |
| phenotype: | FLOWER - Sterile |
| notes: | NONE |
| unique F1 plant ID: | R1 PLANT:ME04065-03 |
| phenotype ID: | 82091 |
| assay: | Soil Gross Morphology: 50% of flowers to be produced have opened |
| phenotype: | INFLORESCENCE - Short |
| notes: | NONE |
| unique F1 plant ID: | R1 PLANT:ME04065-04 |
| phenotype ID: | 82116 |
| assay: | Soil Gross Morphology: 50% of flowers to be produced have opened |
| phenotype: | WHOLE PLANT - Late Senescence |
| notes: | NONE |
| unique F1 plant ID: | R1 PLANT:ME04065-04 |
| phenotype ID: | 82117 |
| assay: | Soil Gross Morphology: 50% of flowers to be produced have opened |
| phenotype: | WHOLE PLANT - Small |
| notes: | 25 percent weight |
| unique F1 plant ID: | R1 PLANT:ME04065-04 |
| phenotype ID: | 82118 |
| assay: | Soil Gross Morphology: 50% of flowers to be produced have opened |
| phenotype: | FLOWER - Reduced fertility |
| notes: | NONE |
| unique F1 plant ID: | R1 PLANT:ME04065-05 |
| phenotype ID: | 82141 |
| assay: | Soil Gross Morphology: 50% of flowers to be produced have opened |
| phenotype: | WHOLE PLANT - Late Senescence |
| notes: | NONE |
| unique F1 plant ID: | R1 PLANT:ME04065-05 |
| phenotype ID: | 82142 |
| assay: | Soil Gross Morphology: 50% of flowers to be produced have opened |
| phenotype: | SILIQUES - Clubbed |
| notes: | NONE |
| unique F1 plant ID: | R1 PLANT:ME04065-08 |
| phenotype ID: | 82254 |
| assay: | Soil Gross Morphology: Flowering complete |
| phenotype: | FLOWER - Sterile |
| notes: | NONE |
| unique F1 plant ID: | R1 PLANT:ME04065-08 |
| phenotype ID: | 82255 |
| assay: | Soil Gross Morphology: Flowering complete |
| phenotype: | WHOLE PLANT - Late Senescence |
| notes: | NONE |
| unique F1 plant ID: | R1 PLANT:ME04065-08 |
| phenotype ID: | 82256 |
| assay: | Soil Gross Morphology: Flowering complete |
| phenotype: | WHOLE PLANT - Small |
| notes: | 10 percent weight |
| unique F1 plant ID: | R1 PLANT:ME04065-09 |
| phenotype ID: | 82292 |
| assay: | Soil Gross Morphology: Flowering complete |
| phenotype: | WHOLE PLANT - Late Senescence |
| notes: | NONE |
| unique F1 plant ID: | R1 PLANT:ME04065-09 |
| phenotype ID: | 82293 |
| assay: | Soil Gross Morphology: Flowering complete |
| phenotype: | WHOLE PLANT - Small |
| notes: | 10 percent weight |
| unique F1 plant ID: | R1 PLANT:ME04065-10 |
| phenotype ID: | 82330 |
| assay: | Soil Gross Morphology: Flowering complete |
| phenotype: | FLOWER - Reduced fertility |
| notes: | NONE |
| unique F1 plant ID: | R1 PLANT:ME04065-10 |
| phenotype ID: | 82331 |
| assay: | Soil Gross Morphology: Flowering complete |
| phenotype: | WHOLE PLANT - Small |
| notes: | 25 percent weight |
| unique F1 plant ID: | R1 PLANT:ME04065-10 |
| phenotype ID: | 82332 |
| assay: | Soil Gross Morphology: Flowering complete |

TABLE 1-continued

| | |
|---|---|
| phenotype: | SILIQUES - Bent |
| notes: | NONE |
| unique F1 plant ID: | R1 PLANT:ME04065-10 |
| phenotype ID: | 82333 |
| assay: | Soil Gross Morphology: Flowering complete |
| phenotype: | SILIQUES - Clubbed |
| notes: | NONE |

Knock-in phenotype in gene(cDNA_id): 13490207

| | |
|---|---|
| clone ID: | 16865 |
| Promoter: | 35S |
| unique F1 plant ID: | R1 PLANT:ME02627-01 |
| phenotype ID: | 55449 |
| assay: | Soil Gross Morphology: 30% of flowers to be produced have opened |
| phenotype: | FLOWER - Reduced fertility |
| notes: | NONE |
| unique F1 plant ID: | R1 PLANT:ME02627-04 |
| phenotype ID: | 55660 |
| assay: | Soil Gross Morphology: 30% of flowers to be produced have opened |
| phenotype: | FLOWER - Reduced fertility |
| notes: | NONE |
| unique F1 plant ID: | R1 PLANT:ME02627-04 |
| phenotype ID: | 55661 |
| assay: | Soil Gross Morphology: 30% of flowers to be produced have opened |
| phenotype: | ROSETTE LEAVES - Other |
| notes: | small rosette leaves |
| unique F1 plant ID: | R1 PLANT:ME02627-05 |
| phenotype ID: | 55763 |
| assay: | Soil Gross Morphology: 30% of flowers to be produced have opened |
| phenotype: | FLOWER - Reduced fertility |
| notes: | NONE |
| unique F1 plant ID: | R1 PLANT:ME02627-10 |
| phenotype ID: | 56099 |
| assay: | Soil Gross Morphology: 30% of flowers to be produced have opened |
| phenotype: | FLOWER - Reduced fertility |
| notes: | NONE |

Knock-in phenotype in gene(cDNA_id): 13496922

| | |
|---|---|
| clone ID: | 14909 |
| Promoter: | 35S |
| unique F1 plant ID: | R1 PLANT:ME06932-02 |
| phenotype ID: | 99919 |
| assay: | Soil Gross Morphology: 6 rosette leaves 1 mm in length |
| phenotype: | WHOLE PLANT - Other |
| notes: | pale green |
| unique F1 plant ID: | R1 PLANT:ME06932-02 |
| phenotype ID: | 99920 |
| assay: | Soil Gross Morphology: 6 rosette leaves 1 mm in length |
| phenotype: | ROSETTE LEAVES - Short Petioles |
| notes: | NONE |
| unique F1 plant ID: | R1 PLANT:ME06932-02 |
| phenotype ID: | 99921 |
| assay: | Soil Gross Morphology: 6 rosette leaves 1 mm in length |
| phenotype: | WHOLE PLANT - Small |
| notes: | 20 pct wt |
| unique F1 plant ID: | R1 PLANT:ME06932-02 |
| phenotype ID: | 99922 |
| assay: | Soil Gross Morphology: 50% of flowers to be produced have opened |
| phenotype: | INFLORESCENCE - Short |
| notes: | 50 pct wt |
| unique F1 plant ID: | R1 PLANT:ME06932-04 |
| phenotype ID: | 99983 |
| assay: | Soil Gross Morphology: 50% of flowers to be produced have opened |
| phenotype: | INFLORESCENCE - Short |
| notes: | 50 pct wt |
| unique F1 plant ID: | R1 PLANT:ME06932-05 |
| phenotype ID: | 100003 |
| assay: | Soil Gross Morphology: 7 rosette leaves 1 mm in length |
| phenotype: | WHOLE PLANT - Other |
| notes: | pale green |
| unique F1 plant ID: | R1 PLANT:ME06932-05 |
| phenotype ID: | 100004 |
| assay: | Soil Gross Morphology: 7 rosette leaves 1 mm in length |
| phenotype: | ROSETTE LEAVES - Short Petioles |
| notes: | NONE |
| unique F1 plant ID: | R1 PLANT:ME06932-05 |
| phenotype ID: | 100005 |
| assay: | Soil Gross Morphology: 7 rosette leaves 1 mm in length |
| phenotype: | INFLORESCENCE - Late Flowering |

TABLE 1-continued

| | |
|---|---|
| notes: | possible |
| unique F1 plant ID: | R1 PLANT:ME06932-05 |
| phenotype ID: | 100006 |
| assay: | Soil Gross Morphology: 50% of flowers to be produced have opened |
| phenotype: | INFLORESCENCE - Short |
| notes: | 50 pct wt |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07569389B2). An electronic copy of the "Sequence Listing" will also be available from the USPTO upon request and payment of the fee set forth in 37 CFR 1.19(b)(3).

What is claimed is:

1. A method of introducing an isolated nucleic acid molecule into a host cell comprising:
    a) providing an isolated nucleic acid molecule having a nucleotide sequence that encodes an amino acid sequence which is at least 95% identical to SEQ ID NO: 48107;
    b) contacting said isolated nucleic acid molecule with said host cell under conditions that permit insertion of said nucleic acid molecule into said host cell; and
    c) obtaining a plant with increased leaf number, increased inflorescence or both when compared to a non-transformed plant of the same species cultivated under the same conditions when said nucleic acid molecule is overexpressed.

2. The method of claim 1, wherein said isolated nucleic acid molecule encodes an amino acid sequence that is at least 97% identical to the sequence set forth in SEQ ID NO: 48107.

3. The method of claim 1, wherein said isolated nucleic acid molecule encodes the amino acid sequence set forth in SEQ ID NO: 48107.

4. A method of producing a plant having increased leaf number, increased inflorescence or both, said method comprising:
    a) transforming a plant, plant cell, plant material or seed of a plant by contacting said plant, plant cell, plant material or seed of a plant with a vector construct, said vector construct comprising:
        a first nucleic acid sequence that is a regulatory sequence which causes transcription in a plant; and
        a second nucleic acid sequence that encodes an amino acid sequence which is at least 95% identical to SEQ ID NO: 48107,
        wherein said first and second nucleic acid sequences are operably linked,
    b) overexpressing said second nucleic acid sequence in said transformed plant, plant cell, plant material or seed of a plant; and
    c) regenerating from said transformed plant, plant cell, plant material or seed of a plant a plant having increased leaf number, increased inflorescence or both as compared to a non-transformed plant of the same species cultivated under the same conditions.

5. The method of claim 4, wherein said transforming nucleic acid molecule encodes an amino acid sequence that is at least 97% identical to the sequence set forth in SEQ ID NO: 48107.

6. The method of claim 4, wherein said transforming nucleic acid molecule encodes the amino acid sequence set forth in SEQ ID NO: 48107.

7. A plant, plant cell, plant material or seed of a plant having increased leaf number, increased inflorescence or both, said plant comprising a nucleic acid molecule having a nucleotide sequence which encodes an amino acid sequence that is at least 95% identical to SEQ ID NO: 48107, wherein said nucleic acid molecule is exogenous or heterologous to said plant, plant cell, plant material or seed of a plant, and wherein overexpression of said nucleic acid molecule in said plant causes said plant to have increased leaf number, increased inflorescence or both as compared to a non-transformed plant of the same species cultivated under the same conditions.

8. A plant, plant cell, plant material or seed of a plant which comprises a vector construct, said vector construct comprising:
    a first nucleic acid sequence that is a regulatory sequence which causes transcription and in a plant; and
    a second nucleic acid sequence that encodes an amino acid sequence which is at least 95% identical to SEQ ID NO: 48107;
    wherein said first and second nucleic acid sequences are operably linked, and wherein transcription of said second nucleic acid sequence causes increased leaf number, increased inflorescence or both in said plant or in a plant regenerated from said plant, plant cell, plant material or seed of a plant.

9. The plant according to claim 7 or 8, wherein said plant has increased leaf number.

10. The plant according to claim 7 or 8, wherein said plant has increased inflorescence.

11. A method for increasing leaf number comprising transforming a plant with a nucleic acid molecule which encodes an amino acid sequence exhibiting at least 95% sequence identity to SEQ ID NO: 48107, wherein the expression of said nucleic acid molecule confers increased leaf number as compared to a non-transformed plant of the same species cultivated under the same conditions.

12. A method for increasing inflorescence comprising transforming a plant with a nucleic acid molecule which encodes an amino acid sequence exhibiting at least 95% sequence identity to SEQ ID NO:48107, wherein the expression of said nucleic acid molecule confers increased inflorescence as compared to a non-transformed plant of the same species cultivated under the same conditions.

13. A plant obtained from the method of claim 11, wherein said plant has increased leaf number as compared to a non-transformed plant of the same species cultivated under the same conditions.

14. The method of claim 11 or 12, wherein said transforming nucleic acid molecule encodes an amino acid sequence that is at least 97% identical to the sequence set forth in SEQ ID NO: 48107.

15. The method of claim 11 or 12, wherein said transforming nucleic acid molecule encodes the amino acid sequence set forth in SEQ ID NO: 48107.

16. A plant obtained from the method of claim 12, wherein said plant has increased inflorescence as compared to a non-transformed plant of the same species cultivated under the same conditions.

* * * * *